US009238818B2

(12) United States Patent
Carter et al.

(10) Patent No.: US 9,238,818 B2
(45) Date of Patent: Jan. 19, 2016

(54) METHODS AND GENETIC CONSTRUCTS FOR MODIFICATION OF LIGNIN COMPOSITION OF CORN COBS

(75) Inventors: Royston E. Carter, Durham, NC (US); John Steffens, Chapel Hill, NC (US); Michael Nuccio, Durham, NC (US); Lawrence M. Lagrimini, Lincoln, NE (US)

(73) Assignee: Syngenta Participations AG, Basel (CH)

( * ) Notice: Subject to any disclaimer, the term of this patent is extended or adjusted under 35 U.S.C. 154(b) by 1027 days.

(21) Appl. No.: 12/549,783

(22) Filed: Aug. 28, 2009

(65) Prior Publication Data
US 2010/0071092 A1 Mar. 18, 2010

Related U.S. Application Data

(63) Continuation-in-part of application No. 11/109,594, filed on Apr. 19, 2005, now Pat. No. 8,129,588, and a continuation-in-part of application No. 11/388,275, filed on Mar. 24, 2006, now abandoned.

(60) Provisional application No. 60/563,687, filed on Apr. 20, 2004, provisional application No. 60/563,678, filed on Apr. 20, 2004, provisional application No. 60/665,695, filed on Mar. 28, 2005.

(51) Int. Cl.
C12N 15/82 (2006.01)
C12P 7/10 (2006.01)
A23K 1/00 (2006.01)

(52) U.S. Cl.
CPC .............. *C12N 15/8255* (2013.01); *A23K 1/00* (2013.01); *C12N 15/827* (2013.01); *C12N 15/8226* (2013.01); *C12P 7/10* (2013.01)

(58) Field of Classification Search
None
See application file for complete search history.

(56) References Cited

U.S. PATENT DOCUMENTS

| | | | |
|---|---|---|---|
| 5,593,874 A | 1/1997 | Brown et al. | 435/172.3 |
| 5,753,475 A | 5/1998 | Houck | 435/172.3 |
| 5,850,020 A | 12/1998 | Bloksberg et al. | |
| 5,866,791 A | 2/1999 | Holt | |
| 5,952,486 A | 9/1999 | Bloksberg et al. | |
| 5,959,178 A | 9/1999 | Fritig et al. | |
| 5,981,837 A | 11/1999 | Chapple | |
| 5,990,386 A | 11/1999 | An | 800/290 |
| 6,066,780 A | 5/2000 | Boudet et al. | |
| 6,140,554 A | 10/2000 | O'Reilly et al. | 800/287 |
| 6,204,434 B1 | 3/2001 | Bloksberg et al. | |
| 6,211,432 B1 | 4/2001 | Boudet et al. | |
| 6,228,645 B1 | 5/2001 | Bruce et al. | 435/424 |
| 6,239,329 B1 | 5/2001 | Weigel et al. | 800/278 |
| 6,342,657 B1 | 1/2002 | Thomas et al. | 800/287 |
| 6,410,826 B1 | 6/2002 | Yanofsky et al. | |
| 6,441,272 B1 | 8/2002 | Ye | |
| 6,537,604 B1 | 3/2003 | Ethington, Jr. | |
| 6,552,249 B1 | 4/2003 | Cahoon et al. | |
| 6,610,521 B1 | 8/2003 | Cahoon | |
| 6,610,908 B1 | 8/2003 | Chapplpe | |
| 6,846,677 B2 | 1/2005 | Yanofsky et al. | |
| 6,855,864 B2 | 2/2005 | Chiang et al. | |
| 2002/0032917 A1 | 3/2002 | Benfey et al. | 800/278 |
| 2002/0081693 A1 | 6/2002 | Cahoon et al. | |
| 2002/0138870 A1 | 9/2002 | Chiang | |
| 2003/0106106 A1 | 6/2003 | Takakura et al. | 800/287 |
| 2003/0131373 A1 | 7/2003 | Bloksberg et al. | |
| 2003/0159170 A1 | 8/2003 | Cahoon | |
| 2004/0014116 A1 | 1/2004 | Cahoon | |
| 2004/0016024 A1 | 1/2004 | Wang et al. | 800/286 |
| 2004/0045053 A1 | 3/2004 | Greenland et al. | 800/284 |
| 2004/0060084 A1 | 3/2004 | An et al. | 800/287 |
| 2004/0214272 A1 | 10/2004 | La Rosa et al. | |

FOREIGN PATENT DOCUMENTS

| | | |
|---|---|---|
| CA | 2005597 | 12/1989 |
| WO | 93/05159 | 3/1993 |
| WO | 9305160 | 3/1993 |
| WO | WO9423044 | 10/1994 |
| WO | 97/12982 | 10/1997 |
| WO | 9803535 | 1/1998 |
| WO | 9910498 | 3/1999 |
| WO | 0022099 | 4/2000 |
| WO | 01/34817 | 5/2001 |
| WO | WO0173090 | 10/2001 |
| WO | 0195702 | 12/2001 |
| WO | 0226994 | 4/2002 |
| WO | 03/018819 | 3/2003 |
| WO | WO 03/087313 A2 | 10/2003 |
| WO | 2004048595 | 6/2004 |
| WO | 2004099413 | 11/2004 |
| WO | 2004099414 | 11/2004 |
| WO | 2006/104891 | 10/2006 |

OTHER PUBLICATIONS

Margulis M. Biodiversity: molecular biological domains, symbiosis and kingdom origins. Biosystems. 1992;27(1):39-51.*
Theissen G. et al. Classification and phylogeny of the MADS-box multigene family suggest defined roles of MADS-box gene subfamilies in the morphological evolution of eukaryotes. J. Mol. Evol. Nov. 1996;43(5):484-516.*
Benfey et al. The Cauliflower Mosaic Virus 35S Promoter: Combinatorial Regulation of Transcription in Plants. Science, 1990, vol. 250, pp. 959-966.*
Piquemal et al. Down-regulation of caffeic acid o-methyltransferase in maize revisited using a transgenic approach. Plant Physiol. Dec. 2002;130(4):1675-85.*

(Continued)

*Primary Examiner* — Cynthia Collins
(74) *Attorney, Agent, or Firm* — Joshua L. Price

(57) ABSTRACT

Expression cassettes causing specific regulatory control of transgene expression in plants, wherein the expression cassettes include regulatory sequences from the MADS gene family for expression of recombinant gene products in the reproductive tissue of plants for the purpose of generating maize plants with altered lignin content of the cobs.

9 Claims, No Drawings

(56) References Cited

OTHER PUBLICATIONS

Shinozuka et al. Isolation and characterization of rice MADS box gene homologues and their RFLP mapping. DNA Res. Apr. 30, 1999;6(2):123-9.*

Jia et al. Characterization and transcriptional profiles of two rice MADS-box genes. Plant Sci. Jun. 29, 2000;155(2):115-122.*

Yu et al. Spatial and temporal expression of the orchid floral homeotic gene DOMADS1 is mediated by its upstream regulatory regions. Plant Mol Biol. May 2002;49(2):225-37.*

Cacharron et al., "Expression of MADS box genes ZMM8 and ZMM14 during inflorescence development of Zea mays discriminates between the upper and the lower floret of each spikelet," Dev Genes Evol (1999) 209: 411-420.

Kang et al., "Isolation and Characterization of a Rice MADS Box Gene Belonging to the AGL2 Gene Family," Mol. Cells (1997) vol. 7, No. 1:45-51.

Larkin et al., "Arabdiopsis Glabrous1 Gene Requires Downstream Sequences for Function," The Plant Cell, vol. 5: 1739-1748, Dec. 1993.

Lopez-Dee et al., OsMADS13, a Novel Rice MADS-Box Gene Expressed During Ovule Development, Developmental Genetics, 25: 237-244 (1999).

Moon et al., "Determination of the Motif Responsible for Interaction between the Rice APETALA1/AGAMOUS-LIKE9 Family Proteins Using a Yeast Two-Hybrid System," Plant Physiology, Aug. 1999, vol. 120: 1193-1203.

Sieburth et al., "Molecular Dissection of the AGAMOUS Control Region Shows That cis Elements for Spatial Regulation Are Located Intragenically," The Plant Cell, vol. 9: 355-365, Mar. 1997.

Yu et al., "Identification and Characterization of Three Orchid MADS-Box Genes of the AP1/AGL9 Subfamily during Floral Transition," Plant Physiology, Aug. 2000, vol. 123: 1325-1336.

Aoki et al., "Molecular Cloning and Expression Analysis of a Gene for a Sucrose Transporter in Maize (Zea mays L.)," Plant Cell Physiol., 40(10), pp. 1072-1078, 1999.

Huijser et al, "Bracteomania, an inflorescence anomaly, is caused by the loss of function of the MADS-box gene squamosa in Antirrhinum majus," The EMBO Journal, vol. 11, No. 4, pp. 1239-1249, 1992.

Syngenta Participations AG, International Application Ser. No. PCT/US2006/010795, International Search Report and Written Opinion, Jul. 1, 2008.

Ballard et al., "Effect of Corn Silage Hybrid on Dry Matter Yield, Nutrient Composition, InVitro Digestion, Intake by Dairy Heifers and Milk Production by Dairy Cows", J. Dairy Sci. 84: 442-452 (2001).

Dwivedi et al., "Modification of Lignin Biosyntehsis in Transgenic Nicotiana Through Expression of an Antisense O-Methyltransferase Gene From Populus", Plant Molecular Biology 26: 61-71 (1994).

Lapierre et al., "Structural Alterations of Lignins in Transgenic Poplars With Depressed Cinnamyl Alcohol Dehydrogenase or Caffeic Acid O-Methyltransferase Activity Have an Opposite Impact on the Efficiency of Industrial Kraft Pulping", Plant Physiology, vol. 119 pp. 153-163 (Jan. 1999).

Morrow et al., "Molecular Characterization of a Brown Midrib3 Deletion Mutation in Maize", Molecular Breeding 3: 351-357, (1997).

Oba et al., "Effects of Brown Midrib 3 Mutation in Corn Silage on Dry Matter Intake and Productivity of High Yielding Dairy Cows"., J. Dairy Sci. 82: 135-142 (1999).

Piquemal et al., Down-Regulation fo Caffeic Acid O-Methyltransferase in Maize Revisited Using a Transgenic Approach, Plant Physiology vol. 130, pp. 1675-1685 (Dec. 2002).

* cited by examiner

METHODS AND GENETIC CONSTRUCTS FOR MODIFICATION OF LIGNIN COMPOSITION OF CORN COBS

CROSS REFERENCE TO RELATED APPLICATIONS

This application is a continuation in part of pending U.S. application Ser. No. 11/388,275, which claims priority to U.S. application Ser. No. 60/665,685, filed Mar. 28, 2005, the disclosure of which is hereby incorporated by reference; and this application is also a continuation in part of pending U.S. application Ser. No. 11/109,594, filed Apr. 19, 2005, which claims priority to U.S. application Ser. No. 60/563,687, filed Apr. 20, 2004 and U.S. application Ser. No. 60/563,678, filed Apr. 20, 2004. The disclosure of all of the foregoing U.S. patent applications are herein incorporated by reference in their entirety.

REFERENCE TO SEQUENCE LISTING SUBMITTED ELECTRONICALLY

The official copy of the sequence listing is submitted concurrently with the specification as a text file via EFS-Web, in compliance with the American Standard Code for Information Interchange (ASCII), with a file name of "70369USCIP Sequence_Listing.txt", a creation date of Oct. 5, 2009, and a size of 150 KB. The sequence listing filed via EFS-Web is part of the specification and is hereby incorporated in its entirety by reference herein.

FIELD OF THE INVENTION

The present invention includes expression cassettes that contain regulatory sequences derived from a target gene, for example, regulatory sequences from the MADS gene family, for tissue specific expression of recombinant gene products in plants.

BACKGROUND OF THE INVENTION

In agricultural biotechnology, plants can be modified according to one's needs. One way to accomplish this is by using modern genetic engineering techniques. For example, by introducing a gene of interest into a plant, the plant can be specifically modified to express a desirable phenotypic trait. For this, plants are transformed most commonly with a heterologous gene comprising a promoter region, a coding region and a termination region. When genetically engineering a heterologous gene for expression in plants, the selection of a promoter is often a critical factor. While it may be desirable to express certain genes constitutively, i.e. throughout the plant at all times and in most tissues and organs, other genes are more desirably expressed only in response to particular stimuli or confined to specific cells or tissues.

Promoters consist of several regions that are necessary for full function of the promoter. Some of these regions are modular, in other words they can be used in isolation to confer promoter activity or they may be assembled with other elements to construct new promoters. The first of these promoter regions lies immediately upstream of the coding sequence and forms the "core promoter region" containing consensus sequences, normally 20-70 base pairs immediately upstream of the coding sequence. The core promoter region contains a TATA box and often an initiator element as well as the initiation site. The precise length of the core promoter region is not fixed but is usually well recognizable. Such a region is normally present, with some variation, in most promoters. The base sequences lying between the various well-characterized elements appear to be of lesser importance. The core promoter region is often referred to as a minimal promoter region because it is functional on its own to promote a basal level of transcription.

The presence of the core promoter region defines a sequence as being a promoter: if the region is absent, the promoter is non-functional. The core region acts to attract the general transcription machinery to the promoter for transcription initiation. However, the core promoter region is insufficient to provide full promoter activity. A series of regulatory sequences, often upstream of the core, constitute the remainder of the promoter. The regulatory sequences determine expression level, the spatial and temporal pattern of expression and, for a subset of promoters, expression under inductive conditions (regulation by external factors such as light, temperature, chemicals and hormones). Regulatory sequences may be short regions of DNA sequence 6-100 base pairs that define the binding sites for trans-acting factors, such as transcription factors. Regulatory sequences may also be enhancers, longer regions of DNA sequence that can act from a distance from the core promoter region, sometimes over several kilobases from the core region. Regulatory sequence activity may be influenced by trans-acting factors including general transcription machinery, transcription factors and chromatin assembly factors.

Frequently, it is desirable to have tissue-specific expression of a gene of interest in a plant. Tissue-specific promoters promote expression primarily in one set of tissues without expression throughout the plant; tissue-preferred promoters promote expression at a higher level in a subset of tissues with significantly less expression in the other tissues of the plant. For example, one may desire to express a value-added product only in corn seed or in the corn cob but not in the remainder of the plant. Another example is the production of male sterility by tissue-specific ablation.

Tissue specific promoters may be expressed in specific tissue at a specific time or times during the plant growth cycle. However, sufficient expression levels of gene products, especially those gene products directed to expression in specific tissues, is difficult to obtain. Iyer M., et al. (2001). It is known that the 5' untranslated leader sequence of mRNA, introns, and the 3' untranslated region of mRNA effect expression for particular genes. For example, Sieburth, L. E. and Meyerowitz, E. M. (1997) show that intragenic sequences appear to be necessary for the expression of the AGAMOUS (AG) gene, an *Arabidopsis* MADS box gene, in the distinct expression patterns of normal early and later flower development. Larkin J. C., et al. (1993) show that deletion of the 3' noncoding region of the *Arabidopsis* GLABROUS1 (GL1) gene negatively affects GL1 function. However, to date, identifying specific regulatory regions and incorporating them into a robust trait delivery platform has not been accomplished.

Important aspects of the present invention are based on the discovery that DNA sequences from the MADS gene family are exceptionally useful in the development of robust expression cassettes that express recombinant genes in the reproductive tissues of plants. An example would be the expression of genes which alter the lignin content of reproduction tissues of a plant such as the cob of a maize plant.

SUMMARY OF THE INVENTION

The present invention includes a number of different aspects, including specific regulatory control of transgene expression in plants by identifying regulatory sequences from the MADS gene family and incorporating such sequences into expression cassettes for expression of recombinant gene products in the reproductive tissue of plants.

The present invention relates to a method of constructing expression cassettes by identifying the target gene, using the relevant cDNA sequence to annotate the gDNA sequence for the purpose of identifying regulatory sequences of the target gene, and incorporating one or more of the regulatory sequences into an expression cassette with a nucleic acid molecule. A plant transformed with an expression cassette of the invention expresses the product of the nucleic acid molecule in a manner that mimics the expression of the target gene.

The present invention relates to the specific regulatory control of transgene expression in plants, and includes targeting transgene expression to developing reproductive tissue in maize, rice and other monocots. Use of the expression cassettes of the present invention includes expressing a glucose or sucrose transporter to increase reproductive sink strength. Sink strength can also be increased by flower-specific expression of an invertase gene or one or more of the trehalose metabolism genes. The invention further encompasses enhancing the capacity for small molecule uptake via increased expression of specific transporters.

The present invention provides methods and genetic expression constructs useful in the control of lignin biosynthesis in plants, and particularly in corn, and more particularly in the cobs of corn plants. In a specific example, double strand RNAi technology is utilized to decrease the expression of (or to knock out) a lignin biosynthesis gene such as either the cinnamyl-alcohol dehydrogenase (CAD) genes of maize or the caffeic acid O-methyl transferase (COMT) genes of maize. Preferred embodiments involve the knock out CAD or COMT genes specifically in the maize cob to reduce lignin content. This will provide improved digestibility of non-digestible fiber in the cob, which would improve whole plant digestibility by ruminants or the use of this plant material in cellulosic conversion to fuel such as ethanol. Limiting expression of brown mid-rib-like traits (i.e. low lignin content) only to the cob, the most highly lignified tissue, will still provide attractive increase in total plant digestibility, but mitigate most of the risk associated with poor agronomic performance such as increased lodging and poor dry-matter yield, as occurs with brown mid-rib mutations, which is associated with their systemic expression. Therefore, CAD or COMT knock out events were generated using double strand RNAi technology with OsMADS6, a cob preferred promoter.

DEFINITIONS

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "abiotic stress" refers to nonliving environmental factors such as frost, drought, excessive heat, high winds, etc., that can have harmful effects on plants.

The term "nucleic acid" refers to a polynucleotide of high molecular weight which can be single-stranded or double-stranded, composed of monomers (nucleotides) containing a sugar, phosphate and a base which is either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. Unless otherwise indicated, a particular nucleic acid sequence of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985); and Rossolini, et al., Mol. Cell. Probes 8:91-98 (1994)). The term nucleic acid is used interchangeably with gene, cDNA, and mRNA encoded by a gene.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Promoter" refers to a nucleotide sequence, usually upstream (5') to its coding sequence, which controls the expression of the coding sequence by providing the recognition for RNA polymerase and other factors required for proper transcription. "Promoter regulatory sequences" consist of proximal and more distal upstream elements. Promoter regulatory sequences influence the transcription, RNA processing or stability, or translation of the associated coding sequence. Regulatory sequences include enhancers, promoters, untranslated leader sequences, introns, and polyadenylation signal sequences. They include natural and synthetic sequences as well as sequences that may be a combination of synthetic and natural sequences. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term "promoter" includes "promoter regulatory sequences."

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Gene" refers to a nucleic acid fragment that expresses mRNA, functional RNA, or specific protein, including regulatory sequences. The term "Native gene" refers to a gene as found in nature. The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but one that is introduced into the organism by gene transfer.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

"Cob specific" or "cob preferred" promoters are plant promoters which show some degree of specificity of expression in the cob of maize plants. The tissue-specificity of some "tissue-specific" or "tissue-preferred" promoters may not be absolute and may be tested by one skilled in the art using the diphtheria toxin sequence. One can also achieve tissue-preferred expression with "leaky" expression by a combination of different tissue-specific promoters (Beals et al., Plant Cell 9:1527 (1997)). Other tissue-preferred promoters can be isolated by one skilled in the art (see U.S. Pat. No. 5,589,379). Tissue-specific or tissue-preferred promoters are not intended to be construed as promoters that only express in a specific tissue. Tissue-specific or tissue-preferred refers to promoters that favor a particular tissue for expression but this favoring of a tissue type is not always absolute.

The terms "MADS" or "MADS box" gene refer to genes which contain a MADS box domain. The MADS box domain is a conserved DNA sequence of about 180 nucleotides which encodes a DNA binding domain. MADS box containing genes are found in animals, fungi and plants. MADS box containing genes are typically transcription factors. A number of MADS box containing genes have been identified in plants including maize, see Munster et al. Maydica 47: 287-301 (2002).

DETAILED DESCRIPTION OF THE INVENTION

Lignin is a complex heterogeneous aromatic polymer which renders membranes impermeable and reinforces the walls of certain plants cells. Lignin is formed by polymerization of free radicals derived from monolignols, such as paracoumaryl, coniferyl and sinapyl alcohols (Higuchi, 1985, in Biosynthesis and degradation of wood components (T. Higuchi, ed.), Academic Press, Orlando, Fla. pp. 141-160). Lignin is formed by polymerization of at least three different monolignols which are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT publication no. WO 94/23044. Furthermore, it has been shown that antisense expression of sequences encoding CAD in poplar leads to the production of lignin having a modified composition (Grand, C. et al. Planta (Berl.) 163:232-237 (1985)).

Lignins have a wide variation in their relative content of monolignols, as a function of the species and the various tissues within the same plant. This variation is probably caused and controlled by different activities and specificities of substrates, the enzymes necessary for biosynthesis of lignin monomers (Higuchi, 1985, loc. cit.).

Beyond its role in the structure and development of plants, lignin represents a major component of the terrestrial biomass and assumes a major economic and ecological significance (Brown, 1985, J. Appl. Biochem. 7, 371-387; Whetten and Sederoff, 1991, Forest Ecology and Management, 43, 301-316). At the level of exploitation of the biomass, it is appropriate first to note that lignin is a limiting factor of the digestibility and nutritional yield of fodder plants. In fact, it is clearly demonstrated that the digestibility of fodder plants by ruminants is inversely proportional to the content of lignin in these plants, the nature of the lignins also being a determining factor in this phenomenon (Buxton and Roussel, 1988, Crop. Sci., 28, 553-558; Jung and Vogel, 1986, J. Anim., Sci., 62, 1703-1712).

Among the main fodder plants in which it would be of interest to reduce the lignin contents there may be mentioned: lucerne, fescue and maize fodder used for silaging. It should also be noted that high lignin contents are partly responsible for the limited quality of sunflower cake intended for feeding cattle, and for the reduction in germinative capacities of certain seeds in the horticultural sector. It may also be emphasized that the intense lignification which results during preservation of plant components after harvesting rapidly renders products such as asparagus, yam, carrots etc, unfit for consumption.

Furthermore, it is also appropriate to note that more than 50 million tons of lignin are extracted from ligneous material each year in the context of production of paper pulp in the paper industry. This extraction operation, which is necessary to obtain cellulose, is costly in energy and, secondly, causes pollution through the chemical compounds used for the extraction, which are found in the environment (Dean and Eriksson, 1992, Holzforschung, 46, 135-147: Whetten and Sederoff, 1991, loc. cit.). To reduce the proportions of lignins (which make up to 20 to 30% of the dry matter, depending on the species) to a few percent (2 to 5%) would represent an increase in yield and a substantial savings (chemical products), and would contribute to improving the environment (reduction in pollution). Given the scale of use of ligneous material, these decreases would have extremely significant repercussions. In this case, the species concerned could be poplar, eucalyptus, *Acacia magnium*, the genus *Casuarina* and all the angiosperms and gymnosperms used for the production of paper pulp.

In addition, lignin is a significant component of biomass which could be converted to fuel (such as ethanol) through the conversion of cellulosic biomass to ethanol. Lignin and cellulose fibers are intimately associated in the biomass of plants. Lignin can create a barrier that prevents cellulose degradation through either chemical methods or through the use of enzymes. The removal of lignin as well as hemicellulose is an important step in the process of converting cellulosic biomass to ethanol independent of the method of converting this biomass to fuel. Lignin poses a challenge to enzyme based conversion of cellulosic biomass to fuel and one of the goals of biomass pretreatment is the removal of lignin. Many pre-treatments associated with the conversion of cellulosic material to ethanol remove the lignin component as well as other components from the plant biomass. Plants with reduced lignin content may be a more efficient biomass for the cellulosic conversion of plant biomass to fuel, such as ethanol. Chen and Dixon, Nature Biotechnology 25: 759-761 (2007) characterized transgenic alfalfa which has been engineered to reduce the expression of a variety of lignin biosynthesis genes regulated under the bean phenylalanine ammonia-lyase promoter. Chen et al demonstrate that plant biomass resistance to acid pretreatment and enzyme mediated digestion of biomass is directly proportional to lignin content.

Corn cobs in particular have been identified as a source of biomass for conversion to ethanol. The corn cobs themselves are a collectable source of plant biomass which is important when considering potential feedstocks for plant biomass. Studies have also indicated that the removal of corn cobs from corn production fields does not prohibitively alter the fertilizer regimen recommended for corn fields which suggests that collecting cobs from the production of field corn will not have intense negative agronomic impacts. Corn cobs are typically tilled back into the soil after harvest of corn grain and hence, there has been investigation into the impact of removing this particular material from the field for use as a source of biomass for ethanol production.

It is clear that in the three sectors under consideration, the reduction in the levels of lignins must be moderated to preserve the characteristics of rigidity and the normal architecture of the plant (or the tree), since the lignins which strengthen the cell walls play a significant role in maintaining the erect habit of plants. The natural variations in the lignin contents observed in nature for the same species (deviations which can be up to 6-8% of the dry matter among individuals) justify the reductions suggested above. The resistance to degradation of lignin, like the difficulties encountered in the context of its extraction, are probably due to the complex structure of this polymer, which is made up of ether bonds and carbon-carbon bonds between the monomers, as well as to the numerous chemical bonds which exist between the lignin and the other components of the cell wall (Sarkanen and Ludwig, 1971, in Lignins: Occurrence, Formation, Structure and Reactions (K. V. Sarkanen and C. H. Kudwig ed.) New York: Wiley—Interscience, pp. 1-18).

An approach to attempt to reduce the level of lignins in plants by genetic engineering would consist of inhibiting the synthesis of one of the enzymes in the biosynthesis chain of these lignins indicated above. A particularly suitable technique in the context of such an approach is to use antisense mRNA which is capable of hybridizing with the mRNA which codes for these enzymes, and consequently to prevent, at least partly, the production of these enzymes from their corresponding mRNA. Such an antisense strategy carried out with the aid of the gene which codes for the CAD in tobacco was the subject matter of European Patent Application no. 584 117, which describes the use of antisense mRNA which is capable of inhibiting the production of lignins in plants by hybridizing with the mRNA which codes for the CAD in these plants. The results in the plants transformed in this way demonstrate a reduction in the activity of the CAD, but paradoxically the contents of lignins show no change. Complementary studies indicate that the lignins of transformed plants are different from control lignins, since the cinnamylaldehydes are incorporated directly into the lignin polymer.

Brown mid-rib (Bmr) corn has been used as an alternative for improving digestibility for silage hybrids for decades. The improvement in ruminal intakes and digestibility is derived from reduced lignin content in Bmr mutated hybrids. The brown mid-rib corn mutants; however, are difficult to develop commercially due to decreased agronomic performance associated with the low lignin content. The agronomic performance problems associated with brown mid-rib include lodging (plants are prone to falling over when exposed to environmental conditions such as wind) is outlined in references within Ballard et al. J. Dairy Sci. 84:442-452 (2001). The Bm1 mutation is relatively mild and causes the fewest pleiotropic effects, but it provides less digestibility improvement than Bm3, has been studied less, and has not been developed commercially. The Bm3 mutation is the best-studied Bm trait, it provides superior digestibility characteristics, but at the expense of moderately poor agronomic performance. Bm3 is the basis of existing commercial products. The Bm1 trait is caused by reduced activity of the biosynthetic enzyme, CAD and the Bm3 trait is caused by reduced activity of a biosynthetic enzyme, COMT.

The maize brown mid-rib mutants display agronomic performance problems which also can be observed in another plant mutant with altered lignin content. The *Arabidopsis* ref8 mutant is compromised in the biosynthesis of sinapate esters which is associated with the lignin biosynthesis pathway (Franke et al Plant Journal 30: 33-45 (2002)). The ref8 mutant has very reduced levels of sinapoylmalate and is deficient in the enzyme C3H (p-coumarate 3-hydroxylase) which is a lignin biosynthesis enzyme. The ref8 mutant is clearly stunted in growth and development which is evident in plants that are 3 weeks of age. The ref8 gene has been characterized as a P450 enzyme.

The following background references are hereby incorporated herein by reference: U.S. Pat. Nos. 6,441,272; 6,855,864; 6,610,908; 5,451,514; 5,866,791; 5,959,178; 6,066,780; 6,211,432; 5,981,837; 5,850,020; 6,204,434; and 6,610,521; U.S. patent applications 20020081693 and 20030159170; PCT applications WO2004080202; WO03054229; European Application EP1425401; and Piquemal et al., Plant Physiology 130:1675-1685 (2002); Vignols et al., The Plant Cell 7:407-416 (1995); Morrow et al., Molecular Breeding 3:351-357 (1997). These references discuss various aspects of lignin biosynthesis in plants, and the control thereof. In particular, U.S. Pat. Nos. 5,451,514; 5,959,178; and 6,066,780 are particularly important with regard to their teaching regarding the role of CAD and COMT expression in lignin biosynthesis in plants.

Altered plant physical phenotypes is also associated with the use of genetic engineering methods to alter lignin content of transgenic plants. Genetic engineering to decrease the expression of lignin biosynthesis genes has been employed to alter the lignin content of plants such as alfalfa as described by Nakashima et al New Phytologist 179: 738-750 (2008). Transgenic tobacco plants silenced for the expression of PAL (phenylalanine ammonia-lyase) have been shown to have both reduced levels of phenylpropanoid compounds as well as to display physical phenotypes of reduced growth and small spoon shaped leaves which curl under at the edges (Korth et al. Physiologia Plantarum 111: 137-143 (2001)). Transgenic tobacco plants engineered to silence the endogenous expression of CCR (cinnamoyl-CoA reductase), a lignin biosynthesis gene, also displayed a stunted growth phenotype which varied with the level of silencing of the endogenous gene (Piquemal et al Plant Journal 13: 71-83 (1998)). The stunted growth was observed in one 1 out 7 primary transformants generated and this particular transformant also displayed a severe morphological alteration to xylem tissue.

Plant cells and tissues can respond to mechanical, chemical or pathogen induced injury by producing various phenolic compounds including mono- or dimethoxylated lignin precursors derived from cinnamic acid via a complex series of biochemical reactions. These lignin precursors are eventually used by the plant to produce the lignin polymer which helps in wound repair by adding hydrophobicity, a physical barrier against pathogen infection and mechanical strength to the injured tissue (Vance, C. P., et al., 1980, Annu Rev Phytopathol 18:259-288). Biosynthesis of the mono- or dimethoxylated lignin precursors occurs, in part, by the action of two enzymes, caffeic acid 3-O-methyltransferase (COMT), also known as caffeic acid/5-hydroxyferulic acid O-methyltransferase and caffeoyl CoA 3-O-methyltransferase (CCOMT). Both enzymes have been isolated and purified from a wide variety of plant species.

Studies have shown that the activities of COMT and CCOMT increase prior to lignin deposition (Inoue, K., et al., 1998, Plant Physiol 117(3):761-770). Synthesis of lignin precursors involves the methylation of caffeic acid to yield ferulic acid followed by 5-hydroxylation of ferulate then a second methyltion to yield sinapate. COMT has been implicated in the methylation of both caffeic acid and 5-hydroxyferulic acid ((Inoue, K., et al., 1998, Plant Physiol 117(3):761-770). Research indicates that COMT transcripts are present at high levels in organs containing vascular tissue and one study suggests that antisense inhibition of COMT can lead to modified lignin content and composition in the xylem and phloem of transgenic plant tissue (Dwivedi, U., et al., 1994, Plant Mol. Biol. 26:61-71).

A promising technology for achieving targeted gene silencing is based on double-stranded RNA (dsRNA) inducing a response called post-transcriptional gene silencing or RNA interference (RNAi). Double-stranded RNA has been introduced into a number of different species, including nematodes, fruit flies, *Trypanosoma*, fungi, plants. See for example, WO9932619. Some limited success has also been demonstrated in mammals, specifically in mouse oocytes and embryos. Introduction of the appropriate dsRNA inhibits gene expression in a sequence-dependent manner, an effect that has been used extensively in *C. elegans* and *D. melanogaster* as a genetic tool for studying gene function. For example, 00/01846 describes methods for characterizing gene function using dsRNA inhibition. However, dsRNA inhibition has been applied with little success in mammalian systems.

Because of the importance of lignins in cell wall architecture and digestibility, and because of the unfavourable agronomics of Bmr corn, there is considerable interest in the prospects for altering lignin quantity or quality by genetic engineering. Thus, there is a great deal of interest in identifying the genes that encode proteins involved in the production of lignin in plants and in modification of the expression of such genes, for example by the use of RNAi methods. These methods may be used in plant cells to control lignin production. Such methods would have significant utility in the production of plant material with improved digestibility either as an animal feed or as a feedstock for fuel production, and if directed at decreasing lignin content of corn cobs, could avoid the agronomic downsides of the Bmr phenotype.

Lignin biosynthesis genes include those genes which are involved in the production of lignin in plants. Several genes are known to contribute to lignin biosynthesis (See Vanholme et al. Current Opinion in Plant Biology 11: 278-285 (2008) for review) which includes but is not limited to phenylalanine ammonia-lyase (PAL), cinnamate 4-hydroxylase (C4H), 4-coumarate:coenzyme A ligase (4CL), hydroxycinnamoyl transferase (HCT), p-coumarate 3-hydroxylase (C3H), caffeic acid O-methyl transferase (COMT), cinnamyl coenzyme A reductase (CCR) and the cinnamyl-alcohol dehydrogenase (CAD). Lignin biosynthesis genes encode lignin biosynthesis enzymes which catalyze biochemical steps in the formation of lignin in plants.

The present invention relates to a method for controlling lignin biosynthesis in a plant, the method comprising down-regulating the expression of an enzyme in the plant, the enzyme selected from the group consisting of CAD, COMT, PAL, C4H, 4CL, HCT, C3H, and CCR wherein the down-regulation is achieved using double-stranded RNAi. The method also relates to down-regulation of expression of both enzymes; to the dsRNAi constructs; and to cob-specific/cob-preferred constructs. The present invention also relates to the use of the low-lignin cobs produced using the method of the invention in biomass conversion applications (for example, in ethanol production) and in feed applications (for example, in animal feed for increased milk production, particularly in dairy cows).

The present invention includes a method for constructing expression cassettes based on identifying a target gene and incorporating into the expression cassettes modified regulatory elements of the selected target gene. For example, regulatory elements from genes that are expressed in roots, stalks, leaves, or reproductive tissues that provide insect resistance, herbicide tolerance, or abiotic stress tolerance are incorporated into expression cassettes for the purpose of producing a transgenic event in a plant that closely mimics the expression profile of the original target gene. Thus, the target gene may be identified from gene expression data.

The present invention is also directed to expression cassettes that incorporate the regulatory mechanisms of target genes of interest to express in plants the products of nucleic acid molecules of interest in a manner that mimics the expression profile of the original target genes.

The present invention further includes expression cassettes that incorporate 5'-MADS gene regulatory sequences to express the products of nucleic acid molecules in plant reproductive tissues, and further includes expression cassettes incorporating both MADS 5'- and 3'-regulatory sequences.

The present invention also includes expression cassettes that incorporate 5'-MADS gene regulatory sequences, and further incorporate a 5'-MADS gene exon.

The present invention also includes expression cassettes that incorporate 5'-MADS gene regulatory sequences, and further incorporates a 5'-MADS gene exon, and a 5'-MADS gene intron.

The present invention further includes expression cassettes that incorporate 5'-MADS gene regulatory sequences, and further incorporates a 5'-MADS gene exon, a 5'-MADS gene intron, and a second exon.

The present invention also includes and further includes expression cassettes incorporating both MADS 5'- and 3'-regulatory sequences, wherein said 3'-regulatory sequence include the 3'-non-translated sequence, and the 3'-nontranscribed sequence.

For purposes of this invention, the definition of the term "3'-non-translated sequence" includes modifications to the nucleotide sequence of a 3'-non-translated sequence derived from a target gene, provided the modified 3'-non-translated sequence does not significantly reduce the activity of its associated 3' regulatory sequence.

For purposes of this invention, the definition of the term "3'-nontranscribed sequence" includes modifications to the nucleotide sequence of a 3'-nontranscribed sequence derived from a target gene, provided the modified 3'-nontranscribed sequence does not significantly reduce the activity of its associated 3' regulatory sequence. The 3'-nontranscribed sequence extends approximately 0.5 to 1.5 kb downstream of the transcription termination site.

The present invention also includes expression cassettes incorporating both MADS 5'- and 3'-regulatory sequences, wherein said 3'-regulatory sequence includes the 3'-non-translated sequence, and the 3'-nontranscribed sequence, and may further include an intron of said MADS gene.

In general MADS genes contribute to the development of plant reproductive structures (De Bodt et al., 2003). For example, the DoMADS3 gene is expressed specifically in pedicel tissue (Yu and Goh, 2000). The genes of the OsMADS gene family were selected for expression cassette development because they encode MADS-transcription factors that are expressed in young rice flowers (Kang and An, 1997). The proteins encoded by genes of the OsMADS gene family are similar to the orchid DoMADS3 gene (GenBank accession AF198176). The present invention recognizes that one method of stabilizing or increasing yield in monocots such as maize is to increase sink strength in reproductive tissue. Thus, transgenic methods for production of plants having increased sink strength in reproductive tissue would benefit from the use of promoters that result in specific expression in a plant's reproductive tissues. The present invention therefore includes the use of OsMADS gene 5'- and 3'-regulatory sequences in expression cassettes to target transgene expression to developing reproductive tissues. The MADS genes from which gene regulatory sequences were identified and utilized according to the present invention encode the following list of MADS proteins (TABLE 1). The MADS proteins are compared by percent identity and similarity to the protein encoded by the DoMADS3 gene.

TABLE 1

| MADS gene | Whole Protein identity | similarity | gaps | MADS Domain Only identity | similarity |
|---|---|---|---|---|---|
| AB003322 | 42% | 58% | 0% | 68% | 78% |
| AB003324 | 59% | 74% | 3% | 80% | 95% |
| AB003328 | 48% | 64% | 0% | 77% | 91% |
| AF077760 | 40% | 59% | 2% | 64% | 80% |

TABLE 1-continued

| MADS gene | Whole Protein identity | similarity | gaps | MADS Domain Only identity | similarity |
|---|---|---|---|---|---|
| AF095645 | 40% | 61% | 5% | 64% | 90% |
| AF139664 | 50% | 66% | 1% | 78% | 95% |
| AF139665 | 48% | 66% | 0% | 80% | 95% |
| AF141964 | 40% | 60% | 11% | 66% | 86% |
| AF141965 | 51% | 67% | 0% | 84% | 91% |
| AY174093 | 42% | 63% | 0% | 63% | 87% |
| AF204063 | 60% | 72% | 3% | 91% | 98% |
| AF345911 | 50% | 68% | 5% | 80% | 95% |
| AF424549 | 39% | 59% | 2% | 63% | 87% |
| AJ293816 | 35% | 52% | 8% | 65% | 79% |
| AY115556 | 39% | 61% | 1% | 60% | 85% |
| AY177695 | 39% | 58% | 0% | 66% | 87% |
| AY177696 | 38% | 62% | 4% | 61% | 87% |
| AY177698 | 41% | 61% | 3% | 68% | 87% |
| AY177699 | 37% | 59% | 3% | 63% | 78% |
| AY177700 | 41% | 61% | 0% | 66% | 87% |
| AY177702 | 38% | 59% | 5% | 70% | 89% |
| AY224482 | 38% | 59% | 5% | 70% | 89% |
| AY250075 | 42% | 67% | 5% | 64% | 88% |
| L37527 | 37% | 60% | 5% | 63% | 85% |
| L37528 | 45% | 68% | 1% | 84% | 94% |
| U78891 | 62% | 75% | 4% | 94% | 99% |
| U78782 (OsMADS6) | 58% | 69% | 4% | 91% | 99% |
| U78892 (OsMADS8) | 60% | 73% | 6% | 94% | 99% |
| U78890 (OsMADS5) | 57% | 72% | 2% | 92% | 97% |
| AF151693 (OsMADS13) | 46% | 67% | 1% | 84% | 94% |
| AF095646 | 55% | 67% | 6% | 94% | 99% |

The present invention therefore includes an expression cassette for expression of a nucleic acid molecule product primarily in the reproductive tissue of a plant comprising a promoter, a first exon; a first intron, and a second exon of a MADS gene, wherein said promoter, first exon, intron, and second exon are the 5'-regulatory sequence of said expression cassette; wherein said 5'-regulatory sequence is engineered to include a translational initiation codon at approximately the 3'-end of said 5'-regulatory sequence, and not to contain restriction endonuclease sites that hinder manipulation by recombinant DNA methods or additional translation initiation codons upstream of said translation initiation codon; a 3'-regulatory sequence of a MADS gene that does not contain restriction endonuclease sites that hinder manipulation by recombinant DNA methods; and a nucleic acid molecule operably linked to said 5'-regulatory sequence and said 3'-regulatory sequence.

Another embodiment of the invention includes a rice floral promoter that functions in transgenic maize plants by expressing in the cob or floral organs of the maize plants. The rice floral promoter may be selected by expression profiling rice to identify genes which preferentially express in the floral organs of rice. These promoters can then be screened by operatively linking the promoter with a reporter gene, such as GUS, and determining the spatial and temporal expression of the promoter in transgenic maize plants. Some of the promoters from MADS box containing genes are an example of a rice floral promoter which functions in transgenic maize by expressing in the cob or floral organs of the maize plant.

Another embodiment of the invention includes any promoter that expresses preferentially in the cob of the maize plants. A variety of promoters are known to be cob preferred such as promoters which are activated by transcription factors which express preferentially in reproductive tissues. Sekhon and Chopra Genetics 181: 81-91 (2009) characterize the interaction of Ufo1 with P1 (a MADS box containing transcription factor, Myb) and demonstrate that several genes including c2, chi1 and a1 preferentially express in the reproductive tissues of maize plants. C2, chi1 and a1 are structural genes associated with the production of pigment in the silks, pericarp and husk of corn plants and appear to be regulated by P1. Additionally, a comparison of genes expressed in immature ear with genes expressed in roots identified several genes which appear to be expressed preferentially in the immature ear (Cho et al. Genome Biology 3(9): 0045.1-0045.16 (2002). Cho identifies a several MADS box containing genes as well as three different heat shock proteins, late elongated hypocotyls and the mudr transposase as preferentially expressed in immature ear indicating that the promoters from these genes may be cob preferred promoters.

Recombinant DNA methods require the presence of specific restriction endonuclease sites at the termini of the DNA molecules to be joined. The most efficient practice requires the sites in one molecule complement the sites in the other molecule. For example, a plasmid with SacI and NotI restriction endonuclease sites is required to clone a gene of interest with SacI and Not I restriction endonuclease sites at its termini. Ideally, these sites are unique, that is they should not occur at any other place in either molecule. If these sites occur internally, they hinder manipulation by recombinant DNA methods and should be eliminated. Site-directed mutagenesis is one method of eliminating such sites. Techniques such as partial digestion followed by gel-purification of the appropriately sized fragment will also accomplish this without eliminating the internal restriction endonuclease sites, but are far less efficient and therefore less desirable.

The present invention recognizes that chemical synthesis, that is use of synthetic chemical technology as opposed enzyme-mediated technology, of a polynucleotide molecule can replace or substitute for recombinant DNA methods in the construction of a polynucleotide molecule comprising a specific nucleotide sequence.

The present invention further includes a method for constructing an expression cassette comprising the steps of selecting a target gene based on its expression data or its encoded protein's similarity to a protein encoded by another gene of interest; identifying the open reading frame on said target gene cDNA; identifying the positions of the translational start codon, translational stop codon, the first intron, first exon, second exon, the 3'-untranslated sequence and the 3'-nontranscribed sequence of said target gene gDNA by using the cDNA to annotate the target gene gDNA; incorporating into an expression cassette a 5'-regulatory sequence comprising said promoter, first exon, first intron, and second exon and a 3'-regulatory sequence comprising the 3'-untranslated sequence and the 3'-nontranscribed sequence; and operably linking a nucleic acid molecule to said 5'-regulatory sequence and said 3'-regulatory sequence of said expression cassette, wherein said nucleic acid molecule is expressed in a manner that mimics the expression profile of said target gene of interest.

In the methods and compositions of the present invention, lignin is altered in plants which express a gene silencing expression cassette under the control of an OsMADS promoter which directs expression of the gene silencing expression cassette to the cob of a maize plant wherein the gene silencing cassette when expressed leads to the down-regulation of a lignin biosynthesis gene. By down-regulating the activity of lignin biosynthesis genes such as CAD, COMT, PAL, C4H, 4CL, HCT, C3H, or CCR it is intended that the level of activity of the lignin biosynthesis enzyme in a plant is decreased or completely suppressed in comparison to the activity in a corresponding control plant which has not been manipulated to decrease the activity of the lignin biosynthesis enzyme. The activity of the lignin biosynthesis enzyme, the target protein, is inhibited, reduced, or eliminated if the activity is less than 95%, less than about 90%, less than about 80%, less than about 70%, less than about 60%, less than about 50%, less than about 40%, less than about 30%, less than about 20%, less than about 10%, or is 100% less than the activity of the lignin biosynthesis enzyme in a plant that is not a mutant or that has not been genetically modified to inhibit the expression of the lignin biosynthesis enzyme. The activity of a lignin biosynthesis enzyme can be measured by measuring the lignin content of the plants.

Methods for inhibiting or eliminating the expression of a gene in a plant are well known in the art, and any such method may be used in the methods of the present invention. Antisense constructions, complementary to at least a portion of the messenger RNA (mRNA) for the target sequence (such as a lignin biosynthesis gene) can be utilized. Antisense nucleotides are constructed to hybridize with the corresponding mRNA. Modifications of the antisense sequences may be made as long as the sequences hybridize to and interfere with expression of the corresponding mRNA. In this manner, antisense constructs having at least about 70%, at least about 80%, at least about 85% or higher sequence identity to the corresponding sense sequences may be used. Furthermore, portions of the antisense nucleotides may be used to disrupt the expression of lignin biosynthesis genes. Generally, sequences of at least about 10 nucleotides, at least about 20 nucleotides, at least about 30 nucleotides, at least about 40 nucleotides, at least about 50 nucleotides, at least about 100 nucleotides, at least about 200 nucleotides, at least about 300, at least about 400, at least about 450, at least about 500, at least about 550, or greater may be used. Antisense methods are known in the art, See, for example, Sheehy et al. (1988) Proc. Natl. Acad. Sci. USA 85:8805-8809; and U.S. Pat. Nos. 5,107,065; 5,453,566; and 5,759,829); herein incorporated by reference.

Cosuppression may also be used to suppress the expression of lignin biosynthesis genes. In this manner, a heterologous lignin biosynthesis gene is expressed in a plant of interest in the sense orientation to suppress the expression of the endogenous lignin biosynthesis gene in the plant. Methods for cosuppression are known in the art. See, for example, Taylor (1997) Plant Cell 9:1245; Jorgensen (1990) Trends Biotech. 8(12):340-344; Jorgensen et al. (1996) Plant Mol. Biol. 31:957-973; Johansen and Carrington (2001) Plant Physiol. 126:930-938; Broin et al. (2002) Plant Cell 14:1417-1432; Stoutjesdijk et al (2002) Plant Physiol. 129:1723-1731; Yu et al. (2003) Phytochemistry 63:753-763; Flavell (1994) Proc. Natl. Acad. Sci. USA 91:3490-3496; Finnegan et al. (1994) Bio/Technology 12:883-888; Neuhuber et al. (1994) Mol. Gen. Genet. 244:230-241; and U.S. Pat. Nos. 5,034,323, 5,283,184, and 5,942,657; all of which are herein incorporated by reference.

Cosuppression involves transforming plants with a DNA construct comprising a promoter that drives expression in a plant operably linked to at least a portion of a polynucleotide that corresponds to the transcript of a lignin biosynthesis gene. The nucleotide sequence is constructed or chosen to have substantial sequence identity to the sequence of the transcript of the endogenous lignin biosynthesis gene, typically greater than about 60% sequence identity, more typically greater than about 80% sequence identity, more typically greater than about 90% sequence identity, and in some instances greater than about 95% sequence identity.

RNA interference (RNAi) can also be used to down-regulate lignin biosynthesis gene activity. See, generally, Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *Proc. Natl. Acad. Sci. USA* 95:15502-15507. In RNAi, long double-stranded RNAs (dsRNAs), typically >200 nucleotides, can be used to silence the expression of a lignin biosynthesis gene in a plant. Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme. These siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate or endogenous RNA. Cleavage of cognate or endogenous RNA takes place near the middle of the region bound by the siRNA strand.

In this manner, double-stranded RNA (dsRNA) interference may be used. For dsRNA interference, a sense and an antisense RNA molecule that is fully or partially complementary to the sense RNA molecule of a lignin biosynthesis gene are expressed in the same cell, resulting in inhibition of the expression of the corresponding endogenous messenger RNA encoding the lignin biosynthesis gene.

The sense and antisense molecules can be expressed from a single or separate expression cassette. Alternatively, multiple plant lines transformed with the dsRNA interference expression cassette or expression cassettes are then screened to identify plant lines that show the greatest inhibition of lignin biosynthetic enzyme expression. Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

In some embodiments of the invention, inhibition of the expression of a lignin biosynthesis gene may be obtained by hairpin RNA (hpRNA) interference or intron-containing hairpin RNA (ihpRNA) interference. A short hairpin RNA (shpRNA) is a sequence of RNA that makes a tight hairpin turn that can be used to silence gene expression. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

Interfering hairpin RNA (ihpRNA) may also be used in the methods of the invention. ihpRNA have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, thus increasing the efficiency of interference. See, for example, Smith et al. (2000) *Nature* 407:319-320. Methods for using ihpRNA interference to inhibit the expression of endogenous plant genes are described, for example, in Smith et al. (2000) *Nature* 407:319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference. See also WO 02/00904 where the hpRNA is designed such that the loop region determines the specificity of the RNA interference.

In some embodiments of the invention, RNA interference by expression of a gene encoding a micro RNA (miRNA) may be used. miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference. For miRNA interference, the expression cassette is designed to express an RNA molecule that is modeled on an endogenous miRNA gene. The miRNA gene encodes an RNA that forms a hairpin structure containing about a 22-nucleotide sequence that is complementary to R1. For example, for suppression of lignin biosynthesis gene expression, the 22-nucleotide sequence is selected from a lignin biosynthesis gene transcript sequence and contains 22 nucleotides of said lignin biosynthesis gene coding sequence in sense orientation and 21 nucleotides of a corresponding antisense sequence that is complementary to the sense sequence.

Other methods for down-regulating the activity of a lignin biosynthesis gene include virus-induced gene silencing (Burton et al. (2000) *Plant Cell* 12:691-705; and Baulcombe (1999) *Curr. Op. Plant Bio.* 2:109-113); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90-96; Dharmapuri and Sonti (1999) *FEMS Microbiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928; Bensen et al. (1995) *Plant Cell* 7:75-84; Mena et al. (1996) *Science* 274:1537-1540; and U.S. Pat. No. 5,962,764); each of which is herein incorporated by reference.

In another preferred embodiment the DNA molecule comprising the nucleotide sequence, or a portion thereof, is comprised in an extrachromosomally replicating molecule. Several publications describing this approach are cited for further illustration (Waterhouse et al. (1998) PNAS 95:13959-13964; Chuang and Meyerowitz (2000) PNAS 97:49854990;

Smith et al. (2000) Nature 407:319-320). Alteration of the expression of a nucleotide sequence by dsRNA interference is also described in, for example WO 99/32619, WO 99/53050 or WO 99/61631, all incorporated herein by reference in their entirety.

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 70% identical to the nucleotide sequence the expression of which is reduced, more preferably it is at least 80% identical, yet more preferably at least 90% identical, yet more preferably at least 95% identical, yet more preferably at least 99% identical.

EXAMPLES

Example 1

Method of Constructing Expression Cassettes Comprising Regulatory Sequences from the MADS Gene Family 1. Identifying target MADS genes.
2. Identifying high quality sequence for both the target's genomic DNA (gDNA) and cDNA.
3. Identifying the target gene's open reading frame on the cDNA. In general this is the longest open reading frame.
4. Using a candidate gene's cDNA sequence to annotate gDNA sequence and marking positions of the translation start codon, translation stop codon, introns, exons, the 5'-untranslated leader and the 3'-untranslated sequence. As is known in the art, marking the translation start codon and the translation stop codon identifies the 5'-regulatory sequence and the 3'-regulatory sequence of the gene. According to the present invention, the promoter, which includes the promoter regulatory sequence, is the sequence that extends approximately 1.5 to 2.5 kb upstream from the translation start codon, wherein the 3'-regulatory sequence of the present invention includes the 3'-untranslated sequence located immediately downstream of the translation stop codon and all or a part of the 3'-nontranscribed sequence, which extends 0.5 to 1.5 kb downstream of the transcription termination site. In one embodiment of the invention, the 5'-regulatory sequence includes the promoter, the first exon, the first intron and the second exon.

The gDNA contigs (AB026295 from GenBank and CL000624.108 plus CL019873.131 were aligned with OsMADS5 cDNA sequence (GenBank accession U78890). The cDNA sequence is broken into corresponding exons. The exons are labeled according to cDNA base numbers. Both sequences align precisely and the intervening sequences (introns) are flanked by GT . . . AG borders. Gaps in between exons represent introns. The AB026295 fragment is a portion of the entire bacterial artificial chromosome (BAC) sequence. The AB026295 (promoter) is an additional fragment from that BAC which defines sequence used for promoter development.

5. Designing expression cassettes that incorporate the following components from a MADS gene(s):
   a. The promoter, a sequence that begins at the translation start codon and extends approximately 1.5 to 2.5 kb upstream of the translation start codon.
   b. The first exon
   c. The first intron
   d. The 5'-most portion of the second exon
   e. The terminus, including the 3'-untranslated sequence and the 3'-nontranscribed sequence, which extends 0.5 to 1.5 kb downstream of the transcription termination site. The terminus can further include an intron.

For simplicity the "5'-regulatory sequence" of the present invention includes components a-d and the "3'-regulatory sequence" of the present invention refers to component e.

6. Amplifying the 5'-regulatory sequence from the appropriate gDNA template by high-fidelity PCR and cloning into a suitable bacterial vector.

The 5'-regulatory sequence from rice genomic DNA (gDNA) is amplified using high-fidelity PCR. A 50 μL reaction mixture contains 100 ng rice gDNA, 200 μM dNTPs (dATP, dCTP, dGTP, TTP), 1 μL 20 μM each of oligonucleotide primers designed to amplify the 5'-regulatory gDNA, 1 μL 10× Expand High Fidelity buffer and 1 μL Expand High Fidelity polymerase (Roche Diagnostics, Cat. No. 1 759 078). The thermocycling program is 95° C. for 2 minutes followed by 40 cycles of (94° C. for 15 seconds, 68° C. for 7.5 minutes) followed by 68° C. for 10 minutes. The 5'-regulatory gDNA product is cloned with the TOPO XL PCR cloning kit (Invitrogen, Cat. No. K4750-20). pCR-XL-TOPO-5'-regulatory-gDNA is identified by digesting 5 μL pCR-XL-TOPO-5'-regulatory-gDNA miniprep DNA (prepared using the QIAprep Spin Miniprep procedure from Qiagen, Cat. No. 27106) with EcoRI (New England Biolabs) in a 20 μL reaction containing 2 μg BSA and 2 μL 10×EcoRI restriction endonuclease buffer (New England Biolabs). The reaction is incubated at 37° C. for 2 hours and the pCR-XL-TOPO-5'-regulatory-gDNA (EcoRI) products are resolved on 1% TAE agarose. The pCR-XL-TOPO-5'-regulatory-gDNA clone is sequenced using the ABI PRISM dye terminator cycle sequencing kit (Perkin Elmer).

7. Amplifying the "3'-regulatory sequence" from the appropriate gDNA template by high-fidelity PCR and clone into a suitable bacterial vector.

The 3'-regulatory sequence from rice gDNA is amplified using high-fidelity PCR. The 50 μL reaction mixture consists of 100 ng rice gDNA, 200 μM dNTPs, 1 μL 20 μM each of the oligonucleotide primers designed to amplify the 3'-regulatory gDNA, 1 μL 10× Expand High Fidelity buffer and 1 μL Expand High Fidelity polymerase. The thermocycling program is 95° C. for 2 minutes followed by 40 cycles of (94° C. for 15 seconds, 68° C. for 7.5 minutes) followed by 68° C. for 10 minutes. The 3'-regulatory gDNA product is cloned with the TOPO XL PCR cloning kit (Invitrogen, Cat. No. K4750-20) following manufactures' instructions. The pCR-XL-TOPO-3'-regulatory-gDNA is identified by digesting 5 μL pCR-XL-TOPO-3'-regulatory-gDNA miniprep DNA with EcoRI in a 20 μL reaction containing 2 μg BSA and 2 μL 10×EcoRI restriction endonuclease buffer. The reaction is incubated at 37° C. for 2 hours and the pCR-XL-TOPO-3'-regulatory-gDNA (EcoRI) products are resolved on 1% TAE agarose. The pCR-XL-TOPO3'-regulatory-gDNA clone is then sequenced.

8. Assembling the 5'-regulatory sequence and 3'-regulatory sequence in any bacterial plasmid.

The expression cassettes of the present invention were assembled in the vector pNOV6901, also known as the "Assembly Vector". This vector contains the coding sequence for GUS reporter gene (which is disrupted by an intron to prevent bacterial expression) flanked at its 5'- and 3'-termini by unique restriction sites (polylinkers) to facilitate recombinant DNA procedures. Any number of other vectors may be used as is known to those persons skilled in the art.

9. Incorporating restriction sites in the expression cassettes, as necessary, to facilitate recombinant DNA procedures.

The "engineered" translation initiation codon, below, is the ATG in the NcoI restriction site (CCATGG). If there are any NcoI restriction sites in the "expression cassette 5'-regulatory sequence" they must be eliminated by mutagenesis. Likewise, restriction sites that are used to assemble the expression cassette must be eliminated by mutagenesis. Incorporation of the first intron in the "expression cassette 5'-regulatory sequence" requires the sequence be modified to avoid creating fusions between native coding sequence, which is normally translated into protein encoded by target gene, and the "gene of interest" (nucleic acid molecule) to be driven by the expression cassette. This is accomplished by any of a number of mutagenic procedures, including the procedure performed by the Stratagene QuikChange Multi Site-Directed Mutagenesis Kit (Cat. No. 200513). Modifications to the expression cassette 5'-regulatory sequence include:

a. Modifying the target gene's natural translation initiation codon so that the target gene's protein coding sequence is silent.

b. Modifying any other translation initiation codons that exist in the sequence between the "silenced" translation initiation codon and the "engineered" translation initiation codon to insure such codons are not operable.

c. Modifying any NcoI sites in the 5'-regulatory sequence.

d. Modifying restriction endonuclease sites, as necessary, to facilitate expression cassette assembly.

In this embodiment of the invention, the procedure does not eliminate nucleotides. Rather, it modifies them to preserve the length of the 5'-regulatory sequence in the expression cassette, yet still silencing the candidate gene's protein coding sequence. However, it is contemplated that one or more of the nucleotides could be eliminated to silence undesired protein expression, provided that 5'- and 3'-regulatory sequences of the cassette continue to enhance expression of the candidate gene in plant reproductive tissue. Furthermore, those skilled in the art do not consider it unreasonable to alter the sequence of nucleotides in a polynucleotide molecule comprising a regulatory sequence so long as the modified regulatory sequence retains a majority of the activity associated with the original regulatory sequence.

Primers were designed to accomplish this task for each 5'-regulatory sequence derived from the MADs gene family. The Stratagene QuikChange Multi Site-Directed Mutagenesis Kit uses each gene's pCR-XL-TOPO-5'-regulatory-gDNA clone as a template and the primers listed to mutagenize that clone according to the present invention. The primers must contain a 5'-phosphate to work. Furthermore, alterations may require more than one round of mutagenesis. The modified pCR-XL-TOPO-5'-regulatory clone is sequenced using the ABI PRISM dye terminator cycle sequencing kit (Perkin Elmer).

10. Modifying, in some cases, the 3'-regulatory sequence to eliminate restriction endonuclease sites to facilitate recombinant DNA procedures. The "engineered" translation initiation codon is the ATG in the NcoI restriction site. If there are any NcoI restriction sites in the "expression cassette 3'-regulatory sequence" they must be eliminated by mutagenesis. Again, this is accomplished any of a number of mutagenic procedures. The present invention therefore includes:

a. Modifying any NcoI sites in the 3'-regulatory sequence.

b. Modifying restriction endonuclease sites, as necessary, to facilitate expression cassette assembly.

In this embodiment of the present invention, the procedure does not eliminate nucleotides. Rather, it modifies them to preserve the length of the 3'-regulatory sequence in the expression cassette. However, it is contemplated that one or more of the nucleotides could be eliminated to silence undesired protein expression, provided that 5'- and 3'-regulatory sequences of the cassette continue to enhance expression of the candidate gene in plant reproductive tissue. Furthermore, those skilled in the art do not consider it unreasonable to alter the sequence of nucleotides in a polynucleotide molecule comprising a regulatory sequence so long as the modified regulatory sequence retains a majority of the activity associated with the original regulatory sequence. Primers were designed to accomplish this task for each 3'-regulatory sequence derived from the MADS gene family. Each gene's pCR-XL-TOPO-3'-regulatory-gDNA clone is used as a template and the primers listed are used to mutagenize these clones. The modified pCR-XL-TOPO-3'-regulatory clones are sequenced.

11. Cloning the 3'-regulatory sequence into pNOV6901, using PCR with the modified pCR-XL-TOPO-3'-regulatory clone as template and the appropriate primer set.

These primers are a 5'-oligonucleotide primer that introduces unique restriction site from the GUS 3'-terminal polylinker in pNOV6901 and 3'-oligonucleotide primer that introduces a rare cutting restriction site (either AscI, PacI, SgfI or RsrII) followed by a restriction endonuclease site unique to the 3'-terminal polylinker.

High-fidelity PCR is used to amplify the 3'-regulatory sequence from the modified pCR-XL-TOPO-3'-regulatory clone. A 50 µL reaction mixture consists of 1 µL miniprep DNA, 200 µM dNTPs, 1 µL each of 20 µM oligonucleotide primers, 5 µL 10× Cloned PFU buffer and 2.5 Units of Pfu-turbo DNA polymerase (Stratagene, Cat. No. 600252). The thermocycling program was 95° C. for 30 seconds then 40 cycles of (95° C. for 10 seconds, 50° C. for 60 seconds, 72° C. for 6 minutes) then 72° C. for 10 minutes. The amplified 3'-regulatory sequence DNA fragment is recovered using the QIAquick PCR purification kit (Qiagen, Cat. No. 28106). The recovered 3'-regulatory sequence DNA fragment is precipitated with 20 µg glycogen, 0.3 M $CH_2COONa$ (pH 5.2) and 2.5 volumes ethanol at −20° C. for more than 2 hours. The 3'-regulatory sequence DNA fragment is recovered by micro centrifugation, washed with 70% ethanol, dried under vacuum and resuspended in 14 µL $ddH_2O$. The 3'-regulatory sequence DNA fragment is digested in a 20 µL reaction containing 2 µg BSA, 2 µL of the appropriate 10× restriction endonuclease buffer and 2 µL of the appropriate restriction endonuclease(s). The reaction is incubated at 37° C. for more than 6 hours. The digested 3'-regulatory sequence DNA products are resolved on 1.0% TAE agarose and the appropriate 3'-regulatory sequence (digested) band is excised. The 3'-regulatory sequence (digested) DNA is extracted and recovered using the QIAquick Gel extraction kit (Qiagen, Cat. No. 28704). The recovered 3'-regulatory sequence (digested) DNA is ethanol precipitated with glycogen carrier. The 3'-regulatory sequence (digested) DNA fragment is recovered by micro centrifugation, washed with 70% ethanol, dried under vacuum and resuspended in 5 µL $ddH_2O$.

2 µg of pNOV6901 miniprep DNA is digested in a 20 µL reaction mixture containing 2 µg BSA, 2 µL of the appropriate 10× restriction endonuclease buffer (used to generate the 3'-gene regulatory sequence) and 2 µL of the appropriate restriction endonuclease (used to generate the 3'-gene regulatory sequence). The reaction mixture is incubated at 37° C. for more than 6 hours, then at 70° C. for 20 minutes. Then 1 µl of the appropriate 10× restriction endonuclease buffer, 1 µL 1 Unit/µL calf-intestinal alkaline phosphatase (CIP-New England Biolabs) and 8 µL $ddH_2O$ is added to the reaction mixture and incubated at 37° C. for 30 minutes. The pNOV6901 (digested/CIP) DNA is resolved on 1.0% TAE agarose and the 4.7 kb pNOV6901 (digested/CIP) band is excised. The pNOV6901 (digested/CIP) DNA is extracted and recovered using the QIAquick Gel extraction kit (Qiagen, Cat. No. 28704). The recovered pNOV6901 (digested/CIP) DNA is ethanol precipitated with glycogen carrier. The pNOV6901 (digested/CIP) DNA is recovered by micro centrifugation, washed with 70% ethanol, and dried under vacuum and resuspend in 5 μL ddH$_2$O.

4.0 μL 3'-regulatory sequence (digested) is ligated to 4.0 μL pNOV6901 (digested/CIP) in a 10 μL ligation mixture containing 1 μL 10×T4 DNA ligase buffer and 1 μL T4 DNA ligase (400 Units/μL-New England Biolabs). The ligation mixture is incubated for more than 8 hours at 16° C. 5.0 μL of ligation mixture is transformed into 50 μL Top10 competent cells (Invitrogen, Cat. No. C4040-03). The pNOV6901-3'-regulatory-sequence recombinants are verified by digesting 2 μL pNOV6901-3'-regulatory-sequence miniprep DNA with 1 μL of the appropriate restriction endonuclease in 10 μL reactions containing 1 μg BSA and 1 μL of the appropriate 10× restriction endonuclease buffer. Digests are incubated at 37° C. for 2 hours then resolved on 1% TAE agarose. The positive pNOV6901-3'-regulatory-sequence recombinants are sequenced.

12. Cloning the 5'-regulatory sequence into pNOV6901-3'-regulatory-sequence, using PCR with the modified pCR-XL-TOPO-5'-regulatory clone as template and the appropriate primer set.

These primers are a 5'-oligonucleotide primer that introduces the same rare cutting restriction site used for the 3'-regulatory sequence preceded by a unique restriction endonuclease site in the 5'-terminal polylinker of pNOV6901 and a 3'-oligonucleotide primer that introduces an NcoI site preceded by a Kozak sequence (CCACC<u>ATG</u>G) at the "engineered" translation initiation codon.

High-fidelity PCR is used to amplify the 5'-regulatory sequence from the modified pCR-XL-TOPO-5'-regulatory clone. A 50 μL reaction mixture consists of 1 μL miniprep DNA, 200 μM dNTPs, 1 μL each of 20 μM oligonucleotide primers, 5 μL 10× Cloned PFU buffer and 2.5 Units of Pfu-turbo DNA polymerase (Stratagene, Cat. No. 600252). The thermocycling program was 95° C. for 30 seconds then 40 cycles of (95° C. for 10 seconds, 50° C. for 60 seconds, 72° C. for 6 minutes) then 72° C. for 10 minutes. The amplified 5'-regulatory sequence DNA fragment is recovered using the QIAquick PCR purification kit. The recovered 5'-regulatory sequence DNA fragment is ethanol precipitated with glycogen carrier. The 5'-regulatory sequence DNA fragment is recovered by micro centrifugation, washed with 70% ethanol, dried under vacuum and resuspended in 14 μL ddH$_2$O. The 5'-regulatory sequence DNA fragment is digested in a 20 μL reaction containing 2 μg BSA, 2 μL of the appropriate 10× restriction endonuclease buffer and 2 μL of the appropriate restriction endonuclease(s). The reaction is incubated at 37° C. for more than 6 hours. The digested 5'-regulatory sequence DNA products are resolved on 1.0% TAE agarose and the appropriate 5'-regulatory sequence (digested) band is excised. The 5'-regulatory sequence (digested) DNA is extracted and recovered using the QIAquick Gel extraction kit (Qiagen, Cat. No. 28704). The recovered 5'-regulatory sequence (digested) DNA is ethanol precipitated with glycogen carrier. The 5'-regulatory sequence (digested) DNA fragment is recovered by micro centrifugation, washed with 70% ethanol, dried under vacuum and resuspended in 5 μL ddH$_2$O.

2 μg of the pNOV6901-3'-regulatory-sequence miniprep DNA is digested in a 20 μL reaction containing 2 μg BSA, 2 μL of the appropriate 10× restriction endonuclease buffer and 2 μL of the appropriate restriction endonuclease. The reaction is incubated at 37° C. for more than 6 hours, then at 70° C. for 20 minutes. Then 1 μL of the appropriate 10× restriction endonuclease buffer, 1 μl Unit/μL CIP and 8 μL ddH$_2$O are added to the reaction and it is further incubated at 37° C. for 30 minutes. The pNOV6901-3'-regulatory-sequence (digested/CIP) DNA is resolved on 1.0% TAE agarose and the pNOV6901-3'-regulatory-sequence (digested/CIP) band is excised. The pNOV6901-3'-regulatory-sequence (digested/CIP) DNA is extracted and recovered. The recovered pNOV6901-3'-regulatory-sequence (digested/CIP) DNA is ethanol precipitated with glycogen carrier. The pNOV6901-3'-regulatory-sequence (digested/CIP) DNA is recovered by micro centrifugation, washed with 70% ethanol, dried under vacuum and resuspended in 5 μL ddH$_2$O.

4.0 μL of the 5'-regulatory sequence (digested) is ligated to 4.0 μL pNOV6901-3'-regulatory-sequence (digested/CIP) in a 10 μL ligation mixture containing 1 μL 10×T4 DNA ligase buffer and 1 μL T4 DNA ligase (400 Units/μL). The ligation mixture is incubated for more than 8 hours at 16° C. 5.0 μL of ligation mixture is transformed into 50 μL Top10 competent cells. The pNOV6901-3'/5'-regulatory-sequence recombinants are verified by digesting 2 μL pNOV6901-3'/5'-regulatory-sequence miniprep DNA with 1 μL of the appropriate restriction endonuclease in 10 μL reaction mixtures containing 1 μg BSA and 1 μL of the appropriate 10× restriction endonuclease buffer. Digests are incubated at 37° C. for 2 hours then pNOV6901-3'/5'-regulatory-sequence (digested) DNA is resolved on 1% TAE agarose. The positive pNOV6901-3'/5'-regulatory-sequence recombinants are sequenced.

The expression cassette of the present invention includes a GUS reporter construct in the Assembly Vector. It is flanked by the engineered, rare-cutting restriction site. In this embodiment of the present invention the GUS reporter gene can be replaced with any gene of interest using methods known to those individuals skilled in the art.

13. The expression cassette can now be mobilized into the *agrobacterium* binary vector pNOV6900, by digesting the assembly vector with the rare-cutting enzyme and purifying the cassette DNA.

2 μg pNOV6900 is digested in a 20 μL reaction mixture containing 2 μg BSA, 2 of the appropriate 10× restriction endonuclease buffer and 2 μL of the appropriate restriction endonuclease. The reaction mixture is incubated at 37° C. for more than 6 hours, then at 70° C. for 20 minutes. Then 1 μL of the appropriate 10× restriction endonuclease buffer, 1 μL 1 Unit/μL CIP and 8 μL ddH$_2$O are added to the reaction and it is further incubated at 37° C. for 30 minutes. 2 μg of the pNOV6901-3'/5'-regulatory-sequence miniprep DNA is digested in a 20 μL reaction containing 2 μg BSA, 2 μL of the same 10× restriction endonuclease buffer used for pNOV6900 and 2 μL of the same restriction endonuclease used for pNOV6900. The reaction is incubated at 37° C. for more than 6 hours.

The digested plasmid DNA, pNOV6900 (digested/CIP) and pNOV6901-3'/5'-regulatory-sequence (digested) are resolved on 1.0% TAE agarose and the 9.2 kb pNOV6900 (digested/CIP) and the appropriate pNOV6901-3'/5'-regulatory-sequence (digested) bands are excised. The pNOV6900 (digested/CIP) and the pNOV6901-3'/5'-regulatory-sequence (digested) DNAs are extracted and recovered. The recovered pNOV6900 (digested/CIP) and the pNOV6901-3'/5'-regulatory-sequence (digested) DNAs are ethanol precipitated with glycogen. The pNOV6900 (digested/CIP) and the pNOV6901-3'/5'-regulatory-sequence (digested) DNA fragments are recovered by micro centrifugation, washed with 70% ethanol, dried under vacuum and resuspended each in 5 µL ddH$_2$O.

4.0 µL of the pNOV6900 (digested/CIP) is ligated to 4.0 µL pNOV6901-3'/5'-regulatory-sequence (digested) in a 10 µL ligation mixture containing 1 µL 10×T4 DNA ligase buffer and 1 µL T4 DNA ligase (400 U/µL). The ligation mixture is incubated for more than 8 hours at 16° C. 5.0 µL of ligation mixture is transformed into 50 µL Top10 competent cells. The pNOV6900-pNOV6901-3'/5'-regulatory-sequence recombinants are verified by digesting 7.5 µL pNOV6900-pNOV6901-3'/5'-regulatory-sequence miniprep DNA with 1.0 µL NcoI in 10 µL reaction mixtures containing 1 µg BSA and 1 µL 10× restriction endonuclease buffer 4 (New England Biolabs). Digests are incubated at 37° C. for 2 hours then resolved on 1% TAE agarose. The junction sequence of positive pNOV6900-pNOV6901-3'/5'-regulatory-sequence recombinants is verified.

14. The expression cassette can now be transformed into *agrobacterium* and then transformed into plants in accordance with methods known to those persons skilled in the art.

Example 2

1. Construction of the Assembly Vector pNOV6901 Containing the β-Glucuronidase (GUS) Coding Sequence A. Preparation of GUS Coding Sequence.

The β-glucuronidase (GUS) coding sequence Narasimhulu, et al 1996, Plant Cell, 8: 873-886, which includes an engineered intron, was amplified from pNOV5003 in a Pfu-turbo polymerase (Stratagene, Cat. No. 600250) reaction. The reaction mixture consisted of 1 µL pNOV5003 miniprep DNA 200 µM dNTPs, 20 µM GUS5 oligonucleotide primer, 20 µM GUS3 oligonucleotide primer 5'-, 5 µL 10× cloned Pfu buffer and 2.5 Units of Pfuturbo DNA polymerase (Stratagene, Cat. No. 600250) in a final volume of 50 µL. The thermocycling program was at 95° C. for 30 seconds then 10 cycles of (95° C. for 5 seconds, 55° C. for 10 seconds, 72° C. for 2.5 minutes) then 20 cycles of (95° C. for 5 seconds, 57° C. for 15 seconds, 72° C. for 2.5 minutes) then 72° C. for 2.5 minutes. The 2.2 kb GUS PCR product was isolated and concentrated using the QIAEX II kit (Qiagen, Cat. No. 20021). The GUS PCR product was recovered in 15 µL ddH$_2$O and subsequently digested in a 20 µL reaction containing 1 µg BSA, 2 µL 10× restriction endonuclease buffer and 1 µL SacI. The reaction was incubated at 37° C. for 2 hours. The GUS PCR product (SacI) was resolved on 1.5% TBE agarose and the 2.2 kb GUS PCR product (SacI) band was excised. The GUS PCR product (SacI) DNA was recovered from the agarose in 15 µL ddH$_2$O with the QIAEX II kit (Qiagen, Cat. No. 20021).

B. Preparation of the pSP73 Vector.

An *E. coli* vector pSP73 (Promega, Cat. No. P2221) miniprep DNA was prepared. 1 µL of the miniprep DNA was digested in a 20 µL reaction mixture containing 1 µg BSA, 2 µL 10× restriction endonuclease, 1 µL SmaI and 1 µL SacI. The reaction was incubated at 25° C. for 1.5 hours then 37° C. for 1.5 hours. The pSP73 (SmaI/SacI) DNA was resolved on 1.5% TBE agarose and the 2.4 kb pSP73 (SmaI/SacI) band was excised. The pSP73 (SmaI/SacI) DNA was recovered from the agarose in 15 µL ddH$_2$O with the QIAEX II kit (Qiagen, Cat No. 20021).

C. Construction of pSP73-GUS

5 µL of pSP73 (SmaI/SacI) was ligated to 5 µL GUS PCR product (SacI) by mixing with an equal volume of Takara DNA Ligation Mix, Version II (Cat. No. TAK 6022) and incubating at 16° C. for 30 minutes. 7.5 µL of the ligation mixture was transformed into 50 µL XL-1 supercompetent cells (Stratagene, Cat. No. 200236). pSP73-GUS recombinants were verified by digesting 2 µL pSP73-GUS miniprep DNA in a 20 µL reaction containing 2 µg BSA, 2 µL 10× restriction endonuclease buffer, 1 µL XbaI and 1 µL SacI and the pSP73-GUS (XbaI/SacI) products were resolved on 1.5% TBE agarose. The positive pSP73-GUS recombinants were sequenced.

D. Addition of Restriction Endonuclease Sites to pSP73-GUS

The pSP73-GUS construct lacks flexibility to clone 3'-regulatory sequence just after the GUS coding sequence. Additional restriction sites were added to the polylinker to increase flexibility at the 3'-terminus of the GUS coding sequence by ligating a synthetic adapter to the construct. The adapter (Synthetic Adaptor I) was made by combining 40 µL of 50 µM oligonucleotide PL-F, 40 µL of 50 µM oligonucleotide PL-R—where P is a 5'-phosphate group—in a 100 µL mixture that is 25 mM in Tris-HCl (pH 8.0) and 10 mM in MgCl$_2$. The mixture was boiled for 5 minutes, removed from heat and naturally cooled to room temperature (about 60 minutes), yielding a 20 µM Synthetic Adaptor I solution.

The pSP73-GUS construct was prepared by digesting 14 µL of miniprep pSP73-GUS DNA with 14 SacI and 1 µL ClaI in a 20 µL reaction mixture containing 2 µg BSA and 2 µL 10× restriction endonuclease buffer. The reaction mixture was incubated at 37° C. for 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. The pSP73-GUS (SacI/ClaI/CIP) DNA was resolved on 1% TAE agarose, excised, recovered and ethanol precipitated with glycogen carrier. The pSP73-GUS (SacI/ClaI/CIP) DNA was recovered by micro centrifugation, washed with 70% ethanol, dried under vacuum and resuspended in 5 µL ddH$_2$O.

4.5 µL of Synthetic Adaptor I solution was ligated to 2.5 µL pSP73-GUS (SacI/ClaI/CIP) in a 10 µL ligation mixture containing 1 µL 10×T4 DNA ligase buffer and 1 µL T4 DNA ligase and incubated more than 8 hours at 16° C. 4 µL of the ligation mixture was transformed into 50 µL XL-1 supercompetent cells (Stratagene, Cat. No. 200236). The pSP73-GUS-mod recombinants were verified by digesting 5 µL pSP73-GUS-mod miniprep DNA in a 20 µL reaction containing 2 µg BSA, 2 µL 10× restriction endonuclease buffer and 1 µL NotI. The digests were resolved on 1.0% TAE agarose, and the sequence of positive pSP73-GUS-mod recombinants was verified. The finished clone was designated pNOV6901.

2. Construction of pNOV6900

It was necessary to construct an *Agrobacterium* binary vector to facilitate mobilization of expression cassettes constructed in pNOV6901 into plants. The pNOV2115 vector was modified by inserting an adaptor that introduces the PacI, SgFI and RsrII restriction endonuclease recognition sites. pNOV2115 miniprep DNA (14 µL) was digested with 1 µL KpnI and 1 µL. HindIII in a 20 µL reaction mixture containing 2 mg BSA and 2 µL 10× restriction endonuclease buffer. Digests were incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. pNOV2115 (KpnI/HindIII/CIP) was resolved on 1% TAE agarose, the 9.2 kb pNOV2115 (KpnI/HindIII/CIP) DNA band was excised, recovered and ethanol precipitated with glycogen carrier. The pNOV2115

(KpnI/HindIII/CIP) DNA was recovered by micro centrifugation, washed with 70% ethanol, dried under vacuum and resuspended in 5 µL ddH₂O.

Additional restriction sites were added to pNOV2115 (KpnI/HindIII/CIP) by ligating the vector to Synthetic Adapter II. The Synthetic Adapter II was made by combining 37 µL of 150 µM oligonucleotide PL1, 37 µL of 150 µM PL2 oligonucleotide—where P is a 5'-phosphate group—in a 100 µL mixture that is 25 mM in Tris-HCl (pH 8.0) and 10 mM in MgCl₂. The mixture was boiled for 5 minutes, removed from heat and naturally cooled to room temperature (about 60 minutes), yielding a 55 µM Synthetic Adapter II solution.

2.5 µL pNOV2115 (KpnI/HindIII/CIP) was ligated to 2.5 µL 55 µM Synthetic Adapter II solution by mixing with an equal volume of Takara DNA Ligation Mix, Version II (Cat. No. TAK 6022), and was incubated at 16° C. for 30 minutes. 5.0 µL of ligation mixture was transformed into 50 µL DH5α competent cells (Invitrogen, Cat. No. 18258-012). pNOV2115-mod recombinants were verified by digesting 2 µL pNOV2115-mod miniprep DNA with KpnI, HindIII, PacI or RsrII in 10 µL reactions containing 1 µg BSA and 1 µL 10× restriction endonuclease buffer. The sequence of positive pNOV2115-mod recombinants was verified. The finished clone was designated pNOV6900.

Example 3

Construction of the OsMADS5 Expression Cassette

A. Cloning the OsMADS5 5'-Regulatory Sequence

High-fidelity PCR was used to amplify the OsMADS5 5'-regulatory sequence from rice genomic DNA (gDNA). The 50 µL reaction mixture consisted of 100 ng rice gDNA, 200 µM dNTPs, 1 µL 20 µM oligonucleotide primer OsMADS5-P3, 1 µL 20 µM oligonucleotide primer OsMADS#5-P2, 1 µL 10× Expand High Fidelity buffer and 1 µL Expand High Fidelity polymerase. The thermocycling program was at 95° C. for 2 minutes followed by 40 cycles of (94° C. for 15 seconds, 68° C. for 7.5 minutes) followed by 68° C. for 10 minutes. The 5.4 kb DNA product, encoding the OsMADS5 5'-regulatory sequence, was cloned with the TOPO XL PCR cloning kit. The pCR-XL-TOPO-OsMADS5-5'-gDNA recombinants, containing the OsMADS5 5'-regulatory sequence, were identified by digesting 5 µL pCR-XL-TOPO-OsMADS5-5'-gDNA miniprep DNA with EcoRI in a 20 µL reaction mixture containing 2 µg BSA and 2 µL 10× restriction endonuclease buffer. The reaction mixture was incubated at 37° C. for 2 hours then the pCR-XL-TOPO-OsMADS5-5'-gDNA (EcoRI) products were resolved on 1% TAE agarose. Positive pCR-XL-TOPO-OsMADS5-5'-gDNA clones were sequenced.

B. Cloning the OsMADS5 3'-Regulatory Sequence

High-fidelity PCR was used to amplify the OsMADS5 3'-regulatory sequence from rice genomic DNA (gDNA). The 50 µL reaction mixture consisted of 100 ng rice gDNA, 200 µM dNTPs, 1 µL 20 µM oligonucleotide primer OsMADS#5-T1, 1 µL 20 µM oligonucleotide primer OsMADS#5-T2, 1 µL 10× Expand High Fidelity buffer and 1 µL Expand High Fidelity polymerase. The thermocycling program was 95° C. for 2 minutes followed by 40 cycles of (94° C. for 15 seconds, 60° C. for 30 seconds, 68° C. for 6 minutes) followed by 68° C. for 15 minutes. The 1.2 kb OsMADS5-3'-gDNA DNA product, encoding the OsMADS5 3'-regulatory sequence, was cloned with the Zero Blunt TOPO PCR cloning kit (Invitrogen, Cat. No. K2875-20). pCR-Blunt II-TOPO-OsMADS5-3'-gDNA recombinants, with the OsMADS5 3'-regulatory sequence, were identified by digesting 5 µL pCR-Blunt II-TOPO-OsMADS5-3'-gDNA miniprep DNA with EcoRI in a 20 µL reaction mixture containing 2 µg BSA and 2 µL 10× restriction endonuclease buffer. The reaction mixture was incubated at 37° C. for 2 hours and then the pCR-Blunt II-TOPO-OsMADS5-3'-gDNA (EcoRI) products were resolved on 1% TAE agarose. Positive pCR-Blunt II-TOPO-OsMADS5-3'-gDNA clones were sequenced.

C. Construction of the OsMADS5 5'-Regulatory Sequence

The OsMADS5 5'-regulatory sequence for the expression cassette was made in several steps. The 3'-half (OsMADS-5Pb, about 3.03 kb) was produced by high-fidelity PCR from the pCR-XL-TOPO-OsMADS5-5'-gDNA clone described above. The reaction mixture consisted of 1 µL pCR-XL-TOPO-OsMADS5-5'-gDNA miniprep DNA, 200 µM dNTPs, 20 µM oligonucleotide primer OsMADS5-C3, 20 µM oligonucleotide primer OsMADS5-C4, 5 µL 10× cloned Pfu buffer and 2.5 Units of Pfuturbo DNA polymerase (Stratagene, Cat. No. 600252) in a final volume of 50 µL. The thermocycling program was at 95° C. for 30 seconds then 40 cycles of (95° C. for 10 seconds, 50° C. for 60 seconds, 72° C. for 6 minutes) then 72° C. for 10 minutes. The OsMADS-5Pb DNA product was recovered using the QIAquick PCR purification kit (Qiagen, Cat. No. 28106). The recovered OsMADS-5Pb DNA was ethanol precipitated with glycogen carrier. The OsMADS-5Pb DNA was recovered by micro centrifugation, washed with 70% ethanol, dried under vacuum and resuspended in 14 µL ddH₂O. The OsMADS-5Pb was digested in a 20 µL reaction mixture containing 2 µg BSA, 2 µL 10× restriction endonuclease buffer, 1 µL SalI and 1 µL NcoI. The reaction mixture was incubated at 37° C. for more than 6 hours. The OsMADS-5Pb (NcoI/SalI) DNA was resolved on 1.0% TAE agarose and the 3.03 kb OsMADS-5Pb (NcoI/SalI) DNA band was excised, recovered and ethanol precipitated with glycogen carrier. The OsMADS-5Pb (NcoI/SalI) DNA was recovered by micro centrifugation, washed with 70% ethanol, dried under vacuum and resuspended in 5 µL ddH₂O.

2 µg of the pNOV6901 miniprep DNA was digested in a 20 µL reaction mixture containing 2 µg BSA, 2 µL 10× restriction endonuclease buffer, 1 µL SalI and 1 µL NcoI. The reaction mixture was incubated at 37° C. for more than 6 hours, then at 70° C. for 20 minutes. Then 1 µL of the appropriate 10× restriction endonuclease buffer, 1 µL 1 Unit/4 CIP and 84 ddH₂O were added to the reaction and it was further incubated at 37° C. for 30 minutes. The pNOV6901 (NcoI/SalI/CIP) DNA was resolved on 1.0% TAE agarose and the 4.7 kb pNOV6901 (NcoI/SalI/CIP) band was excised, recovered and ethanol precipitated with glycogen carrier. The pNOV6901 (NcoI/SalI/CIP) DNA was recovered by micro centrifugation, washed with 70% ethanol, dried under vacuum and resuspended in 54 ddH₂O.

4.0 µL of the OsMADS-5Pb (NcoI/SalI) was ligated to 4.04 pNOV6901 (NcoI/SalI/CIP) in a 10 µL reaction mixture containing 1 µL 10×T4 DNA ligase buffer and 1 µL T4 DNA ligase (400 Units/µL) and incubated more than 8 hours at 16° C. 5.0 µL of the ligation mixture was transformed into 50 µL Top10 competent cells. pNOV6901-OsMADS-5Pb recombinants were verified by digesting 2 µL pNOV6901-OsMADS-5Pb miniprep DNA with 0.5 µL SalI, 0.5 µL NcoI in 10 µL reactions containing 1 µg BSA and 1 µL 10× restriction endonuclease buffer. The digests were incubated at 37° C. for 2 hours and the pNOV6901-OsMADS-5Pb (NcoI/SalI) DNA was resolved on 1% TAE agarose. Positive pNOV6901-OsMADS-5Pb recombinants were sequenced.

The 5'-half (OsMADS-5Pa, about 2.4 kb) was produced by high-fidelity PCR from the pCR-XL-TOPO-OsMADS5-5'-gDNA clone described above. The reaction mixture consisted of 1 µL pCR-XL-TOPO-OsMADS5-5'-gDNA miniprep DNA, 200 µM dNTPs, 20 µM oligonucleotide primer OsMADS5-C1, 20 µM oligonucleotide primer OsMADS5-C2b, 5 µL 10× cloned Pfu buffer and 2.5 Units of Pfuturbo DNA polymerase (Stratagene, Cat. No. 600252) in a final volume of 50 µL. The thermocycling program was at 95° C. for 30 seconds then 40 cycles of (95° C. for 10 seconds, 50° C. for 60 seconds, 72° C. for 6 minutes) then 72° C. for 10 minutes. The 2.4 kb OsMADS-5Pa DNA product was cloned with the Zero Blunt TOPO PCR cloning kit (Invitrogen, Cat. No. K2875-20). pCR-Blunt II-TOPO-OsMADS-5Pa recombinants were identified by digesting 5 µL pCR-Blunt II-TOPO-OsMADS-5Pa miniprep DNA with EcoRI in a 20 µL reaction mixture containing 2 µg BSA and 2 µL 10× restriction endonuclease buffer. The digests were incubated at 37° C. for 2 hours then resolved on 1% TAE agarose. Positive pCR-Blunt II-TOPO-OsMADS-5Pa recombinants were sequenced.

2 µg of the pNOV6901-OsMADS-5Pb miniprep DNA was digested in a 20 µL reaction mixture containing 2 µg BSA, 2 µL 10× restriction endonuclease buffer and 2 µL XhoI. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. 2 µg of the pCR-Blunt II-TOPO-OsMADS-5Pa miniprep DNA was digested in a 20 µL reaction mixture containing 2 µg BSA, 2 µL 10× restriction endonuclease buffer and 2 µL SalI. The digest was incubated at 37° C. for more than 6 hours.

The digested plasmid DNAs, pNOV6901-OsMADS-5Pb (XhoI/CIP) and pCR-Blunt II-TOPO-OsMADS-5Pa (SalI), were resolved on 1.0% TAE agarose and the 7.7 kb pNOV6901-OsMADS-5Pb (XhoI/CIP) and the 2.4 kb OsMADS-5Pa (SalI) bands were excised, extracted, recovered and ethanol precipitated with glycogen. The pNOV6901-OsMADS-5Pb (XhoI/CIP) and OsMADS-5Pa (SalI) DNA fragments were recovered by micro centrifugation, washed with 70% ethanol, dried under vacuum and resuspended each in 5 µL ddH$_2$O.

4.0 µL of the pNOV6901-OsMADS-5Pb (XhoI/CIP) was ligated to 4.0 µL OsMADS-5Pa (SalI) in a 10 µL reaction mixture containing 1 µL 10×T4 DNA ligase buffer and 1 µL T4 DNA ligase (400 U/4). The reaction mixture was incubated more than 8 hours at 16° C. 5.0 µL of the ligation mixture was transformed into 50 µL Top10 competent cells. The pNOV6901-OsMADS5P recombinants were verified by digesting 2 µL pNOV6901-OsMADS5P miniprep DNA with 0.5 µL XhoI, 0.5 µL NcoI in 10 µL reaction mixtures containing 1 µg BSA and 1 µL 10× restriction endonuclease buffer. The digests were incubated at 37° C. for 2 hours then resolved on 1% TAE agarose. Positive pNOV6901-OsMADS5P recombinants were sequenced.

D. Construction of the OsMADS5 3'-Regulatory Sequence

The OsMADS-5 3'-regulatory sequence for the expression cassette was produced by high-fidelity PCR from the pCR-Blunt II-TOPO-OsMADS5-3'-gDNA clone, above. The reaction mixture consisted of 1 µL pCR-Blunt II-TOPO-OsMADS5-3'-gDNA miniprep DNA, 200 µM dNTPs, 20 µM oligonucleotide primer OsMADS5T-F, 20 µM oligonucleotide primer OsMADS5T-R, 5 µL 10× cloned Pfu buffer and 2.5 Units of Pfuturbo DNA polymerase (Stratagene, Cat. No. 600252) in a final volume of 50 µL. The thermocycling program was 95° C. for 30 seconds then 40 cycles of (95° C. for 10 seconds, 50° C. for 60 seconds, 72° C. for 6 minutes) then 72° C. for 10 minutes. The OsMADS5T DNA product was recovered using the QIAquick PCR purification kit (Qiagen, Cat. No. 28106) and ethanol precipitated with glycogen carrier. The OsMADS5T DNA was recovered by micro centrifugation, washed with 70% ethanol, dried under vacuum and resuspended in 14 µL ddH$_2$O. The OsMADS5T DNA was digested in a 20 µL reaction mixture containing 2 µg BSA, 2 µL 10× restriction endonuclease buffer and 2 µL XmaI. The digest was incubated at 37° C. for more than 6 hours. The OsMADS5T (XmaI) DNA was resolved on 1.0% TAE agarose and the 1.1 kb OsMADS5T (XmaI) band was excised, recovered and ethanol precipitated with glycogen carrier. OsMADS5T (XmaI) DNA was recovered by micro centrifugation, washed with 70% ethanol, dried under vacuum and resuspended in 5 µL ddH$_2$O.

2 µg pNOV6901-OsMADS5P miniprep DNA was digested in a 20 µL reaction mixture containing 2 µg BSA, 2 µL 10× restriction endonuclease buffer and 2 µL XmaI. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. The pNOV6901-OsMADS5P (XmaI/CIP) DNA was resolved on 1.0% TAE agarose and the 10.1 kb pNOV6901-OsMADS-5P (XmaI/CIP) band was excised, recovered and ethanol precipitated with glycogen carrier. pNOV6901-OsMADS-5P (XmaI/CIP) DNA was recovered by micro centrifugation, washed with 70% ethanol, dried under vacuum and resuspended each in 5 µL ddH$_2$O.

4.0 µL pNOV6901-OsMADS5P (XmaI/CIP) was ligated to 4.0 µL OsMADS5T (XmaI) in a 10 µL ligation mixture containing 1 µL 10×T4 DNA ligase buffer and 1 µL T4 DNA ligase (400 Units/µL) and incubated more than 8 hours at 16° C. 5.0 µL of ligation mixture was transformed into 50 µL Top10 competent cells. Positive pNOV6901-OsMADS5P/OsMADS5T recombinants were verified by digesting 2 µL miniprep DNA with 1.0 µL AscI in 10 µL reaction mixtures containing 1 µg BSA and 1 µL 10× restriction endonuclease buffer. The digests were incubated at 37° C. for 2 hours then resolved on 1% TAE agarose. Positive pNOV6901-OsMADS5P/OsMADS5T recombinants were sequenced. The construct was designated pNOV6901-OsMADS5P/OsMADS5T. The plasmid's QC number is 11084. 11084 contains the complete OSMADS5 expression cassette depicted by SEQ ID NO: 31.

E. Mobilization of the OsMADS5 GUS Expression Cassette into pNOV6900

2 µg pNOV6900 was digested in a 20 µL reaction mixture containing 2 µg BSA, 2 µL 10× restriction endonuclease buffer and 2 µL AscI. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. 2 µg pNOV6901-OsMADS5P/OsMADS5T miniprep DNA was digested in a 20 µL reaction mixture containing 2 µg BSA, 2 µL 10× restriction endonuclease buffer and 2 µL AscI. The digest was incubated at 37° C. for more than 6 hours.

The digested plasmid DNAs, pNOV6900 (AscI/CIP) and pNOV6901-OsMADS5P/OsMADS5T (AscI), were resolved on 1.0% TAE agarose and the 9.2 kb pNOV6900 (AscI/CIP) and the 8.7 kb pNOV6901-OsMADS5P/OsMADS5T (AscI) DNA bands were excised, recovered and ethanol precipitated with glycogen carrier. The pNOV6900 (AscI/CIP) and pNOV6901-OsMADS5P/OsMADS5T (AscI) DNA fragments were recovered by micro centrifugation, washed with 70% ethanol, dried under vacuum and resuspended in 5 µL ddH$_2$O each.

4.0 µL pNOV6900 (AscI/CIP) was ligated to 4.0 µL pNOV6901-OsMADS5P/OsMADS5T (AscI) in a 10 µL ligation mixture containing 1 µL 10×T4 DNA ligase buffer and 1 µL T4 DNA ligase, which was incubated more than 8 hours at 16° C. 5.0 µL of ligation mixture was transformed into 50 jai, Top10 competent cells. pNOV6900-pNOV6901-OsMADS5P/OsMADS5T recombinants were verified by digesting 7.5 µL pNOV6900-pNOV6901-OsMADS5P/OsMADS5T miniprep DNA with 1.0 µL NcoI in 10 µL reactions containing 1 µg BSA and 1 µL 10× restriction endonuclease buffer. The digests were incubated at 37° C. for 2 hours then resolved on 1% TAE agarose. Positive pNOV6900-pNOV6901-OsMADS5P/OsMADS5T recombinants were sequenced. The finished clone was designated pNOV6911. The plasmid's QC number is 11085.

The engineered alterations in the OsMADS5P sequence include introduction of an XhoI site followed by an AscI site at the 5'-end of the OsMADS5P sequence, elimination the natural translation start codon of the OsMADS5P sequence, elimination of undesired ORFs in the new leader sequence (5'-UTR) of the OsMADS5P sequence, insertion a Kozak sequence upstream of the new translation start codon of the OsMADS5P sequence and insertion of a new translation start codon downstream of the intron1/exon2 junction as an NcoI site in the OsMADS5P sequence. The engineered alterations in the OsMADS5T sequence include introduction of an XmaI site at the 5'-terminus of the OsMADS5T sequence and introduction of an AscI site at the 3'-terminus of the OsMADS5T sequence. In this configuration the GUS coding sequence can be replaced with any gene of interest flanked by NcoI restriction sites. The complete cassette can then be excised as an AscI fragment and cloned into pNOV6900.

The cassette was transformed into A188 X HyII maize and Kaybonnet rice using standard *agrobacterium* mediated methodology.

GUS Expression in T0 Maize

Fifteen T0 transgenic maize lines were generated. Tassel spikelets and leaf punches were harvested just before pollen shed and histochemically screened for GUS activity. The ear from a plant containing multiple transgene copies was sacrificed to examine GUS expression in developing florets. Gus activity localized primarily to transmitting tissue at the base of each floret, and to a lesser extent, the vascular bundles in developing ears. GUS activity was also apparent in developing silks. These data indicate the cassette drives GUS expression primarily in female reproductive tissue.

GUS Expression in T0 Rice

Of forty T0 rice (cv. Kaybonnet) lines containing pNOV6911 (or 11085), eighteen independent transformants were histochemically stained for GUS expression. Only four events had detectable GUS activity in leaf tissue. In most events, activity in spikelets was localized to glume tips, and anthers to a much lesser extent.

GUS Expression in T1 Maize

T1 progeny from three events were sown for expression analysis in vegetative and reproductive tissue. Data for tissue sampled about 5 days before pollination was collected. GUS activity is restricted to developing ears, particularly the vasculature along the outer ear and the transmitting tissue beneath florets. GUS activity was also detected in tissue surrounding the ovule sac. GUS activity was undetectable in the ear node or the node beneath it, tassel, leaf or silk. GUS activity was detected in developing ears. The data show the pattern established at 5 days before pollination persists up to 2 days after pollination. GUS activity becomes restricted to transmitting tissue and maternal tissue at the base of developing kernels during seed development. GUS protein is detectable throughout ovule and kernel development, up to 20 days after pollination. GUS was detected as a very light staining in the aerial tissue, with no GUS activity in the roots In summary, the present invention includes expression cassettes based on the *Oryza sativa* OsMADS5 gene. These cassettes consist of the gene's promoter including the first intron, 5'-UTR, 3'-UTR and 3'-nontranscribed sequence. The cassette's design facilitates replacement of the GUS coding sequence with any gene of interest. The cassette drives gene expression primarily in maternal reproductive tissue. Within developing ears, expression localizes to the outer vasculature along the long axis of the ear, the transmitting tissue in developing florets and kernels, tissue surrounding ovules and maternal tissue at the base of developing kernels. The expression cassettes of the present invention drive gene expression from a very early point in ovule development, perhaps from shortly after differentiation.

Example 4

Construction of the OsMADS6 Expression Cassette

A. Cloning of the OsMADS6 5'-Regulatory Sequence

Used high-fidelity PCR to amplify the OsMADS6 5'-regulatory sequence from rice genomic DNA (gDNA). The 50 µL reaction mixture consisted of 100 ng rice gDNA, 200 µM dNTPs, 1 µL 20 µM oligonucleotide primer OsMADS#6-P1 5'-ctaggacgatggtgtgatgtgggaacacg-3' (SEQ ID NO: 32), 1 µL 20 µM oligonucleotide primer OsMADS#6-P2 5'-gtacctttctaaagtetttgttatgctgcac-3' (SEQ ID NO: 33) 1 µL 10× Expand High Fidelity buffer and 1 µL Expand High Fidelity polymerase. The thermocycling program was at 95° C. for 2 minutes followed by 40 cycles of (94° C. for 15 seconds, 68° C. for 7.5 minutes) followed by 68° C. for 10 minutes. Cloned the 4.5 kb OsMADS6-5'-gDNA DNA product with the TOPO XL PCR cloning kit. pCR-XL-TOPO-OsMADS6-5'-gDNA recombinants were identified by digesting 5 µL pCR-XL-TOPO-OsMADS6-5'-gDNA miniprep DNA with EcoRI in a 20 µL reaction mixture containing 2 µg BSA and 2 µL 10× restriction endonuclease buffer. The digests were incubated at 37° C. for 2 hours then the products were resolved on 1% TAE agarose. The positive pCR-XL-TOPO-OsMADS6-5'-gDNA clones were sequenced.

B. Cloning of the OsMADS6 3'-Regulatory Sequence

The OsMADS6 3'-regulatory sequence from rice genomic DNA (gDNA) was amplified using high-fidelity PCR. The 50 µL reaction mixture consisted of 100 ng rice gDNA, 200 µM dNTPs, 1 µL 20 µM oligonucleotide primer OsMADS#6-T1 5'-gctaagcagccatcgatcagctgtcag-3' (SEQ ID NO: 32), 1 µL 20 µM oligonucleotide primer OsMADS#6-T2 5'-gatgccattgtgtaatgaatggaggagagc-3' (SEQ ID NO: 33), 1 µL 10× Expand High Fidelity buffer and 1 µL Expand High Fidelity polymerase. The thermocycling program was at 95° C. for 2 minutes followed by 40 cycles of (94° C. for 15 seconds, 60° C. for 30 seconds, 68° C. for 6 minutes) followed by 68° C. for 15 minutes. The 1.2 kb DNA product was cloned with the Zero Blunt TOPO PCR cloning kit. The pCR-II-Blunt-OsMADS6-3'-gDNA recombinants were identified by digesting 5 µL pCR-II-Blunt-OsMADS6-3'-gDNA miniprep DNA with EcoRI in a 20 µL reaction mixture containing 2 mg BSA and 2 µL 10× restriction endonuclease buffer. The digests were incubated at 37° C. for 2 hours then resolved on 1% TAE agarose. Positive pCR-II-Blunt-OsMADS6-3'-gDNA clones were sequenced.

C. Construction of the OsMADS6 5'-Regulatory Sequence

The OsMADS6 5'-regulatory sequence for the expression cassette was made in several steps. The 3'-half (OsMADS- 6Pb, about 2.96 kb) was produced by high-fidelity PCR from the OsMADS6 5'-gene regulatory sequence clone, above. The reaction mixture consisted of 1 µL pCR-XL-TOPO-OsMADS6-5'-gDNA miniprep DNA, 200 µM dNTPs, 20 oligonucleotide primer OsMADS6-P3b 5'-cgagtcgacgagggggaa-gagttgagctgag-3' (SEQ ID NO: 34), 20 µM oligonucleotide primer OsMADS6-P4c 5'-gactccatggtggttatgctgcacaaaaatg-3' (SEQ ID NO: 35), 5 µL 10× cloned Pfu buffer and 2.5 Units of Pfuturbo DNA polymerase (Stratagene, Cat. No. 600252) in a final volume of 50 µL. The thermocycling program was at 95° C. for 30 seconds then 40 cycles of (95° C. for 10 seconds, 50° C. for 60 seconds, 72° C. for 6 minutes) then 72° C. for 10 minutes. The DNA product was cloned with the Zero Blunt TOPO PCR cloning kit. The pCR-Blunt-II-TOPO-OsMADS6-Pb recombinants were identified by digesting 5 µL pCR-Blunt-II-TOPO-OsMADS6-Pb miniprep DNA with EcoRI in a 20 µL reaction mixture containing 2 µg BSA and 2 µL 10× restriction endonuclease buffer. The digests were incubated at 37° C. for 2 hours then resolved on 1% TAE agarose. Positive pCR-Blunt-II-TOPO-OsMADS6-Pb recombinants were sequenced.

The 5'-half (OsMADS-6Pa, about 1.5 kb) was produced by high-fidelity PCR from the pCR-XL-TOPO-OsMADS6-5'-gDNA clone, above. The reaction mixture consisted of 1 pCR-XL-TOPO-OsMADS6-5'-gDNA miniprep DNA, 200 µM dNTPs, 20 µM oligonucleotide primer OsMADS6-C1b 5'-cagtgcatgcggaccgctaggacgatggtgtgatgtg-3' (SEQ ID NO: 36), 20 µM oligonucleotide primer OsMADS6-Paa 5'-cctcgtcgactcgcccgatcgatcgaacg-3' (SEQ ID NO: 37), 5 µL 10× cloned Pfu buffer and 2.5 Units of Pfuturbo DNA polymerase in a final volume of 50 µL. The thermocycling program was at 95° C. for 30 seconds then 40 cycles of (95° C. for 10 seconds, 50° C. for 60 seconds, 72° C. for 6 minutes) then 72° C. for 10 minutes. The 1.5 kb OsMADS6-Pa DNA product was cloned with the Zero Blunt TOPO PCR cloning kit. The pCR-Blunt-II-TOPO-OsMADS6-Pa recombinants were identified by digesting 5 µL pCR-Blunt-II-TOPO-OsMADS6-Pa miniprep DNA with EcoRI in a 20 µL reaction mixture containing 2 µg BSA and 2 µL 10× restriction endonuclease. The digests were incubated at 37° C. for 2 hours then resolved on 1% TAE agarose. Positive pCR-Blunt-II-TOPO-OsMADS6-Pa recombinants were sequenced.

14 µL pCR-Blunt-II-TOPO-OsMADS6-Pb miniprep DNA was digested in a 20 reaction mixture containing 2 µg BSA, 2 µL 10× restriction endonuclease buffer, 1 µL SalI and 1 µL NcoI. The digest was incubated at 37° C. for more than 6 hours. The digested DNA was resolved on 1.0% TAE agarose and the 2.96 kb OsMADS6-Pb (SalI/NcoI) DNA band was excised, recovered and ethanol precipitated with glycogen. The OsMADS6-Pb (SalI/NcoI) DNA was recovered by micro centrifugation, washed with 70% ethanol, dried under vacuum and resuspended in 5 µL ddH₂O.

2 µg pNOV6901 miniprep DNA was digested in a 20 µL reaction mixture containing 2 µg BSA, 2 µL 10× restriction endonuclease buffer, 1 µL SalI and 1 µL NcoI. The digest was incubated at 37° C. for more than 6 hours, then at 70° C. for 20 minutes. Then 1 µL of the appropriate 10× restriction endonuclease buffer, 1 µL 1 Unit/µL OP and 8 µL ddH₂O were added to the reaction and it was further incubated at 37° C. for 30 minutes. The digested plasmid DNA was resolved on 1.0% TAE agarose and the 4.7 kb pNOV6901 (SalI/NcoI/CIP) band was excised, recovered and ethanol precipitated with glycogen. The pNOV6901 (SalI/NcoI/CIP) DNA was recovered by micro centrifugation, washed with 70% ethanol, dried under vacuum and resuspended in 5 µL ddH₂O.

4.0 µL OsMADS6-Pb (SalI/NcoI) was ligated to 4.0 µL pNOV6901 (SalI/NcoI/CIP) in a 10 µL ligation mixture containing 1 µL 10×T4 DNA ligase buffer and 1 µL T4 DNA ligase (400 Units/µL). The ligation mixture was incubated for more than 8 hours at 16° C. 5.0 µL of ligation mixture was transformed into 504, Top10 competent cells. The recombinants were verified by digesting 2 µL pNOV6901-OsMADS6-Pb miniprep DNA with 0.5 µL SalI, 0.5 µL NcoI in 10 µL reaction mixtures containing 1 µg BSA and 1 µL 10× restriction endonuclease buffer. The digests were incubated at 37° C. for 2 hours then resolved on 1% TAE agarose. Positive pNOV6901-OsMADS6-Pb recombinants were sequenced.

2 µg pNOV6901-OsMADS6-Pb miniprep DNA was digested in a 20 µL reaction mixture containing 2 µg BSA, 2 µL 10× restriction endonuclease buffer, 1 µL SalI and 1 µL SphI. The digest was incubated at 37° C. for more than 6 hours, then at 70° C. for 20 minutes. Then 1 µL of the appropriate 10× restriction endonuclease buffer, 1 µL 1 Unit/1 µL CIP and 8 µL ddH₂O were added to the reaction and it was further incubated at 37° C. for 30 minutes. 2 µg pCR-Blunt-II-TOPO-OsMADS6-Pa miniprep DNA was digested in a 20 µL reaction containing 2 µg BSA, 2 µL 10× restriction endonuclease buffer, 1 µL SalI and 1 µL SphI. The digest was incubated at 37° C. for more than 6 hours.

The digested plasmid DNAs, pNOV6901-OsMADS6-Pb (SalI/SphI/CIP) and pCR-Blunt-II-TOPO-OsMADS6-Pa (SalI/SphI), were resolved on 1.0% TAE agarose and the 7.7 kb pNOV6901-OsMADS6-Pb (SalI/SphI/CIP) and the 1.5 kb OsMADS6-Pa (SalI/SphI) bands were excised, recovered and ethanol precipitated with glycogen carrier. The pNOV6901-OsMADS6-Pb (SalI/SphI/CIP) and OsMADS6-Pa (SalI/SphI) DNA fragments were recovered by micro centrifugation, washed with 70% ethanol, dried under vacuum and each resuspended in 5 µL ddH₂O.

4.0 µL pNOV6901-OsMADS6-Pb (SalI/SphI/CIP) was ligated to 4.0 µL OsMADS6-Pa (SalI/SphI) in a 10 µL reaction mixture containing 1 µL 10×T4 DNA ligase buffer and 1 µL T4 DNA ligase (400 U/µL). The reaction mixture was incubated for more than 8 hours at 16° C. 5.0 µL of ligation mixture was transformed into 50 µL Top10 competent cells. The pNOV6901-OsMADS6P recombinants were verified by digesting 7.5 µL pNOV6901-OsMADS6P miniprep DNA with 0.5 ml. SphI, 0.5 µL NcoI in 10 µL reactions containing 1 µg BSA and 1 µL 10× restriction endonuclease buffer. Digests were incubated at 37° C. for 2 hours then resolved on 1% TAE agarose. Positive pNOV6901-OsMADS6P recombinants were sequenced.

D. Construction of the OsMADS6 3'-Regulatory Sequence

The OsMADS-6 3'-regulatory sequence for the expression cassette, about 1.3 kb, was produced by high-fidelity PCR from the pCR-II-Blunt-OsMADS6-3'-gDNA clone, above. The reaction mixture consisted of 1 µL pCR-II-Blunt-OsMADS6-3'-gDNA miniprep DNA, 200 µM dNTPs, 20 µM oligonucleotide primer OsMADS6-C4b, 20 µM oligonucleotide primer OsMADS6-C2, 5 µL 10× cloned Pfu buffer and 2.5 Units of Pfuturbo DNA polymerase in a final volume of 50 µL. The thermocycling program was at 95° C. for 30 seconds then 40 cycles of (95° C. for 10 seconds, 50° C. for 60 seconds, 72° C. for 6 minutes) then 72° C. for 10 minutes. The 1.3 kb OsMADS6T DNA product was recovered and ethanol precipitated with glycogen. Recovered the OsMADS6T DNA by micro centrifugation, washed with 70% ethanol, dried under vacuum and resuspended in 14 µL ddH₂O. The OsMADS6T DNA was digested in a 20 µL reaction mixture containing 2 µg BSA, 2 µL 10× restriction endonuclease buffer, and 2 µL SmaI. The digest was incubated at 37° C. for more than 6 hours. The OsMADS6T (SmaI) DNA was resolved on 1.0% TAE agarose and the 1.3 kb OsMADS6T (SmaI) band was excised, recovered and ethanol precipitated with glycogen carrier. The OsMADS6T (SmaI) DNA was recovered by micro centrifugation, washed with 70% ethanol, dried under vacuum and resuspended in 5 µL ddH$_2$O.

2 µg pNOV6901-OsMADS6P miniprep DNA was digested in a 20 µL reaction mixture containing 2 µg BSA, 2 µL 10× restriction endonuclease buffer and 2 µL SmaI. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. The pNOV6901-OsMADS6P (SmaI/CIP) DNA was resolved on 1.0% TAE agarose and the 9.7 kb pNOV6901-OsMADS6P (SmaI/CIP) band was excised, recovered and ethanol precipitated with glycogen carrier. The pNOV6901-OsMADS6P (SmaI/CIP) DNA fragment was recovered by micro centrifugation, washed with 70% ethanol, dried under vacuum and resuspended in 5 µL ddH$_2$O.

4.0 µL pNOV6901-OsMADS6P (SmaI/CIP) was ligated to 4.0 µL OsMADS6T (SmaI) in a 10 µL reaction mixture containing 1 µL 10×T4 DNA ligase buffer and 1 µL T4 DNA ligase (400 Units/µL). The reaction mixture was incubated more than 8 hours at 16° C. 5.0 µL of ligation mixture was transformed into 50 µL Top10 competent cells. The recombinants were verified by digesting 2 µL pNOV6901-OsMADS6P/OsMADS6T miniprep DNA with 1.0 µL RsrII in 10 µL reaction mixtures containing 1 µg BSA and 1 µL 10× restriction endonuclease buffer. The digests were incubated at 37° C. for 2 hours then resolved on 1% TAE agarose. Positive pNOV6901-OsMADS6P/OsMADS6T recombinants were sequenced. Designated the vector pNOV6901-OsMADS6P/OsMADS6T. The plasmid's QC number is 11082. 11082 contains the OsMADS6 expression cassette depicted by SEQ ID NO: 38.

E. Mobilization of the OsMADS6 GUS Expression Cassette into pNOV6900

2 µg pNOV6900 was digested in a 20 µL reaction mixture containing 2 µg BSA, 2 µL 10× restriction endonuclease buffer and 2 µL RsrII. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. 2 µg pNOV6901-OsMADS6P/OsMADS6T miniprep DNA was digested in a 20 µL reaction mixture containing 2 µg BSA, 2 µL 10× restriction endonuclease buffer and 2 µL RsrII. The digest was incubated at 37° C. for more than 6 hours.

The pNOV6900 (RsrII/CIP) and the pNOV6901-OsMADS6P/OsMADS6T (RsrII) plasmid DNAs were resolved on 1.0% TAE agarose, and the 9.2 kb pNOV6900 (RsrII/CIP) and the 8.0 kb pNOV6901-OsMADS6P/OsMADS6T (RsrII) bands were excised, recovered and ethanol precipitated with glycogen carrier. The pNOV6900 (RsrII/CIP) and pNOV6901-OsMADS6P/OsMADS6T (RsrII) DNA fragments were recovered by micro centrifugation, washed with 70% ethanol, dried under vacuum and resuspended in 5 µL ddH$_2$O each.

4.0 µL pNOV6900 (RsrII/CIP) was ligated to 4.0 µL pNOV6901-OsMADS6P/OsMADS6T (RsrII) in a 10 µL ligation mixture containing 1 µL 10×T4 DNA ligase buffer and 1 µL T4 DNA ligase (400 U/µL). The ligation mixture was incubated more than 8 hours at 16° C. 5.0 µL of ligation mixture was transformed into 50 µL Top10 competent cells. The pNOV6900-pNOV6901-OsMADS6P/OsMADS6T recombinants were verified by digesting 2 µL miniprep DNA with 1.0 µL NcoI in 10 µL reaction mixtures containing 1 µg BSA and 1 µL 10× restriction endonuclease buffer. The digests were incubated at 37° C. for 2 hours then resolved on 1% TAE agarose. Positive pNOV6900-pNOV6901-OsMADS6P/OsMADS6T recombinants were sequenced. The finished clone was designated pNOV6907. The plasmid's QC number is 11083.

The engineered alterations in the 5'-regulatory sequence derived from the OsMADS6 gene include introduction of an SphI site followed by an RsrII site at the 5'-end of OsMADS6P, elimination of the natural translation start codon in OsMADS6P, elimination of undesired open reading frames in the new 5'-untranslated leader sequence transcribed from OsMADS6P, insertion of a Kozak sequence upstream of the new translation start codon in OsMADS6P and insertion of the new translation start codon downstream of the intron1/exon2 junction in OsMADS6P as an NcoI site. The engineered alterations in the 3'-gene regulatory sequence derived from the OsMADS6 gene include introduction of a SacI site at the 5'-terminus of OsMADS6T and introduction of an RsrII site at the 3'-terminus of OsMADS6T. In this configuration the GUS coding sequence can be replaced with any gene of interest flanked by NcoI/NotI or NcoI/SacI restriction sites. The complete cassette is mobilized, as an RsrII fragment, to the binary vector pNOV6900.

The cassette was transformed into A188 X HyII maize and Kaybonnet rice using standard *agrobacterium* mediated methodology.

GUS Expression in T0 Maize

One hundred-two T0 transgenic maize lines were generated. Tassel spikelets were histochemically screened for GUS activity. Sixty-four events were positive for GUS activity in the tassel glume, and some also stained positive at the spikelet base. Fifty-six also showed GUS expression in leaf punches. Ears from several plants were sacrificed to examine GUS expression in developing florets. GUS activity localizes primarily to vascular bundles in developing ears, which appears connected to transmitting tissue in each floret. These data indicate the cassette drives GUS expression primarily in female reproductive tissue.

GUS Expression in T0 Rice

Forty-one T0 rice lines containing pNOV6907 were generated. Twenty independent transformants were histochemically stained for GUS expression. Light to strong GUS activity was detected in leaf tissue. In most events, activity in spikelets localized to glumes. Staining intensity varied significantly. Seed were collected for each line, but were not further analyzed.

GUS Expression in T1 Maize

T1 progeny from two independent transformants were sown and analyzed in detail for GUS expression. There was no detectable GUS expression in silk, leaf and tassel. This indicates tassel and leaf expression observed in T0 plants may result from tissue culture associated with the transformation process. Dissected organs from T1 tassel spikelets had no apparent GUS activity (data not shown). GUS activity was detected in the ear node and the developing ear shoot. Residual GUS activity was detected in the central pith, and most activity in the developing ear shoot. Ear activity is confined to the node, the outer whorls and the central region. The pith beneath the ear node has no detectable GUS activity. GUS activity was detected in ears from 8 to 2 days prior to pollination. As in T0 ears, activity is confined to the vaculature, florets and transmitting tissue. Post-pollination GUS activity remains confined to the same tissues. Activity in developing kernels appears restricted to maternal tissue. This pattern persists through kernel development. No activity is detected in the endosperm or developing embryo, it localizes to the placental, funicular and hilar regions of developing kernels. GUS protein is detectable throughout ovule and kernel development, up to 20 days after pollination. These data support the OsMADS6 cassette as a very good candidate for trait expression in developing florets and kernels. When driven by the OsMADS6-based expression cassette, genes that facilitate phloem unloading such as invertase or a sucrose transporter should prove effective in supporting early ear development by increasing sink strength. Very light or no staining in the aerial tissue was detected, with no GUS activity in the roots One embodiment of the invention is an expression cassette based on the *Oryza sativa* OsMADS6 gene. The expression cassette consists of the gene's promoter including the first intron, 5'-UTR, 3'-UTR and 3'-nontranscribed sequence. These components were assembled into a GUS expression cassette and tested in transgenic plants. The cassette's design facilitates replacement of the GUS coding sequence with any gene of interest. The expression cassette drives gene expression primarily in maternal reproductive tissue. Within developing ears, expression localizes to florets, maternal components of developing kernels, the placental or transmitting tissue and vasculature. The expression cassettes of the present invention further drive gene expression from a very early point in ovule development, perhaps from shortly after differentiation.

Example 5

Construction of the OsMADS8 Expression Cassette

A. Cloning of the OsMADS8 5'-Regulatory Sequence

The OsMADS8 5'-regulatory sequence from rice genomic DNA (gDNA) was amplified using high-fidelity PCR. The 50 µL reaction mixture consisted of 100 ng rice gDNA, 200 µM dNTPs, 1 µL 20 µM oligonucleotide primer OsMADS8.P1 5'-ggtatctttccaaagttctggtcatgctgc-3' (SEQ ID NO: 39), 1 µL 20 µM oligonucleotide primer OsMADS8.P2 5'-ccatttttgc-gaaatgccaaatcctggc-3' (SEQ ID NO: 40), 1 µL 10× Expand High Fidelity buffer and 1 µL Expand High Fidelity polymerase. The thermocycling program was at 95° C. for 2 minutes followed by 40 cycles of (94° C. for 15 seconds, 68° C. for 7.5 minutes) followed by 68° C. for 10 minutes. The 5.2 kb OsMADS8-5'-gDNA DNA product was cloned with the TOPO XL PCR cloning kit. The pCR-XL-TOPO-OsMADS8-5'-gDNA was identified by digesting 5 µL pCR-XL-TOPO-OsMADS8-5'-gDNA miniprep DNA with EcoRI in a 20 µL reaction mixture containing 2 µg BSA and 2 µL 10× restriction endonuclease buffer. The digests were incubated at 37° C. for 2 hours then resolved on 1% TAE agarose. Positive pCR-XL-TOPO-OsMADS8-5'-gDNA clones were sequenced.

B. Cloning of the OsMADS8 3'-Regulatory Sequence

The OsMADS8 3'-regulatory sequence from rice genomic DNA (gDNA) was amplified using high-fidelity PCR. The 50 µL reaction mixture consisted of 100 ng rice gDNA, 200 µM dNTPs, 1 µL 20 µM oligonucleotide primer OsMADS8.T1 5'-acgtgagctcactcctgaaggccgatgcgacaacc-3' (SEQ ID NO: 41), 1 µL 20 µM oligonucleotide primer OsMADS8.T2 5'-agtcatcgatcatgacaaaatatcatgtttatttcgagg-3' (SEQ ID NO: 42), 1 µL 10× Expand High Fidelity buffer and 1 µL Expand High Fidelity polymerase. The thermocycling program was 95° C. for 2 minutes followed by 40 cycles of (94° C. for 15 seconds, 60° C. for 30 seconds, 68° C. for 6 minutes) followed by 68° C. for 15 minutes. Cloned the 2.04 kb OsMADS8-3'-gDNA DNA product with the Zero Blunt TOPO PCR cloning kit. The pCR-Blunt-II-OsMADS8-3'-gDNA recombinants were identified by digesting 5 µL miniprep DNA with EcoRI in a 20 µL reaction mixture containing 2 µg BSA and 2 µL 10× restriction endonuclease buffer. The digests were incubated at 37° C. for 2 hours then resolved on 1% TAE agarose. Positive pCR-Blunt-II-OsMADS8-3'-gDNA clones were sequenced.

C. Construction of the OsMADS8 5'-Regulatory Sequence

The OsMADS8 5'-regulatory sequence for the expression cassette was made in several steps. The 3'-half (OsMADS-8Pb, about 2.8 kb) was produced by high-fidelity PCR from pCR-XL-TOPO-OsMADS8-5'-gDNA, above. The reaction mixture consisted of 1 µL pCR-XL-TOPO-OsMADS8-5'-gDNA miniprep DNA, 200 µM dNTP mixture, 20 µM oligonucleotide primer OsMADS8-Pcc 5'-atcgccatggtggtcaagctg-caagtttcaaaaacac-3' (SEQ ID NO: 43), 20 µM oligonucleotide primer OsMADS8-C3 5'-acgtgtcgacgagagggagggtgga-3' (SEQ ID NO: 44), 5 µL 10× cloned Pfu buffer and 2.5 Units of Pfuturbo DNA polymerase in a final volume of 50 µL. The thermocycling program was at 95° C. for 30 seconds then 40 cycles of (95° C. for 10 seconds, 50° C. for 60 seconds, 72° C. for 6 minutes) then 72° C. for 10 minutes. The 2.8 kb OsMADS-8Pb DNA product was cloned with the Zero Blunt TOPO PCR cloning kit. The pCR-Blunt-II-TOPO-OsMADS-8Pb recombinants were identified by digesting 5 µL pCR-Blunt-II-TOPO-OsMADS-8Pb miniprep DNA with EcoRI in a 20 µL reaction mixture containing 2 µL BSA and 2 µL 10× restriction endonuclease buffer. Digests were incubated at 37° C. for 2 hours then resolved on 1% TAE agarose. Positive pCR-Blunt-II-TOPO-OsMADS-8Pb clones were sequenced.

The 5'-half (OsMADS-8Pa, about 2.4 kb) was produced by high-fidelity PCR from pCR-XL-TOPO-OsMADS8-5'-gDNA, above. The reaction mixture consisted of 1 µL pCR-XL-TOPO-OsMADS8-5'-gDNA miniprep DNA, 200 µM dNTP mixture, 20 µM oligonucleotide primer OsMADS8-C5b 5'-tcctcctcctcctcctccacctcacct-3' (SEQ ID NO: 45), 20 µM oligonucleotide primer OsMADS8-C1b 5'-aactaaatcgc-ctgcaggcggaccgttttttgcgaaatgcc-3' (SEQ ID NO: 46), 5 µL 10× cloned Pfu buffer and 2.5 Units of Pfuturbo DNA polymerase in a final volume of 50 µL. The thermocycling program was at 95° C. for 30 seconds then 40 cycles of (95° C. for 10 seconds, 50° C. for 60 seconds, 72° C. for 6 minutes) then 72° C. for 10 minutes. The 2.4 kb OsMADS-8Pa DNA product was cloned with the Zero Blunt TOPO PCR cloning kit. The pCR-Blunt-II-TOPO-OsMADS-8Pa recombinants were identified by digesting 5 µL pCR-Blunt-II-TOPO-OsMADS-8Pa miniprep DNA with EcoRI in a 20 µL reaction mixture containing 2 µg BSA and 2 µL 10× restriction endonuclease buffer. Digests were incubated at 37° C. for 2 hours then resolved on 1% TAE agarose. Positive pCR-Blunt-II-TOPO-OsMADS-8Pb clones were sequenced.

14 µL pCR-Blunt-II-TOPO-OsMADS-8Pb miniprep DNA was digested in a 20 µL reaction mixture containing 2 µg BSA, 2 µL 10× restriction endonuclease buffer, 1 µL SalI and 1 µL NcoI. The digest was incubated at 37° C. for more than 6 hours. The pCR-Blunt-II-TOPO-OsMADS-8Pb (SalI/NcoI) DNA was resolved on 1.0% TAE agarose and the 2.96 kb OsMADS-8Pb (SalI/NcoI) band was excised, recovered and ethanol precipitated with glycogen carrier. OsMADS-8Pb (SalI/NcoI) DNA was recovered by micro centrifugation, washed with 70% ethanol, dried under vacuum and resuspended in 5 µL ddH$_2$O.

2 µg pNOV6901 miniprep DNA was digested in a 20 µL reaction mixture containing 2 µg BSA, 2 µL 10× restriction endonuclease buffer, 1 µL SalI and 1 µL NcoI. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37°

C. for 30 minutes. The pNOV6901 (SalI/NcoI/CIP) plasmid DNA was resolved on 1.0% TAE agarose and the 4.7 kb pNOV6901 (SalI/NcoI/CIP) DNA band was excised, recovered and ethanol precipitated with glycogen carrier. The pNOV6901 (SalI/NcoI/CIP) DNA was recovered by micro centrifugation, washed with 70% ethanol, dried under vacuum and resuspended in 5 µL ddH$_2$O.

4.0 µL OsMADS-8Pb (SalI/NcoI) was ligated to 4.0 µL pNOV6901 (SalI/NcoI/CIP) in a 10 µL reaction mixture containing 1 µL 10×T4 DNA ligase buffer and 1 µL T4 DNA ligase (400 Units/µL), which was incubated more than 8 hours at 16° C. 5.0 µL of ligation mixture was transformed into 50 µL Top10 competent cells. The pNOV6901-OsMADS-8Pb recombinants were verified by digesting 2 µL pNOV6901-OsMADS-8Pb miniprep DNA with 0.5 µL SalI, 0.5 µL NcoI in 10 µL reaction mixtures containing 1 µg BSA and 1 µL 10× restriction endonuclease buffer. The digests were incubated at 37° C. for 2 hours then resolved on 1% TAE agarose. Positive pNOV6901-OsMADS-8Pb recombinants were sequenced.

An SbfI restriction site was introduced to pNOV6901-OsMADS-8Pb by ligating Synthetic Adapter III to the construct. Synthetic Adapter III was made by combining 40 µL of 50 µM oligonucleotide 8PA-1, 40 µL of 50 µM oligonucleotide 8PA-2 in a 100 µL mixture that is 25 mM in Tris-HCl (pH 8.0) and 10 mM in MgCl$_2$. The mixture was boiled for 5 minutes, removed from heat and naturally cooled to room temperature (about 60 minutes). This yielded a 20 µM Synthetic Adapter III mixture.

pNOV6901-OsMADS-8Pb was prepared by digesting 14 µL pNOV6901-OsMADS-8Pb miniprep DNA with 2 µL SalI in a 20 µL reaction mixture containing 2 µg BSA and 2 µL 10× restriction endonuclease buffer. The digest was incubated at 37° C. for 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. The pNOV6901-OsMADS-8Pb (SalI/CIP) DNA was resolved on 1% TAE agarose, excised, recovered and ethanol precipitated with glycogen carrier. The pNOV6901-OsMADS-8Pb (SalI/CIP) DNA was recovered by micro centrifugation, washed with 70% ethanol, dried under vacuum and resuspended in 5 µL ddH$_2$O.

4.5 µL Synthetic Adapter III mixture was ligated to 2.5 µL pNOV6901-OsMADS-8Pb (SalI/CIP) in a 10 µL ligation mixture containing 1 µL 10×T4 DNA ligase buffer and 1 µL T4 DNA ligase (400 U/µL), which was incubated more than 8 hours at 16° C. 4 µL of ligation mixture was transformed into 501.1 µL XL-1 supercompetent cells (Stratagene, Cat. No. 200236). The pNOV6901-OsMADS-8Pb-SbfI recombinants were verified by digesting 7.5 µL pNOV6901-OsMADS-8Pb-SbfI miniprep DNA in a 10 µL reaction mixture containing 1 µg BSA, 1 µL 10× restriction endonuclease buffer and 1 µL SalI. The digests were incubated at 37° C. for 2 hours then resolved on 1.0% TAE agarose. The pNOV6901-OsMADS-8Pb-SbfI recombinants that lost the SalI restriction site were digested with SbfI in a 10 µL reaction mixture containing 1 mg BSA, 1 µL 10×SEBuffer Y restriction endonuclease buffer and 1 µL SbfI (New England Biolabs). The digests were incubated at 37° C. for 2 hours then resolved on 1.0% TAE agarose. Positive pNOV6901-OsMADS-8Pb-SbfI recombinants were sequenced.

2 µg pNOV6901-OsMADS-8Pb-SbfI miniprep DNA was digested in a 20 µL reaction mixture containing 2 µg BSA, 2 µL 10× restriction endonuclease buffer and 2 µL SbfI. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. 2 µg pCR-Blunt-II-TOPO-OsMADS-8Pa miniprep DNA was digested in a 20 µL reaction mixture containing 2 µg BSA, 2 µL 10× restriction endonuclease buffer and 2 µL SbfI. The digest was incubated at 37° C. for more than 6 hours.

The digested plasmid DNAs, pNOV6901-OsMADS-8Pb-SbfI (SbfI/CIP) and pCR-Blunt-II-TOPO-OsMADS-8Pa (SbfI), were resolved on 1.0% TAE agarose and the 7.5 kb pNOV6901-OsMADS-8Pb (SbfI/CIP) and the 2.4 kb OsMADS-8Pa (SbfI) bands were excised, recovered and ethanol precipitated with glycogen carrier. The DNA fragments were recovered by micro centrifugation, washed with 70% ethanol, dried under vacuum and each resuspended in 5 µL ddH$_2$O.

4.0 µL pNOV6901-OsMADS-8Pb (SbfI/CIP) was ligated to 4.0 µL OsMADS-8Pa (SbfI) in a 10 µL ligation mixture containing 1 µL 10×T4 DNA ligase buffer and 1 µL T4 DNA ligase (400 U/µL), which was incubated for more than 8 hours at 16° C. 5.0 µL of ligation mixture was transformed into 504 Top10 competent cells. The pNOV6901-OsMADS-8P recombinants were verified by digesting 7.5 µL pNOV6901-OsMADS-8P miniprep DNA with 0.5 µL SbfI, 0.5 µL NcoI in 10 µL reaction mixtures containing 1 µg BSA and 1 µL 10× restriction endonuclease buffer. The digests were incubated at 37° C. for 2 hours then resolved on 1% TAE agarose. Positive pNOV6901-OsMADS-8P recombinants were sequenced.

D. Construction of the OsMADS8 3'-Regulatory Sequence

The OsMADS-8 3'-regulatory sequence for the expression cassette, about 2.1 kb, was produced by high-fidelity PCR from the pCR-Blunt-II-OsMADS8-3'-gDNA clone, above. The reaction mixture consisted of 1 µL pCR-Blunt-II-OsMADS8-3'-gDNA miniprep DNA, 200 µM dNTP mixture, 20 µM oligonucleotide primer OsMADS8-C2 5'-, 20 µM oligonucleotide primer OsMADS8-C4, 5 µL 10× cloned Pfu buffer and 2.5 Units of Pfuturbo DNA polymerase (Stratagene, Cat. No. 600252) in a final volume of 50 µL. The thermocycling program was 95° C. for 30 seconds then 40 cycles of (95° C. for 10 seconds, 50° C. for 60 seconds, 72° C. for 6 minutes) then 72° C. for 10 minutes. The OsMADS-8T DNA product was recovered using the QIAquick PCR purification kit. The recovered OsMADS-8T DNA was ethanol precipitated with glycogen carrier. The OsMADS-8T DNA was recovered by micro centrifugation, washed with 70% ethanol, dried under vacuum and resuspended in 14 µL ddH$_2$O. The OsMADS-8T DNA was digested in a 20 µL reaction mixture containing 2 µg BSA, 2 µL 10× restriction endonuclease buffer, 1 µL NotI and 1 µL XmaI. The digest was incubated at 37° C. for more than 6 hours. The OsMADS-8T (NotI/XmaI) DNA was resolved on 1.0% TAE agarose, excised, recovered and ethanol precipitated with glycogen carrier. The OsMADS-8T (NotI/XmaI) DNA was recovered by micro centrifugation, washed with 70% ethanol, dried under vacuum and resuspended in 5 µL ddH$_2$O.

2 µg pNOV6901-OsMADS-8P miniprep DNA was digested in a 20 µL reaction mixture containing 2 µg BSA, 2 µL 10× restriction endonuclease buffer, 1 µL NotI and 1 µL XmaI. The digest was incubated at 37° C. for more than 6 hours, then at 70° C. for 20 minutes. Then 1 µL of the appropriate 10× restriction endonuclease buffer, 1 µL 1 Unit/µL CIP and 8 ddH$_2$O were added to the reaction and it was further incubated at 37° C. for 30 minutes. The pNOV6901-OsMADS-8P (NotI/XmaI/CIP) plasmid DNA was resolved on 1.0% TAE agarose and the 9.9 kb pNOV6901-OsMADS-8P band was excised, recovered and ethanol precipitated with glycogen carrier. The pNOV6901-OsMADS-8P (NotI/XmaI/

CIP) DNA fragment was recovered by micro centrifugation, washed with 70% ethanol, dried under vacuum and resuspended in 5 µL ddH$_2$O.

4.0 µL of the pNOV6901-OsMADS-8P (NotI/XmaI/CIP) was ligated to 4.0 µl OsMADS-8T (NotI/XmaI) in a 10 µL ligation mixture containing 1 µL 10×T4 DNA ligase buffer and 1 µL T4 DNA ligase (400 Units/µL), which was incubated more than 8 hours at 16° C. 5.0 µL of ligation mixture was transformed into 50 µL Top10 competent cells. pNOV6901-OsMADS-8P/OsMADS-8T recombinants were verified by digesting 2 µL pNOV6901-OsMADS-8P/OsMADS-8T miniprep DNA with 1.0 µL RsrII in 10 µL reaction mixtures containing 1 µg BSA and 1 µL 10× restriction endonuclease buffer. The digests were incubated at 37° C. for 2 hours then resolved on 1% TAE agarose. Positive pNOV6901-OsMADS-8P/OsMADS-8T recombinants were sequenced. The finished clone was designated pNOV6901-OsMADS-8P/OsMADS-8T. The plasmid's QC number is 11170. 11170 contains the complete OSMADS8 expression cassette depicted by SEQ ID NO: 47.

E. Mobilization of the OsMADS8 GUS Expression Cassette into pNOV6900

2 µg pNOV6900 was digested in a 20 µL reaction mixture containing 2 µg BSA, 2 µL 10× restriction endonuclease buffer and 2 µL RsrII. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. 214 pNOV6901-OsMADS-8P/OsMADS-8T miniprep DNA was digested in a 20 µL reaction mixture containing 2 µg BSA, 2 µL 10× restriction endonuclease buffer and 2 µL RsrII. The digest was incubated the reaction at 37° C. for more than 6 hours.

The digested plasmid DNAs, pNOV6900 (RsrII/CIP) and pNOV6901-OsMADS-8P/OsMADS-8T (RsrII), were resolved on 1.0% TAE agarose and the 9.2 kb pNOV6900 (RsrII/CIP) and the 9.5 kb pNOV6901-OsMADS-8P/OsMADS-8T (RsrII) bands were excised, recovered and ethanol precipitated with glycogen carrier. The pNOV6900 (RsrII/CIP) and the pNOV6901-OsMADS-8P/OsMADS-8T (RsrII) DNA fragments were recovered by micro centrifugation, washed with 70% ethanol, dried under vacuum and each resuspended in 5 µL ddH$_2$O.

4.0 µL of pNOV6900 (RsrII/CIP) was ligated to 4.0 µL pNOV6901-OsMADS-8P/OsMADS-8T (RsrII) in a 10 µL ligation mixture containing 1 µL 10×T4 DNA ligase buffer and 1 µL T4 DNA ligase (400 U/µL). The ligation mixture was incubated more than 8 hours at 16° C. 5.0 µL of ligation mixture was transformed into 50 µL Top10 competent cells. The pNOV6900-pNOV6901-OsMADS-8P/OsMADS-8T recombinants were verified by digesting 7.5 µL pNOV6900-pNOV6901-OsMADS-8P/OsMADS-8T miniprep DNA with 1.0 µL NcoI in 10 µL reaction mixtures containing 1 µg BSA and 1 µL 10× restriction endonuclease buffer. The digests were incubated at 37° C. for 2 hours then resolved on 1% TAE agarose. Positive pNOV6900-pNOV6901-OsMADS-8P/OsMADS-8T recombinants were sequenced. The finished clone was designated pNOV6909. The plasmid's QC number is 11171.

The engineered alterations in the 5'-regulatory sequence derived from the OsMADS8 gene include introduction of an SbfI site followed by an RsrII site at the 5'-end of OsMADS8P, elimination of the natural translation start codon in OsMADS8P, elimination of undesired open reading frames in the new 5'-untranslated leader sequence transcribed from OsMADS8P, insertion of a Kozak sequence upstream of the new translation start codon in OsMADS8P and insertion of the new translation start codon downstream of the intron1/exon2 junction in OsMADS8P as an NcoI site. The engineered alterations in the 3'-gene regulatory sequence derived from the OsMADS8 gene include introduction of a NodI site at the 5'-terminus of OsMADS8T and introduction of an RsrII site at the 3'-terminus of OsMADS8T. In this configuration the GUS coding sequence can be replaced with any gene of interest flanked by NcoI/NotI restriction sites. The complete cassette is mobilized, as an RsrII fragment, to the binary vector pNOV6900.

The cassette was transformed into A188 X HyII maize and Kaybonnet rice using standard *agrobacterium* mediated methodology.

GUS Expression in T0 Maize

Forty T0 transgenic maize lines were generated. Tassel spikelets were histochemically screened for GUS activity. Twenty-nine events were positive for GUS activity. Thirteen also showed GUS expression in leaf punches. In general, the pattern revealed detectable GUS activity in tassels and little to no activity in leaf punches. The ear from one plant reflecting this pattern was sacrificed to examine GUS expression. Strong GUS expression is evident throughout the ear. These data indicate the cassette drives GUS expression primarily in female reproductive tissue.

GUS Expression in T0 Rice

Of thirty-six T0 rice lines containing pNOV6909, thirty-two independent transformants were histochemically stained for GUS expression. No GUS activity was detected in leaf tissue. In most events, activity localized to panicles and could be seen in anthers or the carpel base. Staining intensity varied significantly.

GUS Expression in T1 Maize

T1 progeny from four independent transformants were sown and analyzed in detail for GUS expression. There was no detectable GUS expression in tassels, leaf tissue, developing silk or shoots. This indicates tassel and leaf expression observed in T0 plants may result from tissue culture associated with the transformation process. Dissected organs from T1 tassels indicated no apparent GUS expression (data not shown). No GUS activity was detected in the node attached to the developing ear shoot. The node below this also has no detectable GUS activity, but there is distinct activity in florets on the arrested ear. The expression cassette is activated very early in floret development. GUS activity was detected in the central pith and florets of the developing ear before pollination. This pattern persists from 5 days before pollination to one day before pollination. Central pith expression persists up to 1 day before pollination, after which GUS activity is no longer detected in this zone. Some GUS activity was detected in the ear's outer vasculature and the floret's transmitting tissue from the day of pollination to 1 day after pollination. Afterwards, GUS activity is detected only in the maternal components of developing kernels. GUS expression data was collected during development from 1 day before pollination to 20 days after pollination. GUS protein is detectable throughout ovule and kernel development, up to 20 days after pollination. These data support the OsMADS8 cassette as a very good candidate for trait expression in developing florets. When driven by the OsMADS8-based expression cassette, genes that facilitate phloem unloading such as invertase or a sucrose transporter should prove effective in supporting early ear development by increasing sink strength. Very light staining in the aerial tissue was detected, with no GUS activity in the roots In summary, the present invention includes expression cassettes based on the *Oryza sativa* OsMADS8 gene. It consists of the gene's promoter including the first intron, 5'-UTR, 3'-UTR and 3'-nontranscribed sequence. The cassette's design facilitates replacement of the GUS coding sequence with any gene of interest. The cassette targets gene expression primarily to developing florets and kernels, and the placental tissue beneath each floret. Post-fertilization, expression is detected in the aleurone, hilar region and pedicel. Developmentally, the cassette should drive gene expression from a very early point in ovule development, perhaps from shortly after differentiation.

Example 6

Construction of the OsMADS13 Expression Cassette

A. Cloning of the OsMADS13 5'-Regulatory Sequence

The OsMADS13 5'-regulatory sequence from rice genomic DNA (gDNA) was amplified using high-fidelity PCR. The 50 µL reaction mixture consisted of 100 ng rice gDNA, 200 µM dNTPs, 1 µL 20 µM oligonucleotide primer OsMADS13-C1 5'-gactgcatgcggaccgttccaaaat-taagcacacacatttg-3' (SEQ ID NO: 48), 1 µL 20 µM oligonucleotide primer OsMADS13-C2 5'-gactccatggcttcttgctct-caactgatcaac-3' (SEQ ID NO: 49), 1 µL 10× Expand High Fidelity buffer and 1 µL Expand High Fidelity polymerase. The thermocycling program was at 95° C. for 2 minutes followed by 40 cycles of (94° C. for 15 seconds, 68° C. for 7.5 minutes) followed by 68° C. for 10 minutes. The 1.9 kb OsMADS13-5'-gDNA DNA fragment was recovered and ethanol precipitated with glycogen carrier. The OsMADS13-5'-gDNA fragment was recovered by micro centrifugation, washed with 70% ethanol, dried under vacuum and resuspended in 14 µL ddH$_2$O. The OsMADS13-5'-gDNA fragment was digested in a 20 µL reaction mixture containing 2 µg BSA, 2 µL 10× restriction endonuclease buffer and 2 µL NcoI. The digest was incubated at 37° C. for more than 6 hours. The digest was resolved on 1.0% TAE agarose and the 1.9 kb OsMADS13-5'-gDNA (NcoI) DNA band was excised, recovered and ethanol precipitated with glycogen carrier. The OsMADS13-5'-gDNA (NcoI) DNA as recovered by micro centrifugation, washed with 70% ethanol, dried under vacuum and resuspended in 5 µL ddH$_2$O.

2 µg pNOV6901 miniprep DNA was digested in a 20 µL reaction mixture containing 2 µg BSA, 2 µL 10× restriction endonuclease buffer and 2 µL SphI. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. The pNOV6901 (SphI/blunt) DNA was resolved on 1.0% TAE agarose and the 4.7 kb pNOV6901 (SphI/blunt) band was excised, recovered and ethanol precipitated with glycogen carrier. The pNOV6901 (SphI/blunt) DNA was recovered by micro centrifugation, washed with 70% ethanol, dried under vacuum and resuspended in 14 µL ddH$_2$O.

pNOV6901 (SphI/blunt) miniprep DNA was digested in a 20 µL reaction mixture containing 2 µg BSA, 2 µL 10× restriction endonuclease buffer and 2 µL NcoI. The digest was incubated at 37° C. for more than 6 hours. The pNOV6901 (SphI/blunt/NcoI) plasmid DNA was resolved on 1.0% TAE agarose and the 4.7 kb pNOV6901 (SphI/blunt/NcoI) band was excised, recovered and ethanol precipitated with glycogen carrier. The pNOV6901 (SphI/blunt/NcoI) DNA was recovered by micro centrifugation, washed with 70% ethanol, dried under vacuum and resuspended in 5 µL ddH$_2$O.

4.0 µL OsMADS13-5'-gDNA (NcoI) was ligated to 4.0 µL pNOV6901 (SphI/blunt/NcoI) in a 10 µL ligation mixture containing 1 µL 10×T4 DNA ligase buffer and 1 µL T4 DNA ligase (400 Units/µL). The ligation mixture was incubated more than 8 hours at 16° C. 5.0 µL of the ligation mixture was transformed into 50 µL Top10 competent cells. The pNOV6901-OsMADS13P recombinants were verified by digesting 2 µL pNOV6901-OsMADS13P miniprep DNA with 0.5 µL XhoI, 0.5 µL NcoI in 10 µL reaction mixtures containing 1 µL BSA and 1 µL 10× restriction endonuclease buffer. The digests were incubated at 37° C. for 2 hours then resolved on 1% TAE agarose. Positive pNOV6901-OsMADS13P recombinants were sequenced.

B. Cloning of the OsMADS13 3'-Regulatory Sequence

The OsMADS13 3'-regulatory sequence from rice genomic DNA (gDNA) was amplified using high-fidelity PCR. The 50 µL reaction mixture consisted of 100 ng rice gDNA, 200 µM dNTPs, 1 µL 20 µM oligonucleotide primer OsMADS13-C3 5'-tcgagcggccgctgacatggatatgatgatcag-3' (SEQ ID NO: 50), 1 µL 20 µM oligonucleotide primer OsMADS13-C4 5'-acgtatcgatcggaccgcaacgcacgggcacccaac-3' (SEQ ID NO: 51), 1 µL 10× Expand High Fidelity buffer and 1 µL Expand High Fidelity polymerase. The thermocycling program was at 95° C. for 2 minutes followed by 40 cycles of (94° C. for 15 seconds, 60° C. for 30 seconds, 68° C. for 6 minutes) followed by 68° C. for 15 minutes. The 1.2 kb OsMADS13-3'-gDNA DNA fragment was recovered and ethanol precipitated with glycogen carrier. The OsMADS13-3'-gDNA DNA fragment was recovered by micro centrifugation, washed with 70% ethanol, dried under vacuum and resuspended in 14 µL ddH$_2$O.

The OsMADS13-3'-gDNA fragment was digested in a 20 µL reaction mixture containing 2 µg BSA, 2 µL 10× restriction endonuclease buffer and 2 µL NotI. The digest was incubated at 37° C. for more than 6 hours then resolved on 1.0% TAE agarose and the 1.2 kb OsMADS13-3'-gDNA (NotI) DNA band was excised, recovered and ethanol precipitated with glycogen carrier. The OsMADS13-3'-gDNA (Nod) DNA was recovered by micro centrifugation, washed with 70% ethanol, dried under vacuum and resuspended in 5 ddH$_2$O.

2 µg pNOV6901-OsMADS13P miniprep DNA was digested in a 20 µL reaction mixture containing 2 µg BSA, 2 µL 10× restriction endonuclease buffer, 1 µL NotI and 1 SmaI. The digest was incubated at 37° C. for more than 6 hours, then at 70° C. for 20 minutes. Then 1 µL of the appropriate 10× restriction endonuclease buffer, 1 µL 1 Unit/µL CIP and 8 ddH$_2$O were added to the reaction and it was further incubated at 37° C. for 30 minutes. The pNOV6901-OsMADS13P (NotI/SmaI/CIP) DNA was resolved on 1.0% TAE agarose and the 6.6 kb band was excised, recovered and ethanol precipitated with glycogen carrier. The pNOV6901-OsMADS13P (NotI/SmaI/CIP) DNA fragment was recovered by micro centrifugation, washed with 70% ethanol, dried under vacuum and resuspended each in 5 µL ddH$_2$O.

4.0 µL pNOV6901-OsMADS13P (NotI/SmaI/CIP) was ligated to 4.0 OsMADS13-3'-gDNA (NotI) in a 10 µL ligation mixture containing 1 µL 10×T4 DNA ligase buffer and 1 µL T4 DNA ligase (400 Units/4). The ligation mixture was incubated more than 8 hours at 16° C. 5.0 µL of the ligation mixture was transformed into 50 µL Top10 competent cells. The pNOV6901-OsMADS13P/OsMADS13T recombinants were verified by digesting 7.5 µL pNOV6901-OsMADS13P/OsMADS13T miniprep DNA with 1.0 µL NotI in 10 µL reaction mixtures containing 1 µg BSA and 1 µL 10× restriction endonuclease buffer. Digests were incubated at 37° C. for 2 hours then resolved on 1% TAE agarose. Positive pNOV6901-OsMADS13P/OsMADS13T recombinants were sequenced. The finished clone was designated pNOV6904, which is also the plasmid's QC number. pNOV6904 contains the complete OSMAD13 expression cassette depicted by SEQ ID NO: 52.

C. Mobilization of the OsMADS13 GUS Expression Cassette into pNOV6900

2 µg pNOV6900 was digested in a 20 µL reaction mixture containing 2 µg BSA, 2 µL 10× restriction endonuclease buffer and 2 µL RsrII. The digest was incubated at 37° C. for more than 6 hours, then at 70° C. for 20 minutes. Then 1 µL of the appropriate 10× restriction endonuclease buffer, 1 µL 1 Unit/µL CIP and 8 µL ddH$_2$O were added to the reaction and it was further incubated at 37° C. for 30 minutes. 2 µg pNOV6901-OsMADS13P/OsMADS13T miniprep DNA was digested in a 20 µL reaction mixture containing 2 µg BSA, 2 µL 10× restriction endonuclease buffer and 2 µL RsrII. The digest was incubated the reaction at 37° C. for more than 6 hours.

The digested plasmid DNAs, pNOV6900 (RsrII/CIP) and pNOV6901-OsMADS13P/OsMADS13T (RsrII), were resolved on 1.0% TAE agarose and the 9.2 kb pNOV6900 (RsrII/CIP) and the 5.3 kb pNOV6901-OsMADS13P/OsMADS13T (RsrII) bands were excised, recovered and ethanol precipitated with glycogen carrier. The pNOV6900 (RsrII/CIP) and pNOV6901-OsMADS13P/OsMADS13T (RsrII) DNA fragments were recovered by micro centrifugation, washed with 70% ethanol, dried under vacuum and resuspended each in 5 µL ddH$_2$O.

4.0 µL of pNOV6900 (RsrII/CIP) was ligated to 4.0 µL pNOV6901-OsMADS13P/OsMADS13T (RsrII) in a 10 µL ligation mixture containing 1 µL 10×T4 DNA ligase buffer and 1 µL T4 DNA ligase (400 U/µL). The ligation mixture was incubated more than 8 hours at 16° C. 5.0 µL of ligation mixture was transformed into 50 µL Top10 competent cells. The pNOV6900-pNOV6901-OsMADS13P/OsMADS13T recombinants were verified by digesting 7.5 µL pNOV6900-pNOV6901-OsMADS13P/OsMADS13T miniprep DNA with 1.0 µL NcoI in 10 µL reaction mixtures containing 1 µg BSA and 1 µL 10× restriction endonuclease buffer. The digests were incubated at 37° C. for 2 hours then resolved on 1% TAE agarose. Positive pNOV6900-pNOV6901-OsMADS13P/OsMADS13T recombinants were sequenced. The finished clone was designated pNOV6905, which is also the plasmid's QC number.

The engineered alterations in the 5'-gene regulatory sequence derived from the OsMADS13 gene include introduction of an RsrII site at the 5'-end of OsMADS13P, insertion of a Kozak sequence upstream of the natural OsMADS13P translation start codon and modification of the natural OsMADS13P translation start codon so that it is contained within an NcoI site. The engineered alterations in the 3'-gene regulatory sequence derived from the OsMADS13 gene include introduction of a NotI site at the 5'-terminus of OsMADS13T and introduction of an RsrII site at the 3'-terminus of OsMADS13T. In this configuration the GUS coding sequence can be replaced with any gene of interest flanked by NcoI/NotI restriction sites. The complete cassette is mobilized, as an RsrII fragment, to the binary vector pNOV6900.

The cassette was transformed into A188 X HyII maize and Kaybonnet rice using standard *agrobacterium* mediated methodology.

GUS Expression in T0 Maize

Sixty-seven T0 transgenic maize lines were generated. Tassel spikelets were histochemically screened for GUS expression. Fifty-six were positive for GUS activity. Thirty-five also showed GUS expression in leaf punches. Ten lines had no detectable GUS activity in tassels or leaf punches.

Two T0 lines were selected to analyze GUS expression in developing ears. Both lines had a GUS signal in tassel spikelets and no GUS signal in leaf punches. Ears were harvested approximately 7 days before silking and histochemically stained for GUS expression. Whole sections showed a strong GUS signal only in developing florets, whereas GUS activity is absent in surrounding ear tissue. These data indicate the OsMADS13 expression cassette functions to drive GUS expression in both male and female spikelets in T0 maize transformants.

GUS expression in T0 Rice

Thirty-three T0 rice lines were produced. Fourteen independent transformants were histochemically stained for GUS expression GUS activity was primarily detected in spikelets. Some plants also had GUS activity in leaf tissue.

GUS Expression in T1 Maize

T1 progeny from three independent transformants were sown and analyzed in detail for GUS expression. There was no detectable GUS expression in leaf tissue, developing silk or tassels. This indicates tassel expression observed in T0 plants may result from tissue culture associated with the transformation process. Dissected organs from T1 tassels indicated no apparent GUS expression (data not shown). GUS activity was detected in the developing ear harvested about 5 days before pollination. The longitudinal section showed expression localized to developing ovules and transmitting or placental tissue. The cross section supports this and provides further evidence for expression in ear vasculature. It also localizes to zones where ovules will likely develop.

These data support the OsMADS13 cassette as a very good candidate for trait expression in developing ovules. When driven by the OsMADS13-based expression cassette, genes that facilitate phloem unloading such as invertase or a sucrose transporter should prove effective in supporting early ear development by increasing sink strength.

The observed GUS expression pattern at 4 and 6 days after pollination. Late in kernel development (21 days after pollination) GUS expression remains localized to the pedicel and hilar regions. It also appears in the aleurone. GUS protein is detectable throughout ovule and kernel development, up to 21 days after pollination. Very light staining in the aerial tissue was detected, with no GUS activity in the roots.

The present invention includes an expression cassette based on the *Oryza sativa* OsMADS13 gene. The expression cassette includes the gene's promoter, including the first intron and the 5'-UTR, the 3'-UTR and the 3'-nontranscribed sequence. These components were assembled into a GUS expression cassette and tested in transgenic plants. The cassette's design facilitates replacement of the GUS coding sequence with any gene of interest. The cassette will target gene expression to the vasculature within the placental tissue below the floret of developing ear spikelets. Post-fertilization, expression is also expected in the aleurone, hilar region and pedicel. Developmentally, the cassette should drive gene expression from a very early point, more than 7 days before pollination, in ovule development.

Example 7

Identification of the OsT6PP cDNA Sequence

The first vascular plant trehalose-6-phosphate phosphatase genes were cloned from *Arabidopsis thaliana* by complementation of a yeast tps2 deletion mutant (Vogel et al. 1998). The genes designated AtTPPA and AtTPPB (GenBank accessions AF007778 and AF007779) were shown at that time to have trehalose-6-phosphate phosphatase activity. The AtTPPA and AtTTPB protein sequences were used in TBLASTN queries of maize and rice sequence databases. Sequence alignments organized the hits into individual genes. Three maize and three rice T6PP homologs were identified. The cDNA sequences corresponding to the predicted protein sequence for each gene-ZmT6PP-1, -2 and -3 and OsT6PP-1, -2 and -3—are shown in global alignment with the *Arabidopsis* T6PPs.

The composition and method of the present invention includes using the OsMADS6 promoter operably linked to a nucleic acid molecule that when expressed in a plant cell, increases the expression of T6PP. By doing so, flux through the trehalose pathway is increased only in young developing ears where it functions to increase flux through central carbon metabolism.

The OsT6PP-3 cDNA sequence is amplified using high-fidelity PCR. The 50 μL reaction mixture consists of 1 μL rice cDNA library (prepared from callus mRNA in Stratagene's Lambda Unizap Vector, primary library size >1×10$^6$ pfu, amplified library titer >1×10$^{12}$ pfu/mL), 200 μM dNTPs, 1 μL 20 μM of oligonucleotide primer T6PP-EC-5 and 1 μL 20 μM of oligonucleotide primer T6PP-EC-3, 5 μL 10× Cloned PFU buffer and 2.5 Units of Pfuturbo DNA polymerase. The thermocycling program is 95° C. for 2 minutes followed by 40 cycles of (94° C. for 15 seconds, 50° C. for 1 minute, 72° C. for 1 minute) followed by 72° C. for 10 minutes. The OsT6PP-3 product is cloned with the Zero Blunt TOPO PCR cloning kit. The pCR-Blunt-II-TOPO-OsT6PP-3 is identified by digesting 54, pCR-Blunt-II-TOPO-OsT6PP-3 miniprep DNA with EcoRI in a 20 reaction containing 2 μg BSA and 2 μL 10× EcoRI restriction endonuclease buffer. The reaction is incubated at 37° C. for 2 hours and the pCR-Blunt-II-TOPO-OsT6PP-3 (EcoRI) products are resolved on 1% TAE agarose. The pCR-Blunt-II-TOPO-OsT6PP-3 clone is then sequenced. The OsT6PP-3 cDNA is flanked by NcoI/SacI restriction endonuclease sites.

To facilitate cloning into 11082, an internal NcoI site in OsT6PP was silenced using Stratagene's QuikChange Multi Site-Directed Mutagenesis Kit and the oligonucleotide primer T6PP-QC.

Example 8

Construction of OsMADS6-T6PP

A. Construction of the OsMADS6-OsT6PP-3 Expression Cassette

The pCR-Blunt-II-TOPO-OsT6PP-3 clone (14 μL) DNA was digested in a 20 μL reaction mixture containing 2 μg BSA, 2 μL 10× restriction endonuclease buffer, 1 μL NcoI and 1 μL SacI. The digest was incubated at 37° C. for more than 6 hours. The pCR-Blunt-II-TOPO-OsT6PP-3 (NcoI/SacI) DNA was resolved on 1.0% TAE agarose and the 1.3 kb OsT6PP-3 (NcoI/SacI) band was excised, recovered and ethanol precipitated with glycogen carrier. The OsT6PP-3 (NcoI/SacI) DNA was recovered by micro centrifugation, washed with 70% ethanol, dried under vacuum and resuspended in 5 μL ddH$_2$O.

2 μg 11082 miniprep DNA was digested in a 20 μL reaction mixture containing 2 μg BSA, 2 μL 10× restriction endonuclease buffer, 1 μL NcoI and 1 μL SacI. The digest was incubated at 37° C. for more than 6 hours, then at 70° C. for 20 minutes. Then 1 μL of the appropriate 10× restriction endonuclease buffer, 1 μL 1 Unit/μL CIP and 8 μL ddH$_2$O were added to the reaction and it was further incubated at 37° C. for 30 minutes. The 11082 (NcoI/SacI/CIP) DNA was resolved on 1.0% TAE agarose and the 8.1 kb 11082 (NcoI/SacI/CIP) band was excised, recovered and ethanol precipitated with glycogen carrier. The 11082 (NcoI/SacI/CIP) DNA fragment was recovered by micro centrifugation, washed with 70% ethanol, dried under vacuum and resuspended in 5 μL ddH$_2$O.

4.0 μL 11082 (NcoI/SacI/CIP) was ligated to 4.0 μL OsT6PP-3 (NcoI/SacI) in a 10 μL reaction mixture containing 1 μL 10×T4 DNA ligase buffer and 1 μL T4 DNA ligase (400 Units/μL). The reaction mixture was incubated more than 8 hours at 16° C. 5.0 μL of ligation mixture was transformed into 50 μL Top10 competent cells. The recombinants were verified by digesting 7.5 μL 11082-OsT6PP-3 miniprep DNA with 1.0 μL RsrII in 10 μL reaction mixtures containing 1 μg BSA and 1 μL 10× restriction endonuclease buffer. The digests were incubated at 37° C. for 2 hours then resolved on 1% TAE agarose. Positive 11082-OsT6PP-3 recombinants were sequenced. The vector was designated OsMADS6-OsT6PP-Assembly.

B. Mobilization of the OsMADS6-OsT6PP-Assembly Expression Cassette into pNOV6900

2 μg pNOV6900 was digested in a 20 μL reaction mixture containing 2 μg BSA, 2 μL 10× restriction endonuclease buffer and 2 μL RsrII. The digest was incubated at 37° C. for more than 6 hours, then at 70° C. for 20 minutes. Then 1 μL of the appropriate 10× restriction endonuclease buffer, 1 μL 1 Unit/μL CIP and 8 μL ddH$_2$O were added to the reaction and it was further incubated at 37° C. for 30 minutes. 2 μg pNOV6906-OsT6PP-Assembly miniprep DNA was digested in a 20 μL reaction mixture containing 2 μg BSA, 2 μL 10× restriction endonuclease buffer and 2 μL RsrII. The digest was incubated at 37° C. for more than 6 hours.

The pNOV6900 (RsrII/CIP) and the pNOV6906-OsT6PP-Assembly (RsrII) plasmid DNAs were resolved on 1.0% TAE agarose, and the 9.2 kb pNOV6900 (RsrII/CIP) and the 6.8 kb pNOV6906-OsT6PP-Assembly (RsrII) bands were excised, recovered and ethanol precipitated with glycogen carrier. The pNOV6900 (RsrII/CIP) and pNOV6906-OsT6PP-Assembly (RsrII) DNA fragments were recovered by micro centrifugation, washed with 70% ethanol, dried under vacuum and resuspended in 5 μL ddH$_2$O each.

4.0 μL pNOV6900 (RsrII/CIP) was ligated to 4.0 μL pNOV6906-OsT6PP-Assembly (RsrII) in a 10 μL ligation mixture containing 1 μL 10×T4 DNA ligase buffer and 1 μL T4 DNA ligase (400 U/A). The ligation mixture was incubated more than 8 hours at 16° C. 5.0 μL of ligation mixture was transformed into 50 μL Top10 competent cells. The pNOV6900-pNOV6906-OsT6PP-Assembly recombinants were verified by digesting 7.5 μL miniprep DNA with 1.0 μL NcoI in 10 μL reaction mixtures containing 1 μg BSA and 1 μL 10× restriction endonuclease buffer. The digests were incubated at 37° C. for 2 hours then resolved on 1% TAE agarose. Positive pNOV6900-pNOV6906-OsT6PP-Assembly recombinants were sequenced. The finished clone was designated OsMADS6-OsT6PP-Binary. The plasmid's QC number is 12194.

The OsMADS6-OsT6PP-3 expression cassette (was transformed into A188 maize using standard *agrobacterium* mediated methodology. Regenerated T0 shoots were screened transgene copy number and insert integrity using a Taqman™ assay. Events containing a single copy of the OsMADS6-OsT6PP-3 expression cassette and no other sequence derived from the binary vector were identified.

Expression cassette function in each transgenic Event was verified by RT-PCR. DNA-free total RNA template was prepared from 100 mg of T0 tassel tissue using the RNeasy Plant mini Kit. The RT-PCR assay was performed using the Qiagen One Step RT-PCR kit with 100 ng total RNA template, the T6PP-RTPCRF and 6906-tr primers. This assay produces a transgene-specific 210 by fragment.

Example 9

Greenhouse Growth Conditions

Corn seed is sown into 2.5 SVD pots (Classic 600, ~2 gallon nursery containers) in Universal mix (Sungrow Horticulture, Pine Bluff, Ariz.). Universal mix is 45% Peat moss, 45% bark, 5% perlite, 5% vermiculite. Environmental conditions for greenhouse maize cultivation are typically 16 hour days (average light intensity 600 µmol $m^{-2}s^{-2}$), day time temperature of 80-86° F., night time temperature 70-76° F. and relative humidity greater than 50%. Plants are placed on 2" platforms to avoid contact with the greenhouse floor. Plants are hand watered until daily irrigation as required, then they are placed on irrigation drip. The irrigation schedule is 4 minutes every other day. Plants were routinely treated with insecticides to control pests.

Example 10

Evaluation of Transgenic Maize Expressing OsMADS6-OsT6PP-3 in the Greenhouse

The greenhouse evaluation is a controlled water-stress experiment that quantifies ovule viability in water-stressed and unstressed plants. Data from unstressed plants represent the genotype's potential to set seed under ideal conditions. Data from water-stressed plants quantify kernel abortion that results from drought at the time of flowering. The results of these experiments can be predictive of field performance. We used this tool to select transgenic events for field evaluations.

Transgenic maize segregating for a single copy of the OsMADS6-OsT6PP-3 transgene were sown as above. Taqman analysis was used to divide the progeny into homozygous or hemizygous (containing OsMADS6-OsT6PP-3) and azygous (lost the OsMADS6-OsT6PP-3) groups. These individuals were pollinated with JHAF031 maize pollen to generate hybrid seed (KPOO188RAxJHAF031) for the greenhouse experiment. The hybrid seed were sown as above. Seedlings were transferred to 600 pots, above, and maintained using standard greenhouse procedures until they reached the V6 growth stage (Ritchie et al., 1997). All plants were treated with the systemic pesticide, Marathon, to reduce susceptibility to pests. Water stress was gradually imposed, using salt as the osmoticum (Nuccio et al. 1998). The salt consisted of sodium chloride/calcium chloride at a 10:1 molar ratio, delivered in 0.5x Hoagland's Solution, to prevent sodium-induced disruption of potassium uptake. Salt concentration in the irritant was increased from 50 mM to 100 mM to 150 mM every three days to give plants time to adjust to the salt. Plants were maintained on 150 mM salt solution through the flowering period, typically two weeks, after which pots were thoroughly flushed with water and plants were returned to normal irrigation. This protocol typically reduced kernel set by 40-60%, compared to control plants that received no salt.

Typically 15-20 seed per transgenic event were sown to generate a uniform seedling population. Plants were arranged in a complete, randomized block design consisting of six-eight replicates per treatment. Developing ears were covered with pollination bags before silk emergence. Pollen shed and silk emergence dates were recorded and individual ears were hand pollinated with donor pollen 5 days after silk emergence. Pollination bags were removed after completing all pollinations. Ears were harvested 30 days after pollinations, and dried for 4 days to 15% moisture content. Ears were shelled and the kernels were counted and weighed.

Example 11

Greenhouse Experiment

Two OsMADS6-T6PP-3 events were studied for their ability to set seed under water stress. Twenty-four hybrid seed (A188xJHAF031) from each event were germinated. Taqman analysis was used to establish zygosity in each seedling. Hemizygotes and azygotes were analyzed using the greenhouse water stress protocol described above. In this experiment azygote plants served as the benchmark. In these greenhouse experiments, the hemizygote plants could not be distinguished from the azygote plants. On average the water stress reduced kernel set by 42%. The data in these greenhouse experiments indicate the OsMADS6-T6PP-3 expression cassette does not influence kernel set in maize in these particular greenhouse experiments and when evaluated by the above water stress protocols.

Example 12

Evaluation of Transgenic Maize Expressing OsMADS-T6PP-3 for Drought Stress Tolerance in the Field Hybrid seed were generated for each transgenic Event at the Syngenta Seeds field station in Kauai in late 2004. T1 seed obtained by selfing the T0 plant of the events was sown in four single-row plots, 12.7 feet long separated by 3 foot alleys with about 20 plants per row. Taqman analysis was used to divide the progeny into homozygous or hemizygous (containing OsMADS6-OsT6PP-3) and azygous (lost the OsMADS6-OsT6PP-3) groups. In two of the single-row plots, hemizygous and azygous plants were destroyed and homozygous plants were selfed for seed bulking and also testcrossed to NP2043BT11 and NP2044BT11. In the other two single-row plots homozygous and hemizygous plants were destroyed and azygous plants were selfed and also crossed to NP2043BT11 and NP2044BT11. The azygous and hemizygous testcross seed of the events was used to conduct field trials.

A field evaluation was conducted to test transgene performance in a controlled drought experiment. The experiment was conducted at the Syngenta Crop Protection Facility in Visalia, Calif. in the summer of 2004. The planting site typically gets less than 3" of rainfall during the summer. The NP2043BT11 testcross seed, generated above, was used in this study. This population also contained the BT transgene to control insect pressure. A split-block design, with watering regime as the main plots arranged in a randomised complete blocks and replicated three times, events as the subplots, and in cases where there was seed of the azgous and hemizygous hybrids, genotype as sub-sub-plots was used. Two watering regimes were attempted: water-stressed and well-watered. Each plot consisted of two-rows, 17.5 feet long planted with 40 seeds per row. Alleys between ranges were 2.5 feet. Furrow irrigation was used to water the fields. Each treatment block had a dedicated irrigation source situated at one end of the field. The replication were arranged in such a way that replication one was closest to and replication three was the furthest from the irrigation source. After emergence, stand counts were taken and plots were thinned, as necessary, to establish field uniformity.

The well-watered block was thought to have been irrigated optimally throughout the experiment. The water-stress block was watered optimally until plants reached approximately V, at which time water was withheld. Plants were returned to optimal irrigation after 90% silk emergence.

After plants transitioned to reproductive development, the 50% pollen shed date, the 50% silk emergence date, and leaf scrolling at early-, mid- and late-flowering were recorded for each plot. Plot Barreness was recorded three weeks after silking.

Plots were combine-harvested and grain yield and grain moisture were recorded. The data from hemizygous plots were compared to azygous plots, or wild type plots where necessary, to gauge the transgene's effect on yield. Seven OsMADS6-T6PP-3 events were evaluated. The data show the OsMADS6-T6PP-3 transgene has a positive effect on yield in four of the seven Events. The yield gain is evident in both unstressed and drought-stressed plots. For example in the drought-stressed treatment block the average yield for 5217 Events containing the transgene was 73 Bu/acre and the average yield for 5217 Events lacking the transgene was 54 Bu/acre. Results suggest the transgene improves kernel set by 25% in drought-stressed conditions. In the less stressed treatment block the average yield for 5217 Events containing the transgene was 132 Bu/acre and the average yield for 5217 Events lacking the transgene was 95 Bu/acre. Results suggest the transgene improves kernel set by nearly 28% in less stressed plants. The average yield calculated for each plot in the drought-stressed treatment block was 72 Bu/acre. The average yield calculated for each plot in the less stressed treatment block was 113 Bu/acre. The yield improvement due to the OsMADS6-T6PP-3 gene varies from Event to Event. It is observed in four of the seven Events tested, and is manifest in both less stressed and drought-stressed plants. Results from this field experiment demonstrate the effectiveness of the OsMADS-T6PP-3 transgene in stabilizing kernel set in drought stressed maize.

Example 13

Evaluation of Transgenic Maize Expressing OsMADS-T6PP-3 for Yield in the Field

Hybrid seed was generated for each transgenic Event at the Syngenta Seeds field station in Kauai in late 2004. T1 seed obtained by selfing the T0 plant of the events was sown in four single-row plots, 12.7 feet long separated by 3 foot alleys with about 20 plants per row. Taqman analysis was used to divide the progeny into homozygous or hemizygous (containing OsMADS6-OsT6PP-3) and azygous (lost the OsMADS6-OsT6PP-3) groups. In two of the single-row plots, hemizygous and azygous plants were destroyed and homozygous plants were selfed for seed bulking also testcrossed to NP2043BT11 and NP2044BT11. In the other two single-row plots homozygous and hemizygous plants were destroyed and azygous plants were selfed and also crossed to NP2043BT11 and NP2044BT11. The azygous and hemizygous testcross seed of the events was used to conduct field trials. A series of yield trials were conducted in several mid-West locations to test transgene performance under conditions typically used by growers. The XPOO188RA× NP2043BT11 material, generated above, was used in late maturity zones and the XPOO188RA×JHAF431B material, generated above, was used in early maturity zones. These populations also contained the BT transgene to control insect pressure. The experimental design consisted of randomised complete blocks with three replications. Each experimental unit consisted of two-row plots, 17.5 feet long planted with 34 kernels per row. Ranges were separated by 3 foot alleys. Events for which there was seed of both the azygous and the hemizygous hybrids, randomization was restricted to keep the azygous and hemizygous hybrids of the events in neighboring plots. Most Events were evaluated in eight to nine locations. Event 5124 was evaluated in three locations. After emergence, stand counts were taken and plots were thinned, as necessary, to establish field uniformity. During the growing season plots were evaluated for intactness, greensnap, root lodging, heat units to 50% pollen shed and heat units to 50% silking.

Plots were Combine-harvested and grain yield and grain moisture were recorded. The data from hemizygous plots were compared to azygous plots, or wild type plots where necessary, to gauge the transgene's effect on yield. The data shows that the OsMADS6-T6PP-3 transgene does not significantly affect yield in this experiment. There are two factors to consider. First the standard deviation for grain yield in this experiment was 15-20% of the mean. This is not unusual. Second, growth conditions in the mid-West were ideal for maize in 2004. Depending on location yields in this experiment averaged from 90 to 130 Bu/acre. Results from this field experiment indicate the OsMADS-T6PP-3 transgene did not cause yield drag.

Example 14

Transformation

Once a nucleic acid sequence of the invention has been cloned into an expression system, it is transformed into a plant cell. The receptor and target expression cassettes of the present invention can be introduced into the plant cell in a number of art-recognized ways. Methods for regeneration of plants are also well known in the art. For example, T1 plasmid vectors have been utilized for the delivery of foreign DNA, as well as direct DNA uptake via electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

A. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend on the complement of vir genes carried by the host *Agrobacterium* strain either on a co-resident T1 plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

B. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667-674 (1992)) using particle bombardment into cells of type C long-term regenerable callus, and also by Vasil et al. (Biotechnology 11: 1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

Example 15

Use of Expression Cassettes of the Present Invention to Confer Abiotic Stress Tolerance in Plants Once initiated, maize female spikelets are by definition metabolic sinks. They require a nutrient stream consisting of carbohydrate, amino acids, cofactors, minerals and other material from source tissues to fuel development. Source tissues include leaves, roots, the stalk and other vegetative plant parts. Much of what arrives at each spikelet is rapidly consumed, being converted to cell wall material, protein, lipids, nucleic acids etc. Very little is held in reserve.

The nutrient stream subsides during periods of abiotic stress. This stress is imposed by a number of stimuli including drought, cloud cover, temperature extremes and soil nutrient depletion. Spikelet development continues despite growing conditions, relying on reserves for energy and raw material. Reserves maintain development for, at most, a few days. If the abiotic stress period is prolonged reserves are depleted and spikelet development ceases. The result is kernel abortion and reduced yield.

The OsMADS expression cassettes of the present invention can be used to increase the sink strength in female spikelets by fusing them to genes that function to increase sink strength. These genes include a sucrose transporter, invertase, and trehalose metabolism genes. Many of these genes are not highly expressed in early spikelet development. Early and specific expression in the reproductive organs of plants, spikelets for example, of any of these genes will improve spikelet nourishment without detriment to other plant organs. Improved nutrition will enable spikelets to complete their developmental cycle and become competent for fertilization during ideal growth conditions and, importantly, during prolonged periods of abiotic stress.

Carbon arrives at developing spikelets as sucrose. Spikelets have limited ability to utilize sucrose because enzymes facilitating its entry into metabolism are not highly expressed. These enzymes include sucrose transporter(s) to aid uptake of sucrose unloaded from the phloem. The OsMADS expression cassettes can increase sucrose transporter levels in the transmitting and other maternal tissue. Imported sucrose fuels development and excess sucrose is incorporated into starch and vacuolar reserves. Increased starch and sucrose reserves better enable spikelets to complete development during prolonged periods of abiotic stress.

Carbon nutrition can also be enhanced via increased invertase expression. This enzyme family cleaves sucrose into glucose and fructose. Both monosaccharides can be accumulated to high levels and rapidly enter carbon metabolism. The OSMADS expression cassettes of the present invention can be used to increase glucose and fructose levels in the apoplastic regions of spikelet and other maternal tissues via expression of an apoplastic or cell wall invertase. The monosaccharides enter cells and carbon metabolism more readily than sucrose. Facilitated sucrose utilization should increase sucrose unloading from the phloem, and carbon availability to developing spikelets.

Similarly, carbon nutrition in the cytosol of developing spikelets can be enhanced via expression of a cytosolic or neutral invertase. This enzyme cleaves sucrose in the cytosol, facilitating entry into carbon metabolism. The OSMADS expression cassettes of the present invention can increase neutral invertase expression in developing spikelets. The increased sucrose utilization in the cytosol, in transmitting and related spikelet tissue increases sucrose demand and thus, sucrose import from the apoplast.

Carbon availability and abiotic stress resistance in developing spikelets also can be enhanced via expression of a vacuolar or soluble acid invertase. This enzyme cleaves sucrose into fructose and glucose in the vacuole, making the carbon available for energy metabolism. Sucrose conversion into glucose and fructose also increases the solute potential of the cell, enabling it to maintain water and thus, turgor during periods of drought. This allows spikelets to continue developing despite decreased water availability. Again, the OSMADS expression cassettes of the present invention can increase expression of vacuolar or soluble acid invertase in developing spikelets for the purpose of enhancing abiotic stress tolerance.

The trehalose pathway functions to regulate carbon partitioning between primary metabolism and starch synthesis. Up-regulation of this pathway directs carbon towards starch synthesis. The OsMADS expression cassettes of the present invention can be used to drive expression of trehalose-6-phosphate synthase, trehalose-6-phosphate phosphatase and trehalase in developing spikelets, thereby increasing sink strength and starch synthesis in those tissues. Maintenance of a large starch pool better enables developing spikelets to withstand prolonged periods of abiotic stress and complete their development cycle.

Example 16

*Agrobacterium* Transformation of Maize—Immature Embryos

Preparation of Ear

Harvest ears when immature embryos in the center kernels are approximately 0.5-1.0 mm.

Shuck and sterilize ears in a solution of 20% Chlorox and 3 drops Tween/liter of solution. Put on an orbital shaker for 20 minutes.

Rinse ears three times with sterile ddH$_2$O.

In a sterile environment cut off the tops of the kernels. Rest the ear on a sterile Petri dish and isolate the immature embryos.

Preparing Inoculation Solution for Transformation.

To 100 mL of LP-Lsinf. Medium, add 50 µl of acetosyringone (AS) stock solution (40 mg/ml stock/mL) for a final concentration of 100 µM AS.

Pipet 4 ml (2.5) of the infection medium into a 10 ml disposable tube.

Set up Eppendorf tubes for collecting the embryos at this time and add ~1.4 ml infection medium with AS to them.

Preparation of *Agrobacterium* Suspension

Take one loop of *Agrobacterium* and re-suspend it by vortex in 10 ml disposable tube with 4 ml (2.5 ml) infection medium.

Measure optical density of the *Agrobacterium* suspension. Adjust the OD$_{660}$ to approximately 0.45 to 0.55.

Isolation of Immature Embryos and Transformation

Excise embryos and place them on top of the infection medium in an eppendorf tube.

Excise embryos for 30-45 minutes to obtain a total of ~150 embryos.

Vortex embryos (or hand shake) for 5 seconds.

Heat shock the embryos in a 45° C. water bath for 5 minutes. Do not have lid of eppendorf tube in contact with water (possible contamination issues).

Using a disposable pipet remove infection medium and replace with 1.5 mL *Agrobacterium* suspension. Vortex for 30 seconds.

Allow the tube to sit for 5 minutes.

Shake the tube to suspend embryos and pour into a Petri dish with LS modified As 500 medium.

Pipet off *Agrobacterium* suspension and transfer embryos to an area of the plate that has not been exposed to *Agrobacterium*.

Make absolutely sure that the embryos are all scutellum side up.

Co-Cultivation

Co-culture embryos and *Agrobacterium* at 23° C. for 2-3 days.

Callus/Somatic Embryo Induction

Transfer tissue (18 embryos/plate) to pre-selection/callus induction medium for 10 to 14 days at 28° C. in the dark.

Mannose Selection

Transfer callus clusters on Selection medium. 9 clusters per plate.

Culture for approximately 2 weeks at 28° C. in the dark.

Check cultures for contamination and callus response and culture for additional 2 weeks at 28° C. in the dark.

Transfer 4 events per plate of growing tissue to MS Regeneration (R1) medium and leave in the dark for 10-14 days.

Transfer growing tissue/plants of 4 events per plate to light for 14 days in light.

Transfer events to rooting media in tissue culture containers (2 events/Greiner containers).

Transgenic maize was grown in the greenhouse to the T0 or T1 stage, and cob samples and other materials were selected from the transgenic events produced. The plasmids pSyn12210 containing the CAD RNAi construct (SEQ ID NO: 54), and pSyn12345, containing the COMT RNAi construct (SEQ ID NO: 55) were used in the maize transformation protocol given above. pSYN12210 and pSYN12345 also contained the OsMADS6 promoter (SEQ ID NO: 53) operably linked to the RNAi constructs.

Example 17

T1 CAD (SEQ ID NO: 54) Event Selection pSyn12210

T1 cob samples of a total 15 events (10 low, 3 medium and 2 high copy) include 65 lines (28 low, 14 medium, 5 high copy and 18 null control lines) were sent to MSU for NDF (fiber), ADL (lignin), IVNDFD (in vitro NDF digestibility) analysis. 3 BM3 isolines and 2 hybrid checks were also included. We compared the difference among the lines (transgenic vs. null) of the same event, among the events, or among low, medium and high copy events with the BM3 positive or negative controls and hybrid check. Although a few of these made it into the top 16 lines mentioned below, none of them showed consistent reduction in lignin in future tests. The data are in Table 2, and the methods used for analysis are given below.

T1 COMT (SEQ ID NO: 55) Event Selection (pSyn12345)

T1 cob analysis: total 41 events (23 low, 13 medium, and 5 high copy) include 131 lines (24 low, 13 medium, 8 high copy and 20 null control lines) were sent to MSU for analysis (ADL, NDF, IVNDFD). 3BM3 isolines, one JHAX707 control, and one hybrid check were also included.

T1 Cob analysis: The top 7 lines containing pSyn12210 or pSyn12345 were selected based on the lignin content and in vitro digestibility data. These lines showed a reduction in the lignin content and improved digestibility compared to the control cob, as shown in Table 2. Data pertaining to the two best events containing plasmid pSyn12345 are presented in Table 3.

TABLE 2

Silage characteristics of select events containing RNAi knockouts of either CAD or COMT

| Event | Gene Knockout | Inbred | Generation | DM % MEAN | ASH % MEAN | NDF % MEAN | ADF % MEAN | Lignin % MEAN | IVTD % MEAN | IVNDFD % MEAN |
|---|---|---|---|---|---|---|---|---|---|---|
| 1 | Null | 1 | T2 | 89.4 | 2.6 | 67.0 | 37.1 | 5.0 | 59.6 | 39.9 |
|   | CAD  |   |    | 89.3 | 3.1 | 64.9 | 35.2 | 4.3 | 64.3 | 45.0 |
|   |      |   |    | -0.1 | 0.5 | -2.1 | -1.9 | -0.7 | 4.7 | 5.1 |
| 2 | Null | 1 | T2 | 90.5 | 1.2 | 76.6 | 41.9 | 5.5 | 53.0 | 38.7 |
|   | CAD  |   |    | 89.8 | 2.7 | 70.9 | 39.3 | 5.1 | 59.8 | 43.5 |
|   |      |   |    | -0.7 | 1.5 | -5.7 | -2.6 | -0.5 | 6.7 | 4.8 |
| 3 | Null | 1 | T2 | 94.0 | 3.2 | 77.1 | 44.7 | 6.6 | 49.4 | 34.4 |
|   | COMT |   |    | 94.3 | 3.1 | 75.6 | 43.7 | 5.8 | 53.5 | 38.5 |
|   |      |   |    | 0.3 | -0.1 | -1.5 | -0.9 | -0.8 | 4.1 | 4.1 |
| 4 | Null | 1 | T1 | 92.4 | 2.5 | 77.1 | 45.2 | 6.8 | 48.8 | 33.6 |
|   | COMT |   |    | 90.1 | 3.4 | 75.6 | 43.2 | 6.0 | 53.3 | 38.3 |
|   |      |   |    | -2.2 | 0.9 | -1.5 | -2.1 | -0.8 | 4.5 | 4.7 |
| 4 | Null | 1 | T2 | 88.8 | 3.4 | 78.9 | 45.3 | 6.6 | 50.1 | 36.7 |
|   | COMT |   |    | 87.7 | 3.1 | 72.7 | 40.6 | 5.7 | 57.0 | 40.9 |
|   |      |   |    | -1.1 | -0.2 | -6.2 | -4.7 | -0.9 | 7.0 | 4.2 |
| 5 | Null | 1 | T2 | 89.0 | 2.7 | 78.2 | 44.8 | 6.8 | 51.0 | 37.4 |
|   | COMT |   |    | 88.8 | 3.4 | 70.5 | 39.2 | 5.6 | 59.0 | 42.2 |
|   |      |   |    | -0.2 | 0.7 | -7.7 | -5.6 | -1.2 | 7.9 | 4.7 |
| 6 | Null | 1 | T2 | 89.8 | 2.4 | 82.6 | 46.7 | 6.6 | 43.3 | 31.4 |
|   | COMT |   |    | 89.6 | 3.1 | 78.8 | 43.7 | 5.8 | 50.8 | 37.6 |
|   |      |   |    | -0.2 | 0.6 | -3.9 | -3.0 | -0.8 | 7.5 | 6.2 |
| 7 | Null | 2 | T1 | n/a | n/a | n/a | n/a | 6.3 | n/a | n/a |
|   | COMT |   |    | n/a | n/a | n/a | n/a | 5.6 | n/a | n/a |
|   |      |   |    |     |     |     |     | -0.7 |    |     |
|   | Bmr isogenic normal | | | 89.5 | 3.4 | 84.7 | 48.3 | 6.1 | 47.7 | 38.3 |
|   | Bmr  |   |    | 89.5 | 3.2 | 80.1 | 42.4 | 1.7 | 73.2 | 66.6 |
|   |      |   |    | 0    | -0.2 | -4.6 | -5.9 | -4.4 | 25.5 | 28.3 |

In 2 genetic backgrounds as compared to null lines from the same event. DM = dry matter, NDF = Neutral Detergent Fiber, ADF = Acid Detergent Fiber, IVTD = In vitro true digestibility, IVNDFD = In vitro NDF disappearance.

TABLE 3

Data showing a consistent reduction in percentage lignin and increase in percentage IVNDFD for top two events

|  |  | Lignin (%) | | IVNDFD (%) | | |
|---|---|---|---|---|---|---|
| Event | | Expt 1 T1 | Expt 2 T2 | Expt 1 T1 | Expt 2 T2 | Expt 3 T2 |
| 3 | Null | 6.6 | 5.6 | 34.4 | 35.8 | 27.1 |
|   | COMT | 5.8 | 4.9 | 38.5 | 40.0 | 31.4 |

TABLE 3-continued

Data showing a consistent reduction in percentage lignin
and increase in percentage IVNDFD for top two events

| Event | | Lignin (%) | | IVNDFD (%) | | |
|---|---|---|---|---|---|---|
| | | Expt 1 T1 | Expt 2 T2 | Expt 1 T1 | Expt 2 T2 | Expt 3 T2 |
| 6 | Null | 6.6 | | 31.4 | 33.0 | |
| | COMT | 5.8 | 6.2 | 37.6 | 40.3 | 31.6 |
| bm3* | | 1.7 | 1.2 | 66.6 | 68.0 | 53.5 |
| bm3 iso | | 6.1 | 4.6 | 38.3 | 41.2 | 34.2 |

For general methodologies applicable to these analyses see:

Goering, H. K., and P. J. Van Soest. 1970. Forage Fiber Analyses. Apparatus, Reagents, Procedures, and some applications. Agric. Handbook No. 379. ARS-USDA.

ADF—Acid Detergent Fiber—(Van Soest Method)

Performed under chemical hood, with proper equipment that includes chemical resistant apron, lab coat, chemical resistant rubber gloves, safety glasses.

The ADF method hydrolyzes components of the cell wall that includes pectins and hemicelluloses. The remaining fraction, called ADF contains cellulose, lignin and ash. It is expressed as a percentage of the total cell wall fraction.

The ADL residue is generated from the ADF fraction, and it represents lignin+ash.

The initial step is to recover the cell wall fraction from a particular plant tissue. In other words it will eliminate soluble compounds such as sugars, proteins, oil, and soluble fiber. If the sample contains a large amount of oil (such as soybean seeds) then a wash with acetone is required (grind first, then use a glass tube, or short incubation time in a plastic tube). The tissue is dried and ground in particles of no more than 2 mm in size. Typically about 2-3 gr of tissue is added to a 50 mL conical tube. Then 40 mL of 80% ethanol is added, and mixed for 5 hrs on a rotary shaker. Another wash is required overnight. Then 40 mL of water is added for a 1 hr wash, repeated for a total of 3 washes. Some tissue will be lost during changes of solution. A preliminary wash should be done to estimate the amount of initial tissue to produce about 1 gr of final cell wall sample.

In the case of cob tissue, because the cell wall content is very high, it is not required to do a cell wall preparation. So the ADF and ADL analyses are calculated on a total dry matter basis.

ADF Solution

2% CTAB into 1 $NH_2SO_4$ (for 1 L stock, add 20 gr CTAB to 900 mL deionized (di) water, stir for few min until particle size reduced. Then add 62.5 mL 16 N sulfuric acid (Fisher A298-212, 98% density 1.84 g/mL). As you add the acid, the mixture CTAB+water/acid becomes solubilized. Fill up to 1 L with di water.

The ADF solution can also be purchased at ANKOM (www.ankom.com).

Record weight of ANKOM bag

Weigh 250 mg of air dried sample (from o/n incubation at 37 C of dry sample)

Pour in ANKOM filter bag (F57 type); record weight

Seal with Heat Sealer

Add to a 2000 mL Pyrex glass beaker, typically 20 bags (24 max) with 500 mL ADF solution. Cover with 1000 mL Pyrex dish. Place into glass dish (Pyrex 190 mm diameter×100 mm height), filled with boiling water. Also add some PTFE boiling stones in dish. Water should keep boiling for one hour. Agitate bags every 15 minutes.

Rinse minimum 4 times with 85-90 C $H_2O$. All liquid waste is disposed in sink with continuous water flow. Another 2 minutes rinse with small volume of acetone, which is then disposed of in solvent waste container.

Dry in 70 C oven overnight.

Weight residual tissue=ADF

ADL—Acid Detergent Lignin

Performed under chemical hood, with proper equipment that includes chemical resistant apron, lab coat, chemical resistant rubber gloves, safety glasses.

To the dried ADF residue (20-24 bags), add 500 mL of 72% sulfuric acid, to cover all bags.

Use a 2000 mL Pyrex glass beaker, with 20 bags (24 max) and over with 1000 mL Pyrex dish NOTE: 72% sulfuric acid can be prepared by adding 750 mL of concentrated (95% acid) into 250 mL water. Caution: the mix is very hot and requires pouring the acid very slowly to avoid projections. Also the bottle is then put into a room temperature water bath (2 rinses) for rapid cooling and use. You can also buy the 72% H2SO4 acid from Ankom.

Incubate at RT for 3 hours, stir several times.

Excess acid is disposed of in liquid acid waste.

Then rinse at least 5 times with hot water (85 to 90 C). Washes are performed in the sink.

Final rinse in acetone for 2 minutes, disposed of solvent in waste container.

Dry in oven at 70 C overnight.

Weight residual tissue=ADL

Neutral Detergent Fiber Analysis

Prepare the samples as the standard grinding protocol recommends, without using the Perten Hammer Mill.

Place the samples in the dry balance to assess moisture content.

Number bags with solvent resistant marker.

Record weight of empty Ankom dry sample bags.

Take dried sample and weigh 0.5 g of dried sample into Ankom filter bags.

Seal the bags with the heat sealer.

Dissolve 20 g of Sodium Sulfite (0.5 g/50 ml of NDF solution) into 2000 ml of NDF solution Turn on heat until boil is achieved, once boiling add sample in bags and cover loosely.

Set timer for 105 minutes.

After time is up pour samples into strainer over NDF waste container.

Rinse slowly with 2 L's of 85*-90*C water.

Repeat the rinse process for a total of three rinses.

Add cold water to samples to aid in cooling.

Drain bags and place them in acetone for three minutes.

Spread out bags and allow drying, in the oven is fine after most of the acetone is gone.

Weigh bags, collect data in designated NDF Spreadsheet.

In Vitro True Digestibility Determination

1. Calibrate the balance and weigh 0.5 g (1.0 g for rates of digestion) dry ground (1 mm screen) sample into 125 ml Erlenmeyer flasks. Prepare 6 standard samples for each bath used.

2. Prepare Media by Adding Ingredients Below in Order:

Number of flasks: 24 48 78 110 166

Distilled water 500 ml 1.00 l 1.75 l 2.25 l 3.50 l

Trypticase® Peptonea 2.5 g 5.0 g 8.75 g 11.25 g 17.5 g

Micromineral solution 0.125 ml 0.25 ml 0.438 ml 0.563 ml 0.880 ml

Rumen buffer solution 250 ml 500 ml 875 ml 1.125 l 1.75 l

Macromineral solution 250 ml 500 ml 875 ml 1.125 l 1.75 l

Resazurin 1.25 ml 2.5 ml 4.38 ml 5.63 ml 8.80 ml 1.00 l 2.00 l 3.50 l 4.50 l 7.00 l Mix and add 40 ml per flask. The media should be added to flasks at least 1 h before inoculation to hydrate the samples. Heat water baths overnight.

3. Prepare Reducing Solution:

Add cysteine HCl, H2O, and NaOH and dissolve. Add Na2S.9H2O and dissolve again.

4. While reducing solution is mixing, arrange flasks in water bath. Place flasks with one standard sample in each row arranged diagonally across the water bath. Add 2 ml of reducing solution to each flask with Eppendorf repeater pipette. Stopper each flask with a CO2 flushing tube. Turn on CO2 and allow samples to reduce (red color turns clear or tea colored), before addition of inocula.

5. Prepare Inoculum:

Collect rumen fluid and ingesta from two fistulated animals 2 hours after feeding (cows are fed 7:00 am, collect at 9:15 am). Keep fluid in a clean thermal container which has been preheated by hot tap water. Pour water out into a bucket and place the cannula plug into it to keep it pliable. Form a tunnel through the rumen mat to allow a plastic cup to reach to the ventral rumen. Place a layer of ingesta over the fluid and cover with a lid to eliminate airspace. Replace cannula plugs tightly. Transport fluid to lab and place under CO2. Approximately 2 l unprocessed fluid is needed for a set of 166 samples. Blend fluid and ingesta in the 1 gallon Waring blender taking care to flush with CO2 continuously. Line a large plastic Buchner funnel with 1 layer of nylon mesh and pass the blended inocula through it. Squeeze well.

a Use only Trypticase™ Peptone pancreatic digest of casein (Becton Dickinson BBL #4311921).

Number of flasks: 24 48 78 110 166

Distilled water 48 ml 95 ml 167 ml 261 ml 356 ml

L(+)Cysteine HCl.H2O 313 mg 625 mg 1.094 g 1.719 g 2.344 g

1 N NaOH 2 ml 4 ml 7 ml 11 ml 15 ml

Na2S.9H2O 313 mg 625 mg 1.094 g 1.719 g 2.344 g 50 ml 100 ml 175 ml 275 ml 375 ml

Pass inocula through glass wool into a large plastic beaker to filter small particles. The filtrate must also be kept under CO2 at all times. Transfer inocula to a bottle that the 50 ml Brinkman pipetter attaches to.

Using a Brinkman pipetter, inoculate each flask by first removing the bunsen valve, injecting 10 ml of fluid, and replacing the valve. This procedure will flush each flask with CO2 and displace any O2 that may be present. Swirl the bottle containing rumen fluid frequently during inoculation to keep particles suspended.

6. Seal flasks, notice and correct any CO2 leaks, and adjust CO2 pressure to just enough to produce slow bubbles in the manometer. Water bath temperature throughout the fermentation should be kept at 40° C. (100-102° F.). Digest samples for 30 hr unless otherwise specified. To stop fermentation, remove flasks from bath and add 20 ml of ND solution with the Unispense automatic dispenser. Put a cork on each flask to prevent spilling and store samples in refrigerator or immediately do NDF procedure on the samples if rates are being calculated.

7. Wash flask contents with 80 ml neutral-detergent into a 600 ml Berzelius beaker. Add 0.5 g sodium sulfite. Reflux for 1 hour, timed from the onset of boiling. Add approximately 1 teaspoon of acid purified sea sand (Seesand, Fluka Chemika #84880) into clean Gooch crucibles. Filter sample through a clean, numbered Gooch crucible as in NDF procedure. Wash and rinse with hot water until foam disappears and twice with acetone.

Allow acetone to completely evaporate, dry crucibles overnight at 100° C., calibrate the balance and hot weigh. Ash samples at 500° C. for 6 hr, cool to 200° C., transfer to drying oven and hot weigh crucible plus ash.

8. Calculate in vitro true digestibility of dry matter:

$IVTD=[1-(N-CA)/S]\times 100$ where N=crucible+ND residue weight

CA=empty crucible weight

S=sample dry matter weight

9. Calculate In Vitro NDF Digestibility:

$IVCWD=[1-((N-CA)/(S\times F/100))]\times 100$ where N=crucible+ND residue weight CA=empty crucible weight S=sample dry matter weight F=percent NDF of sample 10. To calculate rates of digestion, prepare a set of 13 samples to be incubated from 0 to 120 hours. Place all flasks in water baths and remove with time. Process residues as listed above. Calculate NDF remaining as a percentage of original NDF for each sample. Either use a non-linear regression method (JMP or SAS) or a log-transform procedure as follows: Subtract the indigestible (~120 hour) residue from each fraction.

Calculate the natural log (ln) of each point and calculate linear regression of the plot. Slope of this line is the rate of digestion of the fraction in question.

This method is a modification of the Tilley-Terry in vitro apparent digestibility procedure. Steps 1 through 5 are common to both techniques. From step 5, continue below with step 6a for the Tilley-Terry method.

6a. After a 48 hour fermentation, carefully add 2 ml 6N HCl to each flask to avoid excessive foaming. This will lower the pH to below 2. Add 0.5 g pepsin, and swirl to dissolve. Add 1 ml toluene, replace flasks in water bath, and incubate another 48 hours.

7a. Remove flasks from water bath and filter on previously tared Whatman #4, 41 or 54 paper without applying vacuum. Rinse filter paper twice by filling with hot water and allowing to drain. Fill filter with acetone, allow to drain and air-dry. Fold papers, dry at 100° C., and weigh. Use a dry matter factor, calculated on separate papers, to correct for tare on papers used for filtering. Separate blanks, containing inocula and medium but no sample, and standard forage samples should also be analyzed.

8a. Calculate In Vitro Apparent Digestibility (Tilley-Terry):

$IVDMD=[1-(R-F)-B]\times 100$ where R=weight of filter paper and residue

F=weight of filter paper

B=blank sample weight

REFERENCES

Goering, H. K. and P. J. Van Soest. 1970. Forage and Fiber Analysis. Agricultural Handbook no. 379. U.S. Dept. Agriculture.

Tilley, J. M. A. and R. A. Terry. 1963. A two-stage technique of the in vitro digestion of forage crops. J. Br. Grassi. Soc. 18:104-111.

Feb. 4, 2000 M. S. Allen, Dairy Nutrition and Forage Analysis Lab Michigan State University Example 18

CAD/COMT Double Knockouts

Co-expression of dsRNAi constructs for CAD & COMT driven by the OsMADs6 promoter can be achieved in single construct. Transgenic maize events containing such constructs are produced using the transformation protocol set forth in Example 16. The sequences of the OsMADs6 promoter and of the RNAi constructs are as presented, and the analyses set forth above are used to determine lignin content etc. Cobs with decreased lignin content produced using this method can be used to the same extent and for the same purposes as those produced using the plasmids pSYN12210 or pSYN12345

Example 19

Low Lignin Plant Material Use in Biomass Conversions

One of the limitations of converting biomass to ethanol is the need for a harsh chemical pretreatment to separate plant fibers which are "glued" together by lignin. The intent of this invention is that the lower the lignin content, the easier fibers can be separated, less harsh pretreatment used, less lose of glucose during the pretreatment, less enzyme required to hydrolyze the biomass and a higher ethanol yield. An example of the technology using corn cob is presented, however it is obvious that this result can be extended to other plant sources. The production of ethanol from cellulose biomass is discussed in Badger, P. C., Ethanol from cellulose: A general review. p. 17-21, in: J. Janick and A Whipkey (eds.), Trends in new crops and new uses. ASHS Press, Alexandria, Va., 2002.

Standard Pretreatment-Saccharification-Fermentation

Eight grams of finely ground cob are suspended with 80 ml of a 1% sodium hydroxide solution and heated for 1 hour at 130° C. The pH is then adjusted to pH 5 and 100 milligrams of dry yeast plus 20 filter paper units (FPU) of cellulose is added and allowed to ferment for 20 hours. The resultant beer would be analyzed for ethanol and it would be expected to be around 3% v/v as is usually obtained from fermenting biomass.

Low Lignin Cob Pretreatment-Saccharification-Fermentation

Eight grams of finely ground cob are suspended with 80 ml of a 1% sodium hydroxide solution and heated for 1 hour at 90° C. The pH is then adjusted to pH 5 and 100 milligrams of dry yeast plus 15 FPU of cellulose is added and allowed to ferment for 20 hours. The resultant beer would be analyzed for ethanol and it would be expected to produce more ethanol than the standard ground cobs in the range of about 3.5% v/v.

Example 20

Cob Compositional Analysis and Preliminary Hydrolytic Data

Saccharide Compositional Analysis of Corncobs

This example describes the saccharide compositional analysis for glucose, xylose, arabinose, and mannose of corn cobs having low lignin. The major saccharide compositional analysis was determined for three varieties of corncob: CPM913 (Isoline control, genotype A), CPM914 (BM3 mutant, genotype A) and CPM916 (BM3 mutant, genotype B). Composition was determined by performing strong acid hydrolysis (72% $H_2SO_4$) for one hour, followed by heated dilute-acid hydrolysis (4% $H_2O_4$ at 121° C. for 1 hour) and calcium carbonate neutralization. Concentrations of individual saccharide monomers were determined via Refractive Index-High Performance Liquid Chromotography (RI-HPLC). Results are presented in Table 4.

TABLE 4

Compositional analysis of triplicate cob samples.

| | glucose | xylose | arabinose | mannose | TOTAL |
|---|---|---|---|---|---|
| CPM 913 | 35% | 21% | 2.9% | 0.3% | 60% |
| CPM 914 | 37% | 23% | 3.2% | 0.3% | 64% |
| CPM 916 | 39% | 23% | 2.9% | 0.1% | 65% |
| | Standard Deviations | | | | |
| CPM 913 | 2.4% | 0.2% | 0.1% | 0.1% | 2.4% |
| CPM 914 | 3.7% | 2.1% | 0.0% | 0.0% | 5.4% |
| CPM 916 | 1.1% | 0.5% | 0.1% | 0.0% | 0.9% |

Cob samples were not analyzed for ferulate, lignin or ash content.

Enzymatic Hydrolysis of Corn Cobs

This experiment was conducted to determine the saccharides produced from various corn cobs upon enzymatic hydrolysis.

A first-pass screen was initiated using high concentrations of corn cob. CPM914 and CPM916 are reduced lignin genotypes A and B, respectively. Large reactions (100 mg of shredded corn cob) were preferred due to the heterogeneous and course nature of the substrate—generally the reactions took place individual eppendorf tubes rather than microtiter plates. Enzyme extracts from fungal supernatants and a cocktail optimized on corn fiber were tested for hydrolysis activities on the three types of cob. Reactions were 1 ml scale containing a) 100 mg shredded cob, supplemented with b) 50 ug fungal enzymes from *Cochliobolus heterotrophus* ('cokie'), c) 50 ug cokie enzymes and 200 ug *Aspergillus niger* enzymes, d) a xylanase-esterase cocktail containing 2 xylanases, an α-arabinofuranosidase, a β-xylosidase, a ferulic acid esterase and an acetyl xylan esterase. The xylanase cocktail contained: 25 ug BD13509, 125 ug BD2157, 62.5 ug BD13715 and BD13457. The esterase cocktail contained: 100 ug BD14441 and BD14104.

The results are presented in Table 5. When using the defined enzyme cocktail, hydrolysis was higher in both reduced-lignin cob varieties as compared to the regular variety cob. Although the xylanase-esterase cocktail was not optimized for cob hydrolysis, the cocktail had a surprisingly high activity on cob, with better activity on the lower lignin mutants. Note that there were no cellulose-degrading enzymes present in the enzyme cocktail: were these enzymes added, it may be possible to further increase the enzymatic hydrolysis of the cobs.

TABLE 5

Enzymatic hydrolysis of three varieties of shredded corn cob to sugar monomer, expressed as a percent dry weight.

| | glucobiose | glucose | xylose | arabinose | TOTAL |
|---|---|---|---|---|---|
| CPM913 control | 0% | 2.1% | 0% | 0% | 2.1% |
| fiber-induced cokie | 0% | 3.7% | 0.9% | 0.1% | 4.7% |
| cokie + 200 ug fungal enz. | 0.1% | 9.3% | 7.7% | 0.5% | 17.6% |

TABLE 5-continued

Enzymatic hydrolysis of three varieties of shredded corn cob to sugar monomer, expressed as a percent dry weight.

|  | glucobiose | glucose | xylose | arabinose | TOTAL |
|---|---|---|---|---|---|
| xylanase-esterase cocktail | 1.0% | 2.9% | 5.7% | 0% | 9.6% |
| Available sugar CPM 913 |  | 35.5% | 20.9% | 2.9% | 59.8% |
| CPM914 control | 0.3% | 2.9% | 0% | 0% | 3.2% |
| fiber-induced cokie | 0.1% | 3.1% | 0.5% | 0% | 3.7% |
| cokie + 200 ug fungal enz. | 0% | 7.1% | 8.5% | 0.7% | 16.3% |
| xylanase-esterase cocktail | 1.2% | 3.1% | 8.5% | 0% | 12.8% |
| Available sugar CPM 914 |  | 37.0% | 23.4% | 3.2% | 64.1% |
| CPM916 control | 0% | 2.9% | 0% | 0% | 2.9% |
| fiber-induced cokie | 0.2% | 3.2% | 0.5% | 0% | 3.9% |
| cokie + 200 ug fungal enz. | 0.1% | 7.9% | 10.8% | 0% | 18.9% |
| xylanase-esterase cocktail | 0.8% | 2.4% | 6.8% | 0.2% | 10.2% |
| Available sugar CPM 916 |  | 38.8% | 22.8% | 2.9% | 64.8% |

Data collected at 48 hour time point, 10% fiber loading
xylanase cocktail: 25 ug BD13509, 125 ug BD2157, 62.5 ug BD13715 and BD13457
esterase cocktail: 100 ug BD14441 and BD14104
Cokie enzymes added at 50 ug Enzymatic Hydrolysis of Corn Cobs Also Including Glucanases, Cellulases and Glucuronidase The positive relationship between the defined enzyme cocktails and CPM913/CPM914 was further explored, this time adding other glucanases, cellulases and a glucuronidase. Hydrolysis reactions were 1 ml scale, 25 mg/ml shredded corn cob incubated for 48 hrs at 37° C. on an eppendorf tube shaker. The xylanase-esterase cocktail is the same as in Example 2 (10 ul xylanase cocktail: 4 ug 13509, 20 ug 2157, Mug 13715 and 13457). Additional enzymes were added to the cocktail: bug α-Glucuronidase BD12669; 100 ug *Trichoderma reesi* cellulose cocktail; 10 ug glucanase CPM516; glucanase with the esterase cocktail (10 ul esterase cocktail: 100 ug BD14104 and 100 ug BD14441); or a cocktail containing all of the above (except the α-Glucuronidase). With defined enzyme cocktails, the low lignin corncob substrate is consistently more prone to enzymatic attack. Addition of a cellulose extract increases overall hydrolysis to 21.8%, or 34% of the total available sugar. A similar reaction using corn fiber yields 5.4%, a substrate for which the enzymes have been optimized.

The same trend of better digestibility was seen in the low lignin cob samples (Table 6). Of particular interest was the ability of esterases and cellulases to increase the amount of xylose hydrolyzed in the low lignin cob. A combination of xylanase cocktail and cellulases were able to convert 34% of the available sugar to monomer in the low-lignin cob, compared to only 25% in the wild-type cob.

TABLE 6

Hydrolysis of two types of shredded cob using defined enzyme cocktails - untreated corn fiber is shown for reference.

|  | Glucose | Xylose | Arabinose | TOTAL |
|---|---|---|---|---|
| Shredded cob (isoline control genotype A) | | | | |
| Control | 2.8% | 0% | 0% | 2.8% |
| xylanase cocktail | 3.5% | 3.7% | 0.2% | 7.4% |
| xylanase w/esterase | 2.9% | 3.4% | 0.2% | 6.5% |
| X-E cocktail w/a-Glrn | 2.8% | 3.8% | 0.2% | 6.8% |
| xylanase w/cellulase | 11.4% | 3.8% | 0.3% | 15.5% |
| glucanase CPM516 | 2.5% | 0.0% | 1.3% | 3.8% |
| CPM516 w/esterase | 2.4% | 0% | 0% | 2.4% |
| CPM516-X-E w/cellulase | 9.3% | 4.4% | 0.2% | 13.9% |
| Available sugar CPM 913 | 35% | 21% | 3% | 60% |
| Shredded low-lignin cob (BM3 mutant genotype A) | | | | |
| Control | 3.0% | 0% | 0% | 3.0% |
| xylanase cocktail | 2.6% | 3.8% | 0.2% | 6.6% |
| xylanase w/esterase | 3.1% | 5.7% | 0.2% | 9.0% |
| X-E cocktail w/a-Glrn | 3.2% | 5.6% | 0.3% | 9.0% |
| xylanase w/cellulase | 13.0% | 8.5% | 0.3% | 21.8% |
| glucanase CPM516 | 3.0% | 0% | 0% | 3.0% |
| CPM516 w/esterase | 3.0% | 0% | 0% | 3.0% |
| CPM516-X-E w/cellulase | 13.4% | 8.8% | 0.3% | 22.5% |
| Available sugar CPM 914 | 37% | 23% | 3% | 64% |
| Untreated corn fiber (w/20% adherent starch) | | | | |
| Control | 2.6% | 0% | 0% | 2.6% |
| xylanase cocktail | 2.7% | 0.2% | 0.4% | 3.3% |
| xylanase w/esterase | 2.9% | 0.2% | 0.3% | 3.4% |
| X-E cocktail w/a-Glrn | 3.0% | 0.3% | 0% | 3.3% |
| xylanase w/cellulase | 4.7% | 0.3% | 0.4% | 5.4% |
| glucanase CPM516 | 2.9% | 0% | 0.4% | 3.2% |
| CPM516 w/esterase | 2.9% | 0% | 0% | 2.9% |
| CPM516-X-E w/cellulase | 4.5% | 0.3% | 0.3% | 5.1% |
| Available sugar CPM 711 | 44% | 19% | 10% | 76% |

Numbers are expressed as a percentage dry weight.

The benefit of improved digestibility of corn silage on dry matter intake and milk yield in dairy cows has been demonstrated by Ballard et al., J. Dairy Sci. 84:442-452 (2001), and by Oba and Allen, J. Dairy Sci. 82:135-142 (1999). Similar feeding trials are established for use of the low-lignin corn cobs of the present invention for demonstration of similar benefits which result from the improved digestibility demonstrated.

Example 21

Low Lignin Cob Events and Seed Set

Transgenic maize plants generated with the transformation vector pSyn12345 were further evaluated in the T1 generation for seed set and lignin content of the cob. Seed set was determined by harvesting the ear from greenhouse grown individual T1 plants and counting the number of seeds. The cobs were then evaluated for lignin (ADF) content essentially as described in Example 17 as performed by MSU. Table 7 outlines a subset of the seed set and lignin content data collected. Evaluation of the data indicates a correlation between seed set and lignin content indicating that events generated with pSyn12345 set lower seed counts when the lignin content of the cob is lower. When all of the data from the T1 generation is analyzed the correlation between seed set and lignin content has an R squared value of 0.602 indicating the relationship between seed set and lignin content is significant.

TABLE 7

Seed set and lignin content of cobs from T1 generation maize plants generated with transformation vector pSyn12345.

| Seed count | Lignin % |
|---|---|
| 22 | 4.3 |
| 11 | 4.95 |
| 1 | 4 |
| 214 | 6.22 |
| 83 | 4.05 |
| 214 | 9.76 |
| 131 | 5.91 |
| 33 | 4.57 |
| 163 | 5.53 |
| 236 | 5.15 |
| 35 | 5.01 |
| 7 | 3.19 |
| 70 | 5.45 |
| 128 | 8.31 |

Without being limited by theory, the correlation between seed set and lignin content of the cob may be influenced by the expression pattern of the cob preferred promoter selected. It is noted that the OsMADS6 promoter does express in tissues intimately associated with the kernel set into the cob, specifically, there is expression in the placental, funicular or hilar tissue of the cob. This tissue is important in the flow of nutrients to the kernel and altering the lignin content of these tissues may influence seed set as observed in plants with a low lignin content in the cob. Selecting promoters which do not express in the placental, funicular or hilar tissue of the cob may overcome this seed set challenge. OsMADS8, OsMADS14 (SEQ ID NO: 56) and OsMADS13 do not demonstrate expression in the placental, funicular or hilar tissue of the cob prior to pollination.

Example 22

OsMADS Promoters and Low Lignin Cobs

Low lignin cobs can be generated by creating expression cassettes comprising an OsMADS promoter operatively linked to an RNAi component composed of a fragment from a lignin biosynthesis gene. For example, any of the OsMADS promoters such as OsMADS8, OsMADS13 or OsMADS14 (SEQ ID NO: 56) can be used to prefer expression of the RNAi component in the cob of a transgenic maize plant. These promoters have the advantage that they do not express in placental, funicular or hilar tissue of developing corn kernels prior to pollination which may alleviate the seed set phenotype observed in Example 21. The RNAi component of the expression cassette can contain a gene fragment from at least one of the maize lignin biosynthesis genes such as CAD, COMT, PAL, C4H, 4CL, HCT, C3H, or CCR. For example, the RNAi component may contain a fragment of the maize CAD gene (SEQ ID NO: 54) or the maize COMT gene (SEQ ID NO: 55) or both of them together. The RNAi component of the expression cassette can be designed based upon any of the silencing approaches described in the above specification (such as co-suppression, RNAi, dsRNAi, ihpRNAi, miRNA or hpRNAi). The RNAi component will be used to decrease the expression of one or more the maize lignin biosynthesis genes. An expression construct will contain an OsMADS promoter operatively linked to a fragment of a maize lignin biosynthesis gene. The expression cassette will also contain a terminator for transcription such that the order of components in the expression cassette is promoter—RNAi component—terminator. The expression cassette will be cloned into a transformation vector appropriate for Agrobacterium mediated transformation of maize callus. The transformation vector will contain a selectable marker appropriate for identifying and selecting transgenic maize callus tissue. Transgenic maize callus will be regenerated into transgenic maize plants and the resulting plants will be evaluated for presence of both the expression cassette containing the RNAi component as well as for the presence of the selectable marker. In addition, maize plants will be grown to produce subsequent generations and in select generations, plants samples will be collected to evaluate lignin content of various tissues including but not limited to the stem and the cob.

Although the foregoing invention has been described in some detail by way of illustration and example for purposes of clarity of understanding, it will be obvious that certain changes and modifications may be practiced with the scope of the present invention.

REFERENCES

Iyer M., Wu L., et al. V (2001) Two step transcriptional amplification as a method for imaging reporter gene expression using weak promoters PNAS 98(25):14595-14600.

De Bodt, S., Raes, J., Van de Peer, Y., and Theien, G. (2003) And then there were many: MADS goes genomic. Trends Plant Sci. 8(10): 475-483.

Larkin, J. C., Oppenheimer, D. G., Pollock, S., and Marks, M. D. (1993) Arabidopsis GLABROUS1 gene requires downstream sequences for function. Plant Cell. 5(12): 1739-1748.

Kang, H.-G. and An, G. (1997) Isolation and characterization of a rice MADS box gene belonging to the AGL2 gene family. Mol. Cells. 7(1), 45-51.

Onodera, Y., Suzuki, A., Wu, C.-Y., Washida, H., and Takaiwa, F. (2001) A rice functional transcriptional activator, RISBZ1, responsible for endosperm-specific expression of storage protein genes through GCN4 motif. J. Biol. Chem. 276(17): 14139-14152.

Sieburth, L. E., and Meyerowitz, E. M. (1997) Molecular dissection of the AGAMOUS control region shows that cis elements for spatial regulation are located intragenically. Plant Cell. 9(3): 355-365.

Yu, H., and Goh, C. J. (2000) Identification and characterization of three orchid MADS-box genes of the AP1/AGL9 subfamily during floral transition. Plant Physiol. 123: 1325-1336.

De Bodt et al (2003) And then there were many: MADS goes genomic. Trends Plant Sci. 8(10): 475-483.

Larkin et al (1993) Arabidopsis GLABROUS1 gene requires downstream sequences for function. Plant Cell. 5(12): 1739-1748.

Kang, H.-G. and An, G. (1997) Isolation and characterization of a rice MADS box gene belonging to the AGL2 gene family. Mol. Cells. 7(1), 45-51.

Onodera et al (2001) A rice functional transcriptional activator, RISBZ1, responsible for endosperm-specific expression of storage protein genes through GCN4 motif. J. Biol. Chem. 276(17): 14139-14152.

Sieburth, L. E., and Meyerowitz, E. M. (1997) Molecular dissection of the AGAMOUS control region shows that cis elements for spatial regulation are located intragenically. Plant Cell. 9(3): 355-365.

Yu, H., and Goh, C. J. (2000) Identification and characterization of three orchid MADS-box genes of the AP1/AGL9 subfamily during floral transition. Plant Physiol. 123: 1325-1336.

Batzer, et al (1991) Enhanced evolutionary PCR using oligonucleotides with inosine at the 3'-terminus. Nucleic Acid Res. 19:5081.

Ohtsuka, et al (1985) An alternative approach to deoxyoligonucleotides as hybridization probes by insertion of deoxyinosine at ambiguous codon positions. J. Biol. Chem. 260:2605-2608.

Rossolini, et al (1994) Use of deoxyinosine-containing primers vs degenerate primers for polymerase chain reaction based on ambiguous sequence information. Mol. Cell. Probes 8:91-98.

Paszkowski et al (1984) Direct Gene Transfer to Plants. EMBO J 3:2717-2722

Potrykus et al (1985) Molecular and general genetics of a hybrid foreign gene introduced into tobacco by direct gene transfer. Mol. Gen. Genet. 199:169-177

Reich et al (1986) Efficient transformation of alfalfa protoplasts by the intranuclear microinjection of T1-plasmids. Bio/Technology 4:1001-1004

Klein et al (1987) High velocity microprojectiles for delivering nucleic acids into living cells. Nature 327:70-73.

Uknes et al (1993) Regulation of pathogenesis-related protein-1a gene expression in tobacco. Plant Cell 5:159-169

Hofgen, R, and Willmitzer, L (1988) Storage of competent cells for *Agrobacterium* transformation. Nucl. Acid Res. 16:9877

Schocher et al (1986) Co-transformation of foreign genes into plants. Biotechnology 4:1093-1096

Gordon-Kamm et al (1990) Transformation of Maize Cells and Regeneration of Fertile Transgenic Plants. Plant Cell 2:603-618

Fromm et al (1990) Inheritance and expression of chimeric genes in the progeny of transgenic maize plants. Bio/Technology 8:833-839.

Koziel et al (1993) Field performance of elite transgenic maize plants expressing an insecticidal protein derived from *Bacillus thuringiensis*. Bio/Technology 11:194-200

Zhang et al (1988) Transgenic rice plants produced by electroporation-mediated plasmid uptake into protoplasts. Plant Cell Rep. 7:379-384

Shimamoto et al (1989) Fertile transgenic rice plants regenerated from transformed protoplasts. Nature 338:274-277.

Datta et al (1990) Genetically engineered fertile Indica-rice recovered from protoplasts. Bio/Technology 8:736-740

Christou et al (1991) Production of transgenic rice (*Oryza sativa* L.) plants from agronomically important indica and japonica varieties via electric-discharge particle acceleration of exogenous DNA into immature zygotic embryos. Bio/Technology 9:957-962

Vasil et al (1992) Herbicide resistant fertile transgenic wheat plants obtained by microprojectile bombardment of regenerable embryogenic callus. Bio/Technology 10:667-674

Vasil et al (1993) Rapid production of transgenic plants by direct bombardment of cultured immature embryos. Bio/Technology 11:1553-1558

Weeks et al (1993) Rapid Production of Multiple Independent Lines of Fertile Transgenic Wheat (*Triticum aestivum*). Plant Physiol. 1102:1077-1084

Murashiga et al (1962) A revised medium for rapid growth and bio-essays with tobacco tissue cultures. Physiologia Plantarum 15:473-497

Negrotto et al (2000) The use of phosphomannose isomerase as a selectable marker to recover transgenic maize plants (*Zea mays* L.) via *Agrobacterium* transformation. Plant Cell Reports 19:798-803

Eastmond, P. J., van Dijken, A. J. H., Spielman, M., Kerr, A., Tissier, A. F., Dickinson, H. G., Jones, J. D. G., Smeekens, S. C., Graham, I. A. (2002). Trehalose-6-phosphate synthase 1, which catalyses the first step in trehalose synthesis, is essential for *Arabidopsis* embryo maturation. Plant J. 29, 225-235.

Nuccio, M. L., Russell, B. L., Nolte, K. D., Rathinasabapathi, B., Gage, D. A., Hanson, D. A. (1998). The endogenous choline supply limits glycine betaine synthesis in transgenic tobacco expressing choline monooxygenase. Plant J. 16, 487-496.

Ranocha, P., McNeil, S. D., Ziemak, M. J., Li, C., Tarczynski, M. C., and Hanson, A. D. (2001). The S-methylmethionine cycle in angiosperms: ubiquity, antiquity and activity. Plant J. 25, 575-584.

Ritchie, S. W., Hanway, J. J., Benson, G. O. (1997). How a Corn Plant Develops. Special Report No. 48. Iowa State University of Science and Technology Cooperative Extension Service. Ames, Iowa.

Rontein, D., Dieuaide-Noubhani, M., Dufourc, E. J., Raymond, P., Rolin, D. (2002b). The metabolic architecture of plant cells. Stability of central metabolism and flexibility of anabolic pathways during the growth cycle of tomato cells. J. Biol. Chem. 277, 42948-43960.

Vogel, G., Aeschbacher, R. A., Müller, J., Boller, T. and Wiemken, A. (1998). Trehalose-6-phosphate phosphatases from *Arabidopsis thaliana*: identification by functional complementation of the yeast tps2 mutant. Plant J. 13, 673-683.

Wingler, A. (2002). The function of trehalose biosynthesis in plants. Phytochem. 60, 437-440.

The invention claimed is:

1. A method for controlling lignin biosynthesis in the cobs of a transformed corn plant, the method comprising down-regulating the expression of one or more lignin biosynthesis genes by transforming a corn plant with one or more double-stranded RNAi constructs, wherein the expression of the double-stranded RNAi is under the control of a cob specific or cob preferred promoter wherein the cob specific or cob preferred promoter is an *Oryza Sativa* MADS (OsMADS) promoter and does not express in placental, funicular or hilar tissue of developing corn kernel prior to pollination, wherein the cob specific or cob preferred promoter is an OsMADS 14 promoter having the sequence of SEQ ID NO:56.

2. The method of claim 1, wherein the one or more lignin biosynthesis genes is selected from the group consisting of CAD, COMT, PAL, C4H, 4CL, HCT, C3H, and CCR.

3. The method of claim 1, wherein the one or more double stranded RNAi constructs comprises SEQ ID NO: 54, SEQ ID NO: 55, or both.

4. A method for using low lignin cobs in biomass conversion applications comprising the steps of: a) providing cobs from a transformed plant produced by the method of claim 1; and b) using said cobs in a biomass conversion application.

5. The method of claim 4, wherein the one or more lignin biosynthesis genes is selected from the group consisting of CAD, COMT, PAL, C4H, 4CL, HCT, C3H, and CCR.

6. The method of claim 4, wherein the one or more double stranded RNAi constructs comprises SEQ ID NO: 54, SEQ ID NO: 55, or both.

7. A method for increasing the nutritional yield of feed to an animal comprising feeding an animal a feed comprising cobs from a transformed plant produced by the method of claim 1.

8. The method of claim 7, wherein the one or more lignin biosynthesis genes is selected from the group consisting of CAD, COMT, PAL, C4H, 4CL, HCT, C3H, and CCR.

9. The method of claim 7, wherein the one or more double stranded RNAi constructs comprises SEQ ID NO: 54, SEQ ID NO: 55, or both.

\* \* \* \* \*

SEQUENCE LISTING

```
<160> NUMBER OF SEQ ID NOS: 56

<210> SEQ ID NO 1
<211> LENGTH: 1027
<212> TYPE: DNA
<213> ORGANISM: Oryza sativa
<220> FEATURE:
<221> NAME/KEY: CDS
<222> LOCATION: (125)..(802)

<400> SEQUENCE: 1
```

```
aagactgcaa gggagaggga gagagaggga agcttgcagg ctgcagctaa ctagctaggc      60
aaggagagag aggagataga tcaagaagag attttgagac cgagagagag ctagagagag     120 atcg atg ggg cga ggg aaa gta gag ctg aag cgg atc gag aac aag ata      169
     Met Gly Arg Gly Lys Val Glu Leu Lys Arg Ile Glu Asn Lys Ile
     1               5                   10                  15 agc cgg cag gtg acg ttc gcg aag agg agg aac ggg ctg ctg aag aag       217
Ser Arg Gln Val Thr Phe Ala Lys Arg Arg Asn Gly Leu Leu Lys Lys
                20                  25                  30 gcg tac gag ctg tcc gtg ctc tgc gac gcc gag gtc gcc ctc atc atc       265
Ala Tyr Glu Leu Ser Val Leu Cys Asp Ala Glu Val Ala Leu Ile Ile
            35                  40                  45 ttc tcc acc cgc ggc cgc ctc ttc gag ttc tcc acc tcc tcc tgt atg       313
Phe Ser Thr Arg Gly Arg Leu Phe Glu Phe Ser Thr Ser Ser Cys Met
50                  55                  60 tac aag aca ctg gag cga tac cgc agt tgc aac tac aac ctt aac tca       361
Tyr Lys Thr Leu Glu Arg Tyr Arg Ser Cys Asn Tyr Asn Leu Asn Ser
65                  70                  75 tgt gaa gca tct gct gca ctg gaa act gaa cta agc aat tac caa gag       409
Cys Glu Ala Ser Ala Ala Leu Glu Thr Glu Leu Ser Asn Tyr Gln Glu
80                  85                  90                  95 tac tta aag tta aag aca aga gtt gag ttc cta caa aca act cag aga       457
Tyr Leu Lys Leu Lys Thr Arg Val Glu Phe Leu Gln Thr Thr Gln Arg
                100                 105                 110 aat ctt ctt ggc gag gac ttg gtt cca ctt agc ttg aag gag ctc gag       505
Asn Leu Leu Gly Glu Asp Leu Val Pro Leu Ser Leu Lys Glu Leu Glu
            115                 120                 125 caa ctt gag aac cag atc gag ata tcc ctc atg aat atc agg tca tca       553
Gln Leu Glu Asn Gln Ile Glu Ile Ser Leu Met Asn Ile Arg Ser Ser
        130                 135                 140 aag aat caa cag ttg ctt gat caa gta ttt gag ctc aaa cgt aag gaa       601
Lys Asn Gln Gln Leu Leu Asp Gln Val Phe Glu Leu Lys Arg Lys Glu
145                 150                 155 caa caa ctt caa gat gct aat aaa gac tta aaa agg aag ata caa gaa       649
Gln Gln Leu Gln Asp Ala Asn Lys Asp Leu Lys Arg Lys Ile Gln Glu
160                 165                 170                 175 act agt gga gaa aat atg ctt cat ata tct tgc caa gat gta ggg ccc       697
Thr Ser Gly Glu Asn Met Leu His Ile Ser Cys Gln Asp Val Gly Pro
                180                 185                 190 agt ggc cat gct agt gaa gct aac caa gag ttt ctc cat cat gca att       745
Ser Gly His Ala Ser Glu Ala Asn Gln Glu Phe Leu His His Ala Ile
            195                 200                 205 tgt gac cct tcc ctg cat ata ggg tat caa gct tac atg gat cac ctc       793
Cys Asp Pro Ser Leu His Ile Gly Tyr Gln Ala Tyr Met Asp His Leu
        210                 215                 220 aac caa tga atgaattgct tatcacatta atggacatct cctatgttgg               842
Asn Gln
    225 atgtggtgtt tgacgtaatg ctctctttta catgcgggtt ttaccttaag tgtgtgtgct     902 aaatttagtg cgtttgttta tgctcttttg aactgaacaa aggaatgatc ccggtttgat     962 tgatgaatgc tgcaagaaca taatctatat gttagtctga attcagtatg taatgaagat    1022 gtttt                                                                1027

<210> SEQ ID NO 2
<211> LENGTH: 225
<212> TYPE: PRT
<213> ORGANISM: Oryza sativa
```

<400> SEQUENCE: 2

Met Gly Arg Gly Lys Val Glu Leu Lys Arg Ile Glu Asn Lys Ile Ser
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Thr Arg Gly Arg Leu Phe Glu Phe Ser Thr Ser Ser Cys Met Tyr
    50                  55                  60

Lys Thr Leu Glu Arg Tyr Arg Ser Cys Asn Tyr Asn Leu Asn Ser Cys
65                  70                  75                  80

Glu Ala Ser Ala Ala Leu Glu Thr Glu Leu Ser Asn Tyr Gln Glu Tyr
                85                  90                  95

Leu Lys Leu Lys Thr Arg Val Glu Phe Leu Gln Thr Thr Gln Arg Asn
            100                 105                 110

Leu Leu Gly Glu Asp Leu Val Pro Leu Ser Leu Lys Glu Leu Glu Gln
        115                 120                 125

Leu Glu Asn Gln Ile Glu Ile Ser Leu Met Asn Ile Arg Ser Ser Lys
    130                 135                 140

Asn Gln Gln Leu Leu Asp Gln Val Phe Glu Leu Lys Arg Lys Glu Gln
145                 150                 155                 160

Gln Leu Gln Asp Ala Asn Lys Asp Leu Lys Arg Lys Ile Gln Glu Thr
                165                 170                 175

Ser Gly Glu Asn Met Leu His Ile Ser Cys Gln Asp Val Gly Pro Ser
            180                 185                 190

Gly His Ala Ser Glu Ala Asn Gln Glu Phe Leu His Ala Ile Cys
        195                 200                 205

Asp Pro Ser Leu His Ile Gly Tyr Gln Ala Tyr Met Asp His Leu Asn
    210                 215                 220

Gln
225

<210> SEQ ID NO 3
<211> LENGTH: 1043
<212> TYPE: DNA
<213> ORGANISM: Oryza sativa
<220> FEATURE:
<221> NAME/KEY: CDS
<222> LOCATION: (34)..(786)

<400> SEQUENCE: 3
tacccgcggg aatcgttcga tcgatcgggc gag atg ggg agg gga aga gtt gag        54
                                    Met Gly Arg Gly Arg Val Glu
                                    1               5 ctg aag cgc atc gag aac aag atc aac agg cag gtc acc ttc tcc aag        102
Leu Lys Arg Ile Glu Asn Lys Ile Asn Arg Gln Val Thr Phe Ser Lys
        10                  15                  20 cgc cgc aac ggc ctc ctc aag aag gcc tac gag ctg tcc gtt ctc tgc        150
Arg Arg Asn Gly Leu Leu Lys Lys Ala Tyr Glu Leu Ser Val Leu Cys
    25                  30                  35 gac gcc gag gtc gcg ctc atc atc ttc tcc agc cgc ggc aag ctc tac        198
Asp Ala Glu Val Ala Leu Ile Ile Phe Ser Ser Arg Gly Lys Leu Tyr
40                  45                  50                  55 gag ttc ggc agc gcc ggc ata aca aag act tta gaa agg tac caa cat        246
Glu Phe Gly Ser Ala Gly Ile Thr Lys Thr Leu Glu Arg Tyr Gln His
                60                  65                  70 tgt tgc tac aat gct caa gat tcc aac aat gca ctt tct gaa act cag        294

```
                Cys Cys Tyr Asn Ala Gln Asp Ser Asn Asn Ala Leu Ser Glu Thr Gln
                            75                  80                  85 agt tgg tac cat gaa atg tca aag ttg aaa gca aaa ttt gaa gct ttg         342
Ser Trp Tyr His Glu Met Ser Lys Leu Lys Ala Lys Phe Glu Ala Leu
        90                  95                  100 cag cgc act caa agg cac ttg ctt ggg gag gat ctt gga cca ctc agc         390
Gln Arg Thr Gln Arg His Leu Leu Gly Glu Asp Leu Gly Pro Leu Ser
105                 110                 115 gtc aaa gaa ttg cag cag ctg gag aaa cag ctt gaa tgt gca cta tca         438
Val Lys Glu Leu Gln Gln Leu Glu Lys Gln Leu Glu Cys Ala Leu Ser
120                 125                 130                 135 cag gcg aga cag aga aag acg caa ctg atg atg gaa cag gtg gag gaa         486
Gln Ala Arg Gln Arg Lys Thr Gln Leu Met Met Glu Gln Val Glu Glu
            140                 145                 150 ctt cgc aga aag gag cgt cag ctg ggt gaa att aat agg caa ctc aag         534
Leu Arg Arg Lys Glu Arg Gln Leu Gly Glu Ile Asn Arg Gln Leu Lys
            155                 160                 165 cac aag ctc gag gtt gaa ggt tcc acc agc aac tac aga gcc atg cag         582
His Lys Leu Glu Val Glu Gly Ser Thr Ser Asn Tyr Arg Ala Met Gln
        170                 175                 180 caa gcc tcc tgg gct cag ggc gcc gtg gtg gag aat ggc gcc gca tac         630
Gln Ala Ser Trp Ala Gln Gly Ala Val Val Glu Asn Gly Ala Ala Tyr
        185                 190                 195 gtg cag ccg ccg cca cac tcc gcg gcc atg gac tct gaa ccc acc ttg         678
Val Gln Pro Pro Pro His Ser Ala Ala Met Asp Ser Glu Pro Thr Leu
200                 205                 210                 215 caa att ggg tat cct cat caa ttt gtg cct gct gaa gca aac act att         726
Gln Ile Gly Tyr Pro His Gln Phe Val Pro Ala Glu Ala Asn Thr Ile
            220                 225                 230 cag agg agc act gcc cct gca ggt gca gag aac aac ttc atg ctg gga         774
Gln Arg Ser Thr Ala Pro Ala Gly Ala Glu Asn Asn Phe Met Leu Gly
            235                 240                 245 tgg gtt ctt tga gctaagcagc catcgatcag ctgtcagaag ttggagctaa             826
Trp Val Leu
        250 taataaaagg gatgtggagt gggctacatg tatctcggat ctctctgcga gccacctaat       886 ggtcttgcgt ggccctttaa tctgtatgtt tttgtgtgta agctactgct agctgtttgc       946 accttctgcg tccgtggttg tgtttccgtg ctaccttttt atgttttgat ttggatcttg      1006 tttgaaaata atcttaccag ctttgggtaa actgttt                               1043

<210> SEQ ID NO 4
<211> LENGTH: 250
<212> TYPE: PRT
<213> ORGANISM: Oryza sativa

<400> SEQUENCE: 4

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Gly Ser Ala Gly Ile Thr Lys
        50                  55                  60

Thr Leu Glu Arg Tyr Gln His Cys Cys Tyr Asn Ala Gln Asp Ser Asn
65                  70                  75                  80

Asn Ala Leu Ser Glu Thr Gln Ser Trp Tyr His Glu Met Ser Lys Leu
```

```
                         85                  90                  95
Lys Ala Lys Phe Glu Ala Leu Gln Arg Thr Gln Arg His Leu Leu Gly
                100                 105                 110

Glu Asp Leu Gly Pro Leu Ser Val Lys Glu Leu Gln Gln Leu Glu Lys
            115                 120                 125

Gln Leu Glu Cys Ala Leu Ser Gln Ala Arg Gln Arg Lys Thr Gln Leu
        130                 135                 140

Met Met Glu Gln Val Glu Glu Leu Arg Arg Lys Glu Arg Gln Leu Gly
145                 150                 155                 160

Glu Ile Asn Arg Gln Leu Lys His Lys Leu Glu Val Glu Gly Ser Thr
                165                 170                 175

Ser Asn Tyr Arg Ala Met Gln Gln Ala Ser Trp Ala Gln Gly Ala Val
            180                 185                 190

Val Glu Asn Gly Ala Ala Tyr Val Gln Pro Pro His Ser Ala Ala
        195                 200                 205

Met Asp Ser Glu Pro Thr Leu Gln Ile Gly Tyr Pro His Gln Phe Val
210                 215                 220

Pro Ala Glu Ala Asn Thr Ile Gln Arg Ser Thr Ala Pro Ala Gly Ala
225                 230                 235                 240

Glu Asn Asn Phe Met Leu Gly Trp Val Leu
                245                 250

<210> SEQ ID NO 5
<211> LENGTH: 5392
<212> TYPE: DNA
<213> ORGANISM: Oryza sativa
<220> FEATURE:
<221> NAME/KEY: misc_feature
<222> LOCATION: (1)..(2245)
<223> OTHER INFORMATION: 5' non-transcribed sequence
<220> FEATURE:
<221> NAME/KEY: misc_feature
<222> LOCATION: (1)..(5392)
<223> OTHER INFORMATION: OsMADS5 5' regulatory sequence
<220> FEATURE:
<221> NAME/KEY: misc_feature
<222> LOCATION: (2246)..(2554)
<223> OTHER INFORMATION: exon
<220> FEATURE:
<221> NAME/KEY: misc_feature
<222> LOCATION: (2555)..(5388)
<223> OTHER INFORMATION: intron
<220> FEATURE:
<221> NAME/KEY: misc_feature
<222> LOCATION: (5389)..(5392)
<223> OTHER INFORMATION: exon

<400> SEQUENCE: 5
tgagcaggta gccggcgacc aatcgcgagc gtcgccaaca cgctgccttt tctcaatgca      60
tggcgtgggc cccaccaggg gccatttttt tctctttaaa aaggagaaaa gcaatcagag     120
ttgagacctc cgagcgcgag acccaacatc tatccctggg cccgcccaaa atccatttcc     180
aggtagttgt agccaaagaa tcaaggatac tccgatcgtt tgagtggaaa taataactcc     240
tacatgtaaa attaattaag gcctctattt gtatgaaaaa acataaaaaa aggattttta     300
atcttattga aaaaaaatcc taaggataac ttcgaataaa tgattaaatc ttaacatttt     360
ctttgaaatt catatggaac aaacaatgct atagagactt tggaggaatt aaagttatta     420
agagctctaa ccttttaaaa gattaccaat gagtctatat aggtagttgt agccaaagaa     480
tcaaggatac tccgatcgtt tgagtggaaa taataactcc tacatgtaaa attaattaag     540
gcctctattt gtatgaaaaa acataaaaaa aggattttta atcttattga aaaaaaatcc     600
```

```
taaggataac ttcgaataaa tgattaaatc ttaacatttt ctttgaaatt catatggaac    660
aaacaatgct atagagactt tggaggaatt aaagttatta agagctctaa ccttttaaaa    720
gattaccaat gagtctatat aggtagttgt agccaaagaa tcaaggatac tccgatcgtt    780
tgagtggaaa taataactcc tacatgtaaa attaattaag gcctctattt gtatgaaaaa    840
acataaaaaa aggatttta atcttattga aaaaaaaatc ctaaagataa cttcgaataa    900
atgattaaat cttaacattt tctttgaaat tcatatggaa caaacaatgc tatagagact    960
ttggaggaat taaagttatt aagagctcta acctttaaa agattaccaa tgagtctata    1020
taggtagttg tagccaaaga atcaaggata ctccgatcgt ttgagtggaa ataataactc    1080
ctacatgtaa aattaattaa ggcctctatt tgtatgaaaa acataaaaa aggatttttt    1140 aatcttattg aaaaaaatc ctaaggataa cttcgaataa atgattaaat cttaacattt    1200
tctttgaaat tcatatggaa caaacaatgc tatagagact ttggaggaat taaagttatt    1260
aagagctcta acctttaaa agattaccaa tgagtctata taggtagttg tagccaaaga    1320
atcaaggata ctccgatcgt ttgagtggaa ataataactc ctacatgtaa aattaattaa    1380
ggcctctatt tgtatgaaaa acataaaaa aggatttttt aatcttattg aaaaaaaat    1440 cctaaagata acttcgaata aatgattaaa tcttaacatt ttctttgaaa ttcatatgga    1500
acaaacaatg ctatagagac tttggaggaa ttaaagttat taagagctct aaccttttaa    1560
aagattacca atgagtctat atcactcatt caattcctac gttttttcaaa tggcctacat    1620 actcaaatgg ttgttcttgg tttttttttt ctctctttcg caattacaat ggacctgctc    1680 gcaactttg caatctgtct atgtttttta tgtttagcag ctgcgctgct gcagctgaac    1740
aaaaaaaaac actgtgacga ttggctgcaa cacaatgaaa atgagtgcag ccgaacagag    1800
ccaatatctt caaaatcttg ttttttcat cttccatttt tcaatcattt attttaaagg    1860
agcccttaat taatggttaa gaaatttat atcttgcatt ttaaaggata atgctgataa    1920
tcaaatagac tacggtgaaa aaaactttaa aactaaatgt aagattaaat ttcacactta    1980
aattttacta gctacggctg ataattaagc taacaactta ctgtgactga cttggtcata    2040
gggggagaga gagagagaga gagagagaga gagagagaga gagagagaga gagagagaga    2100
gagagagaga gagagagaga gagagagaga gaaagaagg caaggagcac tccggccagc    2160
acagccgatg gtacgagagc atggctagct agccgagcta cttagctact acatccatga    2220
tccatccatc cccaacaaac ggagcaagac tgcaagggag agggagagag agggaagctt    2280
gcaggctgca gctaactagc taggcaagga gagagaggag atagatcaag aagagattt    2340 gagaccgaga gagagctaga gagagatcga tggggcgagg gaaagtagag ctgaagcgga    2400
tcgagaacaa gataagccgg caggtgacgt tcgcgaagag gaggaacggg ctgctgaaga    2460
aggcgtacga gctgtccgtg ctctgcgacg ccgaggtcgc cctcatcatc ttctccaccc    2520
gcggccgcct cttcgagttc tccacctcct cctggtacta ctaataattc tctcttgcaa    2580
gctctcgccc cttgcagaga attcatatat atctcgccct aattctaatg caaagttagt    2640
taattagttt gcagccaaga aagactagtt ttctcgttat gagttttga agctccttgt    2700 gatttctggg ctagctactg cccacctagc taccatgttc taattaatca tcagtccgtg    2760
tgtttaatta acatctcatg tttgtccggg aagttcttac acccagtctt ttccctgctg    2820 cttttgtttgt gttaaaaaca tatatatacc agcatttcgt ttgtatttgt tggaattttt    2880
accaatcttt ctcaaagatc ctgattttag ttaatttta ccacctcgat cgtgatcata    2940
```

```
tacatgctca tagctgatta actaacctgt tcctgttgtt gttttggtta aagaaagaga    3000
gacaggacag ccgttctagt cacctgatgg ctgccgatct gtgtgtgttt gccgtcccct    3060
aattcctctt tacggtttgc agttgccata gagactacgt actctgtcaa cagaatcaag    3120
catgcaatct ctccatgctt gcttccattt gtaggctaga gctgcatgct agatatctct    3180
aagctgatct cttccatgct tgtctctcta gctctttcat tagtgcatgc aattttcaga    3240
gtgaagtaga tgagacccct ccagatctgc acaagaacat ggcatatagt actactagta    3300
cgcatattgc atcttaattc tcatattgca caagcacata tactaggctg cagtgccttt    3360
tccaatggca agttattttt gtcagatctt aattaggagc atcttttcca atggcaagtt    3420
gggagggttt cttgctctgg ttttactgtt ccattgggaa ctcgcaacat aggggttgtt    3480
cttgggttcc actgttccat tgagtctctc tctctttctc tctagctagg tttctctctc    3540
tacgtcttgt caaatgtctc ggctgtacta gtgtgcatgc gattgcagct gcagaagcaa    3600
gaggaaaagt agtaatgcag cagcaggagg aaaagtcgta ggagtactcg tggagataag    3660
catctctgta tcgatcgtct cgtcggttgt tatcctccct gtggatatgt acacggtccg    3720
tgtttagatc caaataatt catcaaactt taactttttt catcacatca aaacttttct    3780
acacacataa acttttaact tttacgtcac atcgtttcaa tttcaaccaa acttctaagg    3840
gcccctttga attggaggaa aaacatagga attttagagg atttcaatcc tatagaaaaa    3900
tttcctatga agccctttga aacaaatgat tgaatcctat ccaatccttt gaaattccta    3960
tggaatggac aatcctatag agattttgga ggaaatttag caagagcttc aacctcttgc    4020
taactttcct ttgagtctat ctctctcatc taattcctgc gttttcctg cggttcaatc    4080 aaacggtcat tcatgtgttt ttcctgcgtt ttgcaatcct ctgttttaca cttacattcc    4140
taccaaaatc ctacgttttt cctattccta cgtttttttca atcctgcgat tcaaagggac    4200
cctaattttg gtgtgaacta aacacagcct agttgtagtt gtgtggtacg aaagatcgaa    4260
ttgatttcta gctaggcgtg gccggacaca cacccaagtt aattcactgc attcgtaatt    4320
tcatactcct atgcgattca taattcaca tgcgatgatg cgaatagatt gatttgatca    4380
tttgaacatt gtcatatggt atgcaaacaa cttatcgtgc gagaggcgtg cgtgtcgatt    4440
gccaaaattt tctgtcagcg cacagtacag gctagctagt ctggaacgag gttgtgtcga    4500
tttacaaggc acagttacta gctaccctac cgttagggta tgtagtagga gtacttgtgt    4560
accaaaagtt tggattggtt gaattttcca agctcctagt cacaatgtac tccctccttt    4620
tccctcccca aaaatatac tccttctatc cagtatccac aaagaaaata atgtaactct    4680
agcatttaaa agacaaatta gcaagaagta aaatgattgg gagtgaaatt gtggttgggg    4740
gtaaaatagg gatcataatt tgaatgaggg gggtggttgt agggaaaaat agtactgcac    4800
tcctttagaa ttgcacttat tttgaaacaa aatctgaatg ttagttacaa ttgttttttt    4860
ctaaaaaaac agagtacaat tttctaataa tttaacacaa atcaatcaaa tatatacatg    4920
tttgtaagtg atagtgttta tagctccaaa cagggtttga aatttcggct cgaaatttcg    4980
cccccaccga aatgttcata tctcgcccga aactttcggt tgtttgcaaa ttttttgtgaa   5040 tttggtcaaa tttattcaa atccattcaa aatcagtcaa aaattcaaaa aaaatcgtac    5100
gaaaaaaaaa tctgaaattt tggttatatc gcccacctgc ggtagaaatc cttctttcga    5160
aatttaaaac cctggctcca aacttagggt gcgctgtgca catacccta g aaaatataac    5220 tgatatatgc tccattaatt atgaaaggca aaataaactg atcatgcata tgtaggaaaa    5280
tcgggttgta tatacatgta tttaaacaac aaaatataat ataacaactt taactgatac    5340
```

-continued

```
tgcattgaaa atagttttgt ggtccactga ttttcttttt tgtaacagta tg        5392
```

<210> SEQ ID NO 6
<211> LENGTH: 5412
<212> TYPE: DNA
<213> ORGANISM: Oryza sativa
<220> FEATURE:
<221> NAME/KEY: misc_feature
<222> LOCATION: (1)..(5412)
<223> OTHER INFORMATION: OsMADS5 5' regulatory sequence engineered
<220> FEATURE:
<221> NAME/KEY: misc_feature
<222> LOCATION: (1)..(13)
<223> OTHER INFORMATION: engineered sequence
<220> FEATURE:
<221> NAME/KEY: misc_feature
<222> LOCATION: (1)..(2258)
<223> OTHER INFORMATION: 5' non-transcribed sequence
<220> FEATURE:
<221> NAME/KEY: misc_feature
<222> LOCATION: (2259)..(2567)
<223> OTHER INFORMATION: exon
<220> FEATURE:
<221> NAME/KEY: misc_feature
<222> LOCATION: (2379)..(2384)
<223> OTHER INFORMATION: engineered sequence
<220> FEATURE:
<221> NAME/KEY: misc_feature
<222> LOCATION: (2568)..(5400)
<223> OTHER INFORMATION: intron
<220> FEATURE:
<221> NAME/KEY: misc_feature
<222> LOCATION: (5401)..(5412)
<223> OTHER INFORMATION: partial exon
<220> FEATURE:
<221> NAME/KEY: misc_feature
<222> LOCATION: (5404)..(5412)
<223> OTHER INFORMATION: engineered sequence

<400> SEQUENCE: 6

```
ctcgaggcgc gcctgagcag gtagccggcg accaatcgcg agcgtcgcca acacgctgcc      60
ttttctcaat gcatggcgtg ggccccacca ggggccattt ttttctcttt aaaaaggaga     120
aaagcaatca gagttgagac ctccgagcgc gagacccaac atctatccct gggcccgccc     180
aaaatccatt tccaggtagt tgtagccaaa gaatcaagga tactccgatc gtttgagtgg     240
aaataataac tcctacatgt aaaattaatt aaggcctcta tttgtatgaa aaaacataaa     300
aaaaggattt ttaatcttat tgaaaaaaaa tcctaaggat aacttcgaat aaatgattaa     360
atcttaacat tttctttgaa attcatatgg aacaaacaat gctatagaga ctttggagga     420
attaaagtta ttaagagctc taaccttta aaagattacc aatgagtcta tataggtagt     480
tgtagccaaa gaatcaagga tactccgatc gtttgagtgg aaataataac tcctacatgt     540
aaaattaatt aaggcctcta tttgtatgaa aaaacataaa aaaaggattt ttaatcttat     600
tgaaaaaaaa tcctaaggat aacttcgaat aaatgattaa atcttaacat tttctttgaa     660
attcatatgg aacaaacaat gctatagaga ctttggagga attaaagtta ttaagagctc     720 taaccttta aaagattacc aatgagtcta tataggtagt tgtagccaaa gaatcaagga     780
tactccgatc gtttgagtgg aaataataac tcctacatgt aaaattaatt aaggcctcta     840
tttgtatgaa aaaacataaa aaaaggattt ttaatcttat tgaaaaaaaa tcctaaggat     900
aacttcgaat aaatgattag atcttaacat tttctttgaa attcatatgg aacaaacaat     960
gctatagaga ctttggagga attaaagtta ttaagagctc taaccttta aaagattacc    1020 aatgagtcta tataggtagt tgtagccaaa gaatcaagga tactccgatc gtttgagtgg    1080
```

```
aaataataac tcctacatgt aaaattaatt aaggcctcta tttgtatgaa aaaacataaa    1140
aaaaggattt ttaatcttat tgaaaaaaaa tcctaaggat aacttcgaat aaatgattaa    1200
atcttaacat tttctttgaa attcatatgg aacaaacaat gctatagaga ctttggagga    1260
attaaagtta ttaagagctc taacctttta aaagattacc aatgagtcta tataggtagt    1320
tgtagccaaa gaatcaagga tactccgatc gtttgagtgg aaataataac tcctacatgt    1380
aaaattaatt aaggcctcta tttgtatgaa aaaacataaa aaaaggattt ttaatcttat    1440
tgaaaaaaaa atcctaaaga taacttcgaa taaatgatta atcttaaca ttttctttga    1500 aattcatatg gaacaaacaa tgctatagag actttggagg aattaaagtt attaagagct    1560
ctaacctttt aaaagattac caatgagtct atatcactca ttcaattcct acgtttttca    1620
aatggcctac atactcaaat ggttgttctt gtttttttt tctctctttc gcaattacaa    1680
tggacctgct cgcaactttt gcaatctgtc tatgttttt atgtttagca gctgcgctgc    1740
tgcagctgaa caaaaaaaaa cactgtgacg attggctgca acacaatgaa aatgagtgca    1800
gccgaacaga gccaatatct tcaaaatctt gtttttttca tcttccattt ttcaatcatt    1860
tattttaaag gagcccttaa ttaatggtta agaaattta tatcttgcat tttaaggat     1920 aatgctgata atcaaataga ctacggtgaa aaaaacttta aaactaaatg taagattaaa    1980
tttcacactt aaattttact agctacggct gataattaag ctaacaactt actgtgactg    2040
acttggtcat aggggagag agagagagag agagagagag agagagagag agagagagag    2100
agagagagag agagagagag agagagagag agagagagag agagaaaaga aggcaaggag    2160
cactccggcc agcacagccg atggtacgag agcatggcta gctagccgag ctacttagct    2220
actacatcca tgatccatcc atccccaaca aacggagcaa gactgcaagg gagagggaga    2280
gagagggaag cttgcaggct gcagctaact agctaggcaa ggagagagag gagatagatc    2340
aagaagagat tttgagaccg agagagagct agagagagct cgacggggcg agggaaagta    2400
gagctgaagc ggatcgagaa caagataagc cggcaggtga cgttcgcgaa gaggaggaac    2460
gggctgctga agaaggcgta cgagctgtcc gtgctctgcg acgccgaggt cgccctcatc    2520
atcttctcca cccgcggccg cctcttcgag ttctccacct cctcctggta ctactaataa    2580
ttctctcttg caagctctcg ccccttgcag agaattcata tatatctcgc cctaattcta    2640
atgcaaagtt agttaattag tttgcagcca agaaagacta gttttctcgt tatgagtttt    2700
tgaagctcct tgtgatttct gggctagcta ctgcccacct agctaccatg ttctaattaa    2760
tcatcagtcc gtgtgtttaa ttaacatctc atgtttgtcc gggaagttct tacacccagt    2820
cttttccctg ctgctttgtt tgtgtttaaa acatatatat accagcattt cgtttgtatt    2880
tgttggaatt tttaccaatc tttctcaaag atcctgattt tagttaattt ttaccacctc    2940
gatcgtgatc atatacatgc tcatagctga ttaactaacc tgttcctgtt gttgttttgg    3000
ttaaagaaag agacagga cagccgttct agtcacctga tggctgccga tctgtgtgtg      3060
tttgccgtcc cctaattcct cttacggtt tgcagttgcc atagagacta gtactctgtc     3120
aacagaatca agcatgcaat ctctccatgc ttgcttccat ttgtaggcta gagctgcatg    3180
ctagatatct ctaagctgat ctcttccatg cttgtctctc tagctctttc attagtgcat    3240
gcaattttca gagtgaagta gatgagaccc ctccagatct gcacaagaac atggcatata    3300
gtactactag tacgcatatt gcatcttaat tctcatattg cacaagcaca tatactaggc    3360
tgcagtgcct tttccaatgg caagttattt ttgtcagatc ttaattagga gcatcttttc    3420
caatggcaag ttgggagggt ttcttgctct ggttttactg ttccattggg aactcgcaac    3480
```

```
ataggggttg ttcttgggtt ccactgttcc attgagtctc tctctctttc tctctagcta    3540
ggtttctctc tctacgtctt gtcaaatgtc tcggctgtac tagtgtgcat gcgattgcag    3600
ctgcagaagc aagaggaaaa gtagtaatgc agcagcagga ggaaaagtcg taggagtact    3660
cgtggagata agcatctctg tatcgatcgt ctcgtcggtt gttatcctcc ctgtggatat    3720
gtacacggtc cgtgtttaga tccaaaataa ttcatcaaac ttttaacttt ttcatcacat    3780
caaaactttt ctacacacat aaacttttaa cttttacgtc acatcgtttc aatttcaacc    3840
aaacttctaa gggccccttt gaattggagg aaaaacatag gaattttaga ggatttcaat    3900
cctatagaaa aatttcctat gaagcccttt gaaacaaatg attgaatcct atccaatcct    3960
ttgaaattcc tatggaatgg acaatcctat agagattttg gaggaaattt agcaagagct    4020
tcaacctctt gctaactttc ctttgagtct atctctctca tctaattcct gcgttttcc     4080 tgcggttcaa tcaaacggtc attcatgtgt ttttcctgcg ttttgcaatc ctctgtttta    4140
cacttacatt cctaccaaaa tcctacgttt ttcctattcc tacgtttttt caatcctgcg    4200
attcaaaggg accctaattt tggtgtgaac taaacacagc ctagttgtag ttgtgtggta    4260
cgaaagatcg aattgatttc tagctaggcg tggccggaca cacacccaag ttaattcact    4320
gcattcgtaa tttcatactc ctatgcgatt cataatttca catgcgatga tgcgaataga    4380
ttgatttgat catttgaaca ttgtcatatg gtatgcaaac aacttatcgt gcagaggcg     4440 tgcgtgtcga ttgccaaaat tttctgtcag cgcacagtac aggctagcta gtctggaacg    4500
aggttgtgtc gatttacaag gcacagttac tagctaccct accgttaggg tatgtagtag    4560
gagtacttgt gtaccaaaag tttggattgg ttgaattttc caagctccta gtcacaatgt    4620
actccctcct tttccctccc caaaaaatat actccttcta tccagtatcc acaaagaaaa    4680
taatgtaact ctagcatttta aaagacaaat tagcaagaag taaaatgatt gggagtgaaa    4740
ttgtggttgg gggtaaaata gggatcataa tttgaatgag gggggtggtt gtagggaaaa    4800
atagtactgc actcctttag aattgcactt attttgaaac aaaatctgaa tgttagttac    4860
aattgttttt ttctaaaaaa acagagtaca attttctaat aatttaacac aaatcaatca    4920
aatatataca tgtttgtaag tgatagtgtt tatagctcca aacagggttt gaaatttcgg    4980
ctcgaaattt cgccccccacc gaaatgttca tatctcgccc gaaactttcg gttgtttgca    5040 aattttttgtg aatttggtca aattttattc aaatccattc aaaatcagtc aaaaattcaa    5100
aaaaaatcgt acgaaaaaaa aatctgaaat tttggttata tcgcccacct gcggtagaaa    5160
tccttctttc gaaatttaaa accctggctc caaacttagg gtgcgctgtg cataccct     5220 agaaaatata actgatatat gctccattaa ttatgaaagg caaaataaac tgatcatgca    5280
tatgtaggaa aatcggggttg tatatacatg tatttaaaca acaaaatata atataacaac    5340
tttaactgat actgcattga aaatagtttt gtggtccact gattttcttt tttgtaacag    5400
tatccaccat gg                                                         5412
```

<210> SEQ ID NO 7
<211> LENGTH: 124
<212> TYPE: DNA
<213> ORGANISM: Oryza sativa
<220> FEATURE:
<221> NAME/KEY: misc_feature
<222> LOCATION: (1)..(124)
<223> OTHER INFORMATION: OsMADS5 5' untranslated leader sequence -
      natural

<400> SEQUENCE: 7

```
aagactgcaa gggagaggga gagagaggga agcttgcagg ctgcagctaa ctagctaggc    60
aaggagagag aggagataga tcaagaagag attttgagac cgagagagag ctagagagag   120
atcg                                                                124
```

<210> SEQ ID NO 8
<211> LENGTH: 317
<212> TYPE: DNA
<213> ORGANISM: Oryza sativa
<220> FEATURE:
<221> NAME/KEY: misc_feature
<222> LOCATION: (1)..(317)
<223> OTHER INFORMATION: OsMADS 5 5' untranslated leader sequence
      engineered
<220> FEATURE:
<221> NAME/KEY: misc_feature
<222> LOCATION: (121)..(125)
<223> OTHER INFORMATION: engineered sequence
<220> FEATURE:
<221> NAME/KEY: misc_feature
<222> LOCATION: (313)..(317)
<223> OTHER INFORMATION: engineered sequence

<400> SEQUENCE: 8

```
aagactgcaa gggagaggga gagagaggga agcttgcagg ctgcagctaa ctagctaggc    60
aaggagagag aggagataga tcaagaagag attttgagac cgagagagag ctagagagag   120
ctcgacgggg cgaggaaaag tagagctgaa gcggatcgag aacaagataa gccggcaggt   180
gacgttcgcg aagaggagga acgggctgct gaagaaggcg tacgagctgt ccgtgctctg   240
cgacgccgag gtcgccctca tcatcttctc cacccgcggc cgcctcttcg agttctccac   300
ctcctcctgt atccacc                                                  317
```

<210> SEQ ID NO 9
<211> LENGTH: 1215
<212> TYPE: DNA
<213> ORGANISM: Oryza sativa
<220> FEATURE:
<221> NAME/KEY: misc_feature
<222> LOCATION: (1)..(1215)
<223> OTHER INFORMATION: OsMADS5 terminus
<220> FEATURE:
<221> NAME/KEY: misc_feature
<222> LOCATION: (1)..(228)
<223> OTHER INFORMATION: 3' untranslated sequence
<220> FEATURE:
<221> NAME/KEY: misc_feature
<222> LOCATION: (229)..(1215)
<223> OTHER INFORMATION: 3' non-transcribed sequence

<400> SEQUENCE: 9

```
atgaattgct tatcacatta atggacatct cctatgttgg atgtggtgtt tgacgtaatg    60
ctctctttta catgcgggtt ttaccttaag tgtgtgtgct aaatttagtg cgtttgttta   120
tgctcttttg aactgaacaa aggaatgatc ccggtttgat tgatgaatgc tgcaagaaca   180
taatctatat gttagtctga attcagtatg taatgaagat gttttgttac taattaataa   240
atacgaagta aacaattaac tgaccactaa tcatgtcagc ttagatatat gcttataatt   300
atgttgccta attcttacct taattggtct gtgttcaata tatgtgagta taccacacta   360
gttgtttctc agcatgaact aattaagtgt gagtagataa aacgagtaaa ttggaatgta   420
agaaaaggta aaataaagt acttattaaa gagagagtgc atgccaaaag tacgaagaga   480
aaaacttaga atattagtta caatataata tataatcaag tgcttcgttc gaacccatac   540
atgtttgttt ttcttatttt tctaatattt cttcaccata taggttcccc aggttgcact   600
```

```
ccgaaaggtc gtgtaatgtg tatttagtag cacacatagt tacatcactg cttattttct    660
catccactag ccacaagatt gtgtgcgtgt gaccatctca attagatcca tctcctcctt    720
cacatgcacg gtattgattt gtgctagacc tgccggtgtc tccaatggtg atgatccagc    780
tgattcatcg tcttggagga catcatcgtc ccatgccatt tccatatcta tctcatggcc    840
aatcttgtta gcataatcaa tgtggttgaa gatgtagttc atgtcaacat catcatctat    900
gttgtaaacc tggtacggca tctcgtcctt cgtttcgaac aaatgatcac acatatcaag    960
gcataaatca tcataggtag agaccaggag ttcttcacaa gagttggtct ggatgtagct   1020
gttctcatcc atggtgagta ttccctgggt gaccatttgg ttggatgggt tggaatctgg   1080
cctgatctta ccattcacct ctgctaactt ttgtgtggat gctggtgaag acgatgacac   1140
tgcagtagat tctggtggag cttgacgaac acttgacttg attggaccaa ttccaaggct   1200
cttgatgtag ttttg                                                    1215

<210> SEQ ID NO 10
<211> LENGTH: 1089
<212> TYPE: DNA
<213> ORGANISM: Oryza sativa
<220> FEATURE:
<221> NAME/KEY: misc_feature
<222> LOCATION: (1)..(1089)
<223> OTHER INFORMATION: OsMADS5 3' regulatory sequence engineered
<220> FEATURE:
<221> NAME/KEY: misc_feature
<222> LOCATION: (1)..(31)
<223> OTHER INFORMATION: engineered sequence
<220> FEATURE:
<221> NAME/KEY: misc_feature
<222> LOCATION: (1)..(275)
<223> OTHER INFORMATION: 3' untranslated sequence
<220> FEATURE:
<221> NAME/KEY: misc_feature
<222> LOCATION: (276)..(1089)
<223> OTHER INFORMATION: 3' non-transcribed sequence
<220> FEATURE:
<221> NAME/KEY: misc_feature
<222> LOCATION: (1078)..(1089)
<223> OTHER INFORMATION: engineered sequence

<400> SEQUENCE: 10
gagctccgcg ggcggccgca ctagtcccgg gccatggggg gtctagaatg aattgcttat     60
cacattaatg gacatctcct atgttggatg tggtgtttga cgtaatgctc tcttttacat    120
gcgggtttta ccttaagtgt gtgtgctaaa tttagtgcgt ttgtttatgc tcttttgaac    180
tgaacaaagg aatgatcccg gtttgattga tgaatgctgc aagaacataa tctatatgtt    240
agtctgaatt cagtatgtaa tgaagatgtt ttgttactaa ttaataaata cgaagtaaac    300
aattaactga ccactaatca tgtcagctta gatatatgct tataattatg ttgcctaatt    360
cttaccttaa ttggtctgtg ttcaatatat gtgagtatac cacactagtt gtttctcagc    420
atgaactaat taagtgtgag tagataaaac gagtaaattg gaatgtaaga aaaggtaaaa    480
ataaagtact tattaaagag agagtgcatg ccaaaagtac gaagagaaaa acttagaata    540
ttagttacaa tataatatat aatcaagtgc ttcgttcgaa cccatacatg tttgtttttc    600 ttattttttct aatatttctt caccatatag gttccccagg ttgcactccg aaaggtcgtg    660
taatgtgtat ttagtagcac acatagttac atcactgctt attttctcat ccactagcca    720
caagattgtg tgcgtgtgac catctcaatt agatccatct cctccttcac atgcacggta    780
ttgatttgtg ctagacctgc cggtgtctcc aatggtgatg atccagctga ttcatcgtct    840
```

| tggaggacat catcgtccca tgccatttcc atatctatct catggccaat cttgttagca | 900 |
| taatcaatgt ggttgaagat gtagttcatg tcaacatcat catctatgtt gtaaacctgg | 960 |
| tacggcatct cgtccttcgt ttcgaacaaa tgatcacaca tatcaaggca taaatcatca | 1020 |
| taggtagaga ccaggagttc ttcacaagag ttggtctgga tgtagctgtt ctcatccggc | 1080 |
| gcgcccggg | 1089 |

```
<210> SEQ ID NO 11
<211> LENGTH: 4450
<212> TYPE: DNA
<213> ORGANISM: Oryza sativa
<220> FEATURE:
<221> NAME/KEY: misc_feature
<222> LOCATION: (1)..(4450)
<223> OTHER INFORMATION: OsMADS6
<220> FEATURE:
<221> NAME/KEY: misc_feature
<222> LOCATION: (1)..(1460)
<223> OTHER INFORMATION: 5' non-transcribed sequence
<220> FEATURE:
<221> NAME/KEY: misc_feature
<222> LOCATION: (1461)..(1667)
<223> OTHER INFORMATION: exon
<220> FEATURE:
<221> NAME/KEY: misc_feature
<222> LOCATION: (1668)..(4425)
<223> OTHER INFORMATION: intron
<220> FEATURE:
<221> NAME/KEY: misc_feature
<222> LOCATION: (4426)..(4450)
<223> OTHER INFORMATION: exon
```

<400> SEQUENCE: 11

| gacgatggtg tgatgtggga acacgaagaa acatgagga aaaaatatta aaatgaattt | 60 |
| cccacttaaa atgcatcaaa taaaaaaaat aaagaaacga ccgggaatag acacaggatt | 120 |
| tgtgaactag ctagggcaaa catcatatgg tcccttgctg atgcacaagt acattgagat | 180 |
| gtcatttcaa ttctgtgcat catatgcatg tggtcccttg ctgaatatta ctcttgaaat | 240 |
| atctaccagt gccaatctat tgcatgactt aattaattca caggttttgt tgattacatt | 300 |
| attagtaagc ttgagagcac aagctcaatg gatttttcta taaatgggga tcattttgca | 360 |
| attttctttg tcgtgcaaag ttagccttct ttattactac ttctgttttt aaatatacga | 420 |
| tcctattgac ttttggtcat atatttaacc atgtatctta tttagatagt ttgcgcaaat | 480 |
| atatatacct tcaatgataa aattagttac aatgaaacaa atgatattta cgcaattctt | 540 |
| tttactaaac aagtcacaag aagtacctgc agcaatatat gttggaaccg tgcagtagat | 600 |
| cgagcctagc tacgcaaaaa aacaaaaaga gaaaaaagg gaaaggaaaa acattaatca | 660 |
| tgcatgagca gtatgcccgg caactggaat ttgtcaaaga tatggggaga ggagaataat | 720 |
| acaagtacta ctactaccta gctctaccat gcatatgcac ccaaaggcaa actggattat | 780 |
| tggataaagc acagatgctg gcaaaacaat ccttaagcct cccctccctg cttctttatt | 840 |
| tttgggcagc ctctaccgga cggtgccgtg gtccattgga ccagtaggtg gcgacataca | 900 |
| tggtttgggt taagtctagg agagcagtgt gtgtgcgcgc gcaagagaga gagactgtga | 960 |
| gtctgggagt agccctctcc cctcctttgg ccatcttcct cgtgtatatg catatatgca | 1020 |
| tcatcgcaac ggtgtatatt tgtggtgtgg cgggtgtggc attggattgc ccccattttg | 1080 |
| gctcgtgctt cccagttagg gtaaaacctg tggtaaactt gctagcccca cgccaaagtt | 1140 |
| accctctttt attgttgaaa gggagagrag gtgtgtgaat tgtgatggag ggagagagag | 1200 |
| agagatagaa agagagatgt gtgtcaaagc aagcaagaaa ccagtttcac aaagagctac | 1260 |

```
tactagtact agtgtactac tgtggtacag tgcccaatgt cctttctccg gactcgactc    1320
cactaatatt ctcctcttct cgcgcggctc gttatattct cgtcatcatt ggaggcttta    1380
gcaagcaaga agagaggcag tggtggtggt ggtggaggag gagctagcta gcctgtgctt    1440
gctgatcggt gctgagctga ggaatcgttc gatcgatcgg gcgagatggg gaggggaaga    1500
gttgagctga agcgcatcga gaacaagatc aacaggcagg tcaccttctc caagcgccgc    1560
aacggcctcc tcaagaaggc ctacgagctg tccgttctct gcgacgccga ggtcgcgctc    1620
atcatcttct ccagccgcgg caagctctac gagttcggca gcgccgggta taattaatac    1680
agacacaaca acacacacaa ccaacaaacc agcatcaatt tgaacctgca gatctgctgt    1740
tttctctgat caattgcttc ttttttttg ttcttttttg tttcttttat ctgctgcaac    1800
ggcgtcctgc tcctctgggg tttctcgttt cttttttcat ttattttag caggtgccaa     1860 gtagccgagc tactatactt acctggccat gttaattatt ttattccgtc tgtctgtgtg    1920
tgtctgtgca tactactata gggacatggc gcggtgttct tataaaccgg gaggccggat    1980
ccctaactag catgggagga tatctttca gcggatctat acaaacccta ctcctgctga    2040
cctctttctt ccagtttctc cgggtcttcc ttggattatt attgcccatc ttccgggttg    2100
tgcgtgtgtc agagacagct cgaacgataa atttctcaaa accagtacta gagagggtgt    2160
gttgtgtgtg agaactgagt ggagagttag catgaaggct gcaaactaga aaggaaggta    2220
tgttctttcc ttttgatcc atcaggggag ccccttctgg tattaagatc tttccggcac     2280
attgattttc atactttgtg atgaccctgg aagaatcggc gtagcagcgt agcaccgctc    2340
cattttggtc ttaccctcac ctccccatgc tatgaactga tcaatttcat tgttcttcat    2400
cacccttctc ctagctttcc acttccttcg gatctcatgc catgtttctc agcatgaatc    2460
aaatttaatt cgtgttttct acttccatat atactggaag aaatttaatt agatctattt    2520
ttgctcggga ggtcttcata ctttgagttc tgatgccatc accttatttc cccccccccy    2580
ttctctkgkt ctatcttctt cctcatcttg gcttgatcat tttgatctgt cagttatagc    2640
atgatgcatt ctcaatttga ctgtatgtaa gttcaaccgg aaatatgttg aatggatttt    2700
ctatatatca acacttgatg tcaggcctgc atctgtttcg cttgtggtgg tgtggccaaa    2760
attgtctata tttgatcttt gctcttcttt ctcctcattt catgacgatt cctactacgg    2820
cttaaaccat tcttattct ttactaatca tggatgttgc ttgactccta gttgtttcgt      2880
actagctcaa cttggagatc ttttcattat ttgcctagtt ggtgggtacg tttgtgacag    2940
atctaaaatg gtgcacgaaa agttttactt attatgaaaa aagggagctt aacagggtaa    3000
tttctctatt tattcgtgat gacatttttt ccttgataag ggggatttt tataatctgc      3060 actcacatgt ttatatgtaa aatctagctc ttttgttttg ttttggcat atttcccgct      3120 aagtatagag tttatgtgga taacattata acttttcaag atccaatcca catctttgat    3180
tgtgaaaatc atacaatagg gaaaatcaac tgaagggtta attagatgct atatgcatat    3240
atatatatat gtgcgcgcgc gcgcgcctga atttaactat gtatgcatcc aactgtttca    3300
ttgaaaaaga tttgatattt ttcagtctat tcttttcga gtatataatt aatatgtttc      3360
aatctgtttt gaccattata agataaagcc tatattcacc aggcatttga gatgatcttt    3420
tcatgcatga aaaagctgtt gttatcactt caactaacca gacgatctaa catgtatttg    3480
tataagaaac agaccttgat ttccttctgt aaaatcatgc atgtgttcgt tttgaattgg    3540
agtcggcgcg cctgtgtttt gaccgtcagg aaagtctttt ttttcccctga atagtcaagg    3600
```

| | |
|---|---|
| gtctatactt cttgaagcaa ttgggacact aatcaattat tgtttatacc tcggaccatc | 3660 |
| ttttccttct tcacaccact aatcagttta tgccttggac cattaattgt gttgttcaca | 3720 |
| agcttcttgt ttatggttta caaagcattc gcctagattt gtgtgtgtct ctacacatcg | 3780 |
| atcacttta aatacttgtc gctttcagtt attcttttaa cgtttggtta tttatcttat | 3840 |
| ttaaaaaaat tatcgtatta ttatttattt tgtttgtgat ttactttatt atcaaaagta | 3900 |
| tttcaaatat gacttatctt tttttataag tgcactaatt tttcaaataa gatgaatggt | 3960 |
| caaatgttac aagaaaaagt taaagcaacc actaatttag ggcggaggta gtaaaaccta | 4020 |
| gttattgtaa ccaataattt tatcaatcta taaatgcaac acaaagtcac ttcgtgatat | 4080 |
| ctcacacaaa gccacttcaa cgatgaaagc tgactgcatg ttttatcaaa acacatgtga | 4140 |
| tcagtttgtt ggatgaaaaa aattatctat gtcataaatc aagagttata atataagctt | 4200 |
| ctggctctac aagtaacatt tctatgtttt tttttacgt tcttacatac tatgttttgc | 4260 |
| caaaaaaac atgatcattt tgttggacga aagaaatag taaatataga gtgacctttg | 4320 |
| atatcattat aatataagct tctgcctcta taaataacat ctatgcactt tttacgtcgt | 4380 |
| agtaatttga tatatgagaa atttacatat aacattttg tgcagcataa caaagacttt | 4440 |
| agaaaggtac | 4450 |

```
<210> SEQ ID NO 12
<211> LENGTH: 4457
<212> TYPE: DNA
<213> ORGANISM: Oryza sativa
<220> FEATURE:
<221> NAME/KEY: misc_feature
<222> LOCATION: (1)..(4457)
<223> OTHER INFORMATION: OsMADS6 5' regulatory sequence
<220> FEATURE:
<221> NAME/KEY: misc_feature
<222> LOCATION: (1)..(12)
<223> OTHER INFORMATION: engineered sequence
<220> FEATURE:
<221> NAME/KEY: misc_feature
<222> LOCATION: (1)..(1478)
<223> OTHER INFORMATION: 5' non-transcribed sequence
<220> FEATURE:
<221> NAME/KEY: misc_feature
<222> LOCATION: (1479)..(1685)
<223> OTHER INFORMATION: exon
<220> FEATURE:
<221> NAME/KEY: misc_feature
<222> LOCATION: (1503)..(1508)
<223> OTHER INFORMATION: engineered sequence
<220> FEATURE:
<221> NAME/KEY: misc_feature
<222> LOCATION: (1529)..(1529)
<223> OTHER INFORMATION: mutagenized sequence position
<220> FEATURE:
<221> NAME/KEY: misc_feature
<222> LOCATION: (1686)..(4443)
<223> OTHER INFORMATION: intron
<220> FEATURE:
<221> NAME/KEY: misc_feature
<222> LOCATION: (4444)..(4457)
<223> OTHER INFORMATION: exon
<220> FEATURE:
<221> NAME/KEY: misc_feature
<222> LOCATION: (4450)..(4457)
<223> OTHER INFORMATION: engineered sequence

<400> SEQUENCE: 12
```

| | |
|---|---|
| gcatgcggac cgctaggacg atggtgtgat gtgggaacac gaagaaaaca tgaggaaaaa | 60 |
| atattaaaat gaatttccca cttaaaatgc atcaaataaa aaaataaag aaacgaccgg | 120 |
| gaatagacac agggtttgtg aactagctag ggcaaacatc atatggtccc ttgctgatgc | 180 |

```
acaagtacat tgagatgtca tttcaattct gtgcatcata tgcatgtggt cccttgctga    240
atattactct tgaaatatct accagtgcca atctattgca tgacttaatt aattcacagg    300
ttttgttgat tacattatta gtaagcttga gagcacaagc tcaatggatt tttctataaa    360
tggggatcat tttgcaattt tctttgtcgt gcaaagttag ccttctttat tactacttct    420
gtttttaaat atacgatcct attgactttt ggtcatatat ttaaccatgt atcttattta    480
gatagtttgc gcaaatatat ataccttcaa tgataaaatt agttacaatg aaacaaatga    540
tatttacgca attcttttta ctaaacaagt cacaagaagt acctgcagca atatatgttg    600
gaaccgtgca gtagatcgag cctagctacg caaaaaaaca aaaagagaaa aaagggaaa     660 ggaaaaacat taatcatgca tgagcagtat gcccggcaac tggaatttgt caaagatatg    720
gggagaggag aataatacaa gtactactac tacctagctc taccatgcat atgcacccaa    780
aggcaaactg gattattgga taaagcacag atgctggcaa acaatccttt aagcctcccc    840
tccctgcttc tttattttg ggcagcctct accggacggt gccgtggtcc attggaccag      900
taggtggcga catacatggt ttgggttaag tctaggagag cagtgtgtgt gcgcgcgcaa    960
gagagagaga ctgtgagtct gggagtagcc ctctcccctc ctttggccat cttcctcgtg    1020
tatatgcata tatgcatcat cgcaacggtg tatatttgtg gtgtggcggg tgtggcattg    1080
gattgccccc attttggctc gtgcttccca gttagggtaa aacctgtggt aaacttgcta    1140
gccccacgcc aaagttaccc ttcttttattg ttgaaaggga gaggaggtgt gtgaattgtg   1200
atggagggag agagagagag agatagaaag agagatgtgt gtcaaagcaa gcaagaaacc    1260
agtttcacaa agagctacta ctagtactag tgtactactg tggtacagtg cccaatgtcc    1320
tttctccgga ctcgactcca ctaatattct cctcttctcg cgcggctcgt tatattctcg    1380
tcatcattgg aggctttagc aagcaagaag agaggcagtg gtggtggtgg tggaggagga    1440
gctagctagc ctgtgcttgc tgatcggtgc tgagctgagg aatcgttcga tcgatcgggc    1500
gagtcgacga ggggaagagt tgagctgagg cgcatcgaga acaagatcaa caggcaggtc    1560
accttctcca agcgccgcaa cggcctcctc aagaaggcct acgagctgtc cgttctctgc    1620
gacgccgagg tcgcgctcat catcttctcc agccgcggca agctctacga gttcggcagc    1680
gccgggtata attaatacag acacaacaac acacacaacc aacaaaccag catcaatttg    1740
aacctgcaga tctgctgttt tctctgatca attgcttctt tttttttgtt cttttttgtt    1800
tcttttatct gctgcaacgg cgtcctgctc ctctggggtt tctcgttttc ttttcatttt    1860 attttttagca ggtgccaagt agccgagcta ctatacttac ctggccatgt taattatttt   1920
attccgtctg tctgtgtgtg tctgtgcata ctactatagg gacatggcgc ggtgttctta    1980
taaaccggga ggccggatcc ctaactagca tgggaggata tcttttcagc ggatctatac    2040
aaaccctact cctgctgacc tcttttcttcc agtttctccg ggtcttcctt ggattattat   2100
tgcccatctt ccgggttgtg cgtgtgtcag agacagctcg aacgataaat ttctcaaaac    2160
cagtactaga gagggtgtgt tgtgtgtgag aactgagtgg agagttagca tgaaggctgc    2220
aaactagaaa ggaaggtatg ttcttttcctt tttgatccat caggggagcc ccttctggta    2280
ttaagatctt tccggcacat tgattttcat actttgtgat gacccctggaa gatcggcgt     2340 agcagcgtag caccgctcca ttttggtctt accctcacct ccccatgcta tgaactgatc    2400
aatttcattg ttcttcatca cccttctcct agctttccac ttccttcgga tctcatgcca    2460
tgtttctcag catgaatcaa atttaattcg tgttttctac ttccatatat actggaagaa    2520
```

```
atttaattag atctatttttt gctcgggagg tcttcatact ttgagttctg atgccatcac    2580
cttatttccc ccccccccctt ctcttgttct atcttcttcc tcatcttggc ttgatcattt    2640
tgatctgtca gttatagcat gatgcattct caatttgact gtatgtaagt tcaaccggaa    2700
atatgttgaa tggattttct atatatcaac acttgatgtc aggcctgcat ctgtttcgct    2760
tgtggtggtg tggccaaaat tgtctatatt tgatctttgc tcttctttct cctcatttca    2820
tgacgattcc tactacggct taaaccattc tttattcttt actaatcatg gatgttgctt    2880
gactcctagt tgtttcgtac tagctcaact tggagatctt ttcattattt gcctagttgg    2940
tgggtacgtt tgtgacagat ctaaaatggt gcacgaaaag ttttacttat tatgaaaaaa    3000
gggagcttaa cagggtaatt tctctatttta ttcgtgatga catttttttcc ttgataaggg   3060
ggattttta taatctgcac tcacatgttt atatgtaaaa tctagctctt ttgttttgtt     3120
tttggcatat ttcccgctaa gtatagagtt tatgtggata acattataac ttttcaagat    3180
ccaatccaca tctttgattg tgaaaatcat acaataggga aaatcaactg aagggttaat    3240
tagatgctat atgcatatat atatatatgt gcgcgcgcgc gcgcctgaat ttaactatgt    3300
atgcatccaa ctgtttcatt gaaaagatt tgatatttttt cagtctattc ttttttcgagt   3360
atatatttaa tatgtttcaa tctgttttga ccattataag ataaagccta tattcaccag    3420
gcatttgaga tgatcttttc atgcatgaaa aagctgttgt tatcacttca actaaccaga    3480
cgatctaaca tgtatttgta taagaaacag accttgattt ccttctgtaa aatcatgcat    3540
gtgttcgttt tgaattggag tcggcgcgcc tgtgttttga ccgtcaggaa agtctttttt    3600
ttccctgaat agtcaagggt ctatacttct tgaagcaatt gggacactaa tcaattattg    3660
tttataccctc ggaccatctt ttccttcttc acaccactaa tcagtttatg ccttggacca   3720
ttaattgtgt tgttcacaag cttcttgttt atggtttaca aagcattcgc ctagatttgt    3780
gtgtgtctct acacatcgat cacttttaaa tacttgtcgc tttcagttat tcttttaacg    3840
tttggttatt tatcttatt aaaaaaatta tcgtattatt atttattttg tttgtgattt     3900
actttattat caaaagtatt tcaaatatga cttatctttt tttataagtg cactaatttt    3960
tcaaataaga tgaatggtca aatgttacaa gaaaaagtta aagcaaccac taatttaggg    4020
cggaggtagt aaaacctagt tattgtaacc aataatttta tcaatctata aatgcaacac    4080
aaagtcactt cgtgatatct cacacaaagc cacttcaacg atgaaagctg actgcatgtt    4140
ttatcaaaac acatgtgatc agtttgttgg atgaaaaaaa ttatctatgt cataaatcaa    4200
gagttataat ataagcttct ggctctacaa gtaacatttc tatgtttttt ttttacgttc    4260
ttacatacta tgttttgcca aaaaaaacat gatcattttg ttggacgaaa agaaatagta    4320
aatatagagt gacctttgat atcattataa tataagcttc tgcctctata aataacatct    4380
atgcactttt tacgtcgtag taatttgata tatgagaaat ttacatataa catttttgtg    4440
cagcataacc accatgg                                                   4457
```

<210> SEQ ID NO 13
<211> LENGTH: 25
<212> TYPE: DNA
<213> ORGANISM: Oryza sativa
<220> FEATURE:
<221> NAME/KEY: misc_feature
<222> LOCATION: (1)..(25)
<223> OTHER INFORMATION: OsMADS6 5' untranslated sequence

<400> SEQUENCE: 13
ggaatcgttc gatcgatcgg gcgag                                            25

```
<210> SEQ ID NO 14
<211> LENGTH: 217
<212> TYPE: DNA
<213> ORGANISM: Oryza sativa
<220> FEATURE:
<221> NAME/KEY: misc_feature
<222> LOCATION: (1)..(217)
<223> OTHER INFORMATION: OsMADS6 5' untranslated sequence engineered
<220> FEATURE:
<221> NAME/KEY: misc_feature
<222> LOCATION: (25)..(30)
<223> OTHER INFORMATION: engineered sequence
<220> FEATURE:
<221> NAME/KEY: misc_feature
<222> LOCATION: (51)..(51)
<223> OTHER INFORMATION: mutagenized position
<220> FEATURE:
<221> NAME/KEY: misc_feature
<222> LOCATION: (214)..(217)
<223> OTHER INFORMATION: engineered sequence

<400> SEQUENCE: 14
ggaatcgttc gatcgatcgg gcgagtcgac gaggggaaga gttgagctga ggcgcatcga      60
gaacaagatc aacaggcagg tcaccttctc caagcgccgc aacggcctcc tcaagaaggc     120
ctacgagctg tccgttctct gcgacgccga ggtcgcgctc atcatcttct ccagccgcgg     180
caagctctac gagttcggca gcgccggcat aaccacc                              217

<210> SEQ ID NO 15
<211> LENGTH: 1241
<212> TYPE: DNA
<213> ORGANISM: Oryza sativa
<220> FEATURE:
<221> NAME/KEY: misc_feature
<222> LOCATION: (1)..(1241)
<223> OTHER INFORMATION: OsMADS6 3' regulatory sequence
<220> FEATURE:
<221> NAME/KEY: misc_feature
<222> LOCATION: (1)..(257)
<223> OTHER INFORMATION: 3' untranslated sequence
<220> FEATURE:
<221> NAME/KEY: misc_feature
<222> LOCATION: (258)..(1241)
<223> OTHER INFORMATION: 3' non-transcribed sequence

<400> SEQUENCE: 15
gctaagcagc catcgatcag ctgtcagaag ttggagctaa taataaaagg gatgtggagt      60
gggctacatg tatctcggat ctctctgcga gccacctaat ggtcttgcgt ggcccttaa     120 tctgtatgtt tttgtgtgta agctactgct agctgtttgc accttctgcg tccgtggttg     180
tgtttccgtg ctacctttt atgttttgat ttggatcttg tttgaaaata atcttaccag     240
ctttgggtaa actgtttatt acgtactcta tatagcatat gtgaccgacg acaacggttt     300
cattttagat gatgtgtatg gatgatttct ttccaaaatc acatctttag tataagagca     360
attttaccat ccaataccaa attttatact agaaaatatt ttgggatatc aaaatttatg     420
gtacctccag taccaaatgt tgaatggtaa actttcataa tatacaagtc actctaggat     480
atttaagaca attttagtt ttttcttatt gttgcccttg ttaaatacat gagaaatttt     540
acatcactta aaatgtatca agaggtatca aatttttta atacaaaatt tagtactttc     600
tccgtttata tatgaatgtg gacaatgctt gaaagtctta taacctgaaa ctgaggtagt     660
gtatcgagaa gtacaaaatt ttacactaaa atcccagtac ttactcaata actgtaaaat     720
tactctaaat atgtactccc tctatttcag attataagtt gttttaactt tagtcaaagt     780
```

```
taaactgttt caagtttaac caagtttgta gataaaagta gtaacatatt caacacaaga      840
caaatatatt ataaaaacat attgaattat agatttaatt aaattaattt ggtattgcaa      900
gtattactaa atttgtttat aaatttggtc gaatttaaaa tagtttgact ttaaccaaag      960
tcaaaacaaa ttataatcta aaacaaaggt aatacattgt atcactctca tgaatggatt     1020
gtaacataca ttaatttaat tactatttta gttcttgtgc aaaagttgaa aacgatttat     1080
gtttggaatc tttttgtggt gtatatatat gaaaccattc ctctaccatc cttccccaac     1140
cataatcctc acaaccgtta gccccattgt gatctcaccc agttgctagc ctcttttgtc     1200
accttgtcac agctctcctc cattcattac acaatggcat c                         1241
```

<210> SEQ ID NO 16
<211> LENGTH: 1293
<212> TYPE: DNA
<213> ORGANISM: Oryza sativa
<220> FEATURE:
<221> NAME/KEY: misc_feature
<222> LOCATION: (1)..(1293)
<223> OTHER INFORMATION: OsMADS6 3' regulatory sequence engineered
<220> FEATURE:
<221> NAME/KEY: misc_feature
<222> LOCATION: (1)..(42)
<223> OTHER INFORMATION: engineered sequence
<220> FEATURE:
<221> NAME/KEY: misc_feature
<222> LOCATION: (1)..(299)
<223> OTHER INFORMATION: 3' untranslated sequence
<220> FEATURE:
<221> NAME/KEY: misc_feature
<222> LOCATION: (300)..(1293)
<223> OTHER INFORMATION: 3' non-transcribed sequence
<220> FEATURE:
<221> NAME/KEY: misc_feature
<222> LOCATION: (1283)..(1293)
<223> OTHER INFORMATION: 3' non-transcribed sequence

<400> SEQUENCE: 16

```
acgtgagctc cgcgggcggc cgcactagtc ccacgtgagc tcgctaagca gccatcgatc       60
agctgtcaga agttggagct aataataaaa gggatgtgga gtgggctaca tgtatctcgg      120
atctctctgc gagccaccta atggtcttgc gtggcccttt aatctgtatg ttttgtgtg      180 taagctactg ctagctgttt gcaccttctg cgtccgtggt tgtgtttccg tgctaccttt      240
ttatgttttg atttggatct tgtttgaaaa taatcttacc agctttgggt aaactgttta      300
ttacgtactc tatatagcat atgtgaccga cgacaacggt ttcattttag atgatgtgta      360
tggatgattt ctttccaaaa tcacatcttt agtataagag caattttacc atccaatacc      420
aaattttata ctagaaaata ttttgggata tcaaaattta tggtacctcc agtaccaaat      480
gttgaatggt aaactttcat aatatacaag tcactctagg atatttaaga caattttttag     540 tttttttctta ttgttgccct tgttaaatac atgagaaatt ttacatcact taaaatgtat     600
caagaggtat caaattttttt taatacaaaa tttagtactt tctccgttta tatatgaatg    660
tggacaatgc ttgaaagtct tataacctga aactgaggta gtgtatcgag aagtacaaaa     720
ttttacacta aaatcccagt acttactcaa taactgtaaa attactctaa atatgtactc     780
cctctatttc agattataag tcgttttaac tttagtcaaa gttaaactgt ttcaagttta     840
accaagtttg tagataaaag tagtaacata ttcaacacaa gacaaatata ttataaaaac     900
atattgaatt atagatttaa ttaaattaat tggtattgc aagtattact aaatttgttt     960
ataaatttgg tcgaatttaa aatagtttga ctttaaccaa agtcaaaaca aattataatc    1020
taaaacaaag gtaatacatt gtatcactct catgaatgga ttgtaacata cattaattta    1080
```

-continued

```
attactattt tagttcttgt gcaaaagttg aaaacgattt atgtttggaa tcttttttgtg    1140 gtgtatatat atgaaaccat tcctctacca tccttcccca accataatcc tcacaaccgt    1200
tagccccatt gtgatctcac ccagttgcta gcctcttttg tcaccttgtc acagctctcc    1260
tccattcatt acacaatggc atcggtccgc agt                                  1293

<210> SEQ ID NO 17
<211> LENGTH: 1179
<212> TYPE: DNA
<213> ORGANISM: Oryza sativa
<220> FEATURE:
<221> NAME/KEY: CDS
<222> LOCATION: (109)..(855)
<223> OTHER INFORMATION: OsMADS8

<400> SEQUENCE: 17
gctttcccct ctcttccgct tcgcgagatt ggttgattca tctcgcgatt gatcgagctc     60
gagcggcggt gaggtgaggt ggaggaggag gaggaggagg agatcggg atg ggg aga    117
                                                     Met Gly Arg
                                                       1 ggg agg gtg gag ctg aag agg atc gag aac aag atc aac agg cag gtg    165
Gly Arg Val Glu Leu Lys Arg Ile Glu Asn Lys Ile Asn Arg Gln Val
  5                  10                  15 acg ttc gcg aag cgg agg aat ggg ctc ctc aag aag gcg tac gag ctc    213
Thr Phe Ala Lys Arg Arg Asn Gly Leu Leu Lys Lys Ala Tyr Glu Leu
 20                  25                  30                  35 tcc gtg ctc tgc gac gcc gag gtc gcc ctc atc atc ttc tcc aac cgc    261
Ser Val Leu Cys Asp Ala Glu Val Ala Leu Ile Ile Phe Ser Asn Arg
                 40                  45                  50 ggc aag ctc tac gag ttc tgc agc ggc caa agc atg acc aga act ttg    309
Gly Lys Leu Tyr Glu Phe Cys Ser Gly Gln Ser Met Thr Arg Thr Leu
             55                  60                  65 gaa aga tac caa aaa ttc agt tat ggt ggg cca gat act gca ata cag    357
Glu Arg Tyr Gln Lys Phe Ser Tyr Gly Gly Pro Asp Thr Ala Ile Gln
         70                  75                  80 aac aag gaa aat gag tta gtg caa agc agc cgc aat gag tac ctc aaa    405
Asn Lys Glu Asn Glu Leu Val Gln Ser Ser Arg Asn Glu Tyr Leu Lys
     85                  90                  95 ctg aag gca cgg gtg gaa aat tta cag agg acc caa agg aat ctt ctt    453
Leu Lys Ala Arg Val Glu Asn Leu Gln Arg Thr Gln Arg Asn Leu Leu
100                 105                 110                 115 ggt gaa gat ctt ggg aca ctt ggc ata aaa gag cta gag cag ctt gag    501
Gly Glu Asp Leu Gly Thr Leu Gly Ile Lys Glu Leu Glu Gln Leu Glu
                120                 125                 130 aaa caa ctt gat tca tcc ttg agg cac att aga tcc aca agg aca cag    549
Lys Gln Leu Asp Ser Ser Leu Arg His Ile Arg Ser Thr Arg Thr Gln
            135                 140                 145 cat atg ctt gat cag ctc act gat ctc cag agg agg gaa caa atg ttg    597
His Met Leu Asp Gln Leu Thr Asp Leu Gln Arg Arg Glu Gln Met Leu
        150                 155                 160 tgt gaa gca aat aag tgc ctc aga aga aaa ctg gag gag agc aac cag    645
Cys Glu Ala Asn Lys Cys Leu Arg Arg Lys Leu Glu Glu Ser Asn Gln
    165                 170                 175 ttg cat gga caa gtg tgg gag cac ggc gcc acc cta ctc ggc tac gag    693
Leu His Gly Gln Val Trp Glu His Gly Ala Thr Leu Leu Gly Tyr Glu
180                 185                 190                 195 cgg cag tcg cct cat gcc gtc cag cag gtg cca ccg cac ggt ggc aac    741
Arg Gln Ser Pro His Ala Val Gln Gln Val Pro Pro His Gly Gly Asn
                200                 205                 210
```

```
gga ttc ttc cat tcc ctg gaa gct gcc gcc gag ccc acc ttg cag atc    789
Gly Phe Phe His Ser Leu Glu Ala Ala Ala Glu Pro Thr Leu Gln Ile
            215                 220                 225 ggg ttt act cca gag cag atg aac aac tca tgc gtg act gcc ttc atg    837
Gly Phe Thr Pro Glu Gln Met Asn Asn Ser Cys Val Thr Ala Phe Met
            230                 235                 240 ccg aca tgg cta ccc tga actcctgaag gccgatgcga caaccaataa            885
Pro Thr Trp Leu Pro
            245 aaacggatgt gacgacacag atcaagtcgc accattagat tgatcttctc ctacaagagt    945 gagactagta attccgcgtt tgtgtgctag cgtgttgaaa cttttctgat gtgatgcacg   1005 cacttttaat tattattaag cgttcaagga ctagtatgtg gtataaaagc ccgtacgtga   1065 cagcctatgg ttatatgctg cgcaaaaact acgtatggta cagtgcagtg cctgtacatt   1125 tcataatttg cgggtaaagt ttattgacta tatatccagt gtgtcaaata taat          1179

<210> SEQ ID NO 18
<211> LENGTH: 248
<212> TYPE: PRT
<213> ORGANISM: Oryza sativa

<400> SEQUENCE: 18

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Asn Arg Gly Lys Leu Tyr Glu Phe Cys Ser Gly Gln Ser Met Thr
        50                  55                  60

Arg Thr Leu Glu Arg Tyr Gln Lys Phe Ser Tyr Gly Gly Pro Asp Thr
65                  70                  75                  80

Ala Ile Gln Asn Lys Glu Asn Glu Leu Val Gln Ser Ser Arg Asn Glu
                85                  90                  95

Tyr Leu Lys Leu Lys Ala Arg Val Glu Asn Leu Gln Arg Thr Gln Arg
            100                 105                 110

Asn Leu Leu Gly Glu Asp Leu Gly Thr Leu Gly Ile Lys Glu Leu Glu
        115                 120                 125

Gln Leu Glu Lys Gln Leu Asp Ser Ser Leu Arg His Ile Arg Ser Thr
    130                 135                 140

Arg Thr Gln His Met Leu Asp Gln Leu Thr Asp Leu Gln Arg Arg Glu
145                 150                 155                 160

Gln Met Leu Cys Glu Ala Asn Lys Cys Leu Arg Arg Lys Leu Glu Glu
                165                 170                 175

Ser Asn Gln Leu His Gly Gln Val Trp Glu His Gly Ala Thr Leu Leu
            180                 185                 190

Gly Tyr Glu Arg Gln Ser Pro His Ala Val Gln Val Pro Pro His
        195                 200                 205

Gly Gly Asn Gly Phe Phe His Ser Leu Glu Ala Ala Ala Glu Pro Thr
    210                 215                 220

Leu Gln Ile Gly Phe Thr Pro Glu Gln Met Asn Asn Ser Cys Val Thr
225                 230                 235                 240

Ala Phe Met Pro Thr Trp Leu Pro
                245
```

-continued

```
<210> SEQ ID NO 19
<211> LENGTH: 5229
<212> TYPE: DNA
<213> ORGANISM: Oryza sativa
<220> FEATURE:
<221> NAME/KEY: misc_feature
<222> LOCATION: (1)..(5229)
<223> OTHER INFORMATION: OsMADS8 5' regulatory sequence
<220> FEATURE:
<221> NAME/KEY: misc_feature
<222> LOCATION: (1)..(2303)
<223> OTHER INFORMATION: 5' non-transcribed sequence
<220> FEATURE:
<221> NAME/KEY: misc_feature
<222> LOCATION: (2304)..(2569)
<223> OTHER INFORMATION: exon
<220> FEATURE:
<221> NAME/KEY: misc_feature
<222> LOCATION: (2597)..(5203)
<223> OTHER INFORMATION: intron
<220> FEATURE:
<221> NAME/KEY: misc_feature
<222> LOCATION: (5204)..(5229)
<223> OTHER INFORMATION: exon

<400> SEQUENCE: 19
ccattttttg cgaaatgcca atcctggca  tgcctaagct gacctgagct tgtagttttc     60
aaacgaaccg tgttaattgt ggtatataac acattgggtt ggctactgta tcgtacataa    120
ttttgttggg gttatttctg catgcgtata cgtacggatt agttgtaatt aagaggaaaa    180
acatgcatgt ataatataga tataccctagc atgcaccatt atatacttat taatctaagc    240
tttaaagtgc aaatgatact acatattgaa cattcaactt tattgtattg ataaattgaa    300
ccggatatat ccacaagcac aaaatttgca atgcacttca aaattaatgt aatctttgca    360
cgctactccc tacatttcat attataagtt gatttgactt ttttttttcaa gtttataaaa    420 aaaattagca acatctaaaa tatcaaatta gtttcactta atctaacatt gaatatattt    480
agatactacg tttgttttat cttaaaaatg ttagtatgtt ttttttataa acttggtcag    540
cctttgaaat gttggactag aaaaaaaggt aaaaaaaatt ataatgctga ataagccaca    600
atttaaaaag tttacaggga cggtttaatt cattgacatt tcacatatac atagcacatg    660
tcaaattcat atgttaactt ttctttttat aaactggaca ccccgtgcca acagtcaacc    720
cctaattaaa ttaaccacaa catgaataca tcattaattt tataacatat actagttatt    780
ttgcttttca tatatctccc cctcttgcta atttgagttc ccagcatgca tggatactaa    840
ttaacttaac caaaattagt tagcctgcag cctaatttgt ccatctctag ctagctagtt    900
tgcacttaac atctgtgata cgttaccaca ccaaagttac atacacatta atgattaatc    960
ctttgatcag ttcctatata tcccaggtag aatatatatc gatctcttca gaatcacgac   1020
caattaggta aaatgaaaga acatacactc ctgcctagcc aagacttcaa accttacaca   1080
cacatatata tctactactg caagcactgc aacggcaaag ttctctgcag gcaaagagat   1140
ataccgatcg aagaagcctc tctctatcca aacccaaaca gctccatttt gtctacacga   1200
actatggcaa cttggcaacc acatcgctag ctagctagat atatactatg ctaccttggt   1260
tcattttgct gctttgattt gcaactgcaa cccaagagaa aagttgtaag ggtctgtatg   1320
gggattttct gaccgctgta tcttctctca aaatcatatt aatcctctct acatagtcta   1380 gttttttcatc caaattctca aaagctctaa ttatagaatc taaaaaatta actagaaaac   1440
agaagctgag aaatccacat tctccatatt ctcagaagct tgatactaac tagctatttc   1500
ccaaaatctt aggccttatt tagttgggga aaattttggt gtttgtttgt cacattggat   1560
```

```
atacggacac acattagtat taaatgtggt acaataacaa aacaaattac agattccgtc    1620
aaaaaactgc aagacaaatt tattgagctc aattaatccg tcattagcaa atgtttactg    1680
cagcaccaca ttgtcaaatc aggcgcaatt agacttaaaa gattcgtctc gtaatttaca    1740
cgcaaattgt gtaactggtt ttttttccac atttaatact ccatgcatgt atttaaatat    1800
tcgatgtgat gggtgaaaat tgtttatttt ggaaactaaa caaagcctta agctctccca    1860
acagatcacc caccggctcc tagtggacac aagaagggta ttttccccga aacccgaaaa    1920
ctccgaggtt tcaagtgcaa agcgcccaa ctctactcac ttttccccag cttttccgcg     1980
cttaatttct cgacctgtcg aatcctcagt cgccaccgct gcgtcgacga ggagagagag    2040
agagagagag agagagagag aaaatccaaa gcaatcagtg agagacgcat tgaattgggt    2100
cggagattag tgcgaaatta acctagatag ctttgccttt gcgtacgatg gatcgatcga    2160
ggccgcctag ggttccgcgt cgttccacca ccttgccgga aatggcaatg ccgggtagcc    2220
cccaccgccg ctgcccaccc tctccccctt ccctttttaa accctcatc cccttccccc      2280 tcctcctcct cctcctcgcc ttagcttccc cctctctttc gcttcgcgag attggttgat    2340
tcatctcgcg attgatcgag ctcgagcggc ggtgaggtga ggtggaggag gaggaggagg    2400
aggagatcgg gatggggaga gggagggtgg agctgaagag gatcgagaac aagatcaaca    2460
ggcaggtgac gttcgcgaag cggaggaatg ggctgctcaa gaaggcgtac gagctctccg    2520
tgctctgcga cgccgaggtc gccctcatca tcttctccaa ccgcggcaag ctctacgagt    2580
tctgcagcgg ccaaaggtat atatacatgg acgcactggg cgcgcgcctc gatctgctat    2640
agctagatcg gtagctgctt gcaacgtagc tagctagggt ttcttgcgcg cgcctgcgcc    2700
tccagatctg gagcgcacga tggttttgtg aacttcttgg tggcgatttt gcggggatct    2760
ggggctgcac atggtggatc tgcgagtgtg ctcgtgtttt ggtgagtttt gggagggttt    2820
gggagaagga agttggtgga attctgtggg aataattagg gttttgttc gttcgatcgg     2880 gtgctagcta gcgtaatagg gagtggtgaa atacgtagat ctgagggttt ctgatcccgt    2940
ggtagtagtg gttttgagat ggcgcgctta atggttttga gtttggttta attgcgatta    3000
atttatgtgc atgcatggga tgggacattc aggatttaag cctggatcag caagtcgatt    3060
tttacggaga aaattaatcg ttggaagctt cgaatcttaa ttttatcgat ctcctaatgg    3120
agggtatgcg agtttcgaat tcccttggga tctgttttt tcctcaattt ttagtttttt     3180 gagggcaat ttttttagg gtatatatga tttttttttt ttggggggg ggggtgtgt        3240 gaagggatca tgcatatcat tagccatgta ccggatgtgt gtctaaacaa acgttcactg    3300
catgaattcc acggtttgga ggcagcatac cttacaagat ttgggggttt cacttaagat    3360
tttgtctctt tgttttttta agggatggcc gcggggagt attgttttc aagtgagtta      3420 tggttgcatc attaaaggca acatcaataa atataaagtc tgtttctcct gagataagta    3480
tatgaaaaat catatactac tatatatata attgtctttc agaaacacag agcgtctgat    3540
tggctaggca taattcacaa gccgcatata agctagttga attgattttg aattagaaaa    3600
catttttttt cgggggaag aaaacatttg gtattgtgtt tagagataaa caattagtta     3660
gggtagataa gtcaggcatt catgagcttc atttcatatt tgaatcatac attttccaaa    3720
ctttagaagg ttaaattttc ttgctcattg tattgcactg atcattttaa taatatcttc    3780
tatagtgaat attacatcat tatatatttt agataatgat tacattatta tatgctccgt    3840
tgcagaaaaa accaactttt ttgccaaacc tggacatata taggctatgt ccagatttat    3900
agctagaagt tagggcctca tctttaccc tatgaattat aagccaatat caaatttga      3960
```

```
atttcgaaac ttgatttaga agttgatttt taatgttttg tcaatgtaga ttgtttttca    4020
gcattaactt ttaattcgct aaagacacat atacaatttt actcacaaat tatattttgg    4080
ttgctaataa gccgttatgg cttataatca gccgtaagta tatggggact ttagcattct    4140
ttttcttttt ttatggaggg agtacatgct tgccaatttt tatagttatg tttaaatggt    4200
ttccattata cctaagttac taaattaaaa ttaatacgcc tataaaattc taacattaaa    4260
tatattcaca ataagagta catgatttca ttgaccaggg aattcaattt ggatatgggg    4320
tgagtgaaac atccctcctc tgctcctcgg aagaaatcct gcaagggagt acacaatatt    4380
cctaggactc acttgagtat ctgcagggta cagttagtga cagctttcga ttgtcattcg    4440
attggtctcc tcagctctcg tagctgagct gtcagtacag aagattggtc ttcatcagat    4500
gtctcttcta gttctagcta gagctagttc agtggagtat tttatgccga caattgata     4560 ctcaacgtgt actgtagatc cttttcagaa atctgaattc acgacttgtt taaacaaagg    4620
ctgtgtttgg atccaaactt cagtcctttt ccattacatc aacctgtcat atacacacaa    4680
cattttagtc atatcatctc caatttcaac caaaatctaa actttgcgtt gaactaaaca    4740
cagccaaaag gtcactaaat tgacgcggta gaggggggg ggtgagcatt atagctgtag     4800
tagtagtctg cgtgaagtta tgccatttca ttgtgtgtcg tctgaacttg atatctctct    4860
ttaaagagtg tactccattt tctttacaaa aagtggcctc taggttgata tcatggacat    4920
atataaaatt ataaatcaac ttgaaactac cgatgcaaga attaagataa aacgttattg    4980
tttcttagaa attgtctcca attatgcaag caccttcatc cgtgtcatgg agctaatgtt    5040
catgttttgt gggaaacaag attttcatc tactaattaa tcgatgtggt ccccggaaaa     5100
gaatgtgccc tagattgtta gtatttagtt atgggcgaac tatatatgtt cctttatttc    5160 gttttccat aaacatagcc atttgtgttt ttgaaacttg cagcatgacc agaactttgg     5220
aaagatacc                                                            5229

<210> SEQ ID NO 20
<211> LENGTH: 5226
<212> TYPE: DNA
<213> ORGANISM: Oryza sativa
<220> FEATURE:
<221> NAME/KEY: misc_feature
<222> LOCATION: (1)..(5226)
<223> OTHER INFORMATION: OsMADS8 5' regulatory sequence engineered
<220> FEATURE:
<221> NAME/KEY: misc_feature
<222> LOCATION: (1)..(15)
<223> OTHER INFORMATION: engineered sequence
<220> FEATURE:
<221> NAME/KEY: misc_feature
<222> LOCATION: (1)..(2315)
<223> OTHER INFORMATION: 5' non-transcribed sequence
<220> FEATURE:
<221> NAME/KEY: misc_feature
<222> LOCATION: (2316)..(2605)
<223> OTHER INFORMATION: exon
<220> FEATURE:
<221> NAME/KEY: misc_feature
<222> LOCATION: (2420)..(2425)
<223> OTHER INFORMATION: engineered sequence
<220> FEATURE:
<221> NAME/KEY: misc_feature
<222> LOCATION: (2606)..(5212)
<223> OTHER INFORMATION: intron
<220> FEATURE:
<221> NAME/KEY: misc_feature
<222> LOCATION: (5213)..(5226)
<223> OTHER INFORMATION: exon
<220> FEATURE:
```

<221> NAME/KEY: misc_feature
<222> LOCATION: (5214)..(5214)
<223> OTHER INFORMATION: mutagenized base pair
<220> FEATURE:
<221> NAME/KEY: misc_feature
<222> LOCATION: (5221)..(5226)
<223> OTHER INFORMATION: engineered sequence

<400> SEQUENCE: 20

```
cctgcaggcg gaccgttttt tgcgaaatgc caaatcctgg catgcctaag ctgacctgag      60
cttgtagttt tcaaacgaac cgtgttaatt gtggtatata acacattggg ttggctactg     120
tatcgtacat aattttgttg gggttatttc tgcatgcgta tacgtacgga ttagttgtaa     180
ttaagaggaa aaacatgcat gtataatata gatataccta gcatgcacca ttatatactt     240
attaatctaa gctttaaagt gcaaatgata ctacatattg aacattcaac tttattgtat     300
tgataaattg aaccggatat atccacaagc acaaaatttg caatgcactt caaaattaat     360
gtaatctttg cacgctactc cctacatttc atattataag ttgatttgac ttttttttc      420
aagtttataa aaaaaattag caacatctaa aatatcaaat tagtttcact taatctaaca     480
ttgaatatat ttagatacta cgtttgtttt atcttaaaaa tgttagtatg tttttttat      540
aaacttggtc agcctttgaa atgttggact agaaaaaag gtaaaaaaaa ttataatgct      600
gaataagcca caatttaaaa agtttacagg gacggtttaa ttcattgaca tttcacatat     660
acatagcaca tgtcaaattc atatgttaac ttttcttttt ataaactgga caccccgtgc     720
caacagtcaa cccctaatta aattaaccac aacatgaata catcattaat tttataacat     780
atactagtta ttttgctttt catatatctc cccctcttgc taatttgagt tcccagcatg     840
catggatact aattaactta accaaaatta gttagcctgc agcctaattt gtccatctct     900
agctagctag tttgcactta acatctgtga tacgttacca caccaaagtt acatacacat     960
taatgattaa tcctttgatc agttcctata tatcccaggt agaatatata tcgatctctt    1020
cagaatcacg accaattagg taaaatgaaa gaacatacac tcctgcctag ccaagacttc    1080
aaaccttaca cacacatata tatctactac tgcaagcact gcaacggcaa agttctctgc    1140
aggcaaagag atataccgat cgaagaagcc tctctctatc caaacccaaa cagctccatt    1200
ttgtctacac gaactatggc aacttggcaa ccacatcgct agctagctag atatatacta    1260
tgctaccttg gttcattttg ctgctttgat ttgcaactgc aacccaagag aaagttgta     1320
agggtctgta tggggatttt ctgaccgctg tatcttctct caaaatcata ttaatcctct    1380
ctacatagtc tagtttttca tccaaattct caaaagctct aattatagaa tctaaaaaat    1440
taactagaaa acagaagctg agaaatccac attctccata ttctcagaag cttgatacta    1500
actagctatt tcccaaaatc ttaggcctta tttagttggg gaaaattttt gggtttgttt    1560
gtcacattgg atatacggac acacattagt attaaatgtg gtacaataac aaaacaaatt    1620
acagattccg tcaaaaaact gcaagacaaa tttattgagc tcaattaatc cgtcattagc    1680
aaatgtttac tgcagcacca cattgtcaaa tcaggcgcaa ttagacttaa aagattcgtc    1740
tcgtaattta cacgcaaatt gtgtaactgg ttttttttcc acatttaata ctccatgcat    1800
gtatttaaat attcgatgtg atgggtgaaa attgtttatt ttggaaacta aacaaagcct    1860
taagctctcc caacagatca cccaccggct cctagtggac acaagaaggg tattttttcc    1920
gaaacccgaa aactccgagg tttcaagtgc aaaagcgccc aactctactc acttttcccc    1980
agcttttccg cgcttaattt ctcgacctgt cgaatcctca gtcgccaccg ctgcgtcgac    2040
gaggagagag agagagagag agagagagag agaaaatcca aagcaatcag tgagagacgc    2100
```

-continued

```
attgaattgg gtcggagatt agtgcgaaat taacctagat agctttgcct ttgcgtacga    2160
tggatcgatc gaggccgcct agggttccgc gtcgttccac caccttgccg gaaatggcaa    2220
tgccgggtag cccccaccgc cgctgcccac cctctccccc ttcccttttt aaaccnctca    2280
tccccttccc cctcctcctc ctcctcctcg ccttagcttt cccctctctt tcgcttcgcg    2340
agattggttg attcatctcg cgattgatcg agctcgagcg gcggtgaggt gaggtggagg    2400
aggaggagga ggagatcggg tcgacgagag ggagggtgga gctgaagagg atcgagaaca    2460
agatcaacag gcaggtgacg ttcgcgaagc ggaggaatgg gctgctcaag aaggcgtacg    2520
agctctccgt gctctgcgac gccgaggtcg ccctcatcat cttctccaac cgcggcaagc    2580
tctacgagtt ctgcagcggc caaaggtata tatacatgga cgcactgggc gcgcgcctcg    2640
atctgctata gctagatcgg tagctgcttg caacgtagct agctagggtt tcttgcgcgc    2700
gcctgcgcct ccagatctgg agcgcacgat ggttttgtga acttcttggt ggcgattttg    2760
cggggatctg ggctgcaca tggtggatct gcgagtgtgc tcgtgttttg gtgagttttg    2820
ggagggtttg ggagaaggaa gttggtggaa ttctgtggga ataattaggg ttttgttcg    2880
ttcgatcggg tgctagctag cgtaatagg agtggtgaaa tacgtagatc tgagggtttc    2940
tgatcccgtg gtagtagtgg ttttgagatg gcgcgcttaa tggttttgag tttggtttaa    3000
ttgcgattaa tttatgtgca tgcatgggat gggacattca ggatttaagc ctggatcagc    3060
aagtcgattt ttacggagaa aattaatcgt tggaagcttc gaatcttaat tttatcgatc    3120
tcctaatgga gggtatgcga gtttcgaatt cccttgggat ctgttttttt cctcaatttt    3180
tagttttttg aggggcaatt tttttaggg tatatatgat ttttttttt tggggggggg     3240
ggggtgtgtg aagggatcat gcatatcatt agccatgtac cggatgtgtg tctaaacaaa    3300
cgttcactgc atgaattcca cggtttggag gcagcatacc ttacaagatt tggggggttc    3360
acttaagatt ttgtctcttt gttttttta gggatggccg cggggagta ttgttttca     3420
agtgagttat ggttgcatca ttaaaggcaa catcaataaa tataaagtct gtttctcctg    3480
agataagtat atgaaaaatc atatactact atatatataa ttgtctttca gaaacacaga    3540
gcgtctgatt ggctaggcat aattcacaag ccgcatataa gctagttgaa ttgatttga     3600
attagaaaac atttttttc ggggggaaga aaacatttgg tattgtgttt agagataaac     3660
aattagttag ggtagataag tcaggcattc atgagcttca tttcatattt gaatcataca    3720
ttttccaaac tttagaaggt taaattttct tgctcattgt attgcactga tcattttaat    3780
aatatcttct atagtgaata ttacatcatt atatatttta gataatgatt acattattat    3840
atgctccgtt gcagaaaaaa ccaacttttt tgccaaacct ggacatatat aggctatgtc    3900
cagatttata gctagaagtt agggcctcat cttttaccct atgaattata agccaatatc    3960
aaatttgaa tttcgaaact tgatttagaa gttgattttt aatgttttgt caatgtagat    4020
tgttttcag cattaacttt taattcgcta aagacacata taacaatttta ctcacaaatt    4080
atattttggt tgctaataag ccgttatggc ttataatcag ccgtaagtat atgggactt    4140
tagcattctt tttctttttt tatggaggga gtacatgctt gccaattttt atagttatgt    4200
ttaaatggtt tccattatac ctaagttact aaattaaaat taatacgcct ataaaattct    4260
aacattaaat atattcacaa ataagagtac atgatttcat tgaccaggga attcaatttg    4320
gatatggggt gagtgaaaca tccctcctct gctcctcgga agaaatcctg caagggagta    4380
cacaatattc ctaggactca cttgagtatc tgcagggtac agttagtgac agctttcgat    4440
```

```
tgtcattcga ttggtctcct cagctctcgt agctgagctg tcagtacaga agattggtct    4500
tcatcagatg tctcttctag ttctagctag agctagttca gtggagtatt ttatgccgac    4560
aaattgatac tcaacgtgta ctgtagatcc ttttcagaaa tctgaattca cgacttgttt    4620
aaacaaaggc tgtgtttgga tccaaacttc agtccttttc cattacatca acctgtcata    4680
tacacacaac attttagtca tatcatctcc aatttcaacc aaaatctaaa ctttgcgttg    4740
aactaaacac agccaaaagg tcactaaatt gacgcggtag aggggggggg gtgagcatta    4800
tagctgtagt agtagtctgc gtgaagttat gccatttcat tgtgtgtcgt ctgaacttga    4860
tatctctctt taaagagtgt actccatttt ctttacaaaa agtggcctct aggttgatat    4920
catggacata tataaaatta taaatcaact tgaaactacc gatgcaagaa ttaagataaa    4980
acgttattgt ttcttagaaa ttgtctccaa ttatgcaagc accttcatcc gtgtcatgga    5040
gctaatgttc atgttttgtg ggaaacaaga ttttcatct actaattaat cgatgtggtc     5100
cccggaaaag aatgtgccct agattgttag tatttagtta tgggcgaact atatatgttc    5160
ctttatttcg ttttccata aacatagcca tttgtgtttt tgaaacttgc agcttgacca     5220
ccatgg                                                               5226

<210> SEQ ID NO 21
<211> LENGTH: 108
<212> TYPE: DNA
<213> ORGANISM: Oryza sativa
<220> FEATURE:
<221> NAME/KEY: misc_feature
<222> LOCATION: (1)..(108)
<223> OTHER INFORMATION: OsMADS8 5' untranslated leader sequence native

<400> SEQUENCE: 21
gctttcccct ctcttccgct tcgcgagatt ggttgattca tctcgcgatt gatcgagctc      60
gagcggcggt gaggtgaggt ggaggaggag gaggaggagg agatcggg                  108

<210> SEQ ID NO 22
<211> LENGTH: 300
<212> TYPE: DNA
<213> ORGANISM: Oryza sativa
<220> FEATURE:
<221> NAME/KEY: misc_feature
<222> LOCATION: (1)..(300)
<223> OTHER INFORMATION: OsMADS8 5' untranslated leader sequence
      engineered
<220> FEATURE:
<221> NAME/KEY: misc_feature
<222> LOCATION: (105)..(110)
<223> OTHER INFORMATION: engineered sequence
<220> FEATURE:
<221> NAME/KEY: misc_feature
<222> LOCATION: (292)..(292)
<223> OTHER INFORMATION: mutagenized base pair
<220> FEATURE:
<221> NAME/KEY: misc_feature
<222> LOCATION: (299)..(299)
<223> OTHER INFORMATION: engineered sequence

<400> SEQUENCE: 22
gctttcccct ctctttcgct tcgcgagatt ggttgattca tctcgcgatt gatcgagctc      60
gagcggcggt gaggtgaggt ggaggaggag gaggaggaga tcgggtcgac gagagggagg    120
gtggagctga agaggatcga gaacaagatc aacaggcagg tgacgttcgc gaagcggagg    180
aatgggctgc tcaagaaggc gtacgagctc tccgtgctct cgacgccga ggtcgccctc     240 atcatcttct ccaaccgcgg caagctctac gagttctgca gcggccaaag cttgaccacc    300
```

<210> SEQ ID NO 23
<211> LENGTH: 2034
<212> TYPE: DNA
<213> ORGANISM: Oryza sativa
<220> FEATURE:
<221> NAME/KEY: misc_feature
<222> LOCATION: (1)..(2034)
<223> OTHER INFORMATION: OsMADS8 3' regulatory sequence
<220> FEATURE:
<221> NAME/KEY: misc_feature
<222> LOCATION: (1)..(324)
<223> OTHER INFORMATION: 3' untranslated sequence
<220> FEATURE:
<221> NAME/KEY: misc_feature
<222> LOCATION: (325)..(2034)
<223> OTHER INFORMATION: 3' non-transcribed sequence

<400> SEQUENCE: 23

```
actcctgaag gccgatgcga caaccaataa aaacggatgt gacgacacag atcaagtcgc        60
accattagat tgatcttctc ctacaagagt gagactagta attccgtgtt tgtgtgctag       120
cgtgttgaaa cttttctgat gtgatgcacg cacttttaat tattattaag cgttcaagga       180
ctagtatgtg gtataaaagg ccgtacgtga cagcctatgg ttatatgctg cacaaaaact       240
acgtatggta cagtgcagtg cctgtacatt tcataatttg cggtaaagtt tattgactat       300
atatccagtg tgtcaaatat aataaaaatgt cgaggtttaa ttaccatgct catgtgcatt      360
ctaggttctt tatatatagg agtattaggt taactgatta gttgttgtac atcattgtct       420
aaaaaaatag ctgtcgttgt acataaattg agcatgctgg tctgcatgaa aattaaggaa       480
aagaaacatg caagtagccc aggtagttgg gctgtcaagc agtcgtactt gtccgagtcg       540
cagatagtta gttgacccga aactgtgatt gcgaacgtac gagcgaaaat gtagatgcag       600
gcatttcaac ttgagtgatt tgcttttttat tcatatatat ggttcatttt ttttaaagat      660
ggcttcgact ggatctcgtc ttcgttaagc atgcgtccag gaccaggagt acatgcattt       720
tgcattcagc cctaaccaat acttttttacc aattaaagag cagagcaggc acgacacgca     780
tagacaacgg acatggatct tcgcagtact acatttgcag tagcagtggc tgataggtga       840
acccgatcct acatgtcagt ggctgctact gtagacaatc tccactgata gacaacgggt       900
acaactcgta gtattaattc aaacgccaaa tgcattaatg gtagtttgct tattagtact       960
agtttgcata acgaagcgtg tatatatatt tatacttcct ccgttttatg ttttaatttg      1020
gacttgtcgt tccagaaaat cgtacgaagt catagcaaat tacattgcaa ttcttcttaa      1080
ttacatatta atcatgtttt caaagtaaga attagaattc cttataagag actactacta      1140
gcatggttgt gttagagaaa ggtaagaaga aaaaagcatt taaaaagtga tttggaatat      1200
gagaatgaca agtgttttgg cataactttt aaatggtaga acgacaagta atttaaaaca      1260
tacaaagtac tagtcccttc atttcatatt ataattcgct tcgactttttt ctaagtcaaa     1320
cattgttaaa tttgactagg ttttatagaa gaaaagtaac atttttaaacg tcaaattagt    1380
ttcattaaat ctagcatttg aatatattttt gataatatgt ttgttttgtg gtaaaaatac    1440
tattatattt ttctacaaat ctagtcaaac gtaaaaaaaa agtttgacta ggaaaaaagt     1500
caaaacgatt tataatataa aacataagag cacccgcaat agtaaagtaa ggtgctctct      1560
gtaaaacatg tacatctcag caatagacta gattaatagt aaaccacctt aatagtatgt      1620
ctacttgggt atctatagct ctctaatata ttgcctcgtt tttctctata gactatcttc      1680
acattagtag atagctttgc tctcttttt catctcttcc aagtaggaaa atatgctgac       1740
atggatctct tgtagagagt ttatagataa ccattgtggg tgccctaagt agtactatct      1800
```

-continued

```
tttcttcctg tccaaaaaat ataaagcact tttgagcttc tatacgtaga tttaaatgag    1860
aaatggctat atttgattga gataagtgag taggtaaacg ctctatttaa gataaattgt    1920
aaagttaata tattttgacg gaggggaagt agcatttatg aaaccctagt agagctacgc    1980
ttcgttgacc acactactcg aaataaacat gatattttgt catgatcgat gact          2034
```

```
<210> SEQ ID NO 24
<211> LENGTH: 2051
<212> TYPE: DNA
<213> ORGANISM: Oryza sativa
<220> FEATURE:
<221> NAME/KEY: misc_feature
<222> LOCATION: (1)..(2051)
<223> OTHER INFORMATION: OsMADS8 3' regulatory sequence engineered
<220> FEATURE:
<221> NAME/KEY: misc_feature
<222> LOCATION: (1)..(8)
<223> OTHER INFORMATION: engineered sequence
<220> FEATURE:
<221> NAME/KEY: misc_feature
<222> LOCATION: (1)..(323)
<223> OTHER INFORMATION: 3' untranslated sequence
<220> FEATURE:
<221> NAME/KEY: misc_feature
<222> LOCATION: (324)..(2051)
<223> OTHER INFORMATION: 3' non-transcribed sequence
<220> FEATURE:
<221> NAME/KEY: misc_feature
<222> LOCATION: (2042)..(2047)
<223> OTHER INFORMATION: engineered sequence

<400> SEQUENCE: 24
```

```
gcggccgcag gccgatgcga caaccaataa aaacggatgt gacgacacag atcaagtcgc     60
accattagat tgatcttctc ctacaagagt gagactagta attccgtgtt tgtgtgctag    120
cgtgttgaaa cttttctgat gtgatgcacg cacttttaat tattattaag cgttcaagga    180
ctagtatgtg gtataaaagg ccgtacgtga cagcctatgg ttatatgctg cacaaaaact    240
acgtatggta cagtgcagtg cctgtacatt tcataatttg cggtaaagtt tattgactat    300
atatccagtg tgtcaaatat aataaaatgt cgaggtttaa ttaccatgct catgtgcatt    360
ctaggttctt tatatatagg agtattaggt taactgatta gttgttgtac atcattgtct    420
aaaaaaatag ctgtcgttgt acataaaattg agcatgctgg tctgcatgaa aattaaggaa    480
aagaaacatg caagtagccc aggtagttgg gctgtcaagc agtcgtactt gtccgagtcg    540
cagatagtta gttgacccga aactgtgatt gcgaacgtac gagcgaaaat gtagatgcag    600
gcatttcaac ttgagtgatt tgcttttttat tcatatatat ggttcatttt ttttaaagat    660
ggcttcgact ggatctcgtc ttcgttaagc atgcgtccag gaccaggagt acatgcattt    720
tgcattcagc cctaaccaat acttttttacc aattaaagag cagagcaggc acgacacgca    780
tagacaacgg acatggatct tcgcagtact acatttgcag tagcagtggc tgataggtga    840
acccgatcct acatgtcagt ggctgctact gtagacaatc tccactgata gacaacgggt    900
acaactcgta gtattaattc aaacgccaaa tgcattaatg gtagtttgct tattagtact    960
agtttgcata acgaagcgtg tatatatatt tatacttcct ccgttttatg ttttaatttg   1020
gacttgtcgt tccagaaaat cgtacgaagt catagcaaat tacattgcaa ttcttcttaa   1080
ttacatatta atcatgtttt caaagtaaga attagaattc cttataagag actactacta   1140
gcatggttgt gttagagaaa ggtaagaaga aaaagcatt taaaaagtga tttggaatat    1200
gagaatgaca agtgttttgg cataactttt aaatggtaga acgacaagta atttaaaaca   1260
```

```
tacaaagtac tagtcccttc atttcatatt ataattcgct tcgactttt  ctaagtcaaa   1320 cattgttaaa tttgactagg ttttatagaa gaaaagtaac attttaaacg tcaaattagt   1380
ttcattaaat ctagcatttg aatatatttt gataatatgt ttgttttgtg gtaaaaatac   1440
tattatattt ttctacaaat ctagtcaaac gtaaaaaaaa agtttgacta ggaaaaaagt   1500
caaaacgatt tataatataa aacataagag cacccgcaat agtaaagtaa ggtgctctct   1560
gtaaaacatg tacatctcag caatagacta gattaatagt aaaccacctt aatagtatgt   1620
ctacttgggt atctatagct ctctaatata ttgcctcgtt tttctctata gactatcttc   1680
acattagtag atagctttgc tctctttttt catctcttcc aagtaggaaa atatgctgac   1740
atggatctct tgtagagagt ttatagataa ccattgtggg tgccctaagt agtactatct   1800
tttcttcctg tccaaaaaat ataaagcact tttgagcttc tatacgtaga tttaaatgag   1860
aaatggctat atttgattga gataagtgag taggtaaacg ctctatttaa gataaattgt   1920
aaagttaata tattttgacg gaggggaagt agcatttatg aaaccctagt agagctacgc   1980
ttcgttgacc acactactcg aaataaacat gatattttgt catgatcgat gactcggtcc   2040
gcccgggacg t                                                        2051

<210> SEQ ID NO 25
<211> LENGTH: 1193
<212> TYPE: DNA
<213> ORGANISM: Oryza sativa
<220> FEATURE:
<221> NAME/KEY: CDS
<222> LOCATION: (60)..(872)
<223> OTHER INFORMATION: OsMADS13

<400> SEQUENCE: 25
gaagaagcta gtttcctgcg ccgacctct  tgcttctcac ttttgagag caagaagac     59 atg ggg agg ggc agg att gag atc aag agg atc gag aac acg aca agc    107
Met Gly Arg Gly Arg Ile Glu Ile Lys Arg Ile Glu Asn Thr Thr Ser
1               5                   10                  15 cgc cag gtg acc ttc tgc aag cgc cgc aac ggg ctt ctc aag aag gcg    155
Arg Gln Val Thr Phe Cys Lys Arg Arg Asn Gly Leu Leu Lys Lys Ala
                20                  25                  30 tat gag ctc tcc gtc ctc tgc gat gcc gag gtg gct ctc atc gtc ttc    203
Tyr Glu Leu Ser Val Leu Cys Asp Ala Glu Val Ala Leu Ile Val Phe
        35                  40                  45 tcc agc cgt ggc cgc ctc tac gag tac tcc aac aac aac aat gtg aag    251
Ser Ser Arg Gly Arg Leu Tyr Glu Tyr Ser Asn Asn Asn Asn Val Lys
    50                  55                  60 gct aca att gac agg tac aag aag gcg cat gct tgt ggc tca act tct    299
Ala Thr Ile Asp Arg Tyr Lys Lys Ala His Ala Cys Gly Ser Thr Ser
65                  70                  75                  80 ggt gca cct ctc ata gag gtc aat gct cag caa tac tac cag cag gag    347
Gly Ala Pro Leu Ile Glu Val Asn Ala Gln Gln Tyr Tyr Gln Gln Glu
                85                  90                  95 tct gcc aaa ctg cgc cac cag att cag atg ctg caa aac acc aac aag    395
Ser Ala Lys Leu Arg His Gln Ile Gln Met Leu Gln Asn Thr Asn Lys
            100                 105                 110 cac ctg gtt ggc gat aat gtg agc aac ctg tca ctg aag gag ctg aag    443
His Leu Val Gly Asp Asn Val Ser Asn Leu Ser Leu Lys Glu Leu Lys
        115                 120                 125 caa ctt gaa agc cgc ctg gag aaa ggc att gca aag atc aga gcc agg    491
Gln Leu Glu Ser Arg Leu Glu Lys Gly Ile Ala Lys Ile Arg Ala Arg
    130                 135                 140 aag aat gaa ctg ctg gct tca gag atc aat tac atg gcc aaa agg gag    539
Lys Asn Glu Leu Leu Ala Ser Glu Ile Asn Tyr Met Ala Lys Arg Glu
```

```
Lys Asn Glu Leu Leu Ala Ser Glu Ile Asn Tyr Met Ala Lys Arg Glu
145                 150                 155                 160 att gag ctt cag aac gac aac atg gac ctc aga acc aag att gct gag       587
Ile Glu Leu Gln Asn Asp Asn Met Asp Leu Arg Thr Lys Ile Ala Glu
                165                 170                 175 gag gag cag cag ctg cag cag gtg acg gtg gcc cgg tcg gcc gcc atg       635
Glu Glu Gln Gln Leu Gln Gln Val Thr Val Ala Arg Ser Ala Ala Met
            180                 185                 190 gag ctg cag gct gcg gcg gcg cag cag cag cag aat ccg ttc               683
Glu Leu Gln Ala Ala Ala Ala Gln Gln Gln Gln Asn Pro Phe
        195                 200                 205 gcg gtg gcg gcg gcg cag ttg gac atg aag tgc ttc ttc ccg ttg aac       731
Ala Val Ala Ala Ala Gln Leu Asp Met Lys Cys Phe Phe Pro Leu Asn
    210                 215                 220 ctg ttc gag gcg gcg gcg cag gtg cag gcc gtg gcg gcg cag cgc cag       779
Leu Phe Glu Ala Ala Ala Gln Val Gln Ala Val Ala Ala Gln Arg Gln
225                 230                 235                 240 cag atc atc ccc acc gag ctc aac ctc ggc tac cac cac cac ctc gcc       827
Gln Ile Ile Pro Thr Glu Leu Asn Leu Gly Tyr His His His Leu Ala
                245                 250                 255 att ccc ggc gcc acc gcc gcc gac gcg ccg cct cct cac ttc tga           872
Ile Pro Gly Ala Thr Ala Ala Asp Ala Pro Pro Pro His Phe
            260                 265                 270 acctcatgaa cttcatttg caccggcctg ctgccatgga tatgatgatc agctcatctt       932
ctatatctta tgctgttatg cagacagaca ctgatgtggc tatatatata gtatttgtgt       992
gctgctgcat tttgttaatc ccttataaat tgctacttaa ttatctcatg gagaattgga     1052
gagaccaaat gggcagagct agctagttag ctgtgcccaa ttaagaagct aaatctatca     1112
gaagtgtgta ctgatgagtg atgagtattt tcttcatttt gggatcaaat taaactaagt     1172
aaaacatata tattgactaa a                                               1193
```

<210> SEQ ID NO 26
<211> LENGTH: 270
<212> TYPE: PRT
<213> ORGANISM: Oryza sativa

<400> SEQUENCE: 26

```
Met Gly Arg Gly Arg Ile Glu Ile Lys Arg Ile Glu Asn Thr Thr Ser
1               5                   10                  15

Arg Gln Val Thr Phe Cys Lys Arg Arg Asn Gly Leu Leu Lys Lys Ala
                20                  25                  30

Tyr Glu Leu Ser Val Leu Cys Asp Ala Glu Val Ala Leu Ile Val Phe
            35                  40                  45

Ser Ser Arg Gly Arg Leu Tyr Glu Tyr Ser Asn Asn Asn Asn Val Lys
        50                  55                  60

Ala Thr Ile Asp Arg Tyr Lys Lys Ala His Ala Cys Gly Ser Thr Ser
65                  70                  75                  80

Gly Ala Pro Leu Ile Glu Val Asn Ala Gln Tyr Tyr Gln Gln Glu
                85                  90                  95

Ser Ala Lys Leu Arg His Gln Ile Gln Met Leu Gln Asn Thr Asn Lys
                100                 105                 110

His Leu Val Gly Asp Asn Val Ser Asn Leu Ser Leu Lys Glu Leu Lys
            115                 120                 125

Gln Leu Glu Ser Arg Leu Glu Lys Gly Ile Ala Lys Ile Arg Ala Arg
        130                 135                 140

Lys Asn Glu Leu Leu Ala Ser Glu Ile Asn Tyr Met Ala Lys Arg Glu
```

```
                145                 150                 155                 160
Ile Glu Leu Gln Asn Asp Asn Met Asp Leu Arg Thr Lys Ile Ala Glu
                    165                 170                 175

Glu Glu Gln Gln Leu Gln Gln Val Thr Val Ala Arg Ser Ala Ala Met
                180                 185                 190

Glu Leu Gln Ala Ala Ala Ala Ala Gln Gln Gln Gln Asn Pro Phe
            195                 200                 205

Ala Val Ala Ala Ala Gln Leu Asp Met Lys Cys Phe Phe Pro Leu Asn
        210                 215                 220

Leu Phe Glu Ala Ala Ala Gln Val Gln Ala Val Ala Ala Gln Arg Gln
225                 230                 235                 240

Gln Ile Ile Pro Thr Glu Leu Asn Leu Gly Tyr His His His Leu Ala
                245                 250                 255

Ile Pro Gly Ala Thr Ala Ala Asp Ala Pro Pro Pro His Phe
            260                 265                 270

<210> SEQ ID NO 27
<211> LENGTH: 1901
<212> TYPE: DNA
<213> ORGANISM: Oryza sativa
<220> FEATURE:
<221> NAME/KEY: misc_feature
<222> LOCATION: (1)..(1900)
<223> OTHER INFORMATION: OsMADS13 5' regulatory sequence
<220> FEATURE:
<221> NAME/KEY: misc_feature
<222> LOCATION: (1)..(931)
<223> OTHER INFORMATION: 5' non-transcribed sequence
<220> FEATURE:
<221> NAME/KEY: misc_feature
<222> LOCATION: (932)..(973)
<223> OTHER INFORMATION: exon
<220> FEATURE:
<221> NAME/KEY: misc_feature
<222> LOCATION: (973)..(1881)
<223> OTHER INFORMATION: intron
<220> FEATURE:
<221> NAME/KEY: misc_feature
<222> LOCATION: (1882)..(1900)
<223> OTHER INFORMATION: exon

<400> SEQUENCE: 27
ttccaaaatt aagcacacac atttgcaaga actagctagg catgcatata tgataattaa    60
ccggcaagtt gacttcagtt attctgcaga tgtactaaac ataacaag ggatgatcag    120
ttgcttattt ttttcataac ttgctaggtt gcttataact ccagccttct ggacatcgac   180
caatctctaa acatacttta gcagtgccta caaagtacaa acaactaaat acctctctgc   240
agatcagtgt ttctaggcac aaattacaca agatagaaaa aaggagaggt tataaattct   300
tgcttaaaga atatacatgt aaagatgtct aaatagctat aaatgggtaa gcaagatagc   360
aaagaaggcc agtggccttt gcagctaagc tagctagcta gcccttcttc ctctctttcc   420
tgctttccct tgccttctc ctattaatcc tctgcacctc acacagcagc agaaaaccca    480
ccaactggag ctctcctttc ctactccaag aaacgaaggt agagaaagaa agatcagatc   540
agcttcagga ccaattttag ctaggttata tatctctttg cgtgctaatg tgttttagtt   600
atctgggtgt gtgtagagtt ctttgttaag gcactgattc agctgcagtt tagattcaag   660
tttgtatgtt ctctctttga ggaaaagaaa ccctttttcct gtgcttcgag ttcttgcaaa   720
gagaaactgt gatgcttggc ttccagtttg atgcttcttt gttcagattg gaaattcttc   780
ctagcttctt tctctatttta tgtagcaagg attctttccg gcccagtgat cctggttttct   840
```

```
tttggaaggt tcagttttt tcgttctttc ttgaaatttc tcttcttgcc ttaggcagat    900
ctttgatctt gtgaggagac aggagaaaag gaagaagcta gtttcctgcg gccgacctct    960
tgcttctcac tttgtgatga gttttctttg gtcaattctt agctagatat gttaagatag   1020
ttagttaagc aaatcgaaat tgctagcttt tccatgcttt cttaaacatg attcttcaga   1080
tttggttggt tcttttttt cctttttgtg gagacgtgct gttcttgcat cttatccttc    1140
ttgattcatc tacccatctg gttctttgag ctttcttttt cgcttcttcc cttcattatt   1200
tcgagcaatc tctgcacatc tgaaagtttt gtttcttgag actactttg ctagatcttg    1260 tttactcgat cactctatac ttgcatctag gctccttct aaataggcga tgattgagct    1320
ttgcttatgt caaatgatgg gatagatatt gtccccagtc tccaaatttg atccatatcc   1380
gccaagtctt tcatcatctt tttctttctt tttatgagc aaaaatcatc tttttctttc    1440
aaagttcagc ttttttctct tgtttaccc ctctttagct atagctggtt tcttattcct    1500
tttggattta catgtataaa acatgcttga atttgttaga tcgatcactt tatacacata   1560
ctatgtgaat cacgatctca gatctctcag tatagttgaa ttcattaatt tcttagatcg   1620
atcagcgtgt gatgtagtac tgtaaatcac tactagatct ttcatcagtc tcttttctgc   1680
atctatcaat ttctcatgca agttttagtt gttctcttaa tccggtctct ctctcttttt   1740
taatcagctg agagtttgtg ctgttctttta atcattacca gatctttcat cagtactctc   1800
tcttctgcat ctatcaaact tctcatgcaa tgttttgct gttctttgat ctgatctctg    1860
gtctcctttt tgttgatca gttgagagca agaagccatg g                        1901
```

<210> SEQ ID NO 28
<211> LENGTH: 1913
<212> TYPE: DNA
<213> ORGANISM: Oryza sativa
<220> FEATURE:
<221> NAME/KEY: misc_feature
<222> LOCATION: (1)..(1913)
<223> OTHER INFORMATION: OsMADS13 5' regulatory sequence engineered
<220> FEATURE:
<221> NAME/KEY: misc_feature
<222> LOCATION: (1)..(12)
<223> OTHER INFORMATION: engineered sequence
<220> FEATURE:
<221> NAME/KEY: misc_feature
<222> LOCATION: (1)..(942)
<223> OTHER INFORMATION: 5' non-transcribed sequence
<220> FEATURE:
<221> NAME/KEY: misc_feature
<222> LOCATION: (943)..(985)
<223> OTHER INFORMATION: exon
<220> FEATURE:
<221> NAME/KEY: misc_feature
<222> LOCATION: (986)..(1893)
<223> OTHER INFORMATION: intron
<220> FEATURE:
<221> NAME/KEY: misc_feature
<222> LOCATION: (1894)..(1913)
<223> OTHER INFORMATION: exon
<220> FEATURE:
<221> NAME/KEY: misc_feature
<222> LOCATION: (1908)..(1913)
<223> OTHER INFORMATION: engineered sequence

<400> SEQUENCE: 28

```
gcatgcggac cgttccaaaa ttaagcacac acatttgcaa gaactagcta ggcatgcata     60
tatgataatt aaccggcaag ttgacttcag ttattctgca gatgtactaa acacataaca    120
agggatgatc agttgcttat ttttttcata acttgctagg ttgcttataa ctccagcctt    180
ctggacatcg accaatctct aaacatactt tagcagtgcc tacaaagtac aaacaactaa    240
```

```
atacctctct gcagatcagt gtttctaggc acaaattaca caagatagaa aaaaggagag      300
gttataaatt cttgcttaaa gaatatacat gtaaagatgt ctaaatagct ataaatgggt      360
aagcaagata gcaaagaagg ccagtggcct ttgcagctaa gctagctagc tagcccttct      420
tcctctcttt cctgctttcc ctttgccttc tcctattaat cctctgcacc tcacacagca      480
gcagaaaacc caccaactgg agctctcctt tcctactcca agaaacgaag gtagagaaag      540
aaagatcaga tcagcttcag gaccaatttt agctaggtta tatatctctt tgcgtgctaa      600
tgtgttttag ttatctgggt gtgtgtagag ttctttgtta aggcactgat tcagctgcag      660
tttagattca agtttgtatg ttctctcttt gaggaaaaga aacccttttc ctgtgcttcg      720
agttcttgca aagagaaact gtgatgcttg gcttccagtt tgatgcttct ttgttcagat      780
tggaaattct tcctagcttc tttctctatt tatgtagcaa ggattctttc cggcccagtg      840
atcctggttt cttttggaag gtttcagttt tttcgttctt tcttgaaatt tctcttcttg      900
ccttaggcag atctttgatc ttgtgaggag acaggagaaa aggaagaagc tagtttcctg      960
cggccgacct cttgcttctc actttgtgat gagttttctt tggtcaattc ttagctagat     1020
atgttaagat agttagttaa gcaaatcgaa attgctagct tttccatgct tcttaaaca      1080 tgattcttca gatttggttg gttctttttt ttccttttg tggagacgtg ctgttcttgc      1140
atcttatcct tcttgattca tctacccatc tggttctttg agctttcttt ttcgcttctt     1200
cccttcatta tttcgagcaa tctctgcaca tctgaaagtt ttgtttcttg agactacttt     1260
tgctagatct tgtttactcg atcactctat acttgcatct aggctccttt ctaaataggc     1320
gatgattgag ctttgcttat gtcaaatgat gggatagata ttgtccccag tctccaaatt     1380
tgatccatat ccgccaagtc tttcatcatc tttttctttc tttttatga gcaaaaatca     1440 tcttttcttt tcaaagttca gcttttttct cttgttttac ccctctttag ctatagctgg     1500
tttcttattc cttttggatt tacatgtata aaacatgctt gaatttgtta gatcgatcac     1560
tttatacaca tactatgtga atcacgatct cagatctctc agtatagttg aattcattaa     1620
tttcttagat cgatcagcgt gtgatgtagt actgtaaatc actactagat cttcatcag     1680 tctctttct gcatctatca atttctcatg caagttttag ttgtttcttt aatccggtct     1740
ctctctcttt tttaatcagc tgagagtttg tgctgttctt taatcattac cagatctttc     1800
atcagtactc tctcttctgc atctatcaaa cttctcatgc aatgttttg ctgttctttg     1860 atctgatctc tggtctcctt ttttgttgat cagttgagag caagaagcca tgg           1913
```

<210> SEQ ID NO 29
<211> LENGTH: 1186
<212> TYPE: DNA
<213> ORGANISM: Oryza sativa
<220> FEATURE:
<221> NAME/KEY: misc_feature
<222> LOCATION: (1)..(1186)
<223> OTHER INFORMATION: OsMADS13 3' regulatory sequence
<220> FEATURE:
<221> NAME/KEY: misc_feature
<222> LOCATION: (1)..(335)
<223> OTHER INFORMATION: 3' untranslated sequence
<220> FEATURE:
<221> NAME/KEY: misc_feature
<222> LOCATION: (336)..(1186)
<223> OTHER INFORMATION: 3' non-transcribed sequence

<400> SEQUENCE: 29

```
ccgcctcctc acttctgaac ctcatgaact tcattctgca ccggcctgct gccatggata       60
```

```
tgatgatcag ctcatcttct atatcttatg ctgttatgca gacagacact actgatgtgg      120
ctatatatat agtatttgtg tgctgctgca ttttgttaat cccttataaa ttgctactta      180
attatctcat ggagaattgg agagaccaaa tgggcagagc tagctagtta gctgtgccca      240
attaagaagc taaatctatc agaagtgtgt actgatgagt gatgagtatt tttcttcatt      300
tgggatcaaa ttaaactaag taaaacatat atatttgact tatgttttac gtgcatgcat      360
gcatgcttaa ttgtgtcacc tttggggatt cattttgtac atatgtgcac cattttgtgt      420
gtacaatgca ggtttatatg acttttttcg caattacacg atgcccatg cacataacca       480 ccatgcacac tgcacgtaca tccacaagtg tgccccttta acacaaggca atacaccaaa      540
taaattgtaa tgtgccacta aactttttg aaagtgtaac cgcgcgtatg cttccgtggc       600
ttatatatga ctctggtggc tgacttctag ggcatgtcga cctgagcatc ttcgtgtggg      660
tttcgactct ctaattctcc tggtctctgg cagttgtgga aggggcgaaa ctccagggtt      720
tttgattact ctcttcctc actctcaagg gttctgaaag tcatcctaca ggaagaccgt       780
ttgtggtctt ctgctggcgt cgctgttttt agggggtttat taggagtgta gtggagcttc    840
gccaccaccc tccatctatt taggagcaac atttttttgg tagttttta ctttagcagt      900 cttttttgttt ctttctttgt tcccttatcc acatgcaatg tcgtctgac tggttacgtt     960 gtgtaacaaa aactctgctt ttttctaata tactgacgtg caatccttg gtgcgttcgc     1020 gaaaagaaag ggggatcaat tgcaagtatt ttgtgggaat taaactttc ttgtgaaatt     1080 attgtaaaat tccagcattc taaatgagct ctaatgtgtg ataatttgca ttctctatat    1140
atattgaata attcttttgt tgactagttg ggtgcccgtg cgttgc                   1186
```

<210> SEQ ID NO 30
<211> LENGTH: 1161
<212> TYPE: DNA
<213> ORGANISM: Oryza sativa
<220> FEATURE:
<221> NAME/KEY: misc_feature
<222> LOCATION: (1)..(1161)
<223> OTHER INFORMATION: OsMADS13 3' regulatory sequence engineered
<220> FEATURE:
<221> NAME/KEY: misc_feature
<222> LOCATION: (1)..(8)
<223> OTHER INFORMATION: engineered sequence
<220> FEATURE:
<221> NAME/KEY: misc_feature
<222> LOCATION: (1)..(294)
<223> OTHER INFORMATION: 3' untranslated sequence
<220> FEATURE:
<221> NAME/KEY: misc_feature
<222> LOCATION: (295)..(1161)
<223> OTHER INFORMATION: 3' non-transcribed sequence
<220> FEATURE:
<221> NAME/KEY: misc_feature
<222> LOCATION: (1145)..(1161)
<223> OTHER INFORMATION: engineered sequence

<400> SEQUENCE: 30

```
gcggccgctg acatggatat gatgatcagc tcatcttcta tatcttatgc tgttatgcag       60
acagacacta ctgatgtggc tatatatata gtatttgtgt gctgctgcat tttgttaatc      120
ccttataaat tgctacttaa ttatctcatg gagaattgga gagaccaaat gggcagagct      180
agctagttag ctgtgcccaa ttaagaagct aaatctatca gaagtgtgta ctgatgagtg      240
atgagtattt tcttcattt gggatcaaat taaactaagt aaaacatata tatttgactt      300
atgttttacg tgcatgcatg catgcttaat tgtgtcacct ttggggattc attttgtaca     360
tatgtgcacc attttgtgtg tacaatgcag gtttatatga cttttttcgc aattacacga     420
```

```
tggcccatgc acataaccac catgcacact gcacgtacat ccacaagtgt gcccctttaa    480
cacaaggcaa tacaccaaat aaattgtaat gtgccactaa acttttttga aagtgtaacc    540
gcgcgtatgc ttccgtggct tatatatgac tctggtggct gacttctagg gcatgtcgac    600
ctgagcatct tcgtgtgggt ttcgactctc taattctcct ggtctctggc agttgtggaa    660
ggggcgaaac tccagggttt ttgattactc tctttcctca ctctcaaggg ttctgaaagt    720
catcctacag gaagaccgtt tgtggtcttc tgctggcgtc gctgttttta ggggtttatt    780
aggagtgtag tggagcttcg ccaccaccct ccatctattt aggagcaaca ttttttttggt   840 agttttttac tttagcagtc ttttttgtttc tttctttgtt cccttatcca catgcaatgg   900
tcgtctgact ggttacgttg tgtaacaaaa actctgcttt tttctaatat actgacgtgc    960
aatcctttgg tgcgttcgcg aaagaaagg gggatcaatt gcaagtattt tgtgggaatt    1020
aaacttttct tgtgaaatta ttgtaaaatt ccagcattct aaatgagctc taatgtgtga   1080
taatttgcat tctctatata tattgaataa ttcttttgtt gactagttgg gtgcccgtgc   1140
gttgcggacc gatcgatacg t                                              1161

<210> SEQ ID NO 31
<211> LENGTH: 8709
<212> TYPE: DNA
<213> ORGANISM: Artificial Sequence
<220> FEATURE:
<223> OTHER INFORMATION: OsMADS5 GUS expression cassette

<400> SEQUENCE: 31
ggcgcgcctg agcaggtagc cggcgaccaa tcgcgagcgt cgccaacacg ctgccttttc     60
tcaatgcatg gcgtgggccc caccaggggc cattttttttc tctttaaaaa ggagaaaagc   120
aatcagagtt gagacctccg agcgcgagac ccaacatcta tccctgggcc cgcccaaaat   180
ccatttccag gtagttgtag ccaaagaatc aaggatactc cgatcgtttg agtggaaata   240
ataactccta catgtaaaat taattaaggc ctctatttgt atgaaaaaac ataaaaaaag   300 gattttttaat cttattgaaa aaaaatccta aggataactt cgaataaatg attaaatctt   360 aacatttttct ttgaaattca tatggaacaa acaatgctat agagactttg gaggaattaa   420
agttattaag agctctaacc ttttaaaaga ttaccaatga gtctatatag gtagttgtag   480
ccaaagaatc aaggatactc cgatcgtttg agtggaaata ataactccta catgtaaaat   540
taattaaggc ctctatttgt atgaaaaaac ataaaaaaag gattttttaat cttattgaaa   600 aaaaatccta aggataactt cgaataaatg attaaatctt aacatttttct ttgaaattca   660 tatggaacaa acaatgctat agagactttg gaggaattaa agttattaag agctctaacc   720
ttttaaaaga ttaccaatga gtctatatag gtagttgtag ccaaagaatc aaggatactc   780
cgatcgtttg agtggaaata ataactccta catgtaaaat taattaaggc ctctatttgt   840
atgaaaaaac ataaaaaaag gattttttaat cttattgaaa aaaaatccta aggataactt   900
cgaataaatg attagatctt aacatttttct ttgaaattca tatggaacaa acaatgctat   960
agagactttg gaggaattaa agttattaag agctctaacc ttttaaaaga ttaccaatga  1020
gtctatatag gtagttgtag ccaaagaatc aaggatactc cgatcgtttg agtggaaata  1080
ataactccta catgtaaaat taattaaggc ctctatttgt atgaaaaaac ataaaaaaag  1140 gattttttaat cttattgaaa aaaaatccta aggataactt cgaataaatg attaaatctt  1200 aacatttttct ttgaaattca tatggaacaa acaatgctat agagactttg gaggaattaa  1260
```

```
agttattaag agctctaacc ttttaaaaga ttaccaatga gtctatatag gtagttgtag    1320
ccaaagaatc aaggatactc cgatcgtttg agtggaaata ataactccta catgtaaaat    1380
taattaaggc ctctatttgt atgaaaaaac ataaaaaaag gattttaat cttattgaaa     1440 aaaaaatcct aaagataact tcgaataaat gattaaatct taacattttc tttgaaattc    1500
atatggaaca aacaatgcta tagagacttt ggaggaatta agttattaa gagctctaac     1560 cttttaaaag attaccaatg agtctatatc actcattcaa ttcctacgtt tttcaaatgg    1620
cctacatact caaatggttg ttcttgtttt tttttctct ctttcgcaat tacaatggac     1680
ctgctcgcaa cttttgcaat ctgtctatgt tttttatgtt tagcagctgc gctgctgcag    1740
ctgaacaaaa aaaaacactg tgacgattgg ctgcaacaca atgaaaatga gtgcagccga    1800
acagagccaa tatcttcaaa atcttgtttt tttcatcttc cattttcaa tcatttattt     1860 taaaggagcc cttaattaat ggttaagaaa tttatatct tgcattttaa aggataatgc     1920
tgataatcaa atagactacg gtgaaaaaaa ctttaaaact aaatgtaaga ttaaatttca    1980
cacttaaatt ttactagcta cggctgataa ttaagctaac aacttactgt gactgacttg    2040
gtcatagggg gagagagaga gagagagaga gagagagaga gagagagaga gagagagaga    2100
gagagagaga gagagagaga gagagagaga gagagagaga aaagaaggca aggagcactc    2160
cggccagcac agccgatggt acgagagcat ggctagctag ccgagctact tagctactac    2220
atccatgatc catccatccc caacaaacgg agcaagactg caaggagag ggagagagag     2280 ggaagcttgc aggctgcagc taactagcta ggcaaggaga gagaggagat agatcaagaa    2340
gagattttga gaccgagaga gagctagaga gagctcgacg gggcgaggga aagtagagct    2400
gaagcggatc gagaacaaga taagccggca ggtgacgttc gcgaagagga ggaacgggct    2460
gctgaagaag gcgtacgagc tgtccgtgct ctgcgacgcc gaggtcgccc tcatcatctt    2520
ctccacccgc ggccgcctct tcgagttctc cacctcctcc tggtactact aataattctc    2580
tcttgcaagc tctcgcccct tgcagagaat tcatatatat ctcgccctaa ttctaatgca    2640
aagttagtta attagtttgc agccaagaaa gactagtttt ctcgttatga gttttgaag     2700 ctccttgtga tttctgggct agctactgcc cacctagcta ccatgttcta attaatcatc    2760
agtccgtgtg tttaattaac atctcatgtt tgtccgggaa gttcttacac ccagtctttt    2820
ccctgctgct ttgtttgtgt ttaaaacata tatataccag catttcgttt gtatttgttg    2880 gaattttttac caatctttct caaagatcct gattttagtt aattttacc acctcgatcg     2940 tgatcatata catgctcata gctgattaac taacctgttc ctgttgttgt tttggttaaa    3000
gaaagagaga caggacagcc gttctagtca cctgatggct gccgatctgt gtgtgtttgc    3060
cgtcccctaa ttcctctta cggtttgcag ttgccataga gactagtact ctgtcaacag     3120
aatcaagcat gcaatctctc catgcttgct tccatttgta ggctagagct gcatgctaga    3180
tatctctaag ctgatctctt ccatgcttgt ctctctagct cttcattag tgcatgcaat     3240 tttcagagtg aagtagatga gaccccctcca gatctgcaca agaacatggc atatagtact    3300
actagtacgc atattgcatc ttaattctca tattgcacaa gcacatatac taggctgcag    3360
tgccttttcc aatggcaagt tattttgtc agatcttaat taggagcatc ttttccaatg     3420
gcaagttggg agggtttctt gctctggttt tactgttcca ttgggaactc gcaacatagg    3480
ggttgttctt gggttccact gttccattga gtctctctct ctttctctct agctaggttt    3540
ctctctctac gtcttgtcaa atgtctcggc tgtactagtg tgcatgcgat tgcagctgca    3600
gaagcaagag gaaaagtagt aatgcagcag caggaggaaa agtcgtagga gtactcgtgg    3660
```

```
agataagcat ctctgtatcg atcgtctcgt cggttgttat cctccctgtg gatatgtaca    3720
cggtccgtgt ttagatccaa aataattcat caaactttta actttttcat cacatcaaaa    3780
cttttctaca cacataaact tttaactttt acgtcacatc gtttcaattt caaccaaact    3840
tctaagggcc cctttgaatt ggaggaaaaa cataggaatt ttagaggatt tcaatcctat    3900
agaaaaattt cctatgaagc cctttgaaac aaatgattga atcctatcca atcctttgaa    3960
attcctatgg aatggacaat cctatagaga ttttggagga aatttagcaa gagcttcaac    4020
ctcttgctaa ctttcctttg agtctatctc tctcatctaa ttcctgcgtt tttcctgcgg    4080
ttcaatcaaa cggtcattca tgtgtttttc ctgcgttttg caatcctctg ttttacactt    4140
acattcctac caaaatccta cgttttttcct attcctacgt tttttcaatc ctgcgattca    4200
aagggaccct aattttggtg tgaactaaac acagcctagt tgtagttgtg tggtacgaaa    4260
gatcgaattg atttctagct aggcgtggcc ggacacacac ccaagttaat tcactgcatt    4320
cgtaatttca tactcctatg cgattcataa tttcacatgc gatgatgcga atagattgat    4380
ttgatcattt gaacattgtc atatggtatg caaacaactt atcgtgcgag aggcgtgcgt    4440
gtcgattgcc aaaattttct gtcagcgcac agtacaggct agctagtctg aacgaggtt    4500 gtgtcgattt acaaggcaca gttactagct accctaccgt tagggtatgt agtaggagta    4560
cttgtgtacc aaaagtttgg attggttgaa ttttccaagc tcctagtcac aatgtactcc    4620
ctccttttcc ctccccaaaa aatatactcc ttctatccag tatccacaaa gaaaataatg    4680
taactctagc atttaaaaga caaattagca agaagtaaaa tgattgggag tgaaattgtg    4740 gttggggta aaatagggat cataatttga atgaggggg tggttgtagg gaaaaatagt    4800
actgcactcc tttagaattg cacttatttt gaaacaaaat ctgaatgtta gttacaattg    4860 ttttttttcta aaaaaacaga gtacaatttt ctaataattt aacacaaatc aatcaaatat    4920
atacatgttt gtaagtgata gtgtttatag ctccaaacag ggtttgaaat ttcggctcga    4980
aatttcgccc ccaccgaaat gttcatatct cgcccgaaac tttcggttgt ttgcaaattt    5040
ttgtgaattt ggtcaaattt tattcaaatc cattcaaaat cagtcaaaaa ttcaaaaaaa    5100
atcgtacgaa aaaaaaatct gaaattttgg ttatatcgcc cacctgcggt agaaatcctt    5160
ctttcgaaat ttaaaaccct ggctccaaac ttagggtgcg ctgtgcacat accctagaaa    5220
atataactga tatatgctcc attaattatg aaaggcaaaa taaactgatc atgcatatgt    5280
aggaaaatcg ggttgtatat acatgtattt aaacaacaaa atataatata acaactttaa    5340
ctgatactgc attgaaaata gttttgtggt ccactgattt tcttttttgt aacagtatcc    5400
accatggtac gtcctgtaga aaccccaacc cgtgaaatca aaaaactcga cggcctgtgg    5460
gcattcagtc tggatcgcga aaactgtgga attgatcagc gttggtggga aagcgcgtta    5520
caagaaagcc gggcaattgc tgtgccaggc agttttaacg atcagttcgc cgatgcagat    5580
attcgtaatt atgcgggcaa cgtctggtat cagcgcgaag tctttatacc gaaaggttgg    5640
gcaggccagc gtatcgtgct gcgtttcgat gcggtcactc attacggcaa agtgtgggtc    5700
aataatcagg aagtgatgga gcatcagggc ggctatacgc catttgaagc cgatgtcacg    5760
ccgtatgtta ttgccgggaa aagtgtacgt atcaccgttt gtgtgaacaa cgaactgaac    5820
tggcagacta tcccgccggg aatggtgatt accgacgaaa acggcaagaa aaagcagtct    5880
tacttccatg atttctttaa ctatgccgga atccatcgca gcgtaatgct ctacaccacg    5940
ccgaacacct gggtggacga tatcaccgtg gtgacgcatg tcgcgcaaga ctgtaaccac    6000
```

```
gcgtctgttg actggcaggt accaagctgc gaatcttcgt ttttttaagg aattctcgat   6060
ctttatggtg tataggctct gggttttctg tttttttgtat ctcttaggat tttgtaaatt   6120
ccagatcttt ctatggccac ttagtagtat atttcaaaaa ttctccaatc gagttcttca   6180
ttcgcatttt cagtcatttt ctcttcgacg ttgttttttaa gcctgggtat tactcctatt   6240
tagttgaact ctgcagcaat cttagaaaat tagggttttg aggtttcgat ttctctaggt   6300
aaccgatcta ttgcattcat ctgaatttct gcatatatgt cttagatttc tgataagctt   6360
acgatacgtt aggtgtaatt gaagtttatt tttcaagagt gttattttt gtttctgaat   6420 ttttcaggtg gtggccaatg gtgatgtcag cgttgaactg cgtgatgcgg atcaacaggt   6480
ggttgcaact ggacaaggca ctagcgggac tttgcaagtg gtgaatccgc acctctggca   6540
accgggtgaa ggttatctct atcaactgtg cgtcacagcc aaaagccaga cagagtgtga   6600
tatctacccg cttcgcgtcg gcatccggtc agtggcagta aagggcgaac agttcctgat   6660
taaccacaaa ccgttctact ttactggctt tggtcgtcat gaagatgcgg acttgcgtgg   6720
caaaggattc gataacgtgc tgatggtgca cgaccacgca ttaatggact ggattggggc   6780
caactcctac cgtacctcgc attacccctta cgctgaagag atgctcgact gggcagatga   6840
acatggcatc gtggtgattg atgaaactgc tgctgtcggc tttaacctct ctttaggcat   6900
tggtttcgaa gcgggcaaca agccgaaaga actgtacagc gaagaggcag tcaacgggga   6960
aactcagcaa gcgcacttac aggcgattaa agagctgata gcgcgtgaca aaaccaccc   7020 aagcgtggtg atgtggagta ttgccaacga accggatacc cgtccgcaag gtgcacggga   7080
atatttcgcg ccactggcgg aagcaacgcg taaactcgac ccgacgcgtc cgatcacctg   7140
cgtcaatgta atgttctgcg acgctcacac cgataccatc agcgatctct ttgatgtgct   7200
gtgcctgaac cgttattacg gatggtatgt ccaaagcggc gatttggaaa cggcagagaa   7260
ggtactggaa aaagaacttc tggcctggca ggagaaactg catcagccga ttatcatcac   7320
cgaatacggc gtggatacgt tagccgggct gcactcaatg tacaccgaca tgtggagtga   7380
agagtatcag tgtgcatggc tggatatgta tcaccgcgtc tttgatcgcg tcagcgccgt   7440
cgtcggtgaa caggtatgga attcgccga ttttgcgacc tcgcaaggca tattgcgcgt   7500
tggcggtaac aagaaaggga tcttcactcg cgaccgcaaa ccgaagtcgg cggcttttct   7560
gctgcaaaaa cgctggactg gcatgaactt cggtgaaaaa ccgcagcagg gaggcaaaca   7620
atgagagctc cgcgggcggc cgcactagtc ccgggccatg gggggtctag aatgaattgc   7680
ttatcacatt aatggacatc tcctatgttg gatgtggtgt ttgacgtaat gctctctttt   7740
acatgcgggt tttaccttaa gtgtgtgtgc taaatttagt gcgtttgttt atgctctttt   7800
gaactgaaca aaggaatgat cccggtttga ttgatgaatg ctgcaagaac ataatctata   7860
tgttagtctg aattcagtat gtaatgaaga tgttttgtta ctaattaata aatacgaagt   7920
aaacaattaa ctgaccacta atcatgtcag cttagatata tgcttataat tatgttgcct   7980
aattcttacc ttaattggtc tgtgttcaat atatgtgagt ataccacact agttgtttct   8040
cagcatgaac taattaagtg tgagtagata aaacgagtaa attggaatgt aagaaaaggt   8100
aaaaataaag tacttattaa agagagagtg catgccaaaa gtacgaagag aaaaacttag   8160
aatattagtt acaatataat atataatcaa gtgcttcgtt cgaacccata catgtttgtt   8220
tttcttattt ttctaatatt tcttcaccat ataggttccc caggttgcac tccgaaaggt   8280
cgtgtaatgt gtatttagta gcacacatag ttacatcact gcttattttc tcatccacta   8340
gccacaagat tgtgtgcgtg tgaccatctc aattagatcc atctcctcct tcacatgcac   8400
```

```
ggtattgatt tgtgctagac ctgccggtgt ctccaatggt gatgatccag ctgattcatc    8460
gtcttggagg acatcatcgt cccatgccat ttccatatct atctcatggc caatcttgtt    8520
agcataatca atgtggttga agatgtagtt catgtcaaca tcatcatcta tgttgtaaac    8580
ctggtacggc atctcgtcct tcgtttcgaa caaatgatca cacatatcaa ggcataaatc    8640
atcataggta gagaccagga gttcttcaca agagttggtc tggatgtagc tgttctcatc    8700
cggcgcgcc                                                            8709
```

<210> SEQ ID NO 32
<211> LENGTH: 29
<212> TYPE: DNA
<213> ORGANISM: Artificial Sequence
<220> FEATURE:
<223> OTHER INFORMATION: primer OsMADS6 P1

<400> SEQUENCE: 32

```
ctaggacgat ggtgtgatgt gggaacacg                                        29
```

<210> SEQ ID NO 33
<211> LENGTH: 31
<212> TYPE: DNA
<213> ORGANISM: Artificial Sequence
<220> FEATURE:
<223> OTHER INFORMATION: primer OsMADS6 P2

<400> SEQUENCE: 33

```
gtacctttct aaagtctttg ttatgctgca c                                     31
```

<210> SEQ ID NO 34
<211> LENGTH: 30
<212> TYPE: DNA
<213> ORGANISM: Artificial Sequence
<220> FEATURE:
<223> OTHER INFORMATION: primer OsMADS6 P3b

<400> SEQUENCE: 34

```
cgagtcgacg agggaagag ttgagctgag                                        30
```

<210> SEQ ID NO 35
<211> LENGTH: 31
<212> TYPE: DNA
<213> ORGANISM: Artificial Sequence
<220> FEATURE:
<223> OTHER INFORMATION: primer OsMADS6 P4c

<400> SEQUENCE: 35

```
gactccatgg tggttatgct gcacaaaaat g                                     31
```

<210> SEQ ID NO 36
<211> LENGTH: 37
<212> TYPE: DNA
<213> ORGANISM: Artificial Sequence
<220> FEATURE:
<223> OTHER INFORMATION: primer OsMADS6 C1b

<400> SEQUENCE: 36

```
cagtgcatgc ggaccgctag gacgatggtg tgatgtg                               37
```

<210> SEQ ID NO 37
<211> LENGTH: 29
<212> TYPE: DNA
<213> ORGANISM: Artificial Sequence
<220> FEATURE:

<223> OTHER INFORMATION: primer OsMADS6 Paa

<400> SEQUENCE: 37
cctcgtcgac tcgcccgatc gatcgaacg                                              29

<210> SEQ ID NO 38
<211> LENGTH: 7954
<212> TYPE: DNA
<213> ORGANISM: Artificial Sequence
<220> FEATURE:
<223> OTHER INFORMATION: OsMADS6 GUS expression cassette

<400> SEQUENCE: 38

| cggaccgcta ggacgatggt gtgatgtggg aacacgaaga aaacatgagg aaaaaatatt | 60 |
|---|---|
| aaaatgaatt tcccacttaa aatgcatcaa ataaaaaaaa taaagaaacg accgggaata | 120 |
| gacacagggt ttgtgaacta gctagggcaa acatcatatg gtcccttgct gatgcacaag | 180 |
| tacattgaga tgtcatttca attctgtgca tcatatgcat gtggtcccctt gctgaatatt | 240 |
| actcttgaaa tatctaccag tgccaatcta ttgcatgact taattaattc acaggttttg | 300 |
| ttgattacat tattagtaag cttgagagca caagctcaat ggattttttct ataaatgggg | 360 |
| atcattttgc aattttcttt gtcgtgcaaa gttagccttc tttattacta cttctgtttt | 420 |
| taaatatacg atcctattga cttttggtca tatatttaac catgtatctt atttagatag | 480 |
| tttgcgcaaa tatatatacc ttcaatgata aaattagtta caatgaaaca aatgatattt | 540 |
| acgcaattct ttttactaaa caagtcacaa gaagtacctg cagcaatata tgttggaacc | 600 |
| gtgcagtaga tcgagcctag ctacgcaaaa aaacaaaaag agaaaaaaag ggaaaggaaa | 660 |
| aacattaatc atgcatgagc agtatgcccg gcaactggaa tttgtcaaag atatggggag | 720 |
| aggagaataa tacaagtact actactacct agctctacca tgcatatgca cccaaaggca | 780 |
| aactggatta ttggataaag cacagatgct ggcaaaacaa tccttaagcc tcccctccct | 840 |
| gcttctttat ttttgggcag cctctaccgg acggtgccgt ggtccattgg accagtaggt | 900 |
| ggcgacatac atggtttggg ttaagtctag gagagcagtg tgtgtgcgcg cgcaagagag | 960 |
| agagactgtg agtctgggag tagccctctc ccctcctttg gccatcttcc tcgtgtatat | 1020 |
| gcatatatgc atcatcgcaa cggtgtatat ttgtggtgtg gcgggtgtgg cattggattg | 1080 |
| ccccattttt ggctcgtgct tcccagttag ggtaaaacct gtggtaaact tgctagcccc | 1140 |
| acgccaaagt taccccttctt tattgttgaa agggagagga ggtgtgtgaa ttgtgatgga | 1200 |
| gggagagaga gagagagata gaaagagaga tgtgtgtcaa agcaagcaag aaaccagttt | 1260 |
| cacaaagagc tactactagt actagtgtac tactgtggta cagtgcccaa tgtcctttct | 1320 |
| ccggactcga ctccactaat attctcctct tctcgcgcgg ctcgttatat tctcgtcatc | 1380 |
| attggaggct ttagcaagca agaagagagg cagtggtggt ggtggtggag gaggagctag | 1440 |
| ctagcctgtg cttgctgatc ggtgctgagc tgaggaatcg ttcgatcgat cgggcgagtc | 1500 |
| gacgagggga agagttgagc tgaggcgcat cgagaacaag atcaacaggc aggtcacctt | 1560 |
| ctccaagcgc cgcaacggcc tcctcaagaa ggcctacgag ctgtccgttc tctgcgacgc | 1620 |
| cgaggtcgcg ctcatcatct tctccagccg cggcaagctc tacgagttcg cagcgccgg | 1680 |
| gtataattaa tacagacaca acaacacaca caaccaacaa accagcatca atttgaacct | 1740 |
| gcagatctgc tgttttctct gatcaattgc ttcttttttt ttgttcttttt ttgtttcttt | 1800 |
| tatctgctgc aacggcgtcc tgctcctctg gggtttctcg ttttctttttt catttatttt | 1860 |
| tagcaggtgc caagtagccg agctactata cttacctggc catgttaatt attttattcc | 1920 |

```
gtctgtctgt gtgtgtctgt gcatactact atagggacat ggcgcggtgt tcttataaac    1980
cgggaggccg gatccctaac tagcatggga ggatatcttt tcagcggatc tatacaaacc    2040
ctactcctgc tgacctcttt cttccagttt ctccgggtct tccttggatt attattgccc    2100
atcttccggg ttgtgcgtgt gtcagagaca gctcgaacga taaatttctc aaaaccagta    2160
ctagagaggg tgtgttgtgt gtgagaactg agtggagagt tagcatgaag gctgcaaact    2220
agaaaggaag gtatgttctt tccttttgta tccatcaggg gagcccttc tggtattaag     2280 atctttccgg cacattgatt ttcatacttt gtgatgaccc tggaagaatc ggcgtagcag    2340
cgtagcaccg ctccattttg gtcttaccct cacctcccca tgctatgaac tgatcaattt    2400
cattgttctt catcacccct ctcctagctt tccacttcct tcggatctca tgccatgttt    2460
ctcagcatga atcaaattta attcgtgttt tctacttcca tatatactgg aagaaattta    2520
attagatcta tttttgctcg ggaggtcttc atactttgag ttctgatgcc atcaccttat    2580 ttccccccc cccttctctt gttctatctt cttcctcatc ttggcttgat cattttgatc     2640
tgtcagttat agcatgatgc attctcaatt tgactgtatg taagttcaac cggaaatatg    2700
ttgaatggat tttctatata tcaacacttg atgtcaggcc tgcatctgtt tcgcttgtgg    2760
tggtgtggcc aaaattgtct atatttgatc tttgctcttc tttctcctca tttcatgacg    2820
attcctacta cggcttaaac cattctttat tctttactaa tcatggatgt tgcttgactc    2880
ctagttgttt cgtactagct caacttggag atcttttcat tatttgccta gttggtgggt    2940
acgtttgtga cagatctaaa atggtgcacg aaaagtttta cttattatga aaaaagggag    3000
cttaacaggg taatttctct atttattcgt gatgacattt tttccttgat aaggggatt     3060 ttttataatc tgcactcaca tgtttatatg taaaatctag ctcttttgtt ttgttttttgg   3120 catatttccc gctaagtata gagtttatgt ggataacatt ataacttttc aagatccaat    3180
ccacatcttt gattgtgaaa atcatacaat agggaaaatc aactgaaggg ttaattagat    3240
gctatatgca tatatatata tatgtgcgcg cgcgcgcgcc tgaatttaac tatgtatgca    3300
tccaactgtt tcattgaaaa agatttgata ttttttcagtc tattcttttt cgagtatata   3360
tttaatatgt ttcaatctgt tttgaccatt ataagataaa gcctatattc accaggcatt    3420
tgagatgatc ttttcatgca tgaaaaagct gttgttatca cttcaactaa ccagacgatc    3480
taacatgtat ttgtataaga aacagacctt gatttccttc tgtaaaatca tgcatgtgtt    3540
cgttttgaat tggagtcggc gcgcctgtgt tttgaccgtc aggaaagtct ttttttcccc    3600
tgaatagtca agggtctata cttcttgaag caattgggac actaatcaat tattgtttat    3660
acctcggacc atcttttcct tcttcacacc actaatcagt ttatgccttg gaccattaat    3720
tgtgttgttc acaagcttct tgtttatggt ttacaaagca ttcgcctaga tttgtgtgtg    3780
tctctacaca tcgatcactt ttaaatactt gtcgctttca gttattcttt taacgtttgg    3840
ttatttatct tatttaaaaa aattatcgta ttattattta ttttgtttgt gatttacttt    3900
attatcaaaa gtatttcaaa tatgacttat ctttttttat aagtgcacta attttttcaaa   3960 taagatgaat ggtcaaatgt tacaagaaaa agttaaagca accactaatt tagggcggag    4020
gtagtaaaac ctagttattg taaccaataa ttttatcaat ctataaatgc aacacaaagt    4080
cacttcgtga tatctcacac aaagccactt caacgatgaa agctgactgc atgttttatc    4140
aaaacacatg tgatcagttt gttggatgaa aaaattatc tatgtcataa atcaagagtt     4200
ataatataag cttctggctc tacaagtaac atttctatgt tttttttta cgttcttaca     4260
```

```
tactatgttt tgccaaaaaa aacatgatca ttttgttgga cgaaaagaaa tagtaaatat    4320
agagtgacct ttgatatcat tataatataa gcttctgcct ctataaataa catctatgca    4380
cttttttacgt cgtagtaatt tgatatatga gaaatttaca tataacalltt ttgtgcagca    4440
taaccaccat ggtacgtcct gtagaaaccc caacccgtga aatcaaaaaa ctcgacggcc    4500
tgtgggcatt cagtctggat cgcgaaaact gtggaattga tcagcgttgg tgggaaagcg    4560
cgttacaaga aagccgggca attgctgtgc caggcagttt taacgatcag ttcgccgatg    4620
cagatattcg taattatgcg ggcaacgtct ggtatcagcg cgaagtcttt ataccgaaag    4680
gttgggcagg ccagcgtatc gtgctgcgtt tcgatgcggt cactcattac ggcaaagtgt    4740
gggtcaataa tcaggaagtg atggagcatc agggcggcta tacgccattt gaagccgatg    4800
tcacgccgta tgttattgcc gggaaaagtg tacgtatcac cgtttgtgtg aacaacgaac    4860
tgaactggca gactatcccg ccgggaatgg tgattaccga cgaaaacggc aagaaaaagc    4920
agtcttactt ccatgatttc tttaactatg ccggaatcca tcgcagcgta atgctctaca    4980
ccacgccgaa cacctgggtg gacgatatca ccgtggtgac gcatgtcgcg caagactgta    5040
accacgcgtc tgttgactgg caggtaccaa gctgcgaatc ttcgttttt taaggaattc    5100
tcgatcttta tggtgtatag gctctgggtt ttctgttttt tgtatctctt aggattttgt    5160
aaattccaga tctttctatg gccacttagt agtatatttc aaaaattctc caatcgagtt    5220
cttcattcgc attttcagtc attttctctt cgacgttgtt tttaagcctg ggtattactc    5280
ctatttagtt gaactctgca gcaatcttag aaaattaggg ttttgaggtt tcgatttctc    5340
taggtaaccg atctattgca ttcatctgaa tttctgcata tatgtcttag atttctgata    5400
agcttacgat acgttaggtg taattgaagt ttattttca agagtgttat tttttgtttc    5460
tgaatttttc aggtggtggc aatggtgat gtcagcgttg aactgcgtga tgcggatcaa    5520
caggtggttg caactggaca aggcactagc gggactttgc aagtggtgaa tccgcacctc    5580
tggcaaccgg gtgaaggtta tctctatcaa ctgtgcgtca cagccaaaag ccagacagag    5640
tgtgatatct acccgcttcg cgtcggcatc cggtcagtgg cagtgaaggg cgaacagttc    5700
ctgattaacc acaaaccgtt ctactttact ggctttggtc gtcatgaaga tgcggacttg    5760
cgtggcaaag gattcgataa cgtgctgatg gtgcacgacc acgcattaat ggactggatt    5820
ggggccaact cctaccgtac ctcgcattac ccttacgctg aagagatgct cgactgggca    5880
gatgaacatg gcatcgtggt gattgatgaa actgctgctg tcggctttaa cctctcttta    5940
ggcattggtt tcgaagcggg caacaagccg aaagaactgt acagcgaaga ggcagtcaac    6000
ggggaaactc agcaagcgca cttacaggcg attaaagagc tgatagcgcg tgacaaaaac    6060
cacccaagcg tggtgatgtg gagtattgcc aacgaaccgg ataccgtcc gcaaggtgca    6120
cgggaatatt tcgcgccact ggcggaagca acgcgtaaac tcgacccgac gcgtccgatc    6180
acctgcgtca atgtaatgtt ctgcgacgct cacaccgata ccatcagcga tctctttgat    6240
gtgctgtgcc tgaaccgtta ttacggatgg tatgtccaaa gcggcgattt ggaaacggca    6300
gagaaggtac tggaaaaaga acttctggcc tggcaggaga aactgcatca gccgattatc    6360
atcaccgaat acggcgtgga tacgttagcc gggctgcact caatgtacac cgacatgtgg    6420
agtgaagagt atcagtgtgc atggctggat atgtataccc gcgtctttga tcgcgtcagc    6480
gccgtcgtcg gtgaacaggt atggaatttc gccgattttg cgacctcgca aggcatattg    6540
cgcgttggcg gtaacaagaa agggatcttc actcgcgacc gcaaaccgaa gtcggcggct    6600
tttctgctgc aaaaacgctg gactggcatg aacttcggtg aaaaaccgca gcaggaggc    6660
```

-continued

```
aaacaatgag agctccgcgg gcggccgcac tagtcccacg tgagctcgct aagcagccat    6720
cgatcagctg tcagaagttg gagctaataa taaaagggat gtggagtggg ctacatgtat    6780
ctcggatctc tctgcgagcc acctaatggt cttgcgtggc cctttaatct gtatgttttt    6840
gtgtgtaagc tactgctagc tgtttgcacc ttctgcgtcc gtggttgtgt ttccgtgcta    6900 ccttttatg ttttgatttg gatcttgttt gaaataatc ttaccagctt tgggtaaact      6960
gtttattacg tactctatat agcatatgtg accgacgaca acggtttcat tttagatgat    7020
gtgtatggat gatttcttc caaaatcaca tctttagtat aagagcaatt ttaccatcca     7080
ataccaaatt ttatactaga aaatattttg ggatatcaaa atttatggta cctccagtac    7140
caaatgttga atggtaaact ttcataatat acaagtcact ctaggatatt taagacaatt    7200
tttagttttt tcttattgtt gcccttgtta aatacatgag aaattttaca tcacttaaaa    7260
tgtatcaaga ggtatcaaat tttttaata caaaatttag tactttctcc gtttatatat     7320
gaatgtggac aatgcttgaa agtcttataa cctgaaactg aggtagtgta tcgagaagta    7380
caaattttta cactaaaatc ccagtactta ctcaataact gtaaaattac tctaaatatg    7440
tactccctct atttcagatt ataagtcgtt ttaactttag tcaaagttaa actgtttcaa    7500
gtttaaccaa gtttgtagat aaaagtagta acatattcaa cacaagacaa atatattata    7560
aaaacatatt gaattataga tttaattaaa ttaatttggt attgcaagta ttactaaatt    7620
tgtttataaa tttggtcgaa tttaaaatag tttgacttta accaaagtca aaacaaatta    7680
taatctaaaa caaggtaat acattgtatc actctcatga atggattgta acatacatta     7740
atttaattac tattttagtt cttgtgcaaa agttgaaaac gatttatgtt tggaatcttt    7800
ttgtggtgta tatatatgaa accattcctc taccatcctt ccccaaccat aatcctcaca    7860
accgttagcc ccattgtgat ctcacccagt tgctagcctc ttttgtcacc ttgtcacagc    7920
tctcctccat tcattacaca atggcatcgg accg                                7954
```

```
<210> SEQ ID NO 39
<211> LENGTH: 30
<212> TYPE: DNA
<213> ORGANISM: Artificial Sequence
<220> FEATURE:
<223> OTHER INFORMATION: primer OsMADS8 P1

<400> SEQUENCE: 39
ggtatctttc caaagttctg gtcatgctgc                                     30

<210> SEQ ID NO 40
<211> LENGTH: 29
<212> TYPE: DNA
<213> ORGANISM: Artificial Sequence
<220> FEATURE:
<223> OTHER INFORMATION: primer OsMADS8 P2

<400> SEQUENCE: 40 ccatttttg cgaaatgcca aatcctggc                                       29

<210> SEQ ID NO 41
<211> LENGTH: 35
<212> TYPE: DNA
<213> ORGANISM: Artificial Sequence
<220> FEATURE:
<223> OTHER INFORMATION: primer OsMADS8 T1

<400> SEQUENCE: 41
```

```
acgtgagctc actcctgaag gccgatgcga caacc                                35
```

<210> SEQ ID NO 42
<211> LENGTH: 39
<212> TYPE: DNA
<213> ORGANISM: Artificial Sequence
<220> FEATURE:
<223> OTHER INFORMATION: primer OsMADS8 T2

<400> SEQUENCE: 42

```
agtcatcgat catgacaaaa tatcatgttt atttcgagg                            39
```

<210> SEQ ID NO 43
<211> LENGTH: 37
<212> TYPE: DNA
<213> ORGANISM: Artificial Sequence
<220> FEATURE:
<223> OTHER INFORMATION: primer OsMADS8 Pcc

<400> SEQUENCE: 43

```
atcgccatgg tggtcaagct gcaagtttca aaaacac                              37
```

<210> SEQ ID NO 44
<211> LENGTH: 25
<212> TYPE: DNA
<213> ORGANISM: Artificial Sequence
<220> FEATURE:
<223> OTHER INFORMATION: primer OsMADS8 C3

<400> SEQUENCE: 44

```
acgtgtcgac gagagggagg gtgga                                           25
```

<210> SEQ ID NO 45
<211> LENGTH: 27
<212> TYPE: DNA
<213> ORGANISM: Artificial Sequence
<220> FEATURE:
<223> OTHER INFORMATION: primer OsMADS8 C5b

<400> SEQUENCE: 45

```
tcctcctcct cctcctccac ctcacct                                         27
```

<210> SEQ ID NO 46
<211> LENGTH: 41
<212> TYPE: DNA
<213> ORGANISM: Artificial Sequence
<220> FEATURE:
<223> OTHER INFORMATION: primer OsMADS8 C1b

<400> SEQUENCE: 46

```
aactaaatcg cctgcaggcg gaccgttttt tgcgaaatgc c                         41
```

<210> SEQ ID NO 47
<211> LENGTH: 9487
<212> TYPE: DNA
<213> ORGANISM: Artificial Sequence
<220> FEATURE:
<223> OTHER INFORMATION: OsMADS8 GUS expression cassette

<400> SEQUENCE: 47

```
cggaccgttt tttgcgaaat gccaaatcct ggcatgccta agctgacctg agcttgtagt     60
tttcaaacga accgtgttaa ttgtggtata taacacattg ggttggctac tgtatcgtac    120
ataattttgt tggggttatt tctgcatgcg tatacgtacg gattagttgt aattaagagg    180
aaaaacatgc atgtataata tagatatacc tagcatgcac cattatatac ttattaatct    240
```

```
aagctttaaa gtgcaaatga tactacatat tgaacattca actttattgt attgataaat      300
tgaaccggat atatccacaa gcacaaaatt tgcaatgcac ttcaaaatta atgtaatctt      360
tgcacgctac tccctacatt tcatattata agttgatttg acttttttt tcaagtttat       420 aaaaaaaatt agcaacatct aaaatatcaa attagtttca cttaatctaa cattgaatat     480
atttagatac tacgtttgtt ttatcttaaa aatgttagta tgttttttt ataaacttgg      540 tcagcctttg aaatgttgga ctagaaaaaa aggtaaaaaa aattataatg ctgaataagc     600
cacaatttaa aaagtttaca gggacggttt aattcattga catttcacat atacatagca    660
catgtcaaat tcatatgtta acttttcttt ttataaactg dacaccccgt gccaacagtc    720
aacccctaat taaattaacc acaacatgaa tacatcatta atttataac atatactagt     780 tattttgctt tcatatatc tccccctctt gctaatttga gttcccagca tgcatggata    840
ctaattaact taaccaaaat tagttagcct gcagcctaat ttgtccatct ctagctagct    900
agtttgcact taacatctgt gatacgttac cacaccaaag ttacatacac attaatgatt    960
aatcctttga tcagttccta tatatcccag gtagaatata tatcgatctc ttcagaatca    1020
cgaccaatta ggtaaaatga agaacatac actcctgcct agccaagact tcaaaccta    1080 cacacacata tatatctact actgcaagca ctgcaacggc aaagttctct gcaggcaaag    1140
agatataccg atcgaagaag cctctctcta tccaaaccca aacagctcca ttttgtctac    1200
acgaactatg gcaacttggc aaccacatcg ctagctagct agatatatac tatgctacct    1260
tggttcattt tgctgctttg atttgcaact gcaacccaag agaaaagttg taagggtctg    1320 tatgggggatt ttctgaccgc tgtatcttct ctcaaaatca tattaatcct ctctacatag    1380
tctagttttt catccaaatt ctcaaaagct ctaattatag aatctaaaaa attaactaga    1440
aaacagaagc tgagaaatcc acattctcca tattctcaga agcttgatac taactagcta    1500
tttcccaaaa tcttaggcct tatttagttg gggaaaattt ttgggtttgt ttgtcacatt    1560
ggatatacgg acacacatta gtattaaatg tggtacaata acaaaacaaa ttacagattc    1620
cgtcaaaaaa ctgcaagaca aattttattga gctcaattaa tccgtcatta gcaaatgttt    1680
actgcagcac cacattgtca aatcaggcgc aattagactt aaaagattcg tctcgtaatt    1740
tacacgcaaa ttgtgtaact ggttttttt ccacatttaa tactccatgc atgtatttaa     1800
atattcgatg tgatgggtga aaattgttta ttttggaaac taaacaaagc cttaagctct    1860
cccaacagat cacccaccgg ctcctagtgg acacaagaag ggtattttttc ccgaaacccg    1920 aaaactccga ggtttcaagt gcaaaagcgc ccaactctac tcactttcc ccagcttttc     1980 cgcgcttaat ttctcgacct gtcgaatcct cagtcgccac cgctgcgtcg acgaggagag    2040
agagagagag agagagagag agagaaaatc caaagcaatc agtgagagac gcattgaatt    2100
gggtcggaga ttagtgcgaa attaacctag atagctttgc ctttgcgtac gatggatcga    2160
tcgaggccgc ctagggttcc gcgtcgttcc accaccttgc cggaaatggc aatgccgggt    2220
agcccccacc gccgctgccc accctctccc ccttcccttt ttaaaccct catcccttc     2280 cccctcctcc tcctcctcct cgccttagct ttccctctc tttcgcttcg cgagattggt    2340
tgattcatct cgcgattgat cgagctcgag cggcggtgag gtgaggtgga ggaggaggag    2400
gaggagatcg ggtcgacgag agggagggtg gagctgaaga ggatcgagaa caagatcaac    2460
aggcaggtga cgttcgcgaa gcggaggaat gggctgctca agaaggcgta cgagctctcc    2520
gtgctctgcg acgccgaggt cgccctcatc atcttctcca accgcggcaa gctctacgag    2580
```

```
ttctgcagcg gccaaaggta tatatacatg gacgcactgg gcgcgcgcct cgatctgcta    2640
tagctagatc ggtagctgct tgcaacgtag ctagctaggg tttcttgcgc gcgcctgcgc    2700
ctccagatct ggagcgcacg atggttttgt gaacttcttg gtggcgattt gcggggatc    2760
tggggctgca catggtggat ctgcgagtgt gctcgtgttt tggtgagttt tgggagggtt    2820
tgggagaagg aagttggtgg aattctgtgg gaataattag ggttttttgtt cgttcgatcg    2880
ggtgctagct agcgtaatag ggagtggtga aatacgtaga tctgagggtt tctgatcccg    2940
tggtagtagt ggttttgaga tggcgcgctt aatggttttg agtttggttt aattgcgatt    3000
aatttatgtg catgcatggg atgggacatt caggatttaa gcctggatca gcaagtcgat    3060
ttttacggag aaaattaatc gttggaagct tcgaatctta attttatcga tctcctaatg    3120
gagggtatgc gagtttcgaa ttcccttggg atctgttttt ttcctcaatt tttagttttt    3180
tgagggcaa ttttttttag ggtatatatg atttttttttt tttgggggg gggggtgtg    3240
tgaagggatc atgcatatca ttagccatgt accggatgtg tgtctaaaca aacgttcact    3300
gcatgaattc cacggtttgg aggcagcata ccttacaaga tttgggggtt tcacttaaga    3360
ttttgtctct ttgttttttt aagggatggc cgcgggggag tattgttttt caagtgagtt    3420
atggttgcat cattaaaggc aacatcaata aatataaagt ctgtttctcc tgagataagt    3480
atatgaaaaa tcatatacta ctatatatat aattgtcttt cagaaacaca gagcgtctga    3540
ttggctaggc ataattcaca agccgcatat aagctagttg aattgatttt gaattagaaa    3600
acattttttt tcgggggaa gaaaacattt ggtattgtgt ttagagataa acaattagtt    3660
agggtagata agtcaggcat tcatgagctt catttcatat ttgaatcata cattttccaa    3720
actttagaag gttaaatttt cttgctcatt gtattgcact gatcatttta ataatatctt    3780
ctatagtgaa tattcatca ttatatattt tagataatga ttcattatt atatgctccg    3840
ttgcagaaaa aaccaacttt tttgccaaac ctggacatat ataggctatg tccagattta    3900
tagctagaag ttagggcctc atcttttacc ctatgaatta taagccaata tcaaattttg    3960
aatttcgaaa cttgatttag aagttgattt ttaatgtttt gtcaatgtag attgtttttc    4020
agcattaact tttaattcgc taaagacaca tatacaattt tactcacaaa ttatattttg    4080
gttgctaata agccgttatg gcttataatc agccgtaagt atatgggac tttagcattc    4140
tttttctttt tttatggagg gagtacatgc ttgccaattt ttatagttat gtttaaatgg    4200
tttccattat acctaagtta ctaaattaaa attaatacgc ctataaaatt ctaacattaa    4260
atatattcac aaataagagt acatgatttc attgaccagg gaattcaatt tggatatggg    4320
gtgagtgaaa catccctcct ctgctcctcg gaagaaatcc tgcaagggag tacacaatat    4380
tcctaggact cacttgagta tctgcagggt acagttagtg acagctttcg attgtcattc    4440
gattggtctc ctcagctctc gtagctgagc tgtcagtaca gaagattggt cttcatcaga    4500
tgtctcttct agttctagct agagctagtt cagtggagta ttttatgccg acaaattgat    4560
actcaacgtg tactgtagat ccttttcaga aatctgaatt cacgacttgt ttaaacaaag    4620
gctgtgtttg gatccaaact tcagtccttt tccattacat caacctgtca tatacacaca    4680
acattttagt catatcatct ccaatttcaa ccaaaatcta aactttgcgt tgaactaaac    4740
acagccaaaa ggtcactaaa ttgacgcggt agagggggg gggtgagcat tatagctgta    4800
gtagtagtct gcgtgaagtt atgccatttc attgtgtgtc gtctgaactt gatatctctc    4860
tttaaagagt gtactccatt ttctttacaa aaagtggcct ctaggttgat atcatggaca    4920
tatataaaat tataaatcaa cttgaaacta ccgatgcaag aattaagata aaacgttatt    4980
```

```
gtttcttaga aattgtctcc aattatgcaa gcaccttcat ccgtgtcatg gagctaatgt    5040
tcatgttttg tgggaaacaa gattttcat ctactaatta atcgatgtgg tccccggaaa     5100
agaatgtgcc ctagattgtt agtatttagt tatgggcgaa ctatatatgt tcctttattt    5160 cgttttcca taaacatagc catttgtgtt tttgaaactt gcagcttgac caccatggta     5220
cgtcctgtag aaaccccaac ccgtgaaatc aaaaaactcg acggcctgtg gcattcagt     5280 ctggatcgcg aaaactgtgg aattgatcag cgttggtggg aaagcgcgtt acaagaaagc    5340
cgggcaattg ctgtgccagg cagttttaac gatcagttcg ccgatgcaga tattcgtaat    5400
tatgcgggca acgtctggta tcagcgcgaa gtctttatac cgaaaggttg gcaggccag    5460 cgtatcgtgc tgcgtttcga tgcggtcact cattacggca aagtgtgggt caataatcag    5520
gaagtgatgg agcatcaggg cggctatacg ccatttgaag ccgatgtcac gccgtatgtt    5580
attgccggga aaagtgtacg tatcaccgtt tgtgtgaaca cgaactgaa ctggcagact     5640 atcccgccgg gaatggtgat taccgacgaa aacggcaaga aaaagcagtc ttacttccat    5700
gatttcttta actatgccgg aatccatcgc agcgtaatgc tctacaccac gccgaacacc    5760
tgggtggacg atatcaccgt ggtgacgcat gtcgcgcaag actgtaacca cgcgtctgtt    5820
gactggcagg taccaagctg cgaatcttcg ttttttttaag gaattctcga tctttatggt    5880
gtataggctc tgggttttct gttttttgta tctcttagga ttttgtaaat tccagatctt    5940
tctatggcca cttagtagta tatttcaaaa attctccaat cgagttcttc attcgcattt    6000
tcagtcattt tctcttcgac gttgtttta agcctgggta ttactcctat ttagttgaac    6060
tctgcagcaa tcttagaaaa ttagggtttt gaggtttcga tttctctagg taaccgatct    6120
attgcattca tctgaatttc tgcatatatg tcttagattt ctgataagct tacgatacgt    6180
taggtgtaat tgaagtttat ttttcaagag tgttattttt tgtttctgaa tttttcaggt    6240
ggtggccaat ggtgatgtca gcgttgaact gcgtgatgcg gatcaacagg tggttgcaac    6300
tggacaaggc actagcggga cttttgcaagt ggtgaatccg cacctctggc aaccgggtga    6360
aggttatctc tatcaactgt gcgtcacagc caaaagccag acagagtgtg atatctaccc    6420
gcttcgcgtc ggcatccggt cagtggcagt gaagggcgaa cagttcctga ttaaccacaa    6480
accgttctac tttactggct ttggtcgtca tgaagatgcg gacttgcgtg gcaaaggatt    6540
cgataacgtg ctgatggtgc acgaccacgc attaatggac tggattgggg ccaactccta    6600
ccgtacctcg cattaccctt acgctgaaga gatgctcgac tgggcagatg aacatggcat    6660
cgtggtgatt gatgaaactg ctgctgtcgg ctttaacctc tctttaggca ttggtttcga    6720
agcgggcaac aagccgaaag aactgtacag cgaagaggca gtcaacgggg aaactcagca    6780
agcgcactta caggcgatta agagctgatg agcgcgtgac aaaaaccacc caagcgtggg    6840
gatgtggagt attgccaacg aaccggatac ccgtccgcaa ggtgcacggg aatatttcgc    6900
gccactggcg gaagcaacgc gtaaactcga cccgacgcgt ccgatcacct gcgtcaatgt    6960
aatgttctgc gacgctcaca ccgataccat cagcgatctc tttgatgtgc tgtgcctgaa    7020
ccgttattac ggatggtatg tccaaagcgg cgatttggaa acggcagaga aggtactgga    7080
aaaagaactt ctggcctggc aggagaaact gcatcagccg attatcatca ccgaatacgg    7140
cgtggatacg ttagccgggc tgcactcaat gtacaccgac atgtggagtg aagagtatca    7200
gtgtgcatgg ctggatatgt atcaccgcgt ctttgatcgc gtcagcgccg tcgtcggtga    7260
acaggtatgg aatttcgccg attttgcgac ctcgcaaggc atattgcgcg ttggcggtaa    7320
```

-continued

```
caagaaaggg atcttcactc gcgaccgcaa accgaagtcg gcggcttttc tgctgcaaaa    7380
acgctggact ggcatgaact tcggtgaaaa accgcagcag ggaggcaaac aatgagagct    7440
ccgcgggcgg ccgcaggccg atgcgacaac caataaaaac ggatgtgacg acacagatca    7500
agtcgcacca ttagattgat cttctcctac aagagtgaga ctagtaattc cgtgtttgtg    7560
tgctagcgtg ttgaaacttt tctgatgtga tgcacgcact tttaattatt attaagcgtt    7620
caaggactag tatgtggtat aaaaggccgt acgtgacagc ctatggttat atgctgcaca    7680
aaaactacgt atggtacagt gcagtgcctg tacatttcat aatttgcggt aaagtttatt    7740
gactatatat ccagtgtgtc aaatataata aaatgtcgag gtttaattac catgctcatg    7800
tgcattctag gttctttata tataggagta ttaggttaac tgattagttg ttgtacatca    7860
ttgtctaaaa aaatagctgt cgttgtacat aaattgagca tgctggtctg catgaaaatt    7920
aaggaaaaga aacatgcaag tagcccaggt agttgggctg tcaagcagtc gtacttgtcc    7980
gagtcgcaga tagttagttg acccgaaact gtgattgcga acgtacgagc gaaaatgtag    8040
atgcaggcat ttcaacttga gtgatttgct ttttattcat atatatggtt catttttttt    8100
aaagatggct tcgactggat ctcgtcttcg ttaagcatgc gtccaggacc aggagtacat    8160
gcattttgca ttcagcccta accaatactt tttaccaatt aaagagcaga gcaggcacga    8220
cacgcataga caacggacat ggatcttcgc agtactacat ttgcagtagc agtggctgat    8280
aggtgaaccc gatcctacat gtcagtggct gctactgtag acaatctcca ctgatagaca    8340
acgggtacaa ctcgtagtat taattcaaac gccaaatgca ttaatggtag tttgcttatt    8400
agtactagtt tgcataacga agcgtgtata tatatttata cttcctccgt tttatgtttt    8460
aatttggact tgtcgttcca gaaaatcgta cgaagtcata gcaaattaca ttgcaattct    8520
tcttaattac atattaatca tgttttcaaa gtaagaatta gaattcctta taagagacta    8580
ctactagcat ggttgtgtta gagaaaggta agaagaaaaa agcatttaaa aagtgatttg    8640
gaatatgaga atgacaagtg ttttggcata acttttaaat ggtagaacga caagtaattt    8700
aaaacataca aagtactagt cccttcattt catattataa ttcgcttcga cttttttctaa   8760
gtcaaacatt gttaaatttg actaggtttt atagaagaaa agtaacattt taaacgtcaa    8820
attagtttca ttaaatctag catttgaata tattttgata atatgtttgt tttgtggtaa    8880
aaatactatt atattttcct acaaatctag tcaaacgtaa aaaaaagtt tgactaggaa    8940
aaaagtcaaa acgatttata atataaaaca taagagcacc cgcaatagta aagtaaggtg    9000
ctctctgtaa aacatgtaca tctcagcaat agactagatt aatagtaaac caccttaata    9060
gtatgtctac ttgggtatct atagctctct aatatattgc ctcgtttttc tctatagact    9120
atcttcacat tagtagatag ctttgctctc tttttcatc tcttccaagt aggaaaatat    9180
gctgacatgg atctcttgta gagagtttat agataaccat tgtgggtgcc ctaagtagta    9240
ctatctttc ttcctgtcca aaaaataaa agcacttttg agcttctata cgtagattta    9300
aatgagaaat ggctatattt gattgagata agtgagtagg taaacgctct atttaagata    9360
aattgtaaag ttaatatatt ttgacggagg ggaagtagca tttatgaaac cctagtagag    9420
ctacgcttcg ttgaccacac tcctcgaaat aaacatgata ttttgtcatg atcgatgact    9480
cggaccg                                                              9487
```

<210> SEQ ID NO 48
<211> LENGTH: 41
<212> TYPE: DNA
<213> ORGANISM: Artificial Sequence

```
<220> FEATURE:
<223> OTHER INFORMATION: primer OsMADS13 C1

<400> SEQUENCE: 48
gactgcatgc ggaccgttcc aaaattaagc acacacattt g                  41

<210> SEQ ID NO 49
<211> LENGTH: 33
<212> TYPE: DNA
<213> ORGANISM: Artificial Sequence
<220> FEATURE:
<223> OTHER INFORMATION: primer OsMADS13 C2

<400> SEQUENCE: 49
gactccatgg cttcttgctc tcaactgatc aac                           33

<210> SEQ ID NO 50
<211> LENGTH: 33
<212> TYPE: DNA
<213> ORGANISM: Artificial Sequence
<220> FEATURE:
<223> OTHER INFORMATION: primer OsMADS13 C3

<400> SEQUENCE: 50
tcgagcggcc gctgacatgg atatgatgat cag                           33

<210> SEQ ID NO 51
<211> LENGTH: 36
<212> TYPE: DNA
<213> ORGANISM: Artificial Sequence
<220> FEATURE:
<223> OTHER INFORMATION: primer OsMADS13 C4

<400> SEQUENCE: 51
acgtatcgat cggaccgcaa cgcacgggca cccaac                        36

<210> SEQ ID NO 52
<211> LENGTH: 5286
<212> TYPE: DNA
<213> ORGANISM: Artificial Sequence
<220> FEATURE:
<223> OTHER INFORMATION: OsMADS13 GUS expression cassette

<400> SEQUENCE: 52
cggaccgttc aaaattaag cacacacatt tgcaagaact agctaggcat gcatatatga    60
taattaaccg gcaagttgac ttcagttatt ctgcagatgt actaaacaca taacaaggga   120
tgatcagttg cttattttt tcataacttg ctaggttgct tataactcca gccttctgga   180
catcgaccaa tctctaaaca tactttagca gtgcctacaa agtacaaaca actaaatacc   240
tctctgcaga tcagtgtttc taggcacaaa ttacacaaga tagaaaaaag gagaggttat   300
aaattcttgc ttaaagaata tacatgtaaa gatgtctaaa tagctataaa tgggtaagca   360
agatagcaaa gaaggccagt ggcctttgca gctaagctag ctagctagcc cttcttcctc   420
tctttcctgc tttcccttg ccttctccta ttaatcctct gcacctcaca cagcagcaga   480
aaacccacca actggagctc tcctttccta ctccaagaaa cgaaggtaga gaaagaaaga   540
tcagatcagc ttcaggacca attttagcta ggttatatat ctctttgcgt gctaatgtgt   600
tttagttatc tgggtgtgtg tagagttctt tgttaaggca ctgattcagc tgcagtttag   660
attcaagttt gtatgttctc tctttgagga aaagaaaccc ttttcctgtg cttcgagttc   720
ttgcaaagag aaactgtgat gcttggcttc cagtttgatg cttcttgtt cagattggaa    780
```

```
attcttccta gcttctttct ctatttatgt agcaaggatt ctttccggcc cagtgatcct      840
ggtttctttt ggaaggtttc agttttttcg ttctttcttg aaatttctct tcttgcctta      900
ggcagatctt tgatcttgtg aggagacagg agaaaaggaa gaagctagtt tcctgcggcc      960
gacctcttgc ttctcacttt gtgatgagtt ttctttggtc aattcttagc tagatatgct     1020
aagatagtta gttaagcaaa tcgaaattgc tagcttttcc atgctttctt aaacatgatt     1080
cttcagattt ggttggttct tttttttcct ttttgtggag acgtgctgtt cttgcatctt     1140
atccttcttg attcatctac ccatctggtt ctttgagctt tcttttttcgc ttcttcccctt   1200
cattatttcg agcaatctct gcacatctga aagttttgtt tcttgagact acttttgcta     1260
gatcttgttt actcgatcac tctatacttg catctaggct cctttctaaa taggcgatga     1320
ttgagctttg cttatgtcaa atgatgggat agatattgtc ccagtctcca aatttgatcc     1380
atatccgcca agtctttcat catctttttc tttctttttt atgagcaaaa atcatctttt     1440
tctttcaaag ttcagctttt ttctcttgtt ttacccctct ttagctatag ctggtttctt     1500
attccttttg gatttacatg tataaaacat gcttgaattt gttagatcga tcactttata     1560
cacatactat gtgaatcacg atctcagatc tctcagtata gttgaattca ttaatttctt     1620
agatcgatca gcgtgtgatg tagtactgta aatcactact agatctttca tcagtctctt     1680
ttctgcatct atcaatttct catgcaagtt ttagttgttt ctttaatccg gtctctctct     1740
ctttttttaat cagctgagag tttgtgctgt tctttaatca ttaccagatc tttcatcagt    1800
actctctctt ctgcatctat caaacttctc atgcaatgtt tttgctgttc tttgatctga     1860
tctctggtct ccttttttgt tgatcagttg agagcaagaa gccatggtac gtcctgtaga     1920
aaccccaacc cgtgaaatca aaaaactcga cggcctgtgg gcattcagtc tggatcgcga     1980
aaactgtgga attgatcagc gttggtggga aagcgcgtta caagaaagcc gggcaattgc     2040
tgtgccaggc agttttaacg atcagttcgc cgatgcagat attcgtaatt atgcgggcaa     2100
cgtctggtat cagcgcgaag tctttatacc gaaaggttgg gcaggccagc gtatcgtgct     2160
gcgtttcgat gcggtcactc attacggcaa agtgtgggtc aataatcagg aagtgatgga     2220
gcatcagggc ggctatacgc catttgaagc cgatgtcacg ccgtatgtta ttgccgggaa     2280
aagtgtacgt atcaccgttt gtgtgaacaa cgaactgaac tggcagacta tcccgccggg     2340
aatggtgatt accgacgaaa acggcaagaa aaagcagtct tacttccatg atttctttaa     2400
ctatgccgga atccatcgca cgtaatgct ctacaccacg ccgaacacct gggtggacga      2460
tatcaccgtg gtgacgcatg tcgcgcaaga ctgtaaccac cgtctgttg actggcaggt      2520
accaagctgc gaatcttcgt ttttttaagg aattctcgat ctttatggtg tataggctct     2580
gggttttctg tttttttgtat ctcttaggat tttgtaaatt ccagatcttt ctatggccac    2640
ttagtagtat atttcaaaaa ttctccaatc gagttcttca ttcgcatttt cagtcatttt     2700
ctcttcgacg ttgtttttaa gcctgggtat tactcctatt tagttgaact ctgcagcaat     2760
cttagaaaat tagggttttg aggtttcgat ttctctaggt aaccgatcta ttgcattcat     2820
ctgaatttct gcatatatgt cttagatttc tgataagctt acgatacgtt aggtgtaatt     2880
gaagtttatt tttcaagagt gttatttttt gtttctgaat ttttcaggtg gtggccaatg     2940
gtgatgtcag cgttgaactg cgtgatgcgg atcaacaggt ggttgcaact ggacaaggca     3000
ctagcgggac tttgcaagtg gtgaatccgc acctctggca accgggtgaa ggttatctct     3060
atcaactgtg cgtcacagcc aaaagccaga cagagtgtga tatctacccg cttcgcgtcg     3120
gcatccggtc agtggcagtg aagggcgaac agttcctgat taaccacaaa ccgttctact     3180
```

```
ttactggctt tggtcgtcat gaagatgcgg acttgcgtgg caaaggattc gataacgtgc    3240
tgatggtgca cgaccacgca ttaatggact ggattggggc caactcctac cgtacctcgc    3300
attacccttg cgctgaagag atgctcgact gggcagatga acatggcatc gtggtgattg    3360
atgaaactgc tgctgtcggc tttaacctct ctttaggcat tggtttcgaa gcgggcaaca    3420
agccgaaaga actgtacagc gaagaggcag tcaacgggga aactcagcaa gcgcacttac    3480
aggcgattaa agagctgata gcgcgtgaca aaaaccaccc aagcgtggtg atgtggagta    3540
ttgccaacga accggatacc cgtccgcaag gtgcacggga atatttcgcg ccactggcgg    3600
aagcaacgcg taaactcgac ccgacgcgtc cgatcacctg cgtcaatgta atgttctgcg    3660
acgctcacac cgataccatc agcgatctct ttgatgtgct gtgcctgaac cgttattacg    3720
gatggtatgt ccaaagcggc gatttggaaa cggcagagaa ggtactggaa aaagaacttc    3780
tggcctggca ggagaaactg catcagccga ttatcatcac cgaatacggc gtggatacgt    3840
tagccgggct gcactcaatg tacaccgaca tgtggagtga agagtatcag tgtgcatggc    3900
tggatatgta tcaccgcgtc tttgatcgcg tcagcgccgt cgtcggtgaa caggtatgga    3960
atttcgccga ttttgcgacc tcgcaaggca tattgcgcgt tggcggtaac aagaaaggga    4020
tcttcactcg cgaccgcaaa ccgaagtcgg cggcttttct gctgcaaaaa cgctggactg    4080
gcatgaactt cggtgaaaaa ccgcagcagg gaggcaaaca atgagagctc cgcgggcggc    4140
cgctgacatg gatatgatga tcagctcatc ttctatatct tatgctgtta tgcagacaga    4200
cactactgat gtggctatat atatagtatt tgtgtgctgc tgcattttgt taatcccttg    4260
taaattgcta cttaattatc tcatggagaa ttggagagac caaatgggca gagctagcta    4320
gttagctgtg cccaattaag aagctaaatc tatcagaagt gtgtactgat gagtgatgag    4380
tatttttctt catttgggat caaattaaac taagtaaaac atatatattt gacttatgtt    4440
ttacgtgcat gcatgcatgc ttaattgtgt caccttttggg gattcatttt gtacatatgt    4500
gcaccatttt gtgtgtacaa tgcaggttta tatgactttt ttcgcaatta cacgatggcc    4560
catgcacata accaccatgc acactgcacg tacatccaca agtgtgcccc tttaacacaa    4620
ggcaatacac caaataaatt gtaatgtgcc actaaacttt tttgaaagtg taaccgcgcg    4680
tatgcttccg tggcttatat atgactctgg tggctgactt ctagggcatg tcgacctgag    4740
catcttcgtg tgggtttcga ctctctaatt ctcctggtct ctgcagttg tggaaggggc    4800 gaaactccag ggttttgat tactctcttt cctcactctc aagggttctg aaagtcatcc    4860
tacaggaaga ccgtttgtgg tcttctgctg gcgtcgctgt ttttagggg ttattaggag    4920 tgtagtggag cttcgccacc accctccatc tatttaggag caacattttt ttggtagttt    4980 tttacttta cagtctttttt gtttctttct ttgttccctt atccacatgc aatggtcgtc    5040
tgactggtta cgttgtgtaa caaaaactct gcttttttct aatatactga cgtgcaatcc    5100
tttggtgcgt tcgcgaaaag aaagggggat caattgcaag tatttgtgg gaattaaact    5160 tttcttgtga aattattgta aaattccagc attctaaatg agctctaatg tgtgataatt    5220
tgcattctct atatatattg aataattctt ttgttgacta gttgggtgcc cgtgcgttgc    5280
ggaccg                                                              5286
```

<210> SEQ ID NO 53
<211> LENGTH: 4439
<212> TYPE: DNA
<213> ORGANISM: Oryza sativa
<220> FEATURE:

<221> NAME/KEY: promoter
<222> LOCATION: (1)..(4439)
<223> OTHER INFORMATION: OsMADS6 promoter in RNAi constructs

<400> SEQUENCE: 53

```
ctaggacgat ggtgtgatgt gggaacacga agaaaacatg aggaaaaaat attaaaatga    60
atttcccact taaaatgcat caaataaaaa aaataaagaa acgaccggga atagacacag   120
ggtttgtgaa ctagctaggg caaacatcat atggtccctt gctgatgcac aagtacattg   180
agatgtcatt tcaattctgt gcatcatatg catgtggtcc cttgctgaat attactcttg   240
aaatatctac cagtgccaat ctattgcatg acttaattaa ttcacaggtt ttgttgatta   300
cattattagt aagcttgaga gcacaagctc aatggatttt tctataaatg gggatcattt   360
tgcaattttc tttgtcgtgc aaagttagcc ttctttatta ctacttctgt ttttaaatat   420
acgatcctat tgacttttgg tcatatattt aaccatgtat cttatttaga tagtttgcgc   480
aaatatatat accttcaatg ataaaattag ttacaatgaa acaaatgata tttacgcaat   540
tcttttttact aaacaagtca caagaagtac ctgcagcaat atatgttgga accgtgcagt   600
agatcgagcc tagctacgca aaaaaacaaa aagagaaaaa aagggaaagg aaaaacatta   660
atcatgcatg agcagtatgc ccggcaactg gaatttgtca aagatatggg gagagggaaa   720
taatacaagt actactacta cctagctcta ccatgcatat gcacccaaag gcaaactgga   780
ttattggata aagcacagat gctggcaaaa caatccttaa gcctcccctc cctgcttctt   840
tattttgggg cagcctctac cggacggtgc cgtggtccat tggaccagta ggtggcgaca   900
tacatggttt gggttaagtc taggagagca gtgtgtgtgc gcgcgcaaga gagagagact   960
gtgagtctgg gagtagcct ctccctcct ttggccatct tcctcgtgta tatgcatata   1020
tgcatcatcg caacggtgta tatttgtggt gtggcgggtg tggcattgga ttgccccat   1080
tttggctcgt gcttcccagt tagggtaaaa cctgtggtaa acttgctagc cccacgccaa   1140
agttacccctt ctttattgtt gaaagggaga ggaggtgtgt gaattgtgat ggagggagag   1200
agagagagat agaaagagag atgtgtgtca aagcaagcaa gaaaccagtt tcacaaagag   1260
ctactactag tactagtgta ctactgtggt acagtgccca atgtcctttc tccggactcg   1320
actccactaa tattctcctc ttctcgcgcg gctcgttata ttctcgtcat cattggaggc   1380
tttagcaagc aagaagagag gcagtggtgg tggtggtgga ggaggagcta gctagcctgt   1440
gcttgctgat cggtgctgag ctgaggaatc gttcgatcga tcgggcgagt cgacgagggg   1500
aagagttgag ctgaggcgca tcgagaacaa gatcaacagg caggtcacct tctccaagcg   1560
ccgcaacggc ctcctcaaga aggcctacga gctgtccgtt ctctgcgacg ccgaggtcgc   1620
gctcatcatc ttctccagcc gcggcaagct ctacgagttc ggcagcgccg ggtataatta   1680
atacagacac aacaacacac acaaccaaca aaccagcatc aatttgaacc tgcagatctg   1740
ctgtttttctc tgatcaattg cttcttttt tttgttcttt tttgtttctt ttatctgctg   1800
caacggcgtc ctgctcctct ggggtttctc gttttctttt tcatttattt ttagcaggtg   1860
ccaagtagcc gagctactat acttacctgg ccatgttaat tattttattc cgtctgtctg   1920
tgtgtgtctg tgcatactac tatagggaca tggcgcggtg ttcttataaa ccggaggcc   1980
ggatccctaa ctagcatggg aggatatctt ttcagcggat ctatacaaac cctactcctg   2040
ctgacctctt tcttccagtt tctccgggtc ttccttggat tattattgcc catcttccgg   2100
gttgtgcgtg tgtcagagac agctcgaacg ataaatttct caaaaccagt actagagagg   2160
gtgtgttgtg tgtgagaact gagtggagag ttagcatgaa ggctgcaaac tagaaaggaa   2220
```

```
ggtatgttct ttccttttg atccatcagg ggagcccctt ctggtattaa gatctttccg    2280
gcacattgat tttcatactt tgtgatgacc ctggaagaat cggcgtagca gcgtagcacc    2340
gctccatttt ggtcttaccc tcacctcccc atgctatgaa ctgatcaatt tcattgttct    2400
tcatcaccct tctcctagct ttccacttcc ttcggatctc atgccatgtt tctcagcatg    2460
aatcaaattt aattcgtgtt ttctacttcc atatatactg gaagaaattt aattagatct    2520
attttgctc gggaggtctt catactttga gttctgatgc catcaccta tttccccccc     2580
cccttctct tgttctatct tcttcctcat cttggcttga tcattttgat ctgtcagtta    2640
tagcatgatg cattctcaat ttgactgtat gtaagttcaa ccggaaatat gttgaatgga    2700
ttttctatat atcaacactt gatgtcaggc ctgcatctgt ttcgcttgtg gtggtgtggc    2760
caaaattgtc tatatttgat ctttgctctt ctttctcctc atttcatgac gattcctact    2820
acggcttaaa ccattcttta ttctttacta atcatggatg ttgcttgact cctagttgtt    2880
tcgtactagc tcaacttgga gatcttttca ttatttgcct agttggtggg tacgtttgtg    2940
acagatctaa aatggtgcac gaaaagttt acttattatg aaaaagggga gcttaacagg    3000
gtaatttctc tatttattcg tgatgacatt ttttccttga taagggggat ttttatat     3060
ctgcactcac atgtttatat gtaaaatcta gctcttttgt tttgttttg gcatatttcc    3120
cgctaagtat agagtttatg tggataacat tataacttt caagatccaa tccacatctt    3180
tgattgtgaa aatcatacaa tagggaaaat caactgaagg gttaattaga tgctatatgc    3240
atatatatat atatgtgcgc gcgcgcgcgc ctgaatttaa ctatgtatgc atccaactgt    3300
ttcattgaaa aagatttgat atttttcagt ctattctttt tcgagtatat atttaatatg    3360
tttcaatctg ttttgaccat tataagataa agcctatatt caccaggcat ttgagatgat    3420
cttttcatgc atgaaaaagc tgttgttatc acttcaacta accagacgat ctaacatgta    3480
tttgtataag aaacagacct tgatttcctt ctgtaaaatc atgcatgtgt tcgttttgaa    3540
ttggagtcgg cgcgcctgtg ttttgaccgt caggaaagtc ttttttttcc ctgaatagtc    3600
aagggtctat acttcttgaa gcaattggga cactaatcaa ttattgttta tacctcggac    3660
catctttcc ttcttcacac cactaatcag tttatgcctt ggaccattaa ttgtgttgtt    3720
cacaagcttc ttgtttatgg tttacaaagc attcgcctag atttgtgtgt gtctctacac    3780
atcgatcact tttaaatact tgtcgctttc agttattctt ttaacgtttg gttatttatc    3840
ttatttaaaa aaattatcgt attattatt atttttgtttg tgatttactt tattatcaaa    3900
agtatttcaa atatgactta tcttttttta taagtgcact aatttttcaa ataagatgaa    3960
tggtcaaatg ttacaagaaa aagttaaagc aaccactaat ttagggcgga ggtagtaaaa    4020
cctagttatt gtaaccaata attttatcaa tctataaatg caacacaaag tcacttcgtg    4080
atatctcaca caaagccact tcaacgatga aagctgactg catgttttat caaaacacat    4140
gtgatcagtt tgttggatga aaaaaattat ctatgtcata aatcaagagt tataatataa    4200
gcttctggct ctacaagtaa catttctatg ttttttttt acgttcttac atactatgtt    4260
ttgccaaaaa aaacatgatc attttgttgg acgaaaagaa atagtaaata tagagtgacc    4320
tttgatatca ttataatata agcttctgcc tctataaata acatctatgc acttttacg    4380
tcgtagtaat ttgatatatg agaaatttac atataacatt tttgtgcagc ataaccacc    4439
```

<210> SEQ ID NO 54
<211> LENGTH: 411
<212> TYPE: DNA

```
<213> ORGANISM: Zea mays
<220> FEATURE:
<221> NAME/KEY: misc_feature
<222> LOCATION: (1)..(411)
<223> OTHER INFORMATION: CAD RNAi fragment

<400> SEQUENCE: 54
atggggagcc tggcgtccga gaggaaggtg gtcgggtggg ccgccaggga cgccaccgga      60
cacctctccc cctactccta caccctcagg aacacaggcc ctgaagatgt ggtggtgaag     120
gtgctctact gcgggatctg ccacacggac atccaccagg ccaagaacca cctcggggct     180
tcaaagtatc ctatggtccc tgggcacgag gtggtcggcg aggtggtgga ggtcgggccc     240
gaggtggcca agtacggcgt cggcgacgtg gtaggcgtcg gggtgatcgt tgggtgctgc     300
cgcgagtgca gccgctgcaa ggccaacgtt gagcagtact gcaacaagaa gatctggtca     360
tacaacgacg tctacactga tggacggccc acgcagggtg gattcgccct c             411

<210> SEQ ID NO 55
<211> LENGTH: 363
<212> TYPE: DNA
<213> ORGANISM: Zea mays
<220> FEATURE:
<221> NAME/KEY: misc_feature
<222> LOCATION: (1)..(363)
<223> OTHER INFORMATION: COMT RNAi fragment

<400> SEQUENCE: 55
atgcagctgg cgtcgtcgtc catcctgccc atgacgctga agaacgccat cgagctgggc      60
ctgctggagg tgctgcagaa ggaggccggc ggcggcaagg cggcgctggc gcccgaggag     120
gtggtggcgc ggatgcccgc ggcgcccggc gaccccgccg ccgcggcggc catggtggac     180
cgcatgctcc gcctgctcgc ctcctacgac gtcgtccggt gccagatgga ggaccgggac     240
ggccggtacg agcgccgcta ctccgccgcg cccgtctgca gtggctcac ccccaacgag      300 gacggcgtgt ccatggccgc cctcgcgctc atgaaccagg acaaggtcct catggagagc     360
tgg                                                                    363

<210> SEQ ID NO 56
<211> LENGTH: 2492
<212> TYPE: DNA
<213> ORGANISM: Oryza sativa
<220> FEATURE:
<221> NAME/KEY: misc_feature
<222> LOCATION: (1)..(2492)
<223> OTHER INFORMATION: promoter OsMADS14

<400> SEQUENCE: 56
tggaagtttg aagaaattga aacgatgtga tggaaaagtt gaaagtttga agaaaaaagt      60
tggaatctaa ataggggccca acatactcaa ggctttggaa tattactcac acacacacac    120
acacaaattc atgtgggtca aatagcttgt cctttagaat tttggaattt cccccattct    180
ccaactagaa tatccaatga aattattgcg tttaaaagaa agagttgggc ggtgacgata    240
tggggtttta tcaactttca aaatgaacac ctatgaaatt tctacttaac ctcaacttca    300
atatgagaaa tgtaaagtaa aaggaaaaat tttctacaaa acatctaaaa aacatgatct    360
ttgctggtgg acaccgttaa aaatgtagct tttgtcttag ggcactaaaa aacgtgataa    420
tttgctggag aacatcacgg cctttaaaat gtaaaatcca cttaattgag aagagatgag    480
gcatatgaaa tgtttatttt gccctcctct tcttcctcgc cactcatgtc atcgcctcgc    540
tgcctgctaa tagggggtttg agtgagagag cacaaagatt gagaggcggg gatatgatca    600
```

```
gttcgaactg agacatactc cttcgttcac atatgcggga tagggcctc ctaaaatatt      660
tttctatcaa ataggatgaa aacaataaaa taatcgatgt ttatgttctt cagcaaatta      720
ccatattttt atagtgttct cggaaaatcc acgttttgat ttagatatac tgtagcaaat      780
ttgccaaatt aaaactaacc ggtttaatta attttaggtt ttagcaagta ctgtacgctc      840
ttcaagttgt ggcaactact ttgattgcag ctacagtaca cccccgatc gagagcgaga       900
ccgagggtta cgtggtgggc ccagcgcggc agccacactg taggagtgac agtgctaggc      960
tacagctact gtgctgggcg tagtagttgt tccgctcact gtgcagatga ggtcatgcgc     1020
tcatcgatcc ccctcctctc ctcctcctcc tctctgtcct ctgccatccc ccccacccgt     1080
cacgtgaggc gacgccgccg acctgatggc tcgacatgcc ccccgtcccg gtcgacgcga     1140
cgtgcactgt gaccggccgg aagaacgccc ccctgccag ccggcgacac gcacgcgtcc      1200
ggccaaggct gcctagctag cgtatcgctc ccccagctac cggcctcgcc gtgtggcccg     1260
gcgcccggc gtgcgtacgc gtcgggtacg taggaaacac ggcggcagcg tcgaggcgag      1320
gacggggaag cggctggacc ggcgggccgg gggaagagag gcagccatcc tgtactctcc     1380
tacgtacagc caccttacct gttgcgtcaa cgagagcttg ggcgttgctc gctacagccg     1440
ctggctagct tagcttatag ctagtctccg cttagcctgt gggcataaaa gcacccggca     1500
ccagcgtccg ctcgacacgt cgcgattccg cctctgtgcg cgctgctgcc cgggccgcac     1560
cgtgtgatac gtacacaacc tcgggttcga cgcccccgcc ggcccggtcg cttccctcgc     1620
ctcgctgtta acgtcgctgt tacaagcttg cgaattgcga ttgtgcgagc gctcgcggcg     1680
gtattaattt ttgctatacc tggggcgatg gaaacgtaac gtactactac tacgtgacct     1740
agggtgagag acgagacgag acgagaatat gagatgagat ccaaattcaa tctgcctctc     1800
taccccacga aagaaaagat tcttctcttc gtcgacgacc cggcctctcg ctctcgttgc     1860
ctttctttcg cgctcagtct ctctcggcca attaagctgt agatcggcca ccaccaccac     1920
caccaccacc accatccaca gggcgctgca agctgggcca ggcctctctc tatctctctc     1980
tcttgagagg agagattaag tagggcatag agagaaaaaa gctactccta attaagccac     2040
agcttgagca gatcagctgc aggccggccg gtgtgcgtgt gtgacagtag gagagagagc     2100
tagcgagaga gagcaaggaa tcggaattga tttcatgcac tgatcgatcc atccatcatg     2160
cagatgctgc atggatgaga agagctagca gctaagcttt gctgaagaaa attcttcaga     2220
ggtttgtgtt gatttgctgg tctgctagag atcgatctag agagagagag aggaagggaa     2280
gactgaagag agatctcgag cgggagatcg agatcgggcg aggcaaggtg gtgcttcagc     2340
ggatcgagaa caagatcagc cggcaggtga cgttcgccaa gcggcggaac ggcctgctca     2400
agaaggccta cgagctgtcc atcctctgcg acgccgaggt cgccctcgtc ctcttctccc     2460
acgccggccg cctctaccag ttctcctcct ca                                   2492
```